United States Patent
Weiner et al.

(10) Patent No.: US 12,194,086 B2
(45) Date of Patent: Jan. 14, 2025

(54) MAYARO VIRUS CONSENSUS ANTIGENS, DNA ANTIBODY CONSTRUCTS FOR USE AGAINST MAYARO VIRUS, AND COMBINATIONS THEREOF

(71) Applicant: THE WISTAR INSTITUTE OF ANATOMY AND BIOLOGY, Philadelphia, PA (US)

(72) Inventors: David B. Weiner, Merion, PA (US); Kar Muthumani, Cherry Hill, NJ (US); Sagar Kudchodkar, Philadelphia, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 16/755,257

(22) PCT Filed: Oct. 12, 2018

(86) PCT No.: PCT/US2018/055572
§ 371 (c)(1),
(2) Date: Apr. 10, 2020

(87) PCT Pub. No.: WO2019/075300
PCT Pub. Date: Apr. 18, 2019

(65) Prior Publication Data
US 2020/0237895 A1 Jul. 30, 2020

Related U.S. Application Data

(60) Provisional application No. 62/571,487, filed on Oct. 12, 2017, provisional application No. 62/571,498, filed on Oct. 12, 2017, provisional application No. 62/571,514, filed on Oct. 12, 2017.

(51) Int. Cl.
| | |
|---|---|
| A61K 39/12 | (2006.01) |
| C07K 16/10 | (2006.01) |
| C12N 15/86 | (2006.01) |
| A61K 39/00 | (2006.01) |

(52) U.S. Cl.
CPC .......... *A61K 39/12* (2013.01); *C07K 16/1081* (2013.01); *C12N 15/86* (2013.01); *A61K 2039/505* (2013.01); *C12N 2770/36122* (2013.01)

(58) Field of Classification Search
None
See application file for complete search history.

(56) References Cited

U.S. PATENT DOCUMENTS

| | | | |
|---|---|---|---|
| 2014/0170186 A1* | 6/2014 | Nabel | C12N 7/00 424/218.1 |
| 2016/0215282 A1 | 7/2016 | Lin | |
| 2017/0073377 A1 | 3/2017 | Nabel | |

FOREIGN PATENT DOCUMENTS

WO 2017165460 9/2017

OTHER PUBLICATIONS

Choi et al., PLoS Neglected Tropical Diseases, 2019, 13(2):e0007042, 21 pages. (Year: 2019).*
Auguste et al., Emerging Infectious Diseases, Oct. 2015, 21(10):1742-1750. (Year: 2015).*
GenBank Accession No. ALI88617.1, Oct. 14, 2015. (Year: 2015).*
Terzian et al., Am. J. Trop. Med. Hyg., 2015, Epub 2014, 92(2):401-404. (Year: 2014).*
GenBank Accession No. AJA30086.1 (2014) (Year: 2014).*
GenBank Accession No. KM400598.1 (2014) (Year: 2014).*
Abad-Franch F et al. "Mayaro virus infection in amazonia: a multimodel inference approach to risk factor assessment". PLoS Negl Trop Dis. 2012;6(10):e1846. doi: 839 10.1371/journal.pntd. 0001846.
Aitken TH et al., "Mayaro virus isolated from a Trinidadian mosquito", *Mansonia venezuelensis*. Science. 1960;131(3405):986.
Auguste AJ, et al., "Evolutionary and Ecological Characterization of Mayaro Virus Strains Isolated during an Outbreak", Venezuela, 2010. Emerg Infect Dis. 2015;21(10):1742-50. doi: 10.3201/eid2110. 141660.
Duperret et al., 2018, "Synergy of Immune Checkpoint Blockade with a Novel Synthetic Consensus DNA Vaccine Targeting TERT", Mol Ther 26(2):435-445.
El-Bacha et al., 2004, "Mayaro virus infection alters glucose metabolism in cultured cells through activation of the enzyme 6-phosphofructo 1-kinase", Mol Cell Biochem 266(1-2):191-8.
Fisher et al., 2017, "Adipose tissue: a new target for electroporation-enhanced DNA vaccines", Gene Ther 24(12):757-67.
Forshey BM, Guevara C, Laguna-Torres VA, Cespedes M, Vargas J, Gianella A, et al. Arboviral etiologies of acute febrile illnesses in Western South America, 2000-2007. PLoS Negl Trop Dis. 2010;4(8):e787. doi: 10.1371/journal.pntd.0000787.
Fox et al., 2015, "Broadly Neutralizing Alphavirus Antibodies Bind an Epitope on E2 and Inhibit Entry and Egress", Cell 163(5):1095-107.
Fox et al., 2016, "Immune-Mediated Protection and Pathogenesis of Chikungunya Virus", J Immunol 197(11):4210-18.
Genbank Accession No. KM400598, "Mayaro virus strain FSB1131 structural polyprotein gene, partial cds," 2014.
Gorchakov et al., 2012, "Attenuation of Chikungunya virus vaccine strain 181/clone 25 is determined by two amino acid substitutions in the E2 envelope glycoprotein", J Virol 86(11):6084-96.
Haist et al., 2017, "Inflammatory monocytes mediate control of acute alphavirus infection in mice", PLoS Pathog. 13(12):e1006748.

(Continued)

*Primary Examiner* — Stacy B Chen
(74) *Attorney, Agent, or Firm* — Riverside Law LLP

(57) ABSTRACT

Disclosed herein is a composition comprising a nucleic acid sequence encoding a Mayaro Virus antigen that elicits an immune response in a mammal. Also disclosed herein is a nucleic acid sequence encoding an anti-Mayaro Virus antibody, a fragment thereof, a variant thereof. Also disclosed herein is a method of generating a synthetic antibody in a subject by administering the composition to the subject. The disclosure also provides a method of preventing and/or treating a Mayaro virus infection in a subject using said composition and method of generation.

11 Claims, 34 Drawing Sheets
Specification includes a Sequence Listing.

(56) References Cited

OTHER PUBLICATIONS

Hassing RJ et al., "Imported Mayaro virus infection in the Netherlands", J Infect. 2010;61(4):343-5. doi: 10.1016/j.jinf.2010.06.009.
Herrero LJ, Nelson M, Srikiatkhachorn A, Gu R, Anantapreecha S, Fingerle-Rowson G, et al. Critical role for macrophage migration inhibitory factor (MIF) in Ross River virus-induced arthritis and myositis. Proc Natl Acad Sci U S A. 2011;108(29):12048-53.
Herrero LJ, Sheng KC, Jian P, Taylor A, Her Z, Herring BL, et al. Macrophage migration inhibitory factor receptor CD74 mediates alphavirus-induced arthritis and myositis in murine models of alphavirus infection. Arthritis Rheum. 2013;65(10):2724-2736. doi: 10.1002/art.38090.
Lavergne A, de Thoisy B, Lacoste V, Pascalis H, Pouliquen JF, Mercier V, et al. Mayaro virus: complete nucleotide sequence and phylogenetic relationships with other alphaviruses. Virus Res. 2006;117(2):283-90.
Lednicky et al., 2016, "Mayaro Virus in Child with Acute Febrile Illness", Emerg Infect Dis 22(11):2000-2.
Lin F, Shen X, Kichaev G, Mendoza JM, Yang M, Armendi P, et al. Optimization of electroporation-enhanced intradermal delivery of DNA vaccine using a minimally invasive surface device. Hum Gene Ther Methods. 2012;23(3):157-68.
Llagonne-Barets et al., "A case of Mayaro virus infection imported from French Guiana". J Clin Virol. 2016;77:66-68. doi: 10.1016/j.jcv.2016.02.013.
Long KC et al., "Experimental transmission of Mayaro virus by Aedes aegypti". Am J Trop Med Hyg. 2011;85(4):750-7. doi: 10.4269/ajtmh.2011.11-0359.
Mackay et al., 2016, "Mayaro virus: a forest virus primed for a trip to the city?", Microbes Infect 18(12):724-34.
Mallilankaraman et al., 2011, "A DNA vaccine against chikungunya virus is protective in mice and induces neutralizing antibodies in mice and nonhuman primates", PLoS Negl Trop Dis 5(1):e298.
Muthumani et al., 2015, "A synthetic consensus anti-spike protein DNA vaccine induces protective immunity against Middle East respiratory syndrome coronavirus in nonhuman primates", Sci Transl. Med. 7(301):301ra132.
Muthumani et al., 2016, "In vivo protection against ZIKV infection and pathogenesis through passive antibody transfer and active immunisation with a prMEnv DNA vaccine", NPJ Vaccines 1:1602.
Muthumani et al., 2016, "Rapid and Long-Term Immunity Elicited by DNA-Encoded Antibody Prophylaxis and DNA Vaccination Against Chikungunya Virus", J Infect Dis 214(3):369-78.

Robinson et al., "Inactivated Mayaro vaccine produced in human diploid cell cultures", Mil Med. 1976;141(3):163-166.
Rodriguez-Morales et al., 2017, "Mayaro, Oropouche and Venezuelan Equine Encephalitis viruses: Following in the footsteps of Zika?", Travel Med Infect Dis 15:72-73.
Rulli NE, Melton J, Wilmes A, Ewart G, Mahalingam S. The molecular and cellular aspects of arthritis due to alphavirus infections: lesson learned from Ross River virus. Ann N Y Acad Sci. 2007;1102:96-108.
Santiago et al., "Long-Term Arthralgia after Mayaro Virus Infection Correlates with Sustained Pro-inflammatory Cytokine Response", PLoS Negl Trop Dis 9(10):e0004104 (2015).
Smith GC et al., "Laboratory studies of a Brazilian strain of Aedes albopictus as a potential vector of Mayaro and Oropouche viruses". J Am Mosq Control Assoc. 1991;7(1).
Snyder JE, Kulcsar KA, Schultz KL, Riley CP, Neary JT, Marr S, et al. Functional characterization of the alphavirus TF protein. J Virol. 2013;87(15):8511-23. doi: 10.1128/JVI.00449-13.
Suhrbier A, Jaffar-Bandjee MC, Gasque P. Arthritogenic alphaviruses—an overview. Nat Rev Rheumatol. 2012;8(7):420-9.
Tebas P, Roberts CC, Muthumani K, Reuschel EL, Kudchodkar SB, Zaidi FI, et al. Safety and Immunogenicity of an Anti-Zika Virus DNA Vaccine—Preliminary Report. N Engl J Med. 2017. doi: 10.1056/NEJMoa1708120.
Trimble CL, Morrow MP, Kraynyak KA, Shen X, Dallas M, Yan J, et al. Safety, efficacy, and immunogenicity of VGX-3100, a therapeutic synthetic DNA vaccine targeting human papillomavirus 16 and 18 E6 and E7 proteins for cervical intraepithelial neoplasia 2/3: a randomised, double-blind, placebo-controlled phase 2b trial. Lancet. 2015;386(10008):2078-88.
Tsetsarkin KA, McGee CE, Volk SM, Vanlandingham DL, Weaver SC, Higgs S. Epistatic roles of E2 glycoprotein mutations in adaption of chikungunya virus to Aedes albopictus and Ae. aegypti mosquitoes. PLoS One. 2009;4(8):e6835.
Tsetsarkin KA, Vanlandingham DL, McGee CE, Higgs S. A single mutation in chikungunya virus affects vector specificity and epidemic potential. PLoS Pathog. 2007;3(12):e201. doi: 10.1371/journal.ppat.0030201.
UniProtKB Accession No. A0A0A7RBR8, "Structural polyprotein, Mayaro virus," 2015.
Wang et al., 2011, "Chimeric Chikungunya viruses are nonpathogenic in highly sensitive mouse models but efficiently induce a protective immune response", J Virol 85(17):9249-9252.
Weise WJ et al., "A novel live-attenuated vaccine candidate for mayaro Fever." PLoS Negl Trop Dis. 2014;8(8):e2969.

\* cited by examiner

A

```
                              A0A0P0CE34
                              ALI88590.1
                              ALI88593.1
                              ALI88596.1
                              ALI88599.1
                              ALI88602.1
                              ALI88605.1
                              A0A0N7HUW8
                              ALI88614.1
                              A0A0P0C1J9
                              ALI88620.1
                              A0A0P0BS91
                              A0A0P0CJP2
                              AHM95189.2
                              X2FA82
                              A0A0N7HUX1
                              AAO33335.1
                              AAY45742.1
                              Q1L7V0
                              A0A0P0C1L0
                              ALI88656.1
                              MAYV-Consensus ★
                              ALI88653.1
                              A0A0P0BWK0
                              ALI886.23
                              ALI88626.1
                              A0A0P0BSS5
                              A0A0A7RQX5
                              AJA37502.1
                              A0A0P0BS97
                              A0A0P0CH64
                              ALI88659.1
                              A0A0P0CKR8
                              A0A0P0BWJ4
                              ALI88611.1
                              A0A0P0C894
                              ALI88608.1
                              A0A0P0CJN2
                              A0A0P0CE87
                              A0A0P0FQ16
                              ALJ56197.1
                              A0A0P0BWN1
                              ALI88668.1
                              ALI88668.1
                              A0A0N7HUX4
                              Q8QZ72.1
                              Q8QZ72
                              A0A0P0C8D1
                              ALI88665.1
                              A0A0N9LW36
                              ALG64706.1
2.3
     2   Amino Acid Substitutions Per 100 residues    0
```

| MW kDa | MAYV Env | pVax1 | MAYV Capsid | pVax1 |

Primary Ab: Immune sera (day 35)

Figure 10

Construction of DNA-based monoclonal antibody (DMAb) against MAYV-Env

MAYARO VIRUS CONSENSUS ANTIGENS, DNA ANTIBODY CONSTRUCTS FOR USE AGAINST MAYARO VIRUS, AND COMBINATIONS THEREOF

CROSS-REFERENCE TO RELATED APPLICATIONS

This application is the U.S. national phase application filed under 35 U.S.C. § 371 claiming benefit to International Patent Application No. PCT/US2018/055572, filed on Oct. 12, 2018, which is entitled to priority to U.S. Provisional Application No. 62/571,487, filed Oct. 12, 2017, U.S. Provisional Application No. 62/571,497, filed Oct. 12, 2017, and U.S. Provisional Application No. 62/571,514, filed Oct. 12, 2017, which are incorporated by reference herein in their entireties.

TECHNICAL FIELD

The present invention relates to compositions comprising an immunological Mayaro virus antigen, compositions comprising a recombinant nucleic acid sequence for generating one or more synthetic antibodies, and functional fragments thereof, in vivo, and combinations thereof. The compositions of the invention provide improved methods for inducing immune responses, and for prophylactically and/or therapeutically immunizing individuals against Mayaro virus.

BACKGROUND

Mayaro virus (MAYV) is an emerging mosquito-transmitted alphavirus that causes signs and symptoms including an acute febrile illness and rash. However, it may also cause incapacitating arthralgias that develop into persistent, severe joint pain which continues for years after infection. MAYV is typically found in South America, but has recently been reported in the Caribbean Sea, as well as in travelers returning to the USA and Europe. Past epidemics have been associated with mosquito vectors, such as those in the genus *Haemagogus*, that are not likely to sustain transmission in humans, but concerns over the potential emergence of urban transmission were raised after a laboratory study showed that vector competence in Aedes mosquitoes is possible. There is a risk for endemic establishment within neotropical and subtropical regions inhabited by Aedes, as well as within temperate areas of the U.S. that are populated by this anthropophilic vector. Humans experience high-titer viremia after infection with MAYV, and an urban cycle of transmission may develop that is identical to what has been seen for DENV, ZIKV, and CHIKV, where a single viremic traveler could initiate endemic or epidemic MAYV transmission. The dramatic spread of DENV since 1980 and the recent spread of CHIKV and ZIKV throughout tropical America, via the same vectors and human hosts, underscores the risk to public health in the Americas. Despite its importance as an emerging virus, there are no licensed vaccines to prevent Mayaro infection, nor therapeutics to treat it.

Thus, there is need in the art for improved therapeutics that prevent and/or treat Mayaro virus infection. The current invention satisfies this need.

SUMMARY

The present invention is directed to combinations of one or more nucleic acid molecules encoding one or more anti-MAYV synthetic antibodies and one or more or more nucleic acid molecules encoding one or more MAYV antigens.

In one embodiment, the present invention provides a composition comprising a first nucleic acid sequence wherein the nucleic acid sequence encodes a Mayaro Virus (MAYV) antigen and a second nucleic acid sequence encoding one or more anti-MAYV synthetic antibodies or fragments thereof or one or more anti-MAYV monoclonal antibodies.

In one embodiment, the MAYV antigen comprises an antigen selected from the group consisting of MAYV-E1, MAYV-E2, MAYV-E3, MAYV-6K and MAYV-Capsid (CA).

In one embodiment, MAYV-CA comprises an amino acid sequence selected from the group consisting of SEQ ID NO:104, an amino acid sequence that is 90% identical or greater to SEQ ID NO:104, a fragment of SEQ ID NO:104 and a fragment of an amino acid sequence that is 90% identical or greater to SEQ ID NO:104. In one embodiment, the nucleic acid molecule encoding MAYV-CA comprises nucleotide sequence selected from the group consisting of: SEQ ID NO:105, a nucleotide sequence that is 90% identical or greater to SEQ ID NO:105, a fragment of SEQ ID NO:105 and a fragment of a nucleotide sequence that is 90% identical or greater to SEQ ID NO:105.

In one embodiment, MAYV-E1 comprises an amino acid sequence selected from the group consisting of SEQ ID NO:106, an amino acid sequence that is 90% identical or greater to SEQ ID NO:106, a fragment of SEQ ID NO:106 and a fragment of an amino acid sequence that is 90% identical or greater to SEQ ID NO:106. In one embodiment, the nucleic acid molecule encoding MAYV-E1 comprises nucleotide sequence selected from the group consisting of: SEQ ID NO:107, a nucleotide sequence that is 90% identical or greater to SEQ ID NO:107, a fragment of SEQ ID NO:107 and a fragment of a nucleotide sequence that is 90% identical or greater to SEQ ID NO:107.

In one embodiment, MAYV-E2 comprises an amino acid sequence selected from the group consisting of SEQ ID NO:108, an amino acid sequence that is 90% identical or greater to SEQ ID NO:108, a fragment of SEQ ID NO:108 and a fragment of an amino acid sequence that is 90% identical or greater to SEQ ID NO:108. In one embodiment, the nucleic acid molecule encoding MAYV-E2 comprises nucleotide sequence selected from the group consisting of: SEQ ID NO:109, a nucleotide sequence that is 90% identical or greater to SEQ ID NO:109, a fragment of SEQ ID NO:109 and a fragment of a nucleotide sequence that is 90% identical or greater to SEQ ID NO:109.

In one embodiment, MAYV-E3 comprises an amino acid sequence selected from the group consisting of SEQ ID NO:110, an amino acid sequence that is 90% identical or greater to SEQ ID NO:110, a fragment of SEQ ID NO:110 and a fragment of an amino acid sequence that is 90% identical or greater to SEQ ID NO:110. In one embodiment, the nucleic acid molecule encoding MAYV-E3 comprises nucleotide sequence selected from the group consisting of: SEQ ID NO:111, a nucleotide sequence that is 90% identical or greater to SEQ ID NO:111, a fragment of SEQ ID NO:111 and a fragment of a nucleotide sequence that is 90% identical or greater to SEQ ID NO:111.

In one embodiment, MAYV-6K comprises an amino acid sequence selected from the group consisting of SEQ ID NO:112, an amino acid sequence that is 90% identical or greater to SEQ ID NO:112, a fragment of SEQ ID NO:112 and a fragment of an amino acid sequence that is 90% identical or greater to SEQ ID NO:112. In one embodiment, the nucleic acid molecule encoding MAYV-6K comprises nucleotide sequence selected from the group consisting of: SEQ ID NO:10, a nucleotide sequence that is 90% identical or greater to SEQ ID NO:10, a fragment of SEQ ID NO:113 and a fragment of a nucleotide sequence that is 90% identical or greater to SEQ ID NO:113.

In one embodiment, the MAYV antigen comprises MAYV-E2 and MAYV-E3. In one embodiment, the MAYV antigen comprises an amino acid sequence selected from the group consisting of SEQ ID NO:114, an amino acid sequence that is 90% identical or greater to SEQ ID NO:114, a fragment of SEQ ID NO:114 and a fragment of an amino acid sequence that is 90% identical or greater to SEQ ID NO:114. In one embodiment. the nucleic acid molecule encoding MAYV antigen comprises nucleotide sequence selected from the group consisting of: SEQ ID NO:115, a nucleotide sequence that is 90% identical or greater to SEQ ID NO:115, a fragment of SEQ ID NO:115 and a fragment of a nucleotide sequence that is 90% identical or greater to SEQ ID NO:115.

In one embodiment, the MAYV antigen comprises MAYV-E1, MAYV-E2, MAYV-E3, and MAYV-6K. In one embodiment, the MAYV antigen comprises an amino acid sequence selected from the group consisting of SEQ ID NO:116, an amino acid sequence that is 90% identical or greater to SEQ ID NO:116, a fragment of SEQ ID NO:116 and a fragment of an amino acid sequence that is 90% identical or greater to SEQ ID NO:116. In one embodiment, the nucleic acid molecule encoding MAYV antigen comprises nucleotide sequence selected from the group consisting of: SEQ ID NO:117, a nucleotide sequence that is 90% identical or greater to SEQ ID NO:117, a fragment of SEQ ID NO:117 and a fragment of a nucleotide sequence that is 90% identical or greater to SEQ ID NO:117.

In one embodiment, the composition further comprises a nucleic acid sequence further comprising a nucleic acid sequences that encode one or more proteins selected from the group consisting of: IL-12, IL-15 and IL-28. In one embodiment, the MAYV antigen is linked to an IgE leader sequence.

In one embodiment, the one or more anti-MAYV synthetic antibodies binds to a MAYV antigen. In one embodiment, the MAYV antigen is selected from the group consisting of MAYV-Capsid, MAYV-E1, MAYV-E2, MAYV-E3, MAYV-6K, and any combination thereof. In one embodiment, the MAYV antigen comprises an amino acid sequence selected from EGHYNWHYGAVQYTG (SEQ ID NO:101), GRSVIHFSTASAAPS (SEQ ID NO: 102) and LAKCPPGEVISVSFV (SEQ ID NO: 103).

In one embodiment, the second nucleic acid sequence further comprising a nucleotide sequence encoding a cleavage domain.

In one embodiment, the second nucleic acid sequence encodes an anti-MAYV antibody.

In one embodiment, the second nucleic acid sequence comprises a nucleotide sequence encoding an amino acid sequence at least 90% homologous to SEQ ID NO:1 or 3. the second nucleic acid sequence comprises a nucleotide sequence at least 90% homologous to SEQ ID NO:2 or 4.

In one embodiment, the second nucleic acid sequence comprises a nucleotide sequence encoding an anti-MAYV heavy chain comprising an amino acid sequence at least 90% homologous to one of SEQ ID NOs: 5-16.

In one embodiment, the second nucleic acid sequence comprises a sequence encoding an anti-MAYV light chain comprising an amino acid sequence at least 90% homologous to one of SEQ ID NOs: 17-28.

In one embodiment, the second nucleic acid sequence comprises sequence encodes a leader sequence.

In one or more embodiment, the one or more anti-MAYV monoclonal antibodies comprises a heavy chain and a light chain, wherein the heavy chain comprises an amino acid sequence at least 90% homologous to one of SEQ ID NOs: 5-16 and the light chain comprises an amino acid sequence at least 90% homologous to one of SEQ ID NOs: 17-28.

The present invention also provides methods for inducing an immune response by administering a combination of one or more nucleic acid molecules encoding one or more anti-MAYV synthetic antibodies and one or more or more nucleic acid molecules encoding one or more MAYV antigens. In some embodiments, immune response is an anti-MAYV immune response. In some embodiments, the immune response is persistent. In some embodiments, the immune response is immediate. In some embodiments, the immune response is systemic.

The present invention also provides methods for preventing or treating a disease in a subject. In one embodiment, the disease is a Mayaro virus infection. In one embodiment, the method comprises administering to the subject the composition of the invention.

BRIEF DESCRIPTION OF THE DRAWINGS

FIG. 1, comprising FIG. 1A through FIG. 1E, depicts the development and characterization of a synthetic consensus Mayaro DNA vaccine. FIG. 1A depicts phylogenic analysis based on neighbor joining evaluation of MAYV-envelope sequences deposited in GenBank. The position of the scMAYV-E vaccine sequence in this tree is noted with an asterisk '*' FIG. 1B depicts a schematic of the scMAYV-E vaccine construct generated. scMAYV-E encodes all three envelope glycoproteins (E1, E2, and E3) and the 6K/TF polypeptide linked by protease cleavage sites. The IgE-leader sequence was inserted at the 5' end to increase protein expression. FIG. 1C depicts computer-generated MAYV antigen model. FIG. 1D depicts a view of E1 showing fusion loop in cyan. The fusion loop is generally conserved among the alphaviruses. E3 (transparent red) is shown to provide orientation. The highly conserved MWGG sequence is visible at the loop's rightmost position. The M residue is buried and predicted to interact with nearby TYR and PRO residues of E2. The backbone portion of M participates in H-bonds with the nearby G at position i+3 to form a b-turn. FIG. 1E depict western analyses of lysates from scMAYV-E or pVax1 transfected 293T cells incubated with pooled day 35 sera from scMAYV-E immunized mice. A lane shown left of the ladder represents 2 μg of rE1 probed with the same pooled day 35 sera from scMAYV-E-vaccinated mice.

FIG. 2, comprising FIG. 2A through FIG. 2D, depicts generation of recombinant MAYV-E1 (rE1) protein. FIG. 2A depicts MAYV-E1 from the consensus full-length envelope sequence of scMAYV-E cloned downstream of a 6×His Tag in the pET-30a E. coli expression vector. Lysates from E. coli transfected with the pET-30a MAYV-E1 plasmid were subjected to nickel chromatography to isolate and purify recombinant MAYV-E1 (rE1) protein after which the 6×His tag was removed. FIG. 2B depicts pooled purified proteins collected from the nickel columns run on a SDS-PAGE gel and subjected to silver staining. Lane 1 signifies crude pooled-E1 proteins. Lane 2 indicates the purified pooled-E1 proteins. Bands at expected MW of rE1 are shown. FIG. 2C depicts western blot analysis of pooled purified protein collected from nickel columns ran on a 12% SDS-PAGE gel and transferred to a nitrocellulose membrane subsequently blotted with a pan-alphavirus monoclonal antibody (ThermoFisher; clone: G77L) and IRDye800-tagged anti-mouse secondary antibody, scanned on the Licor Odyssey system. FIG. 2D depicts ELISA of sera from scMAYV-E1 or scMAYV-E immunized individual mice (n=4) using rE1 as a capture antigen for both groups.

FIG. 3, comprising FIG. 3A through FIG. 3F, depicts experimental results demonstrating scMAYV-E vaccine induces a robust, MAYV-specific humoral response in mice including neutralizing antibodies. FIG. 3A depicts ELISA of sera from scMAYV-E immunized mice. C57BL/6 mice (n=4) were immunized three times using EP-enhanced i.m. injection with 25 µg of scMAYV-E or pVax1 empty vector plasmid at 2-week intervals with sera collected one week after each immunization. Half-log dilutions of sera from individual mice were evaluated for their binding capacity to a recombinant MAYV-E1 (rE1) capture antigen. FIG. 3B depicts rE1-specific IgG endpoint titers of scMAYV-E vaccinated mouse sera after each immunization. The antibody endpoint titer was defined as the highest dilution of a serum sample with OD values>(mean+3SD) of pVax1 vaccinated mice. Samples with a titer <50 were given an endpoint titer of 1. FIG. 3C depicts IgG subclass isotyping of C57BL/6 pVax1 mouse sera and scMAYV-E mouse sera one week post third immunization (day 35). IgG1, IgG2a, IgG2b, and IgG3 for both groups shown (n=4). FIG. 3D depicts an indirect immunofluorescence assay of MAYV-infected Vero cells incubated with pooled day 35 sera from pVax1 or scMAYV-E immunized mice followed by FITC-tagged anti-mouse IgG secondary antibody (green) and DAPI (blue) to identify nuclei. FIG. 3E depicts an indirect immunofluorescence assay of MAYV-infected U87 neuronal cells incubated with pooled day 35 sera from scMAYV-E DNA immunized mice followed by FITC-tagged anti-mouse IgG secondary antibody (green) and DAPI (blue) to identify nuclei. FIG. 3F depicts a plaque reduction neutralization assay ($PRNT_{50}$) of heat-inactivated pooled day 35 sera from uninfected naive, pVax1, or scMAYV-E immunized mice. Serial two-fold dilutions of sera were incubated with $10^2$ PFU of MAYV for 1.5 hours and then added to wells of confluent Vero cells. Plaque formation in wells was scored at 3 days post infection and % reduction of plaque formation was calculated in comparison to plaques formed in wells receiving virus only. $PRNT_{50}$ value is calculated by a non-linear regression analysis using PRISM software.

FIG. 4, comprising FIG. 4A depicts phase contrast images of MAYV-infected MDMs over time. Magnification: ×20. FIG. 4B depicts phase contrast and fluorescent images of MDMs infected with MAYV preincubated with immune sera. 3-day-old cultures of MDMs were treated with DMEM media only, MAYV plus pVax1 sera, or MAYV preincubated with 1:100 dilution of pooled day 35 (post third immunization) immune sera from scMAYV-E immunized mice. After 48 hours of co-culture, the cells were fixed, permeabilized, and stained with Live Cell Labeling Kit-Green Fluorescence-Cytopainter, which stains only live cells with Labelling Dye Green. Magnification: ×40. FIG. 4C depicts a histogram comparing the percentage of live cells in the control and experimental groups evaluated by Labelling Dye Green signals from six independent evaluations of the infected MDMs in FIG. 4B. FIG. 4D depicts percent viability of Vero CCL-81 cells inoculated 36 hours with supernatants from the infected MDM cultures from experiments described in FIG. 4B. The cell viabilities of Vero cells were assessed by Trypan Blue dye exclusion staining using a Countess™ II Automated Cell Counter. Each dot represents the cell viability from a single well +/−SEM counted in triplicates.

FIG. 5, comprising FIG. 5A through FIG. 5C, depicts experimental results demonstrating scMAYV-E induces a robust antigen specific cellular immune response to multiple epitopes in mice. C57BL/6 mice were immunized with 25 µg of either pVax1 empty vector or scMAYV-E plasmid once and euthanized 2 weeks later, or three times at 2-week intervals then euthanized one week after the last immunization. Splenocytes were harvested and cultured overnight in the presence of linear peptide pools spanning the full-length envelope protein. FIG. 5A depicts an IFN-g ELISpot assay used to measure IFN-g-producing spot-forming units (SFUs) generated per $10^6$ splenocytes+/−SEM. FIG. 5B depicts IFN-g ELISpot assay performed on splenocytes from immunized animals after ex vivo stimulation with matrix peptide pools spanning the E1 protein. FIG. 5C depicts IFN-g ELISpot assay performed on splenocytes from immunized animals after ex vivo stimulation with matrix peptide pools spanning the E3+E2 proteins. Average IFN-g SFUs generated per $10^6$ splenocytes+/−SEM for each peptide pool shown. The immunodominant epitopes in E1 and E3+E2 identified via the matrix peptide pools are indicated with arrows.

FIG. 6, comprising FIG. 6A depicts evaluation of splenocytes from immunized mice by polychromatic flow cytometry to identify the frequency of CD4+ T cells that produce the cytokines IFN-g, IL-2, and TNF-a following a 5-hour ex vivo stimulation with pooled MAYV envelope peptides spanning the entire length of the envelope protein. FIG. 6B depicts evaluation of splenocytes from immunized mice by polychromatic flow cytometry to identify the frequency of $CD8^+$ T cells that produce the cytokines IFN-g, IL-2, and TNF-a following a 5 hour ex vivo stimulation with pooled MAYV envelope peptides spanning the entire length of the envelope protein. One representative experiment of three is shown in FIGS. 6A and 6B. FIG. 6C depicts the frequency of total $CD4^+$ and $CD8^+$ T cells expressing each of the seven analyzed combinations of IFN-g, TNF-a, and IL-2 using Boolean gating is shown as bar graphs. The pie charts represent the proportion of CD4+ and CD8+ T cells producing one, two, or all three cytokines.

FIG. 7, comprising FIG. 7A through FIG. 7G, depicts experimental results demonstrating scMAYV-E protects immunized mice from MAYV challenge. $IFNAR^{-/-}$ mice aged 4-6 weeks old were immunized twice, two weeks apart with pVax1 or scMAYV-E using EP-enhanced i.m. injection. Groups of mice for immunogenicity studies were euthanized one week after the final immunization. FIG. 7A depicts evaluation of cellular responses in vaccinated $IFNAR^{-/-}$ mice. IFN-g ELISpot of pVax1 or scMAYV-E immunized splenocytes is shown (n=4). FIG. 7B depicts evaluation of humoral responses in vaccinated $IFNAR^{-/-}$ mice. Binding ELISA of pVax1 or scMAYV-E immunized sera is shown using rE1 as a capture antigen (n=4). Groups of mice for challenge were then injected intraperitoneally (i.p.) one week after the second immunization (day 21) with $10^2$ PFU of MAYV TRVL 15537. All mice were observed daily for clinical signs of disease up to 8 days post challenge. FIG. 7C depicts the percent change in bodyweight from day 0 in individual immunized mice post challenge (n=10). FIG. 7D depicts a Kaplan-Meier survival curve of scMAYV-E or pVax1 immunized mice for 8 days post-MAYV challenge (n=10). FIG. 7E depicts representative pictures of rear footpad of uninfected mouse (naive), pVax1 immunized mouse (Infected/pVax1), and scMAYV-E immunized mouse (Infected/scMAYV-E) at 6 days post challenge. FIG. 7F depicts the quantification of rear footpad size as measured by a caliper on day 6 post-MAYV challenge (n=6 pVax1; n=8 scMAYV-E). (G) MAYV PFU/ml in sera collected from pVax1 and scMAYV-E immunized mice at day 6 post MAYV challenge (n=8).

Figures 8A, 8B:
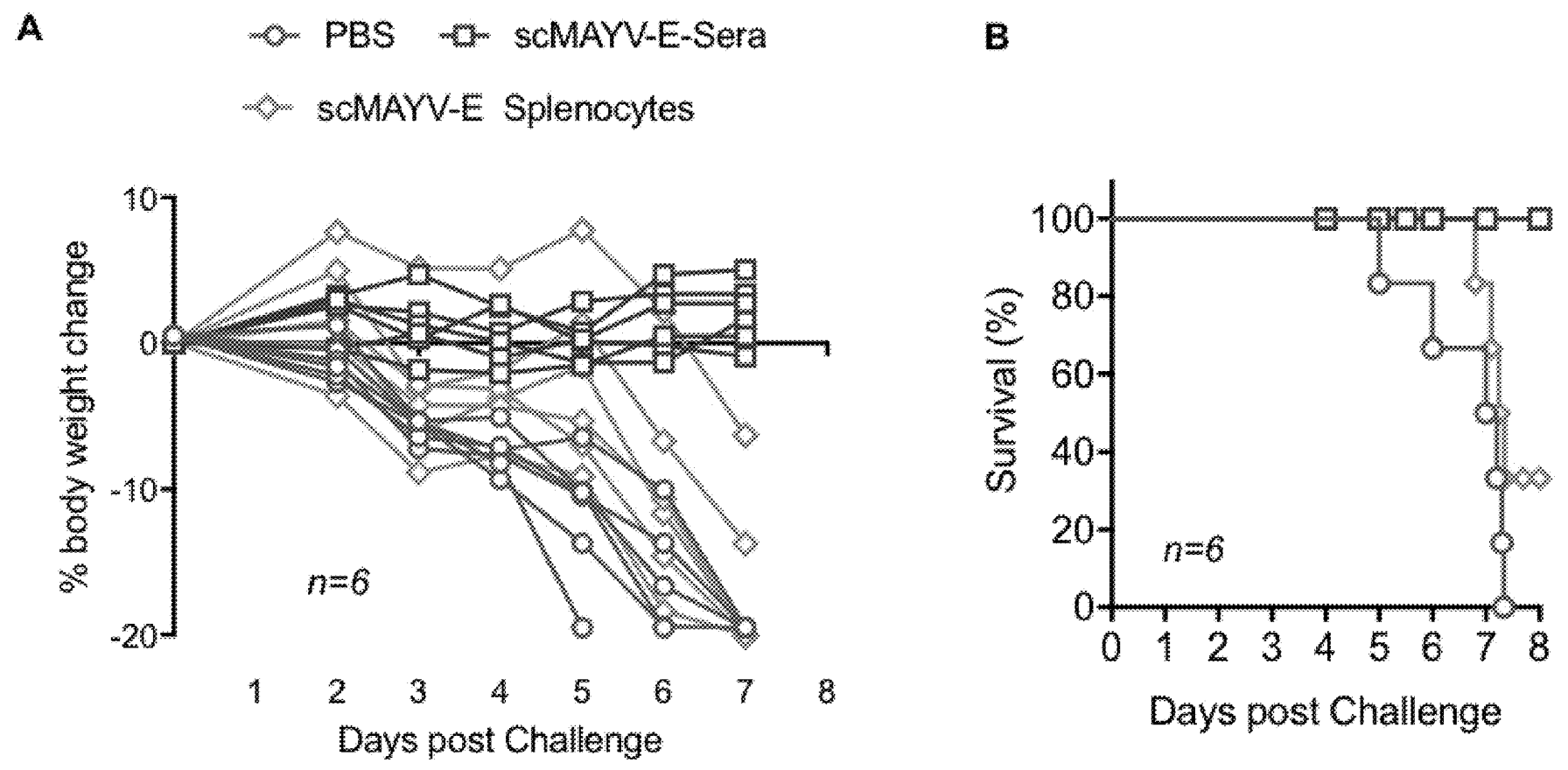

FIG. 8, comprising FIG. 8A and FIG. 8B, depicts experimental results demonstrating scMAYV-E induced humoral responses drive protection from MAYV challenge. IFNAR$^{-/-}$ mice aged 4-6 weeks were immunized twice with 25 µg of scMAYV-E two weeks apart using EP-enhanced i.m. injection then euthanized one week after last immunization; immune sera and bulk splenocytes were collected. A naive batch of IFNAR$^{-/-}$ mice of mixed sex aged 4-6 weeks were divided into three groups and injected i.p. with 1) 200 µl of immune sera from scMAYV-E immunized mice, 2) 2×10$^6$ bulk splenocytes from scMAYV-E immunized mice, or 3) PBS as a negative control. One hour post passive transfer, all mice were challenged with 10$^2$ PFU of MAYV TRVL 15537 and observed daily for clinical signs of disease up to 8 days post challenge (n=6). FIG. 8A depicts the percent change in bodyweight from day 0 shown for individual mice in each group. FIG. 8B depicts a Kaplan-Meier survival curve for each group.

FIG. 9 depicts the Mayaro Virus DNA vaccine approach.

FIG. 10 depicts the characterization of MAYV-Vaccine by Western blot analysis.

FIG. 19 depicts the construction of DNA-based monoclonal antibody (DMAb) against MAYV-Env.

Figure 20:
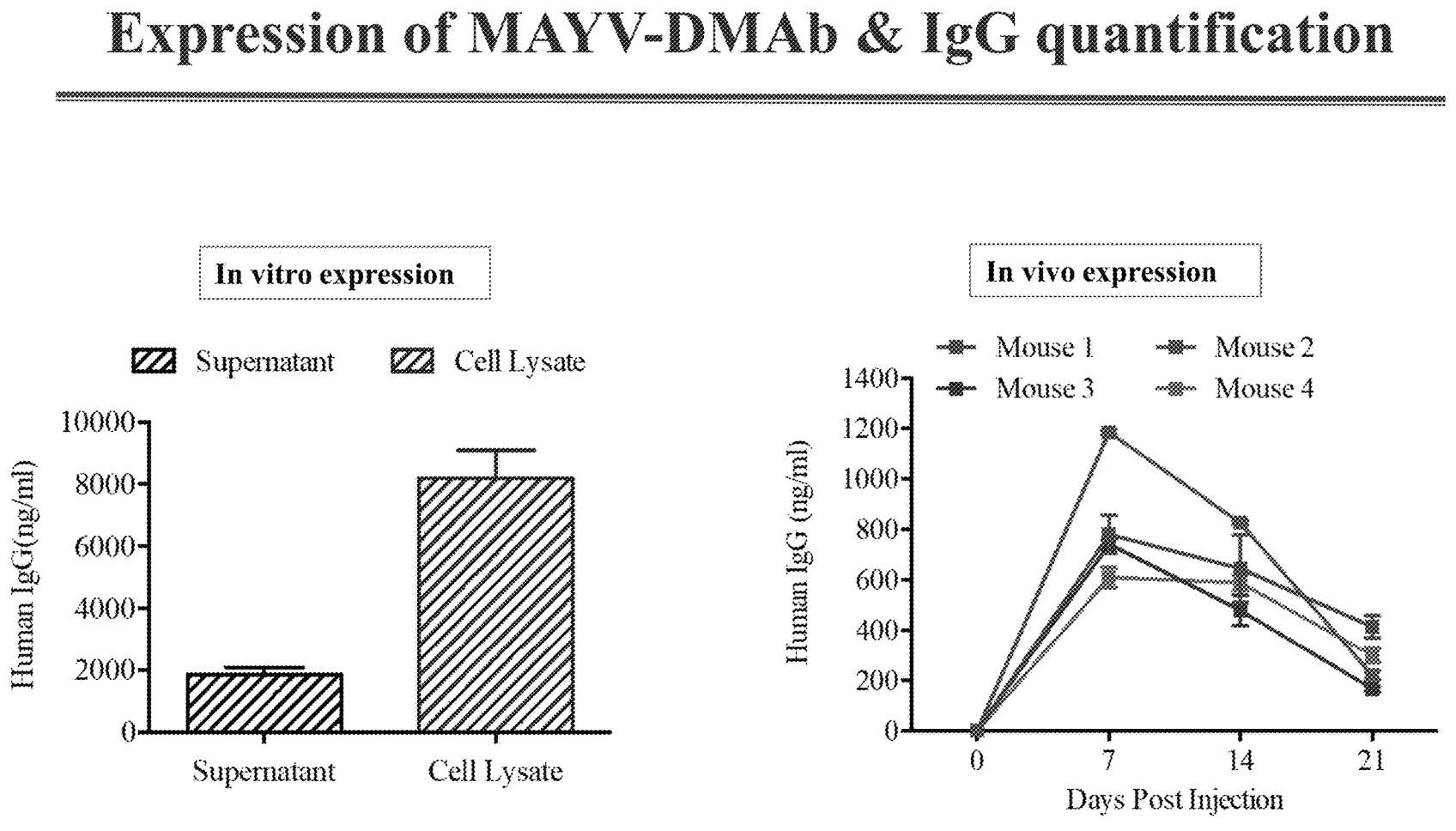

FIG. 20 depicts the expression of MAYV-DMAb and IgG quantification.

DETAILED DESCRIPTION

Figures 2A, 2B, 2C:
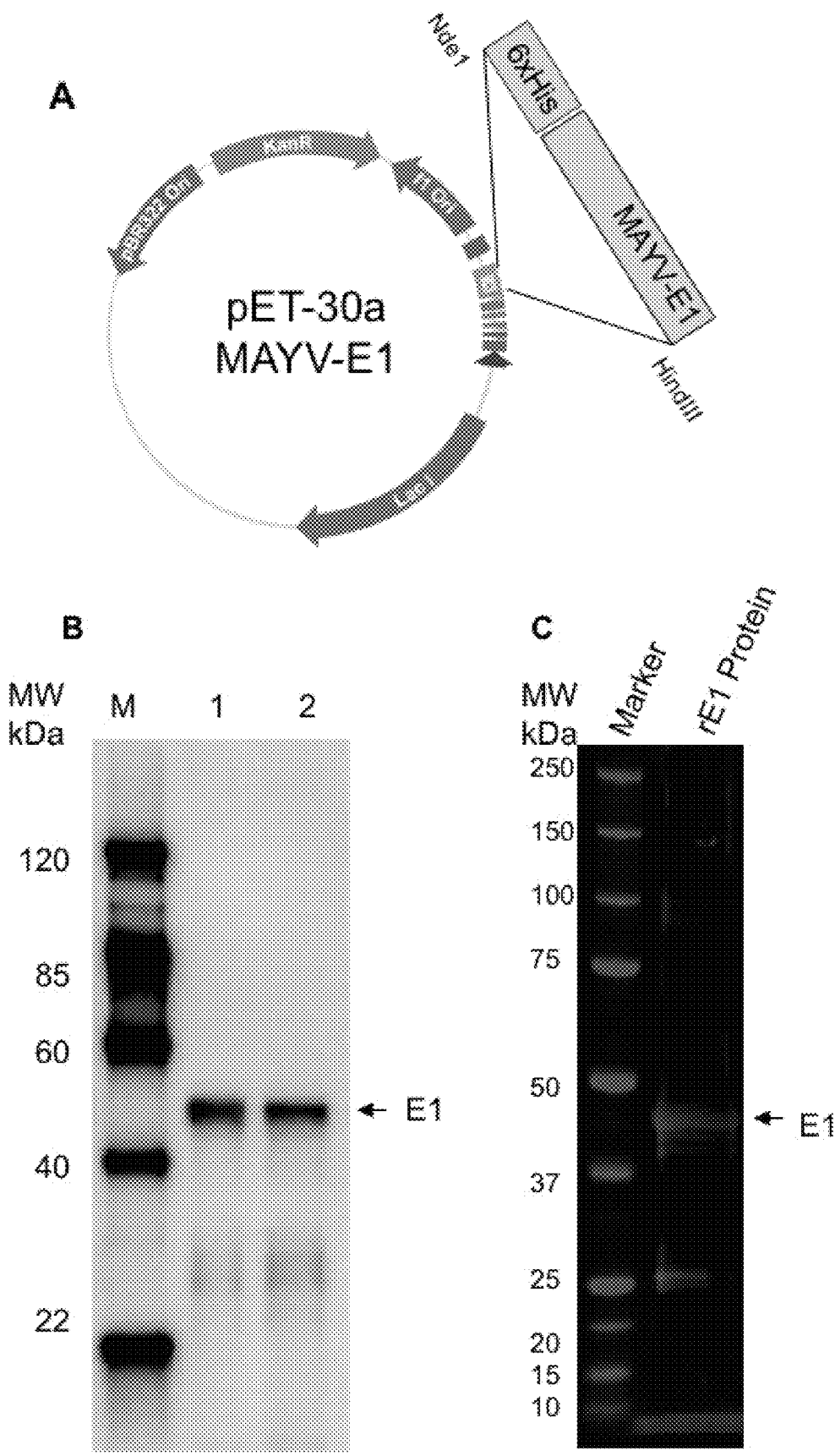

In one embodiment, the invention provides composition comprising one or more nucleotide sequences encoding one or more Mayaro virus (MAYV) antigens and one or more nucleotide sequences encoding one or more anti-MAYV synthetic antibodies or fragments thereof.

In one embodiment, the invention provides a composition comprising a combination of a composition that elicits an immune response in a mammal against a MAYV antigen and a composition comprising a recombinant nucleic acid sequence encoding an anti-MAYV antibody, a fragment thereof, a variant thereof, or a combination thereof.

In one embodiment, the recombinant nucleic acid sequence encoding an anti-MAYV antibody comprises sequences that encode a heavy chain and light chain. In particular, the heavy chain and light chain polypeptides expressed from the recombinant nucleic acid sequences can assemble into the synthetic antibody. The heavy chain polypeptide and the light chain polypeptide can interact with one another such that assembly results in the synthetic antibody being capable of binding a MAYV antigen, being more immunogenic as compared to an antibody not assembled as described herein, and being capable of eliciting or inducing an immune response against the MAYV antigen.

Additionally, these synthetic antibodies are generated more rapidly in the subject than antibodies that are produced in response to antigen induced immune response. The synthetic antibodies are able to effectively bind and neutralize a range of MAYV antigens. The synthetic antibodies are also able to effectively protect against and/or promote survival of MAYV infection and disease.

Another aspect of the present invention provides nucleic acid vaccines, such as DNA plasmid vaccines, that are capable of generating in a mammal an immune response against a MAYV antigen. The nucleic acid vaccines are comprised of a nucleic acid capable of expressing a MAYV antigen in a mammal. The nucleic acid is comprised of a promoter operably linked to a coding sequence that encodes the MAYV antigen.

The present invention also provides methods for inducing an immune response by administering a combination of one or more nucleic acid molecules encoding one or more anti-MAYV synthetic antibodies and one or more or more nucleic acid molecules encoding one or more MAYV antigens. In some embodiments, immune response is an anti-MAYV immune response. In some embodiments, the immune response is persistent. In some embodiments, the immune response is immediate. In some embodiments, the immune response is systemic.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments, "comprising," "consisting of" and "consisting essentially of," the embodiments, or elements presented herein, whether explicitly set forth or not.

"Antibody" may mean an antibody of classes IgG, IgM, IgA, IgD or IgE, or fragments, fragments or derivatives thereof, including Fab, F(ab')2, Fd, and single chain antibodies, and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

"Antibody fragment" or "fragment of an antibody" as used interchangeably herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Antigen" refers to proteins that have the ability to generate an immune response in a host. An antigen may be recognized and bound by an antibody. An antigen may originate from within the body or from the external environment.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

"Coding sequence" or "encoding nucleic acid" as used herein may mean refers to the nucleic acid (RNA or DNA molecule) that comprise a nucleotide sequence which encodes an antibody as set forth herein. The coding sequence may also comprise a DNA sequence which encodes an RNA sequence. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a biomembrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is administered an effective dose of an antigen for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a polypeptide fragment of an antibody that is function, i.e., can bind to desired target and have the same intended effect as a full length antibody. A fragment of an antibody may be 100% identical to the full length except missing at least one amino acid from the N and/or C terminal, in each case with or without signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length antibody, excluding any heterologous signal peptide added. The fragment may comprise a fragment of a polypeptide that is 95% or more, 96% or more, 97% or more, 98% or more or 99% or more identical to the antibody and additionally comprise an N terminal methionine or heterologous signal peptide which is not included when calculating percent identity. Fragments may further comprise an N terminal methionine and/or a signal peptide such as an immunoglobulin signal peptide, for example an IgE or IgG signal peptide. The N terminal methionine and/or signal peptide may be linked to a fragment of an antibody.

A fragment of a nucleic acid sequence that encodes an antibody may be 100% identical to the full length except missing at least one nucleotide from the 5' and/or 3' end, in each case with or without sequences encoding signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length coding sequence, excluding any heterologous signal peptide added. The fragment may comprise a fragment that encode a polypeptide that is 95% or more, 96% or more, 97% or more, 98% or more or 99% or more identical to the antibody and additionally optionally comprise sequence encoding an N terminal methionine or heterologous signal peptide which is not included when calculating percent identity. Fragments may further comprise coding sequences for an N terminal methionine and/or a signal peptide such as an immunoglobulin signal peptide, for example an IgE or IgG signal peptide. The coding sequence encoding the N terminal methionine and/or signal peptide may be linked to a fragment of coding sequence.

"Genetic construct" as used herein refers to the DNA or RNA molecules that comprise a nucleotide sequence which encodes a protein, such as an antibody. The genetic construct may also refer to a DNA molecule which transcribes an RNA. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more nucleic acids and/or peptides. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV 40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human. The subject or patient may be undergoing other forms of treatment.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

"Synthetic antibody" as used herein refers to an antibody that is encoded by the recombinant nucleic acid sequence described herein and is generated in a subject.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a vaccine of the present invention to a subject after induction of the disease but before its clinical appearance. Repressing the disease involves administering a vaccine of the present invention to a subject after clinical appearance of the disease.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOSITIONS

In one aspect, the present invention provides a combination of a composition that elicits an immune response in a mammal against a MAYV antigen with a composition comprising a recombinant nucleic acid sequence encoding an anti-MAYV antibody, a fragment thereof, a variant thereof, or a combination thereof. The composition comprising a recombinant nucleic acid sequence encoding an anti-MAYV antibody can be administered to a subject in need thereof to facilitate in vivo expression and formation of a synthetic anti-MAYV antibody.

In one embodiment, the present invention relates to a combination of a first composition that elicits an immune response in a mammal against a MAYV antigen and a second composition comprising a recombinant nucleic acid sequence encoding an anti-MAYV antibody, a fragment thereof, a variant thereof, or a combination thereof. I In one embodiment, the first composition comprises a nucleic acid encoding one or more MAYV antigens. In one embodiment, the first composition comprises a nucleic acid vaccine, such as a DNA vaccine. In one embodiment, the first composition comprises a protein antigen, such as a MAYV antigen.

In one embodiment, the second composition comprises a recombinant nucleic acid sequence encoding an anti-MAYV antibody, a fragment thereof, a variant thereof, or a combination thereof. The second composition, when administered to a subject in need thereof, can result in the generation of a synthetic anti-MAYV antibody in the subject. The synthetic antibody can bind a MAYV antigen present in the subject. Such binding can neutralize the antigen, block recognition of the antigen by another molecule, for example, a protein or nucleic acid, and elicit or induce an immune response to the antigen.

The synthetic antibody can treat, prevent, and/or protect against MAYV infection or MAYV associated disease in the subject administered the composition. The synthetic antibody by binding the MAYV antigen can treat, prevent, and/or protect against MAYV infection in the subject administered the composition. The synthetic antibody can promote survival of the subject administered the composition. The synthetic antibody can provide at least about 50%, 55%, 60%, 65%, 70%, 75%, 80%, 85%, 90%, 95%, or 100% survival of the subject administered the composition. In other embodiments, the synthetic antibody can provide at least about 65%, 66%, 67%, 68%, 69%, 70%, 71%, 72%, 73%, 74%, 75%, 76%, 77%, 78%, 79%, or 80% survival of the subject administered the composition.

Another aspect of the present invention provides nucleic acid vaccines that are capable of generating in a mammal an immune response against a MAYV antigen. The nucleic acid vaccines are comprised of a nucleotide sequence capable of expressing a consensus antigen in the mammal and a pharmaceutically acceptable excipient. For example, in one embodiment, the nucleic acid vaccine is a DNA plasmid vaccine. The DNA plasmid is comprised of a promoter operably linked to a coding sequence that encodes the consensus MAYV antigen.

In one embodiment, the compositions of the invention, when administered, generate an immediate and persistent immune responses. For example, in one embodiment, the first composition comprising a nucleic acid encoding one or more MAYV antigens generates a persistent immune response. In one embodiment, the second composition comprising a recombinant nucleic acid sequence encoding an anti-MAYV antibody, a fragment thereof, a variant thereof generates an immediate immune response. In some embodiments, the immune response is an anti-MAYV immune response.

3. PROTEIN ANTIGENS

Provided herein are antigens capable of eliciting an immune response in a mammal against one or more Mayaro virus (MAYV) subtypes. In one embodiment, the MAYV antigens described herein can be used to induce broad immunity against multiple subtypes or serotypes of Mayaro virus. In some embodiments, the MAYV antigen includes a MAYV capsid (CA) protein or MAYV-envelope (ENV) protein, a consensus thereof, a variant thereof, a fragment thereof or a combination thereof. For example, in some embodiments, the MAYV antigen includes MAYV-CA, MAYV-E1, MAYV-E2, MAYV-E3, MAYV-6K, a consensus thereof, a variant thereof, a fragment thereof or any combination thereof. In one embodiment, antigen includes MAYV-E3 and MAYV-E2 or MAYV-E1 and MAYV-E2. In one embodiment, antigen includes MAYV-E3, MAYV-E2, MAYV-6K and MAYV-E1.

In one embodiment, the sequences of the MAYV antigen include SEQ ID NOs: 104, 106, 108, 110, 112, 114, 116 and variants thereof, and fragments of SEQ ID NOs: 104, 106, 108, 110, 112, 114, 116, and variants thereof, optionally including a signal peptide such as for example an IgE or IgG signal peptide.

In some embodiments, the immunogens may comprise a signal peptide from a different protein such as an immunoglobulin protein, for example an IgE signal peptide or an IgG signal peptide. For example, in one embodiment, the MAYV antigen linked to a signal peptide may comprise a sequence of SEQ ID NOs:118, 120, 122, 124, 126, 128, 130, and fragments or variants thereof.

Fragments of a full-length MAYV antigen can comprise at least 10%, at least 20%, at least 30%, at least 40%, at least 50%, at least 60%, at least 70%, at least 80%, at least 90%, or at least 95% of one or more of the amino sequences set forth below In one embodiment, the MAYV antigen comprises MAYV-CA, a consensus thereof, a variant thereof, or a fragment thereof. In one embodiment, the MAYV-CA antigen can comprise the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:104. In one embodiment, the MAYV antigen comprises a fragment of a MAYV-CA. In one embodiment, the fragment of MAYV-CA can comprise a fragment of SEQ ID NO:104. In one embodiment, the fragment of a MAYV-CA antigen can comprise a fragment of a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:104. In one embodiment, the fragment of MAYV-CA can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids, at least 190 amino acids, at least 200 amino acids, at least 210 amino acids, at least 220 amino acids, at least 230 amino acids, at least 240 amino acids, at least 250 amino acids or more of a protein comprising the amino acid sequence set forth in SEQ ID NO:104 or a protein comprising a sequence at least 80% identical to the amino acid sequence set forth in SEQ ID NO:104.

In one embodiment, the MAYV antigen comprises MAYV-E1, a consensus thereof, a variant thereof, or a fragment thereof. In one embodiment, the MAYV-E1 antigen can comprise the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:106. In one embodiment, the MAYV antigen comprises a fragment of a MAYV-E1. the In one embodiment, the fragment of MAYV-E1 can comprise a fragment of SEQ ID NO:106. In one embodiment, the fragment of a MAYV-E1 antigen can comprise a fragment of a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:106. In one embodiment, the fragment of MAYV-E1 can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids, at least 190 amino acids, at least 200 amino acids, at least 210 amino acids, at least 220 amino acids, at least 230 amino acids, at least 240 amino acids, at least 250 amino acids, at least 260 amino acids, at least 270 amino acids, at least 280 amino acids, at least 290 amino acids, at least 300 amino acids, at least 310 amino acids, at least 320 amino acids, at least 330 amino acids, at least 340 amino acids, at least 350 amino acids, at least 360 amino acids, at least 370 amino acids, at least 380 amino acids, at least 390 amino acids, at least 400 amino acids, at least 410 amino acids, at least 420 amino acids, at least 430 amino acids or more of a protein comprising the amino acid sequence set forth in SEQ ID NO:106 or a protein comprising a sequence at least 80% identical to the amino acid sequence set forth in SEQ ID NO:106.

In one embodiment, the MAYV antigen comprises MAYV-E2, a consensus thereof, a variant thereof, or a fragment thereof. In one embodiment, the MAYV-E2 antigen can comprise the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:108. In one embodiment, the MAYV antigen comprises a fragment of a MAYV-E2. the In one embodiment, the fragment of MAYV-E2 can comprise a fragment of SEQ ID NO:108. In one embodiment, the fragment of a MAYV-E2 antigen can comprise a fragment of a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:108. In one embodiment, the fragment of MAYV-E2 can comprise at least 20 amino acids or more, at least 30 amino acids or more, at least 40 amino acids or more, at least 50 amino acids or more, at least 60 amino acids or more, or more of a protein comprising the amino acid sequence set forth in SEQ ID NO:108 or a protein comprising a sequence at least 80% identical to the amino acid sequence set forth in SEQ ID NO:108.

In one embodiment, the MAYV antigen comprises MAYV-E3, a consensus thereof, a variant thereof, or a fragment thereof. In one embodiment, the MAYV-E3 antigen can comprise the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:110. In one embodiment, the MAYV antigen comprises a fragment of a MAYV-E3. the In one embodiment, the fragment of MAYV-E3 can comprise a fragment of SEQ ID NO:110. In one embodiment, the fragment of a MAYV-E3 antigen can comprise a fragment of a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:110. In one embodiment, the fragment of MAYV-E3 can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids, at least 190 amino acids, at least 200 amino acids, at least 210 amino acids, at least 220 amino acids, at least 230 amino acids, at least 240 amino acids, at least 250 amino acids, at least 260 amino acids, at least 270 amino acids, at least 280 amino acids, at least 290 amino acids, at least 300 amino acids, at least 310 amino acids, at least 320 amino acids, at least 330 amino acids, at least 340 amino acids, at least 350 amino acids, at least 360 amino acids, at least 370 amino acids, at least 380 amino acids, at least 390 amino acids, at least 400 amino acids, at least 410 amino acids, at least 420 amino acids or more of a protein comprising the amino acid sequence set forth in SEQ ID NO:110 or a protein comprising a sequence at least 80% identical to the amino acid sequence set forth in SEQ ID NO:110.

In one embodiment, the MAYV antigen comprises MAYV-6K, a consensus thereof, a variant thereof, or a fragment thereof. In one embodiment, the MAYV-6K antigen can comprise the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:112. In one embodiment, the MAYV antigen comprises a fragment of a MAYV-6K. the In one embodiment, the fragment of MAYV-6K can comprise a fragment of SEQ ID NO:112. In one embodiment, the fragment of a MAYV-6K antigen can comprise a fragment of a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:112. In one embodiment, the fragment of MAYV-6K can comprise at least 20 amino acids or more, at least 30 amino acids or more, at least 40 amino acids or more, at least 50 amino acids or more, at least 60 amino acids or more, or more of a protein comprising the amino acid sequence set forth in SEQ ID NO:112 or a protein comprising a sequence at least 80% identical to the amino acid sequence set forth in SEQ ID NO:112.

In one embodiment, the MAYV antigen comprises MAYV-E3 and MAYV-E2 (MAYV-E3+E2), a consensus thereof, a variant thereof, or a fragment thereof. In one embodiment, the MAYV-E3+E2 antigen can comprise the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:114. In one embodiment, the MAYV antigen comprises a fragment of a MAYV-E3+E2. In one embodiment, the fragment of MAYV-E3+E2 can comprise a fragment of SEQ ID NO:114. In one embodiment, the fragment of a MAYV-E3+E2 antigen can comprise a fragment of a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:114. In one embodiment, the fragment of MAYV-E3+E2 can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids, at least 190 amino acids, at least 200 amino acids, at least 210 amino acids, at least 220 amino acids, at least 230 amino acids, at least 240 amino acids, at least 250 amino acids, at least 260 amino acids, at least 270 amino acids, at least 280 amino acids, at least 290 amino acids, at least 300 amino acids, at least 310 amino acids, at least 320 amino acids, at least 330 amino acids, at least 340 amino acids, at least 350 amino acids, at least 360 amino acids, at least 370 amino acids, at least 380 amino acids, at least 390 amino acids, at least 400 amino acids, at least 410 amino acids, at least 420 amino acids, at least 430 amino acids, at least 440 amino acids, at least 450 amino acids, at least 460 amino acids, at least 470 amino acids, at least 480 amino acids or more of a protein comprising the amino acid sequence set forth in SEQ ID NO:114 or a protein comprising a sequence at least 80% identical to the amino acid sequence set forth in SEQ ID NO:114.

In one embodiment, the MAYV antigen is a MAYV-envelope (ENV) antigen. In one embodiment, the MAYV-ENV antigen comprises MAYV-E3, MAYV-E2, MAYV-6K, and MAYV-E1, a consensus thereof, a variant thereof, or a fragment thereof. In one embodiment, the MAYV-ENV antigen can comprise the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:116. In one embodiment, the MAYV antigen comprises a fragment of a MAYV-ENV. In one embodiment, the fragment of MAYV-ENV can comprise a fragment of SEQ ID NO:116. In one embodiment, the fragment of a MAYV-ENV antigen can comprise a fragment of a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:116. In one embodiment, the fragment of MAYV-ENV can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids, at least 190 amino acids, at least 200 amino acids, at least 210 amino acids, at least 220 amino acids, at least 230 amino acids, at least 240 amino acids, at least 250 amino acids, at least 260 amino acids, at least 270 amino acids, at least 280 amino acids, at least 290 amino acids, at least 300 amino acids, at least 310 amino acids, at least 320 amino acids, at least 330 amino acids, at least 340 amino acids, at least 350 amino acids, at least 360 amino acids, at least 370 amino acids, at least 380 amino acids, at least 390 amino acids, at least 400 amino acids, at least 410 amino acids, at least 420 amino acids, at least 430 amino acids, at least 440 amino acids, at least 450 amino acids, at least 460 amino acids, at least 470 amino acids, at least 480 amino acids, at least 490 amino acids, at least 500 amino acids, at least 510 amino acids, at least 520 amino acids, at least 530 amino acids, at least 540 amino acids, at least 550 amino acids, at least 560 amino acids, at least 570 amino acids, at least 580 amino acids, at least 590 amino acids, at least 600 amino acids, at least 610 amino acids, at least 620 amino acids, at least 630 amino acids, at least 640 amino acids, at least 650 amino acids, at least 660 amino acids, at least 670 amino acids, at least 680 amino acids, at least 690 amino acids, at least 700 amino acids, at least 710 amino acids, at least 720 amino acids, at least 730 amino acids, at least 740 amino acids, at least 750 amino acids, at least 760 amino acids, at least 770 amino acids, at least 780 amino acids, at least 790 amino acids, at least 800 amino acids, at least 810 amino acids, at least 820 amino acids, at least 830 amino acids, at least 840 amino acids, at least 850 amino acids, at least 860 amino acids, at least 870 amino acids, at least 880 amino acids, at least 890 amino acids, at least 900 amino acids, at least 910 amino acids, at least 920 amino acids, at least 930 amino acids or more of a protein comprising the amino acid sequence set forth in SEQ ID NO:116 or a protein comprising a sequence at least 80% identical to the amino acid sequence set forth in SEQ ID NO:116.

In some embodiments, the MAYV antigen further comprises a protease sequence. For example, in one embodiment, MAYV-E3+E2 comprises a protease sequence between MAYV-E3 and MAYV-E2. In one embodiment, MAYV-ENV comprises a proteinase a protease sequence between two or more of MAYV-E3, MAYV-E2, MAYV-6K and MAYV-E1. In one embodiment, the protease sequence is a native protease sequence. In one embodiment, the protease sequence is a heterologous protease sequence. In one embodiment, the protease sequence is a furin protease sequence. In one embodiment, the furin protease sequence comprises the amino acid sequence RGRKRRS (SEQ ID NO:126).

4. NUCLEIC ACIDS AND CODING SEQUENCES ENCODING ANTIGENS

Provided herein are coding sequences of antigens capable of eliciting an immune response against one or more MAYV subtypes. Coding sequences encoding the proteins set forth herein may be generated using routine methods. Also described herein are isolated nucleic acids comprising nucleic acid sequences that encode MAYV antigens. The antigen may be a MAYV antigen comprising CA protein E1, E2, E3, 6K, a consensus thereof, a variant thereof, a fragment thereof or a combination thereof. The MAYV antigen may contain at least one antigenic epitope that may be effective against particular MAYV immunogens against which an immune response can be induced. Nucleic acid sequences encoding a MAYV-E1 antigen, a MAYV-E2 antigen, a MAYV-E3 antigen, a MAYV-6K immunogen and a MAYV-CA antigen can be generated based upon the amino acid sequences disclosed. The nucleic acid sequences may optionally comprise coding sequences that encode a signal peptide such as for example an IgE or IgG signal peptide.

The nucleic acid sequence may encode a full-length MAYV-E1 antigen, a full-length MAYV-E2 antigen, a full-length MAYV-E3 antigen, a full-length MAYV-6K antigen or a full-length MAYV-CA antigen. The MAYV antigen may be a MAYV polyprotein. For example, the nucleic acid may encode a full length MAYV polyprotein. For example, in one embodiment, the nucleic acid sequence may encode MAYV-E3 and MAYV-E2 (MAYV-E3+E2). In one embodiment, the nucleic acid sequence may encode MAYV-envelope (ENV). On one embodiment, MAYV-ENV comprise MAYV-E3, MAYV-E2, MAYV-6K and MAYV-E1. The nucleic acid sequences may comprise a sequence that encodes one or more of SEQ ID NOs: 104, 106, 108, 110, 112, 114, 116, a variant thereof, a fragment thereof or any combination thereof. In one embodiment, the nucleic acid sequence comprises an RNA sequence encoding a full-length consensus MAYV immunogen sequence described herein. For example, nucleic acids may comprise an RNA sequence encoding one or more of SEQ ID NOs: 104, 106, 108, 110, 112, 114, 116, a variant thereof, a fragment thereof or any combination thereof.

The nucleic acid sequence may encode a fragment of a MAYV antigen. Fragments of a full-length MAYV antigen can comprise at least 10%, at least 20%, at least 30%, at least 40%, at least 50%, at least 60%, at least 70%, at least 80%, at least 90%, or at least 95% of one or more of the amino acid sequences set forth herein. Fragments of a nucleic acid encoding a MAYV antigen can comprise at least 10%, at least 20%, at least 30%, at least 40%, at least 50%, at least 60%, at least 70%, at least 80%, at least 90%, or at least 95% of one or more of the nucleic acid sequences set forth herein.

The nucleic acid sequence may encode a protein homologous to a MAYV antigen. For example, the nucleic acid sequence may encode a protein homologous to MAYV-E1, a protein homologous to MAYV-E2, a protein homologous to MAYV-E3, a protein homologous to MAYV-6K or a protein homologous to MAYV-CA. The MAYV antigen may be homologous to a MAYV polyprotein. For example, the nucleic acid may encode a protein homologous to a MAYV polyprotein. For example, in one embodiment, the nucleic acid sequence may encode a protein homologous to MAYV-E3 and MAYV-E2 (MAYV-E3+E2). In one embodiment, the nucleic acid sequence may encode a protein homologous to MAYV-envelope (ENV). On one embodiment, MAYV-ENV comprises MAYV-E3, MAYV-E2, MAYV-6K and MAYV-E1. Nucleic acid sequence may comprise a sequence that encodes a protein homologous to one or more of SEQ ID NOs: 104, 106, 108, 110, 112, 114, and 116.

The nucleic acid sequence may encode a protein homologous to a MAYV antigen. For example, the nucleic acid sequence may encode a protein homologous to MAYV-E1, a protein homologous to MAYV-E2, a protein homologous to MAYV-E3, a protein homologous to MAYV-6K or a protein homologous to MAYV-CA. The MAYV antigen may be homologous to a MAYV polyprotein. For example, the nucleic acid may encode a protein homologous to a MAYV polyprotein. For example, in one embodiment, the nucleic acid sequence may encode a protein homologous to MAYV-E3 and MAYV-E2 (MAYV-E3+E2). In one embodiment, the nucleic acid sequence may encode a protein homologous to MAYV-envelope (ENV). On one embodiment, MAYV-ENV comprises MAYV-E3, MAYV-E2, MAYV-6K and MAYV-E1. Nucleic acid sequence may comprise a sequence that encodes a protein homologous to one or more of SEQ ID NOs: 104, 106, 108, 110, 112, 114, and 116. Fragments of a protein homologous to a MAYV antigen can comprise at least 10%, at least 20%, at least 30%, at least 40%, at least 50%, at least 60%, at least 70%, at least 80%, at least 90%, or at least 95% of one or more of the amino acid sequences set forth herein. Fragments of a nucleic acid encoding a protein homologous to a MAYV antigen can comprise at least 10%, at least 20%, at least 30%, at least 40%, at least 50%, at least 60%, at least 70%, at least 80%, at least 90%, or at least 95% of one or more of the nucleic acid sequences set forth herein.

In one embodiment, the nucleic acid encodes an antigen comprising MAYV-CA. In one embodiment, MAYV-CA can be encoded by a nucleic acid sequence encoding a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino sequence set forth in the SEQ ID NO:104. In some embodiments, MAYV-CA can be encoded by a nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:105. In some embodiments, the MAYV-CA antigen can be encoded by an RNA that is a transcript from a DNA sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:105. In some embodiments, the MAYV-CA antigen can be encoded by an RNA that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:104.

In one embodiment, the nucleic acid sequence encodes a fragment of MAYV-CA. In one embodiment, the fragment of MAYV-CA can comprise a fragment of SEQ ID NO:104. In one embodiment, the nucleic acid encodes a fragment of a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:104. In one embodiment, the nucleic acid comprises a fragment of a nucleic acid sequence set forth in SEQ ID NO:105 or a fragment of a nucleic acid sequence at having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:105. The fragment can comprise at least 50, at least 75, at least 100, at least 125, at least 150, at least 175, at least 200, at least 225, at least 250, at least 275, at least 300, at least 325, at least 350, at least 375, at least 400, at least 425, at least 450, at least 475, at least 500, at least 525, at least 550, at least 575, at least 600, at least 625, at least 650, at least 675, at least 700, at least 725, at least 750, or more nucleic acids of a nucleic acid sequence comprising the nucleic acid sequence set forth in SEQ ID NO:105 or a nucleic acid sequence comprising a sequence at least 80% identical to the nucleic acid sequence set forth in SEQ ID NO:105.

In one embodiment, the nucleic acid encodes an antigen comprising MAYV-E1. In one embodiment, MAYV-E1 can be encoded by a nucleic acid sequence encoding a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino sequence set forth in the SEQ ID NO:106. In some embodiments, MAYV-E1 can be encoded by a nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:107. In some embodiments, the MAYV-E1 antigen can be encoded by an RNA that is a transcript from a DNA sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:107. In some embodiments, the MAYV-E1 antigen can be encoded by an RNA that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:106.

In one embodiment, the nucleic acid sequence encodes a fragment of MAYV-E1. In one embodiment, the fragment of MAYV-E1 can comprise a fragment of SEQ ID NO:106. In one embodiment, the nucleic acid encodes a fragment of a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:106. In one embodiment, the nucleic acid comprises a fragment of a nucleic acid sequence set forth in SEQ ID NO:107 or a fragment of a nucleic acid sequence at having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:107. The fragment can comprise at least 50, at least 75, at least 100, at least 125, at least 150, at least 175, at least 200, at least 225, at least 250, at least 275, at least 300, at least 325, at least 350, at least 375, at least 400, at least 425, at least 450, at least 475, at least 500, at least 525, at least 550, at least 575, at least 600, at least 625, at least 650, at least 675, at least 700, at least 725, at least 750, at least 775, at least 800, at least 825, at least 850, at least 875, 900, at least 925, at least 950, at least 975, 1000, at least 1025, at least 1050, at least 1075, 1100, at least 1125, at least 1150, at least 1175, at least 1200, at least 1225, at least 1250, at least 1275 or more nucleic acids of a nucleic acid sequence comprising the nucleic acid sequence set forth in SEQ ID NO:107 or a nucleic acid sequence comprising a sequence at least 80% identical to the nucleic acid sequence set forth in SEQ ID NO:107.

In one embodiment, the nucleic acid encodes an antigen comprising MAYV-E2. In one embodiment, MAYV-E2 can be encoded by a nucleic acid sequence encoding a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino sequence set forth in the SEQ ID NO:108. In some embodiments, MAYV-E2 can be encoded by a nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:109. In some embodiments, the MAYV-E2 antigen can be encoded by an RNA that is a transcript from a DNA sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:109. In some embodiments, the MAYV-E2 antigen can be encoded by an RNA that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:108.

In one embodiment, the nucleic acid sequence encodes a fragment of MAYV-E2. In one embodiment, the fragment of MAYV-E2 can comprise a fragment of SEQ ID NO:108. In one embodiment, the nucleic acid encodes a fragment of a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:108. In one embodiment, the nucleic acid comprises a fragment of a nucleic acid sequence set forth in SEQ ID NO:109 or a fragment of a nucleic acid sequence at having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:109. The fragment can comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or more nucleic acids of a nucleic acid sequence comprising the nucleic acid sequence set forth in SEQ ID NO:109 or a nucleic acid sequence comprising a sequence at least 80% identical to the nucleic acid sequence set forth in SEQ ID NO:109.

In one embodiment, the nucleic acid encodes an antigen comprising MAYV-E3. In one embodiment, MAYV-E3 can be encoded by a nucleic acid sequence encoding a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino sequence set forth in the SEQ ID NO:110. In some embodiments, MAYV-E3 can be encoded by a nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:111. In some embodiments, the MAYV-E3 antigen can be encoded by an RNA that is a transcript from a DNA sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:111. In some embodiments, the MAYV-E3 antigen can be encoded by an RNA that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:110.

In one embodiment, the nucleic acid sequence encodes a fragment of MAYV-E3. In one embodiment, the fragment of MAYV-E3 can comprise a fragment of SEQ ID NO:110. In one embodiment, the nucleic acid encodes a fragment of a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:110. In one embodiment, the nucleic acid comprises a fragment of a nucleic acid sequence set forth in SEQ ID NO:111 or a fragment of a nucleic acid sequence at having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:111. The fragment can comprise at least 50, at least 75, at least 100, at least 125, at least 150, at least 175, at least 200, at least 225, at least 250, at least 275, at least 300, at least 325, at least 350, at least 375, at least 400, at least 425, at least 450, at least 475, at least 500, at least 525, at least 550, at least 575, at least 600, at least 625, at least 650, at least 675, at least 700, at least 725, at least 750, at least 775, at least 800, at least 825, at least 850, at least 875, 900, at least 925, at least 950, at least 975, 1000, at least 1025, at least 1050, at least 1075, 1100, at least 1125, at least 1150, at least 1175, at least 1200, at least 1225, at least 1250, or more nucleic acids of a nucleic acid sequence comprising the nucleic acid sequence set forth in SEQ ID NO:111 or a nucleic acid sequence comprising a sequence at least 80% identical to the nucleic acid sequence set forth in SEQ ID NO:111.

In one embodiment, the nucleic acid encodes an antigen comprising MAYV-6K. In one embodiment, MAYV-6K can be encoded by a nucleic acid sequence encoding a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino sequence set forth in the SEQ ID NO:112. In some embodiments, MAYV-6K can be encoded by a nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:113. In some embodiments, the MAYV-6K antigen can be encoded by an RNA that is a transcript from a DNA sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:113. In some embodiments, the MAYV-6K antigen can be encoded by an RNA that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:112.

In one embodiment, the nucleic acid sequence encodes a fragment of MAYV-6K. In one embodiment, the fragment of MAYV-6K can comprise a fragment of SEQ ID NO:112. In one embodiment, the nucleic acid encodes a fragment of a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:112. In one embodiment, the nucleic acid comprises a fragment of a nucleic acid sequence set forth in SEQ ID NO:113 or a fragment of a nucleic acid sequence at having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:113. The fragment can comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200 or more nucleic acids of a nucleic acid sequence comprising the nucleic acid sequence set forth in SEQ ID NO:113 or a nucleic acid sequence comprising a sequence at least 80% identical to the nucleic acid sequence set forth in SEQ ID NO:113.

In one embodiment, the nucleic acid encodes an antigen comprising MAYV-E2+E3. In one embodiment, MAYV-E2+E3 can be encoded by a nucleic acid sequence encoding a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino sequence set forth in the SEQ ID NO:114. In some embodiments, MAYV-E2+E3 can be encoded by a nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:115. In some embodiments, the MAYV-E2+E3 antigen can be encoded by an RNA that is a transcript from a DNA sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:115. In some embodiments, the MAYV-E2+E3 antigen can be encoded by an RNA that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:114.

In one embodiment, the nucleic acid sequence encodes a fragment of MAYV-E2+E3. In one embodiment, the fragment of MAYV-E2+E3 can comprise a fragment of SEQ ID NO:114. In one embodiment, the nucleic acid encodes a fragment of a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:114. In one embodiment, the nucleic acid comprises a fragment of a nucleic acid sequence set forth in SEQ ID NO:115 or a fragment of a nucleic acid sequence at having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:115. The fragment can comprise at least 50, at least 75, at least 100, at least 125, at least 150, at least 175, at least 200, at least 225, at least 250, at least 275, at least 300, at least 325, at least 350, at least 375, at least 400, at least 425, at least 450, at least 475, at least 500, at least 525, at least 550, at least 575, at least 600, at least 625, at least 650, at least 675, at least 700, at least 725, at least 750, at least 775, at least 800, at least 825, at least 850, at least 875, 900, at least 925, at least 950, at least 975, 1000, at least 1025, at least 1050, at least 1075, 1100, at least 1125, at least 1150, at least 1175, at least 1200, at least 1225, at least 1250, at least 1300, at least 1325, at least 1350, at least 1375, at least 1400, at least 1425, at least 1450 or more nucleic acids of a nucleic acid sequence comprising the nucleic acid sequence set forth in SEQ ID NO:115 or a nucleic acid sequence comprising a sequence at least 80% identical to the nucleic acid sequence set forth in SEQ ID NO:115.

In one embodiment, the nucleic acid encodes an antigen comprising MAYV-E2+E3. In one embodiment, MAYV-E2+E3 can be encoded by a nucleic acid sequence encoding a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino sequence set forth in the SEQ ID NO:114. In some embodiments, MAYV-E2+E3 can be encoded by a nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:115. In some embodiments, the MAYV-E2+E3 antigen can be encoded by an RNA that is a transcript from a DNA sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:115. In some embodiments, the MAYV-E2+E3 antigen can be encoded by an RNA that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:114.

In one embodiment, the nucleic acid sequence encodes a fragment of MAYV-E2+E3. In one embodiment, the fragment of MAYV-E2+E3 can comprise a fragment of SEQ ID NO:114. In one embodiment, the nucleic acid encodes a fragment of a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:114. In one embodiment, the nucleic acid comprises a fragment of a nucleic acid sequence set forth in SEQ ID NO:115 or a fragment of a nucleic acid sequence at having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:115. The fragment can comprise at least 50, at least 75, at least 100, at least 125, at least 150, at least 175, at least 200, at least 225, at least 250, at least 275, at least 300, at least 325, at least 350, at least 375, at least 400, at least 425, at least 450, at least 475, at least 500, at least 525, at least 550, at least 575, at least 600, at least 625, at least 650, at least 675, at least 700, at least 725, at least 750, at least 775, at least 800, at least 825, at least 850, at least 875, 900, at least 925, at least 950, at least 975, 1000, at least 1025, at least 1050, at least 1075, 1100, at least 1125, at least 1150, at least 1175, at least 1200, at least 1225, at least 1250, at least 1300, at least 1325, at least 1350, at least 1375, at least 1400, at least 1425, at least 1450 or more nucleic acids of a nucleic acid sequence comprising the nucleic acid sequence set forth in SEQ ID NO:115 or a nucleic acid sequence comprising a sequence at least 80% identical to the nucleic acid sequence set forth in SEQ ID NO:115.

In one embodiment, the nucleic acid encodes an antigen comprising MAYV-ENV. In one embodiment, MAYV-ENV can be encoded by a nucleic acid sequence encoding a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino sequence set forth in the SEQ ID NO:116. In some embodiments, MAYV-ENV can be encoded by a nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:117. In some embodiments, the MAYV-ENV antigen can be encoded by an RNA that is a transcript from a DNA sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:117. In some embodiments, the MAYV-ENV antigen can be encoded by an RNA that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:116.

In one embodiment, the nucleic acid sequence encodes a fragment of MAYV-ENV. In one embodiment, the fragment of MAYV-ENV can comprise a fragment of SEQ ID NO:116. In one embodiment, the nucleic acid encodes a fragment of a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:116. In one embodiment, the nucleic acid comprises a fragment of a nucleic acid sequence set forth in SEQ ID NO:117 or a fragment of a nucleic acid sequence at having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:117. The fragment can comprise at least 50, at least 75, at least 100, at least 125, at least 150, at least 175, at least 200, at least 225, at least 250, at least 275, at least 300, at least 325, at least 350, at least 375, at least 400, at least 425, at least 450, at least 475, at least 500, at least 525, at least 550, at least 575, at least 600, at least 625, at least 650, at least 675, at least 700, at least 725, at least 750, at least 775, at least 800, at least 825, at least 850, at least 875, 900, at least 925, at least 950, at least 975, 1000, at least 1025, at least 1050, at least 1075, 1100, at least 1125, at least 1150, at least 1175, at least 1200, at least 1225, at least 1250, at least 1300, at least 1325, at least 1350, at least 1375, at least 1400, at least 1425, at least 1450, at least 1500, at least 1525, at least 1550, at least 1575, at least 1600, at least 1625, at least 1650, at least 1675, at least 1700, at least 1725, at least 1750, at least 1775, at least 1800, at least 1825, at least 1850, at least 1875, at least 1900, at least 1925, at least 1950, at least 1975, at least 2000, at least 2025, at least 2050, at least 2075, at least 2100, at least 2125, at least 2150, at least 2175, at least 2200, at least 2225, at least 2250, at least 2275, at least 2300, at least 2325, at least 2350, at least 2375, at least 2400, at least 2425, at least 2450, at least 2475, at least 2500, at least 2525, at least 2550, at least 2575, at least 2600, at least 2625, at least 2650, at least 2675, at least 2700, at least 2725, at least 2750, at least 2775 at least 1475, or more nucleic acids of a nucleic acid sequence comprising the nucleic acid sequence set forth in SEQ ID NO:117 or a nucleic acid sequence comprising a sequence at least 80% identical to the nucleic acid sequence set forth in SEQ ID NO:117.

5. VACCINES AND IMMUNOLOGICAL COMPOSITIONS

Provided herein is a vaccine or immunologic composition capable of generating in a mammal an immune response against Mayaro virus. The vaccine may a nucleic acid molecule as discussed above. The vaccine may comprise a plurality of the nucleic acid molecules, or combinations thereof. The vaccine may be provided to induce a therapeutic or prophylactic immune response.

The vaccine can be a DNA vaccine. DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome.

The vaccine can be an RNA of the one or more MAYV antigens. The RNA vaccine can be introduced into the cell.

The vaccine can be an attenuated live vaccine, a vaccine using recombinant vectors to deliver antigen, subunit vaccines, and glycoprotein vaccines, for example, but not limited, the vaccines described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,3 64; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine of the present invention can have features required of effective vaccines such as being safe so that the vaccine itself does not cause illness or death; being protective against illness; inducing neutralizing antibody; inducing protective T cell responses; and providing ease of administration, few side effects, biological stability, and low cost per dose.

The vaccine may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. In one embodiment, the concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be one or more adjuvants. An adjuvant may be other genes that are expressed from the same or from an alternative plasmid or are delivered as proteins in combination with the plasmid above in the vaccine. The one or more adjuvants may be proteins and/or nucleic acid molecules that encode proteins selected from the group consisting of: CCL20, α-interferon (IFN-α), β-interferon (IFN-β, γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence or coding sequence that encodes the signal sequence deleted and optionally including a different signal peptide such as that from IgE or coding sequence that encodes a difference signal peptide such as that from IgE, IL-28, MHC, CD80, CD86, IL-1, IL-2, IL-4, IL-5, IL-6, IL-10, IL-18, MCP-1, MIP-1α, MIP-1β, IL-8, L-selectin, P-selectin, E-selectin, CD34, Gly-CAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL- R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or a combination thereof.

In some embodiments, the adjuvant may be one or more proteins and/or nucleic acid molecules that encode proteins selected from the group consisting of: CCL-20, IL-12, IL-15, IL-28, CTACK, TECK, MEC or RANTES. Examples of IL-12 constructs and sequences are disclosed in PCT application no. PCT/US1997/019502 and corresponding U.S. application Ser. No. 08/956,865, and U.S. Provisional Application Ser. No 61/569,600 filed Dec. 12, 2011, which are each incorporated herein by reference. Examples of IL-15 constructs and sequences are disclosed in PCT application no. PCT/US04/18962 and corresponding U.S. application Ser. No. 10/560,650, and in PCT application no. PCT/US07/00886 and corresponding U.S. application Ser. No. 12/160,766, and in PCT application no. PCT/US10/048827, which are each incorporated herein by reference. Examples of IL-28 constructs and sequences are disclosed in PCT application no. PCT/US09/039648 and corresponding U.S. application Ser. No. 12/936,192, which are each incorporated herein by reference. Examples of RANTES and other constructs and sequences are disclosed in PCT application no. PCT/US1999/004332 and corresponding U.S. application Ser. No. and 09/622,452, which are each incorporated herein by reference. Other examples of RANTES constructs and sequences are disclosed in PCT application no. PCT/US11/024098, which is incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of chemokines CTACK, TECK and MEC constructs and sequences are disclosed in PCT application no. PCT/US2005/042231 and corresponding U.S. application Ser. No. 11/719,646, which are each incorporated herein by reference. Examples of OX40 and other immunomodulators are disclosed in U.S. application Ser. No. 10/560,653, which is incorporated herein by reference. Examples of DR5 and other immunomodulators are disclosed in U.S. application Ser. No. 09/622,452, which is incorporated herein by reference.

The vaccine may further comprise a genetic vaccine facilitator agent as described in U.S. Ser. No. 021,579 filed Apr. 1, 1994, which is fully incorporated by reference.

The vaccine may comprise the consensus antigens and plasmids at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the consensus antigen or plasmid thereof.

In some embodiments, pharmaceutical compositions according to the present invention comprise at least 10, 15, 20, 25, 30, 35, 40, 45, 50, 55, 60, 65, 70, 75, 80, 85, 90, 95 or 100 nanograms of DNA of the vaccine. In some embodiments, the pharmaceutical compositions can comprise at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms of DNA of the vaccine. In some embodiments, the pharmaceutical composition can comprise at least 1.5, 2, 2.5, 3, 3.5, 4, 4.5, 5, 5.5, 6, 6.5, 7, 7.5, 8, 8.5, 9, 9.5 or 10 mg or more of DNA of the vaccine.

In other embodiments, the pharmaceutical composition can comprise up to and including 15, 20, 25, 30, 35, 40, 45, 50, 55, 60, 65, 70, 75, 80, 85, 90, 95 or 100 nanograms of DNA of the vaccine. In some embodiments, the pharmaceutical composition can comprise up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms of DNA of the vaccine. In some embodiments, the pharmaceutical composition can comprise up to and including 1.5, 2, 2.5, 3, 3.5, 4, 4.5, 5, 5.5, 6, 6.5, 7, 7.5, 8, 8.5, 9, 9.5 or 10 mg of DNA of the vaccine.

The vaccine may be formulated according to the mode of administration to be used. An injectable vaccine pharmaceutical composition may be sterile, pyrogen free and particulate free. An isotonic formulation or solution may be used. Additives for isotonicity may include sodium chloride, dextrose, mannitol, sorbitol, and lactose. The vaccine may comprise a vasoconstriction agent. The isotonic solutions may include phosphate buffered saline. Vaccine may further comprise stabilizers including gelatin and albumin. The stabilizing may allow the formulation to be stable at room or ambient temperature for extended periods of time such as LGS or polycations or polyanions to the vaccine formulation.

The vaccine may be stable for is stable at room temperature (25° C.) for more than 1 week, in some embodiments for more than 2 weeks, in some embodiments for more than 3 weeks, in some embodiments for more than 4 weeks, in some embodiments for more than 5 weeks, and in some embodiments for more than 6 weeks. In some embodiments, the vaccine is stable for more than one month, more than 2 months, more than 3 months, more than 4 months, more than 5 months, more than 6 months, more than 7 months, more than 8 months, more than 9 months, more than 10 months, more than 11 months, or more than 12 months. In some embodiments, the vaccine is stable for more than 1 year, more than 2 years, more than years, or more than 5 years. In one embodiment, the vaccine is stable under refrigeration (2-8° C.). Accordingly, in one embodiment, the vaccine does not require frozen cold-chain. A vaccine is stable if it retains its biological activity for a sufficient period to allow its intended use (e.g., to generate an immune response in a subject). For example, for vaccines that are to be stored, shipped, etc., it may be desired that the vaccines remain stable for months to years.

The immunogenic composition can induce an immune response in the subject administered the composition. The induced immune response can be specific for a native antigen. The induced immune response can be reactive with a native antigen related to the optimized consensus-encoded antigen. In various embodiments, related antigens include antigens having amino acid sequences having at least 90%, at least 91%, at least 92%, at least 93%, at least 94%, at least 95%, at least 96%, at least 97%, at least 98%, at least 99%, or 100% homology to the amino acid sequence of the optimized consensus-encoded antigen. In various embodiments, related antigens include antigens encoded by nucleotide sequences having at least 90%, at least 91%, at least 92%, at least 93%, at least 94%, at least 95%, at least 96%, at least 97%, at least 98%, at least 99%, or 100% homology to the optimized consensus nucleotide sequences disclosed herein.

The immunogenic composition can induce a humoral immune response in the subject administered the immunogenic composition. The induced humoral immune response can be specific for a native antigen. The induced humoral immune response can be reactive with the native antigen related to the optimized consensus-encoded antigen. The humoral immune response can be induced in the subject administered the immunogenic composition by about 1.5-fold to about 16-fold, about 2-fold to about 12-fold, or about 3-fold to about 10-fold. The humoral immune response can be induced in the subject administered the immunogenic composition by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized MAYV antigen.

The humoral immune response induced by the immunogenic composition can include an increased level of neutralizing antibodies associated with the subject administered the immunogenic composition as compared to a subject not administered the immunogenic composition. The neutralizing antibodies can be specific for a native antigen related to the optimized consensus-encoded antigen. The neutralizing antibodies can be reactive with the native antigen genetically related to the optimized consensus antigen. The neutralizing antibodies can provide protection against and/or treatment of tumor growth, metastasis or tumor associated pathologies in the subject administered the immunogenic composition.

The humoral immune response induced by the immunogenic composition can include an increased level of IgG antibodies associated with the subject administered the immunogenic composition as compared to a subject not administered the immunogenic composition. These IgG antibodies can be specific for the native antigen genetically related to the optimized consensus antigen. These IgG antibodies can be reactive with the native antigen genetically related to the optimized consensus antigen. The level of IgG antibody associated with the subject administered the immunogenic composition can be increased by about 1.5-fold to about 16-fold, about 2-fold to about 12-fold, or about 3-fold to about 10-fold as compared to the subject not administered the immunogenic composition. The level of IgG antibody associated with the subject administered the immunogenic composition can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized MAYV antigen.

The immunogenic composition can induce a cellular immune response in the subject administered the immunogenic composition. The induced cellular immune response can be specific for a native antigen related to the optimized consensus-encoded antigen. The induced cellular immune response can be reactive to the native antigen related to the optimized consensus-encoded antigen. The induced cellular immune response can include eliciting a $CD8^+$ T cell response. The elicited $CD8^+$ T cell response can be reactive with the native antigen genetically related to the optimized consensus antigen. The elicited $CD8^+$ T cell response can be polyfunctional. The induced cellular immune response can include eliciting a $CD8^+$ T cell response, in which the $CD8^+$ T cells produce interferon-gamma (IFN-γ), tumor necrosis factor alpha (TNF-α), interleukin-2 (IL-2), or a combination of IFN-γ and TNF-α.

The induced cellular immune response can include an increased $CD8^+$ T cell response associated with the subject administered the immunogenic composition as compared to the subject not administered the immunogenic composition. The $CD8^+$ T cell response associated with the subject administered the immunogenic composition can be increased by about 2-fold to about 30-fold, about 3-fold to about 25-fold, or about 4-fold to about 20-fold as compared to the subject not administered the immunogenic composition. The CD8⁺ T cell response associated with the subject administered the immunogenic composition can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to a subject not administered the immunogenic composition or a subject administered a non-optimized MAYV antigen.

The induced cellular immune response can include an increased frequency of CD107a/IFNγ/T-bet triple-positive CD8 T cells that are reactive against the native antigen. The frequency of CD107a/IFNγ/T-bet triple-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized MAYV antigen.

The induced cellular immune response can include an increased frequency of CD107a/IFNγ double-positive CD8 T cells that are reactive against the native antigen. The frequency of CD107a/IFNγ double-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to a subject not administered the immunogenic composition or a subject administered a non-optimized MAYV antigen.

The cellular immune response induced by the immunogenic composition can include eliciting a CD4⁺ T cell response. The elicited CD4⁺ T cell response can be reactive with the native antigen genetically related to the optimized consensus antigen. The elicited CD4⁺ T cell response can be polyfunctional. The induced cellular immune response can include eliciting a CD4⁺ T cell response, in which the CD4⁺ T cells produce IFN-γ, TNF-α, IL-2, or a combination of IFN-γ and TNF-α.

The induced cellular immune response can include an increased frequency of CD4⁺ T cells that produce IFN-γ. The frequency of CD4⁺IFN-γ⁺ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized MAYV antigen.

The induced cellular immune response can include an increased frequency of CD4⁺ T cells that produce TNF-α. The frequency of CD4⁺TNF-γ⁺ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to a subject not administered the immunogenic composition or a subject administered a non-optimized MAYV antigen.

The induced cellular immune response can include an increased frequency of CD4⁺ T cells that produce both IFN-γ and TNF-α. The frequency of CD4⁺IFN-γ⁺TNF-α⁺ associated with the subject administered the immunogenic composition can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to a subject not administered the immunogenic composition or a subject administered a non-optimized MAYV antigen.

The immunogenic composition of the present invention can have features required of effective vaccines such as being safe so the vaccine itself does not cause illness or death; is protective against illness resulting from exposure to live pathogens such as viruses or bacteria; induces neutralizing antibody to prevent invention of cells; induces protective T cells against intracellular pathogens; and provides ease of administration, few side effects, biological stability, and low cost per dose.

The immunogenic composition can further induce an immune response when administered to different tissues such as the muscle or skin. The immunogenic composition can further induce an immune response when administered via electroporation, or injection, or subcutaneously, or intramuscularly.

6. DNA MONOCLONAL ANTIBODIES

The present invention relates to a composition comprising a recombinant nucleic acid sequence encoding an antibody, a fragment thereof, a variant thereof, or a combination thereof. The composition, when administered to a subject in need thereof, can result in the generation of a synthetic antibody in the subject. The synthetic antibody can bind a target molecule (i.e., an antigen) present in the subject. Such binding can neutralize the antigen, block recognition of the antigen by another molecule, for example, a protein or nucleic acid, and elicit or induce an immune response to the antigen.

In one embodiment, the composition comprises a nucleotide sequence encoding a synthetic antibody. In one embodiment, the composition comprises a nucleic acid molecule comprising a first nucleotide sequence encoding a first synthetic antibody and a second nucleotide sequence encoding a second synthetic antibody. In one embodiment, the nucleic acid molecule comprises a nucleotide sequence encoding a cleavage domain.

In one embodiment, the nucleic acid molecule comprises a nucleotide sequence encoding an anti-Mayaro virus (anti-MAYV) antibody.

In one embodiment, the nucleotide sequence encoding an anti-MAYV antibody comprises one or more codon optimized nucleic acid sequences encoding an amino acid sequence at least 90% homologous to SEQ ID NO:1 or 3, or a fragment of an amino acid sequence at least 90% homologous to SEQ ID NO:1 or 3. In one embodiment, the nucleotide sequence encoding an anti-MAYV antibody comprises one or more codon optimized nucleic acid sequences encoding an amino acid sequence as set forth in SEQ ID NO:1 or 3 or a fragment of an amino acid sequence as set forth in SEQ ID NO:1 or 3.

In one embodiment, the nucleotide sequence encoding an anti-MAYV antibody comprises one or more RNA sequence transcribed from one or more DNA sequences encoding an amino acid sequence at least 90% homologous to SEQ ID NO:1 or 3 or a fragment of an amino acid sequence at least 90% homologous to SEQ ID NO:1 or 3. In one embodiment, the nucleotide sequence encoding an anti-MAYV antibody comprises one or more RNA sequence transcribed from one or more DNA sequences encoding an amino acid sequence as set forth in SEQ ID NO:1 or 3 or a fragment of an amino acid sequence as set forth in SEQ ID NO:1 or 3.

In one embodiment, the nucleotide sequence encoding an anti-MAYV antibody comprises one or more codon optimized nucleic acid sequences at least 90% homologous to SEQ ID NO: 2 or 4 or a fragment of a nucleic acid sequence at least 90% homologous to SEQ ID NO: 2 or 4. In one embodiment, the nucleotide sequence encoding an anti-MAYV antibody comprises one or more codon optimized nucleic acid sequences as set forth in SEQ ID NO: 2 or 4 or a fragment of a nucleic acid sequence as set forth in SEQ ID NO: 2 or 4.

In one embodiment, the nucleotide sequence encoding an anti-MAYV antibody comprises one or more RNA sequence transcribed from one or more DNA sequences at least 90% homologous to SEQ ID NO: 2 or 4 or a fragment of a DNA sequence at least 90% homologous to SEQ ID NO: 2 or 4. In one embodiment, the nucleotide sequence encoding an anti-MAYV antibody comprises one or more RNA sequence transcribed from one or more DNA sequences as set forth in SEQ ID NO: 2 or 4 or a fragment of a DNA sequence as set forth in SEQ ID NO:2 or 4.

In one embodiment, the composition comprises a nucleotide sequence encoding a synthetic MAYV heavy chain. In one embodiment, the composition comprises a nucleotide sequence encoding a synthetic MAYV light chain. In one embodiment, the composition comprises a nucleotide sequence encoding a synthetic MAYV antibody. In one embodiment, the sequence encoding a synthetic MAYV antibody comprises a first sequence encoding a synthetic MAYV heavy chain and a second sequence encoding a synthetic MAYV light chain.

In one embodiment, the nucleotide sequence encoding a synthetic MAYV heavy chain comprises one or more codon optimized nucleic acid sequences encoding an amino acid sequence at least 90% homologous to one of SEQ ID NOs:5-16, or a fragment of an amino acid sequence at least 90% homologous to one of SEQ ID NOs:5-16. In one embodiment, the nucleotide sequence encoding a synthetic MAYV heavy chain comprises one or more codon optimized nucleic acid sequences encoding an amino acid sequence as set forth in one of SEQ ID NOs:5-16 or a fragment of an amino acid sequence as set forth in one of SEQ ID NOs:5-16.

In one embodiment, the nucleotide sequence encoding a synthetic MAYV heavy chain comprises one or more codon optimized nucleic acid sequences encoding one or more CDRs each individually comprising an amino acid sequence at least 90% homologous to one of SEQ ID NO:29-64. In one embodiment, the nucleotide sequence encoding a synthetic MAYV heavy chain comprises one or more codon optimized nucleic acid sequences encoding one or more CDRs each individually comprising an amino acid sequence as set forth in one of SEQ ID NOs: 29-64.

In one embodiment, the nucleotide sequence encoding a synthetic MAYV heavy chain comprises one or more RNA sequence transcribed from one or more DNA sequences encoding an amino acid sequence at least 90% homologous to one of SEQ ID NOs:5-16, or a fragment of an amino acid sequence at least 90% homologous to one of SEQ ID NOs:5-16. In one embodiment, the nucleotide sequence encoding a synthetic MAYV heavy chain comprises one or more RNA sequence transcribed from one or more DNA sequences encoding an amino acid sequence as set forth in one of SEQ ID NOs:5-16, or a fragment of an amino acid sequence as set forth in one of SEQ ID NOs:5-16.

In one embodiment, the nucleotide sequence encoding a synthetic MAYV heavy chain comprises one or more RNA sequence transcribed from one or more DNA sequences encoding one or more CDRs each individually comprising an amino acid sequence at least 90% homologous to one of SEQ ID NO:29-64. In one embodiment, the nucleotide sequence encoding a synthetic MAYV heavy chain one or more RNA sequence transcribed from one or more DNA sequences encoding one or more CDRs each individually comprising an amino acid sequence as set forth in one of SEQ ID NOs: 29-64.

In one embodiment, the nucleotide sequence encoding a synthetic MAYV light chain comprises one or more codon optimized nucleic acid sequences encoding an amino acid sequence at least 90% homologous to one of SEQ ID NOs: 17-28, or a fragment of an amino acid sequence at least 90% homologous to one of SEQ ID NOs: 17-28. In one embodiment, the nucleotide sequence encoding a synthetic MAYV light chain comprises one or more codon optimized nucleic acid sequences encoding an amino acid sequence as set forth in one of SEQ ID NOs: 17-28 or a fragment of an amino acid sequence as set forth in one of SEQ ID NOs: 17-28.

In one embodiment, the nucleotide sequence encoding a synthetic MAYV light chain comprises one or more codon optimized nucleic acid sequences encoding one or more CDRs each individually comprising an amino acid sequence at least 90% homologous to one of SEQ ID NO:65-100. In one embodiment, the nucleotide sequence encoding a synthetic MAYV light chain comprises one or more codon optimized nucleic acid sequences encoding one or more CDRs each individually comprising an amino acid sequence as set forth in one of SEQ ID NOs:65-100.

In one embodiment, the nucleotide sequence encoding a synthetic MAYV light chain comprises one or more RNA sequence transcribed from one or more DNA sequences encoding an amino acid sequence at least 90% homologous to one of SEQ ID NOs: 17-28, or a fragment of an amino acid sequence at least 90% homologous to one of SEQ ID NOs: 17-28. In one embodiment, the nucleotide sequence encoding a synthetic MAYV light chain comprises one or more RNA sequence transcribed from one or more DNA sequences encoding an amino acid sequence as set forth in one of SEQ ID NOs:17-28, or a fragment of an amino acid sequence as set forth in one of SEQ ID NOs: 17-28.

In one embodiment, the nucleotide sequence encoding a synthetic MAYV light chain comprises one or more RNA sequence transcribed from one or more DNA sequences encoding one or more CDRs each individually comprising an amino acid sequence at least 90% homologous to one of SEQ ID NO:65-100. In one embodiment, the nucleotide sequence encoding a synthetic MAYV light chain one or more RNA sequence transcribed from one or more DNA sequences encoding one or more CDRs each individually comprising an amino acid sequence as set forth in one of SEQ ID NOs: 65-100.

The composition of the invention can treat, prevent and/or protect against any disease, disorder, or condition associated with Mayaro virus infection. In certain embodiments, the composition can treat, prevent, and or/protect against viral infection. In certain embodiments, the composition can treat, prevent, and or/protect against condition associated with Mayaro virus infection.

The composition can result in the generation of the synthetic antibody in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 20 hours, 25 hours, 30 hours, 35 hours, 40 hours, 45 hours, 50 hours, or 60 hours of administration of the composition to the subject. The composition can result in generation of the synthetic antibody in the subject within at least about 1 day, 2 days, 3 days, 4 days, 5 days, 6 days, 7 days, 8 days, 9 days, or 10 days of administration of the composition to the subject. The composition can result in generation of the synthetic antibody in the subject within about 1 hour to about 6 days, about 1 hour to about 5 days, about 1 hour to about 4 days, about 1 hour to about 3 days, about 1 hour to about 2 days, about 1 hour to about 1 day, about 1 hour to about 72 hours, about 1 hour to about 60 hours, about 1 hour to about 48 hours, about 1 hour to about 36 hours, about 1 hour to about 24 hours, about 1 hour to about 12 hours, or about 1 hour to about 6 hours of administration of the composition to the subject.

The composition, when administered to the subject in need thereof, can result in the generation of the synthetic antibody in the subject more quickly than the generation of an endogenous antibody in a subject who is administered an antigen to induce a humoral immune response. The composition can result in the generation of the synthetic antibody at least about 1 day, 2 days, 3 days, 4 days, 5 days, 6 days, 7 days, 8 days, 9 days, or 10 days before the generation of the endogenous antibody in the subject who was administered an antigen to induce a humoral immune response.

The composition of the present invention can have features required of effective compositions such as being safe so that the composition does not cause illness or death; being protective against illness; and providing ease of administration, few side effects, biological stability and low cost per dose.

7. RECOMBINANT NUCLEIC ACID SEQUENCE

As described above, the composition can comprise a recombinant nucleic acid sequence. The recombinant nucleic acid sequence can encode an anti-MAYV synthetic antibody, a fragment thereof, a variant thereof, or a combination thereof. The antibody is described in more detail below. The recombinant nucleic acid sequence can encode a MAYV antigen, a fragment thereof, a variant thereof, or a combination thereof.

The recombinant nucleic acid sequence can be a heterologous nucleic acid sequence. The recombinant nucleic acid sequence can include one or more heterologous nucleic acid sequences.

The recombinant nucleic acid sequence can be an optimized nucleic acid sequence. Such optimization can increase or alter the immunogenicity of the antibody. Optimization can also improve transcription and/or translation. Optimization can include one or more of the following: low GC content leader sequence to increase transcription; mRNA stability and codon optimization; addition of a kozak sequence (e.g., GCC ACC) for increased translation; addition of an immunoglobulin (Ig) leader sequence encoding a signal peptide; addition of an internal IRES sequence and eliminating to the extent possible cis-acting sequence motifs (i.e., internal TATA boxes).

Recombinant Nucleic Acid Sequence Construct

The recombinant nucleic acid sequence can include one or more recombinant nucleic acid sequence constructs. The recombinant nucleic acid sequence construct can include one or more components, which are described in more detail below.

The recombinant nucleic acid sequence construct can include a heterologous nucleic acid sequence that encodes a heavy chain polypeptide, a fragment thereof, a variant thereof, or a combination thereof. The recombinant nucleic acid sequence construct can include a heterologous nucleic acid sequence that encodes a light chain polypeptide, a fragment thereof, a variant thereof, or a combination thereof. The recombinant nucleic acid sequence construct can also include a heterologous nucleic acid sequence that encodes a protease or peptidase cleavage site. The recombinant nucleic acid sequence construct can also include a heterologous nucleic acid sequence that encodes an internal ribosome entry site (IRES). An IRES may be either a viral IRES or a eukaryotic IRES. The recombinant nucleic acid sequence construct can include one or more leader sequences, in which each leader sequence encodes a signal peptide. The recombinant nucleic acid sequence construct can include one or more promoters, one or more introns, one or more transcription termination regions, one or more initiation codons, one or more termination or stop codons, and/or one or more polyadenylation signals. The recombinant nucleic acid sequence construct can also include one or more linker or tag sequences. The tag sequence can encode a hemagglutinin (HA) tag.

(1) Heavy Chain Polypeptide

The recombinant nucleic acid sequence construct can include the heterologous nucleic acid encoding the heavy chain polypeptide, a fragment thereof, a variant thereof, or a combination thereof. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

In one embodiment, the amino acid sequence of CDR1, CDR2, and CDR3 of the heavy chain polypeptide each independently comprise an amino acid sequence at least 90% homologous to one of SEQ ID NO:29-64. In one embodiment. the amino acid sequence of CDR1, CDR2, and CDR3 of the heavy chain polypeptide each independently comprise a comprises an amino acid sequence set forth in one of SEQ ID NO:29-64.

(2) Light Chain Polypeptide

The recombinant nucleic acid sequence construct can include the heterologous nucleic acid sequence encoding the light chain polypeptide, a fragment thereof, a variant thereof, or a combination thereof. The light chain polypeptide can include a variable light chain (VL) region and/or a constant light chain (CL) region.

The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

In one embodiment, the amino acid sequence of CDR1, CDR2, and CDR3 of the light chain polypeptide each independently comprise an amino acid sequence at least 90% homologous to one of SEQ ID NO:65-100. In one embodiment. the amino acid sequence of CDR1, CDR2, and CDR3 of the light chain polypeptide each independently comprise a comprises an amino acid sequence set forth in one of SEQ ID NO: 65-100.

(3) Protease Cleavage Site

The recombinant nucleic acid sequence construct can include heterologous nucleic acid sequence encoding a protease cleavage site. The protease cleavage site can be recognized by a protease or peptidase. The protease can be an endopeptidase or endoprotease, for example, but not limited to, furin, elastase, HtrA, calpain, trypsin, chymotrypsin, trypsin, and pepsin. The protease can be furin. In other embodiments, the protease can be a serine protease, a threonine protease, cysteine protease, aspartate protease, metalloprotease, glutamic acid protease, or any protease that cleaves an internal peptide bond (i.e., does not cleave the N-terminal or C-terminal peptide bond).

The protease cleavage site can include one or more amino acid sequences that promote or increase the efficiency of cleavage. The one or more amino acid sequences can promote or increase the efficiency of forming or generating discrete polypeptides. The one or more amino acids sequences can include a 2A peptide sequence.

(4) Linker Sequence

The recombinant nucleic acid sequence construct can include one or more linker sequences. The linker sequence can spatially separate or link the one or more components described herein. In other embodiments, the linker sequence can encode an amino acid sequence that spatially separates or links two or more polypeptides.

(5) Promoter

The recombinant nucleic acid sequence construct can include one or more promoters. The one or more promoters may be any promoter that is capable of driving gene expression and regulating gene expression. Such a promoter is a cis-acting sequence element required for transcription via a DNA dependent RNA polymerase. Selection of the promoter used to direct gene expression depends on the particular application. The promoter may be positioned about the same distance from the transcription start in the recombinant nucleic acid sequence construct as it is from the transcription start site in its natural setting. However, variation in this distance may be accommodated without loss of promoter function.

The promoter may be operably linked to the heterologous nucleic acid sequence encoding the heavy chain polypeptide and/or light chain polypeptide. The promoter may be a promoter shown effective for expression in eukaryotic cells.

The promoter operably linked to the coding sequence may be a CMV promoter, a promoter from simian virus 40 (SV40), such as SV40 early promoter and SV40 later promoter, a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, human polyhedrin, or human metalothionein.

The promoter can be a constitutive promoter or an inducible promoter, which initiates transcription only when the host cell is exposed to some particular external stimulus. In the case of a multicellular organism, the promoter can also be specific to a particular tissue or organ or stage of development. The promoter may also be a tissue specific promoter, such as a muscle or skin specific promoter, natural or synthetic. Examples of such promoters are described in US patent application publication no. US20040175727, the contents of which are incorporated herein in its entirety.

The promoter can be associated with an enhancer. The enhancer can be located upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

(6) Intron

The recombinant nucleic acid sequence construct can include one or more introns. Each intron can include functional splice donor and acceptor sites. The intron can include an enhancer of splicing. The intron can include one or more signals required for efficient splicing.

(7) Transcription Termination Region

The recombinant nucleic acid sequence construct can include one or more transcription termination regions. The transcription termination region can be downstream of the coding sequence to provide for efficient termination. The transcription termination region can be obtained from the same gene as the promoter described above or can be obtained from one or more different genes.

(8) Initiation Codon

The recombinant nucleic acid sequence construct can include one or more initiation codons. The initiation codon can be located upstream of the coding sequence. The initiation codon can be in frame with the coding sequence. The initiation codon can be associated with one or more signals required for efficient translation initiation, for example, but not limited to, a ribosome binding site.

(9) Termination Codon

The recombinant nucleic acid sequence construct can include one or more termination or stop codons. The termination codon can be downstream of the coding sequence. The termination codon can be in frame with the coding sequence. The termination codon can be associated with one or more signals required for efficient translation termination.

(10) Polyadenylation Signal

The recombinant nucleic acid sequence construct can include one or more polyadenylation signals. The polyadenylation signal can include one or more signals required for efficient polyadenylation of the transcript. The polyadenylation signal can be positioned downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, CA).

(11) Leader Sequence

The recombinant nucleic acid sequence construct can include one or more leader sequences. The leader sequence can encode a signal peptide. The signal peptide can be an immunoglobulin (Ig) signal peptide, for example, but not limited to, an IgG signal peptide and a IgE signal peptide. Arrangement of the DMAb Recombinant Nucleic Acid Sequence Construct As described above, the recombinant nucleic acid sequence encoding a synthetic antibody can include one or more recombinant nucleic acid sequence constructs, in which each recombinant nucleic acid sequence construct can include one or more components. The one or more components are described in detail above. The one or more components, when included in the recombinant nucleic acid sequence construct, can be arranged in any order relative to one another. In some embodiments, the one or more components can be arranged in the recombinant nucleic acid sequence construct as described below.

(12) Arrangement 1

In one arrangement, a first recombinant nucleic acid sequence construct can include the heterologous nucleic acid sequence encoding the heavy chain polypeptide and a second recombinant nucleic acid sequence construct can include the heterologous nucleic acid sequence encoding the light chain polypeptide. For example, in one embodiment, the first recombinant nucleic acid sequence encodes a heavy chain polypeptide having an amino acid sequence at least 90% homologous to one of SEQ ID NOs: 5-16. In one embodiment, the second recombinant nucleic acid sequence encodes a light chain polypeptide having an amino acid sequence at least 95% homologous to one of SEQ ID NOs: 17-28.

The first recombinant nucleic acid sequence construct can be placed in a vector. The second recombinant nucleic acid sequence construct can be placed in a second or separate vector. Placement of the recombinant nucleic acid sequence construct into the vector is described in more detail below.

The first recombinant nucleic acid sequence construct can also include the promoter, intron, transcription termination region, initiation codon, termination codon, and/or polyadenylation signal. The first recombinant nucleic acid sequence construct can further include the leader sequence, in which the leader sequence is located upstream (or 5') of the heterologous nucleic acid sequence encoding the heavy chain polypeptide. Accordingly, the signal peptide encoded by the leader sequence can be linked by a peptide bond to the heavy chain polypeptide.

The second recombinant nucleic acid sequence construct can also include the promoter, initiation codon, termination codon, and polyadenylation signal. The second recombinant nucleic acid sequence construct can further include the leader sequence, in which the leader sequence is located upstream (or 5') of the heterologous nucleic acid sequence encoding the light chain polypeptide. Accordingly, the signal peptide encoded by the leader sequence can be linked by a peptide bond to the light chain polypeptide.

Accordingly, one example of arrangement 1 can include the first vector (and thus first recombinant nucleic acid sequence construct) encoding the heavy chain polypeptide that includes VH and CH1, and the second vector (and thus second recombinant nucleic acid sequence construct) encoding the light chain polypeptide that includes VL and CL. A second example of arrangement 1 can include the first vector (and thus first recombinant nucleic acid sequence construct) encoding the heavy chain polypeptide that includes VH, CH1, hinge region, CH2, and CH3, and the second vector (and thus second recombinant nucleic acid sequence construct) encoding the light chain polypeptide that includes VL and CL.

(13) Arrangement 2

In a second arrangement, the recombinant nucleic acid sequence construct can include the heterologous nucleic acid sequence encoding the heavy chain polypeptide and the heterologous nucleic acid sequence encoding the light chain polypeptide. The heterologous nucleic acid sequence encoding the heavy chain polypeptide can be positioned upstream (or 5') of the heterologous nucleic acid sequence encoding the light chain polypeptide. Alternatively, the heterologous nucleic acid sequence encoding the light chain polypeptide can be positioned upstream (or 5') of the heterologous nucleic acid sequence encoding the heavy chain polypeptide.

The recombinant nucleic acid sequence construct can be placed in the vector as described in more detail below.

The recombinant nucleic acid sequence construct can include the heterologous nucleic acid sequence encoding the protease cleavage site and/or the linker sequence. If included in the recombinant nucleic acid sequence construct, the heterologous nucleic acid sequence encoding the protease cleavage site can be positioned between the heterologous nucleic acid sequence encoding the heavy chain polypeptide and the heterologous nucleic acid sequence encoding the light chain polypeptide. Accordingly, the protease cleavage site allows for separation of the heavy chain polypeptide and the light chain polypeptide into distinct polypeptides upon expression. In other embodiments, if the linker sequence is included in the recombinant nucleic acid sequence construct, then the linker sequence can be positioned between the heterologous nucleic acid sequence encoding the heavy chain polypeptide and the heterologous nucleic acid sequence encoding the light chain polypeptide.

The recombinant nucleic acid sequence construct can also include the promoter, intron, transcription termination region, initiation codon, termination codon, and/or polyadenylation signal. The recombinant nucleic acid sequence construct can include one or more promoters. The recombinant nucleic acid sequence construct can include two promoters such that one promoter can be associated with the heterologous nucleic acid sequence encoding the heavy chain polypeptide and the second promoter can be associated with the heterologous nucleic acid sequence encoding the light chain polypeptide. In still other embodiments, the recombinant nucleic acid sequence construct can include one promoter that is associated with the heterologous nucleic acid sequence encoding the heavy chain polypeptide and the heterologous nucleic acid sequence encoding the light chain polypeptide.

The recombinant nucleic acid sequence construct can further include two leader sequences, in which a first leader sequence is located upstream (or 5') of the heterologous nucleic acid sequence encoding the heavy chain polypeptide and a second leader sequence is located upstream (or 5') of the heterologous nucleic acid sequence encoding the light chain polypeptide. Accordingly, a first signal peptide encoded by the first leader sequence can be linked by a peptide bond to the heavy chain polypeptide and a second signal peptide encoded by the second leader sequence can be linked by a peptide bond to the light chain polypeptide.

Accordingly, one example of arrangement 2 can include the vector (and thus recombinant nucleic acid sequence construct) encoding the heavy chain polypeptide that includes VH and CH1, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A second example of arrangement of 2 can include the vector (and thus recombinant nucleic acid sequence construct) encoding the heavy chain polypeptide that includes VH and CH1, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

A third example of arrangement 2 can include the vector (and thus recombinant nucleic acid sequence construct) encoding the heavy chain polypeptide that includes VH, CH1, hinge region, CH2, and CH3, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A forth example of arrangement of 2 can include the vector (and thus recombinant nucleic acid sequence construct) encoding the heavy chain polypeptide that includes VH, CH1, hinge region, CH2, and CH3, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

Expression from the Recombinant Nucleic Acid Sequence Construct

As described above, the recombinant nucleic acid sequence construct can include, amongst the one or more components, the heterologous nucleic acid sequence encoding the heavy chain polypeptide and/or the heterologous nucleic acid sequence encoding the light chain polypeptide. Accordingly, the recombinant nucleic acid sequence construct can facilitate expression of the heavy chain polypeptide and/or the light chain polypeptide.

When arrangement 1 as described above is utilized, the first recombinant nucleic acid sequence construct can facilitate the expression of the heavy chain polypeptide and the second recombinant nucleic acid sequence construct can facilitate expression of the light chain polypeptide. When arrangement 2 as described above is utilized, the recombinant nucleic acid sequence construct can facilitate the expression of the heavy chain polypeptide and the light chain polypeptide.

Upon expression, for example, but not limited to, in a cell, organism, or mammal, the heavy chain polypeptide and the light chain polypeptide can assemble into the synthetic antibody. In particular, the heavy chain polypeptide and the light chain polypeptide can interact with one another such that assembly results in the synthetic antibody being capable of binding the antigen. In other embodiments, the heavy chain polypeptide and the light chain polypeptide can interact with one another such that assembly results in the synthetic antibody being more immunogenic as compared to an antibody not assembled as described herein. In still other embodiments, the heavy chain polypeptide and the light chain polypeptide can interact with one another such that assembly results in the synthetic antibody being capable of eliciting or inducing an immune response against the antigen.

Vector

The recombinant nucleic acid sequence construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. In some embodiments, the vector includes linear DNA, enzymatic DNA or synthetic DNA. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The one or more vectors can be a heterologous expression construct, which is generally a plasmid that is used to introduce a specific gene into a target cell. Once the expression vector is inside the cell, the heavy chain polypeptide and/or light chain polypeptide that are encoded by the recombinant nucleic acid sequence construct is produced by the cellular-transcription and translation machinery ribosomal complexes. The one or more vectors can express large amounts of stable messenger RNA, and therefore proteins.

(14) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid sequence construct may be chimeric, meaning that at least one of its components is heterologous with respect to at least one of its other components.

(15) Plasmid

The one or more vectors can be a plasmid. The plasmid may be useful for transfecting cells with the recombinant nucleic acid sequence construct. The plasmid may be useful for introducing the recombinant nucleic acid sequence construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, CA), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif), which may be used for protein production in *Escherichia coli* (*E. coli*). The plasmid may also be pYES2 (Invitrogen, San Diego, Calif.), which may be used for protein production in Saccharomyces cerevisiae strains of yeast. The plasmid may also be of the MAXBAC™ complete baculovirus expression system (Invitrogen, San Diego, Calif.), which may be used for protein production in insect cells. The plasmid may also be pcDNAI or pcDNA3 (Invitrogen, San Diego, Calif.), which may be used for protein production in mammalian cells such as Chinese hamster ovary (CHO) cells.

(16) RNA

In one embodiment, the nucleic acid is an RNA molecule. In one embodiment, the RNA molecule is transcribed from a DNA sequence described herein. For example, in some embodiments, the RNA molecule is encoded by a DNA sequence at least 90% homologous to one of SEQ ID NOs:2 and 4. In another embodiment, the nucleotide sequence comprises an RNA sequence transcribed by a DNA sequence encoding a polypeptide sequence at least 90% homologous to one of SEQ ID NOs:1, 3, and 5-28, or a variant thereof or a fragment thereof. Accordingly, in one embodiment, the invention provides an RNA molecule encoding one or more of the MAbs or DMAbs. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. A RNA molecule useful with the invention may comprise synthetic RNA. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

(17) Circular and Linear Vector

The one or more vectors may be circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid sequence construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid sequence construct. The LEC may be any linear DNA devoid of any phosphate backbone. The LEC may not contain any antibiotic resistance genes and/or a phosphate backbone. The LEC may not contain other nucleic acid sequences unrelated to the desired gene expression.

The LEC may be derived from any plasmid capable of being linearized. The plasmid may be capable of expressing the heavy chain polypeptide and/or light chain polypeptide encoded by the recombinant nucleic acid sequence construct. The plasmid can be pNP (Puerto Rico/34) or pM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleic acid sequence construct.

The LEC can be perM2. The LEC can be perNP. perNP and perMR can be derived from pNP (Puerto Rico/34) and pM2 (New Caledonia/99), respectively.

(18) Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

(19) Method of Preparing the Vector

Provided herein is a method for preparing the one or more vectors in which the recombinant nucleic acid sequence construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in a licensed, co-pending U.S. provisional application U.S. Ser. No. 60/939,792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

8. ANTIBODY

As described above, the recombinant nucleic acid sequence can encode the antibody, a fragment thereof, a variant thereof, or a combination thereof. The antibody can bind or react with the antigen, which is described in more detail below.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites. Accordingly, the antibody can be the Fab or F(ab')$_2$. The Fab can include the heavy chain polypeptide and the light chain polypeptide. The heavy chain polypeptide of the Fab can include the VH region and the CH1 region. The light chain of the Fab can include the VL region and CL region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

The antibody can be a bispecific antibody as described below in more detail. The antibody can be a bifunctional antibody as also described below in more detail.

As described above, the antibody can be generated in the subject upon administration of the composition to the subject. The antibody may have a half-life within the subject. In some embodiments, the antibody may be modified to extend or shorten its half-life within the subject. Such modifications are described below in more detail.

The antibody can be defucosylated as described in more detail below.

The antibody may be modified to reduce or prevent antibody-dependent enhancement (ADE) of disease associated with the antigen as described in more detail below.

Bispecific Antibody

The recombinant nucleic acid sequence can encode a bispecific antibody, a fragment thereof, a variant thereof, or a combination thereof. The bispecific antibody can bind or react with two antigens, for example, two of the antigens described below in more detail. The bispecific antibody can be comprised of fragments of two of the antibodies described herein, thereby allowing the bispecific antibody to bind or react with two desired target molecules, which may include the antigen, which is described below in more detail, a ligand, including a ligand for a receptor, a receptor, including a ligand-binding site on the receptor, a ligand-receptor complex, and a marker.

The invention provides novel bispecific antibodies comprising a first antigen-binding site that specifically binds to a first target and a second antigen-binding site that specifically binds to a second target, with particularly advantageous properties such as producibility, stability, binding affinity, biological activity, specific targeting of certain T cells, targeting efficiency and reduced toxicity. In some instances, there are bispecific antibodies, wherein the bispecific antibody binds to the first target with high affinity and to the second target with low affinity. In other instances, there are bispecific antibodies, wherein the bispecific antibody binds to the first target with low affinity and to the second target with high affinity. In other instances, there are bispecific antibodies, wherein the bispecific antibody binds to the first target with a desired affinity and to the second target with a desired affinity.

In one embodiment, the bispecific antibody is a bivalent antibody comprising a) a first light chain and a first heavy chain of an antibody specifically binding to a first antigen, and b) a second light chain and a second heavy chain of an antibody specifically binding to a second antigen.

A bispecific antibody molecule according to the invention may have two binding sites of any desired specificity. In some embodiments, one of the binding sites is capable of binding a tumor associated antigen. In some embodiments, the binding site included in the Fab fragment is a binding site specific for a MAYV antigen. In some embodiments, the binding site included in the single chain Fv fragment is a binding site specific for a MAYV antigen such as a MAYV capsid antigen or a MAYV envelope antigen, for example MAYV-E1, MAYV-E2, MAYV-E3, or MAYV-6K.

In some embodiments, one of the binding sites of an antibody molecule according to the invention is able to bind a T-cell specific receptor molecule and/or a natural killer cell (NK cell) specific receptor molecule. A T-cell specific receptor is the so called "T-cell receptor" (TCRs), which allows a T cell to bind to and, if additional signals are present, to be activated by and respond to an epitope/antigen presented by another cell called the antigen-presenting cell or APC. The T cell receptor is known to resemble a Fab fragment of a naturally occurring immunoglobulin. It is generally monovalent, encompassing .alpha.- and .beta.-chains, in some embodiments, it encompasses .gamma.-chains and .delta.-chains (supra). Accordingly, in some embodiments, the TCR is TCR (alpha/beta) and in some embodiments, it is TCR (gamma/delta). The T cell receptor forms a complex with the CD3 T-Cell co-receptor. CD3 is a protein complex and is composed of four distinct chains. In mammals, the complex contains a CD3γ chain, a CD3δ chain, and two CD3ε chains. These chains associate with a molecule known as the T cell receptor (TCR) and the ζ-chain to generate an activation signal in T lymphocytes. Hence, in some embodiments, a T-cell specific receptor is the CD3 T-Cell co-receptor. In some embodiments, a T-cell specific receptor is CD28, a protein that is also expressed on T cells. CD28 can provide co-stimulatory signals, which are required for T cell activation. CD28 plays important roles in T-cell proliferation and survival, cytokine production, and T-helper type-2 development. Yet a further example of a T-cell specific receptor is CD134, also termed Ox40. CD134/OX40 is being expressed after 24 to 72 hours following activation and can be taken to define a secondary costimulatory molecule. Another example of a T-cell receptor is 4-1 BB capable of binding to 4-1 BB-Ligand on antigen presenting cells (APCs), whereby a costimulatory signal for the T cell is generated. Another example of a receptor predominantly found on T-cells is CD5, which is also found on B cells at low levels. A further example of a receptor modifying T cell functions is CD95, also known as the Fas receptor, which mediates apoptotic signaling by Fas-ligand expressed on the surface of other cells. CD95 has been reported to modulate TCR/CD3-driven signaling pathways in resting T lymphocytes.

An example of a NK cell specific receptor molecule is CD16, a low affinity Fc receptor and NKG2D. An example of a receptor molecule that is present on the surface of both T cells and natural killer (NK) cells is CD2 and further members of the CD2-superfamily. CD2 is able to act as a co-stimulatory molecule on T and NK cells.

In some embodiments, the first binding site of the antibody molecule binds a MAYV antigen and the second binding site binds a T cell specific receptor molecule and/or a natural killer (NK) cell specific receptor molecule.

In some embodiments, the first binding site of the antibody molecule binds one of MAYV-capsid, MAYV-E1, MAYV-E1, MAYV-E2, MAYV-E3, or MAYV-6K or a polyprotein comprising any combination thereof, and the second binding site binds a T cell specific receptor molecule and/or a natural killer (NK) cell specific receptor molecule. In some embodiments, the first binding site of the antibody molecule binds a MAYV antigen and the second binding site binds one of CD3, the T cell receptor (TCR), CD28, CD16, NKG2D, Ox40, 4-1BB, CD2, CD5 and CD95.

In some embodiments, the first binding site of the antibody molecule binds a T cell specific receptor molecule and/or a natural killer (NK) cell specific receptor molecule and the second binding site binds a MAYV antigen. In some embodiments, the first binding site of the antibody binds a T cell specific receptor molecule and/or a natural killer (NK) cell specific receptor molecule and the second binding site binds one of MAYV-capsid, MAYV-E1, MAYV-E1, MAYV-E2, MAYV-E3, or MAYV-6K or a polyprotein comprising any combination thereof. In some embodiments, the first binding site of the antibody binds one of CD3, the T cell receptor (TCR), CD28, CD16, NKG2D, Ox40, 4-1BB, CD2, CD5 and CD95, and the second binding site binds a MAYV antigen.

Bifunctional Antibody

The recombinant nucleic acid sequence can encode a bifunctional antibody, a fragment thereof, a variant thereof, or a combination thereof. The bifunctional antibody can bind or react with the antigen described below. The bifunctional antibody can also be modified to impart an additional functionality to the antibody beyond recognition of and binding to the antigen. Such a modification can include, but is not limited to, coupling to factor H or a fragment thereof. Factor H is a soluble regulator of complement activation and thus, may contribute to an immune response via complement-mediated lysis (CML).

Extension of Antibody Half-Life

As described above, the antibody may be modified to extend or shorten the half-life of the antibody in the subject. The modification may extend or shorten the half-life of the antibody in the serum of the subject.

The modification may be present in a constant region of the antibody. The modification may be one or more amino acid substitutions in a constant region of the antibody that extend the half-life of the antibody as compared to a half-life of an antibody not containing the one or more amino acid substitutions. The modification may be one or more amino acid substitutions in the CH2 domain of the antibody that extend the half-life of the antibody as compared to a half-life of an antibody not containing the one or more amino acid substitutions.

In some embodiments, the one or more amino acid substitutions in the constant region may include replacing a methionine residue in the constant region with a tyrosine residue, a serine residue in the constant region with a threonine residue, a threonine residue in the constant region with a glutamate residue, or any combination thereof, thereby extending the half-life of the antibody.

In other embodiments, the one or more amino acid substitutions in the constant region may include replacing a methionine residue in the CH2 domain with a tyrosine residue, a serine residue in the CH2 domain with a threonine residue, a threonine residue in the CH2 domain with a glutamate residue, or any combination thereof, thereby extending the half-life of the antibody.

Defucosylation

The recombinant nucleic acid sequence can encode an antibody that is not fucosylated (i.e., a defucosylated antibody or a non-fucosylated antibody), a fragment thereof, a variant thereof, or a combination thereof. Fucosylation includes the addition of the sugar fucose to a molecule, for example, the attachment of fucose to N-glycans, O-glycans and glycolipids. Accordingly, in a defucosylated antibody, fucose is not attached to the carbohydrate chains of the constant region. In turn, this lack of fucosylation may improve FcγRIIIa binding and antibody directed cellular cytotoxic (ADCC) activity by the antibody as compared to the fucosylated antibody. Therefore, in some embodiments, the non-fucosylated antibody may exhibit increased ADCC activity as compared to the fucosylated antibody.

The antibody may be modified so as to prevent or inhibit fucosylation of the antibody. In some embodiments, such a modified antibody may exhibit increased ADCC activity as compared to the unmodified antibody. The modification may be in the heavy chain, light chain, or a combination thereof. The modification may be one or more amino acid substitutions in the heavy chain, one or more amino acid substitutions in the light chain, or a combination thereof.

Reduced ADE Response

The antibody may be modified to reduce or prevent antibody-dependent enhancement (ADE) of disease associated with the antigen, but still neutralize the antigen.

In some embodiments, the antibody may be modified to include one or more amino acid substitutions that reduce or prevent binding of the antibody to FcγR1a. The one or more amino acid substitutions may be in the constant region of the antibody. The one or more amino acid substitutions may include replacing a leucine residue with an alanine residue in the constant region of the antibody, i.e., also known herein as LA, LA mutation or LA substitution. The one or more amino acid substitutions may include replacing two leucine residues, each with an alanine residue, in the constant region of the antibody and also known herein as LALA, LALA mutation, or LALA substitution. The presence of the LALA substitutions may prevent or block the antibody from binding to FcγR1a, and thus, the modified antibody does not enhance or cause ADE of disease associated with the antigen, but still neutralizes the antigen.

Monoclonal Antibodies

In one embodiment, the invention provides anti-MAYV antibodies. The antibodies may be intact monoclonal antibodies, and immunologically active fragments (e.g., a Fab or (Fab)₂ fragment), a monoclonal antibody heavy chain, or a monoclonal antibody light chain.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

In one embodiment, the anti-MAYV antibody comprises a heavy chain comprising an amino acid sequence at least 90% homologous to one of SEQ ID NO:5-16, or a fragment thereof. In one embodiment, the anti-MAYV antibody comprises a heavy chain comprising an amino acid sequence set forth in one of SEQ ID NO:5-16, or a fragment thereof.

In one embodiment, the anti-MAYV antibody comprises a heavy chain comprising 3 CDRs wherein each CDR independently comprises an amino acid sequence at least 90% homologous to one of SEQ ID NO:29-64. In one embodiment, the anti-MAYV antibody comprises a heavy chain comprising 3 CDRs wherein each CDR independently comprises an amino acid sequence set forth in one of SEQ ID NO:29-64.

In one embodiment, the anti-MAYV antibody comprises a light chain comprising an amino acid sequence at least 90% homologous to one of SEQ ID NO:17-28, or a fragment thereof. In one embodiment, the anti-MAYV antibody comprises a light chain comprising an amino acid sequence set forth in one of SEQ ID NO:17-28, or a fragment thereof.

In one embodiment, the anti-MAYV antibody comprises a light chain comprising 3 CDRs wherein each CDR independently comprises an amino acid sequence at least 90% homologous to one of SEQ ID NO:65-100. In one embodiment, the anti-MAYV antibody comprises a light chain comprising 3 CDRs wherein each CDR independently comprises an amino acid sequence set forth in one of SEQ ID NO:65-100.

In one embodiment, the anti-MAYV antibody comprises an amino acid sequence at least 90% homologous to one of SEQ ID NO:1 and 3, or a fragment thereof. In one embodiment, the anti-MAYV antibody comprises an amino acid sequence set forth in one of SEQ ID NO:1 and 3, or a fragment thereof.

9. ANTIGEN

The synthetic antibody is directed to the antigen or fragment or variant thereof. The antigen can be a nucleic acid sequence, an amino acid sequence, a polysaccharide or a combination thereof. The nucleic acid sequence can be DNA, RNA, cDNA, a variant thereof, a fragment thereof, or a combination thereof. The amino acid sequence can be a protein, a peptide, a variant thereof, a fragment thereof, or a combination thereof. The polysaccharide can be a nucleic acid encoded polysaccharide.

The antigen can be from a virus. The antigen can be associated with viral infection. In one embodiment, the antigen can be associated with Mayaro virus infection. In one embodiment, the antigen can be a Mayaro Capsid protein or a Mayaro envelope protein. In one embodiment, the Mayaro envelope protein can include Mayaro-E1, E2, E3, or 6K.

In one embodiment, the antigen can be a fragment of a Mayaro Capsid protein or a Mayaro envelope protein. For example, in one embodiment, the antigen is a fragment of a Mayaro Capsid, wherein the fragment comprises the amino acid sequence EGHYNWHYGAVQYTG (SEQ ID NO:101). In one embodiment, the antigen is a fragment of a Mayaro Envelope protein, wherein the fragment comprises the amino acid sequence GRSVIHFSTASAAPS (SEQ ID NO: 102) or LAKCPPGEVISVSFV (SEQ ID NO: 103)

In one embodiment, a synthetic antibody of the invention targets two or more antigens. In one embodiment, at least one antigen of a bispecific antibody is selected from the antigens described herein. In one embodiment, the two or more antigens are selected from the antigens described herein.

Viral Antigens

The viral antigen can be a viral antigen or fragment or variant thereof. The virus can be a disease-causing virus. The virus can be a Mayaro virus.

The antigen may be a Mayaro viral antigen, or fragment thereof, or variant thereof. The Mayaro antigen can be from a factor that allows the virus to replicate, infect or survive. Factors that allow a Mayaro virus to replicate or survive include, but are not limited to structural proteins and non-structural proteins. Such a protein can be an envelope protein or a capsid protein. In one embodiment, a capsid protein is Mayaro Capsid. In one embodiment, an envelope protein is Mayaro E1, E2, E3, 6K or a polyprotein comprising any combination thereof.

10. EXCIPIENTS AND OTHER COMPONENTS OF THE COMPOSITION

The composition may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the composition. The composition may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The composition may further comprise a genetic facilitator agent as described in U.S. Ser. No. 021,579 filed Apr. 1, 1994, which is fully incorporated by reference.

The composition may comprise DNA at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, composition according to the present invention comprises about 5 nanogram to about 1000 micrograms of DNA. In some preferred embodiments, composition can contain about 10 nanograms to about 800 micrograms of DNA. In some preferred embodiments, the composition can contain about 0.1 to about 500 micrograms of DNA. In some preferred embodiments, the composition can contain about 1 to about 350 micrograms of DNA. In some preferred embodiments, the composition can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of DNA.

The composition can be formulated according to the mode of administration to be used. An injectable pharmaceutical composition can be sterile, pyrogen free and particulate free. An isotonic formulation or solution can be used. Additives for isotonicity can include sodium chloride, dextrose, mannitol, sorbitol, and lactose. The composition can comprise a vasoconstriction agent. The isotonic solutions can include phosphate buffered saline. The composition can further comprise stabilizers including gelatin and albumin. The stabilizers can allow the formulation to be stable at room or ambient temperature for extended periods of time, including LGS or polycations or polyanions.

11. METHOD OF GENERATING THE SYNTHETIC ANTIBODY

The present invention also relates a method of generating the synthetic antibody. The method can include administering the composition to the subject in need thereof by using the method of delivery described in more detail below. Accordingly, the synthetic antibody is generated in the subject or in vivo upon administration of the composition to the subject.

The method can also include introducing the composition into one or more cells, and therefore, the synthetic antibody can be generated or produced in the one or more cells. The method can further include introducing the composition into one or more tissues, for example, but not limited to, skin and muscle, and therefore, the synthetic antibody can be generated or produced in the one or more tissues.

12. METHOD OF IDENTIFYING OR SCREENING FOR THE ANTIBODY

The present invention further relates to a method of identifying or screening for the antibody described above, which is reactive to or binds the antigen described above. The method of identifying or screening for the antibody can use the antigen in methodologies known in those skilled in art to identify or screen for the antibody. Such methodologies can include, but are not limited to, selection of the antibody from a library (e.g., phage display) and immunization of an animal followed by isolation and/or purification of the antibody.

13. METHOD OF DELIVERY OF THE COMPOSITION

The present invention also relates to a method of delivering the composition to the subject in need thereof. The method of delivery can include, administering the composition to the subject. Administration can include, but is not limited to, DNA injection with and without in vivo electroporation, liposome mediated delivery, and nanoparticle facilitated delivery.

The mammal receiving delivery of the composition may be human, primate, non-human primate, cow, cattle, sheep, goat, antelope, bison, water buffalo, bison, bovids, deer, hedgehogs, elephants, llama, alpaca, mice, rats, and chicken.

The composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal, intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The composition may be administered by traditional syringes, needleless injection devices, "microprojectile bombardment gone guns", or other physical methods such as electroporation ("EP"), "hydrodynamic method", or ultrasound.

Electroporation

Administration of the composition via electroporation may be accomplished using electroporation devices that can be configured to deliver to a desired tissue of a mammal, a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, PA) or Elgen electroporator (Inovio Pharmaceuticals, Plymouth Meeting, PA) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the composition of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the composition include those provided in co-pending and co-owned U.S. patent application, Ser. No. 11/874,072, filed Oct. 17, 2007, which claims the benefit under 35 USC 119(e) to U.S. Provisional Application Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments, that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

14. METHOD OF TREATMENT

Also provided herein is a method of treating, protecting against, and/or preventing a MAYV infection or MAYV disease in a subject in need thereof by administering one or more compositions described herein. In one embodiment, the methods comprise administering one or more DMAb constructs such that a synthetic anti-MAYV antibody is generated in the subject. In one embodiment, the methods comprise administering one or more genetic constructs and proteins of the one or more MAYV antigens such that secreted proteins, or synthetic antigens, will be recognized as foreign by the immune system, which will mount an immune response that can include antibodies made against the one or more MAYV antigens. In one embodiment, the methods comprise administering one or more DMAb constructs and one or more genetic constructs and proteins of the one or more MAYV antigens. In one embodiment, administering a MAYV DMAb and a nucleic acid encoding a MAYV antigen provides an immediate, persistent and systemic anti-MAYV immune response. The method can include administering the composition to the subject. Administration of the composition to the subject can be done using the method of delivery described above.

In certain embodiments, the invention provides a method of treating protecting against, and/or preventing a Mayaro Virus infection. In one embodiment, the method treats, protects against, and/or prevents a disease associated with Mayaro Virus.

Upon generation of the synthetic antibody in the subject, the synthetic antibody can bind to or react with the antigen. Such binding can neutralize the antigen, block recognition of the antigen by another molecule, for example, a protein or nucleic acid, and elicit or induce an immune response to the antigen, thereby treating, protecting against, and/or preventing the disease associated with the antigen in the subject.

The method of delivering the vaccine or vaccination may be provided to induce a therapeutic and prophylactic immune response. The vaccination process may generate in the mammal an immune response against the antigen. The vaccine may be delivered to an individual to modulate the activity of the mammal's immune system and enhance the immune response. The delivery of the vaccine may be the transfection of the consensus antigen as a nucleic acid molecule that is expressed in the cell and delivered to the surface of the cell upon which the immune system recognized and induces a cellular, humoral, or cellular and humoral response. The delivery of the vaccine may be used to induce or elicit and immune response in mammals against the antigen by administering to the mammals the vaccine as discussed above.

The composition dose can be between 1 μg to 10 mg active component/kg body weight/time, and can be 20 μg to 10 mg component/kg body weight/time. The composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of composition doses for effective treatment can be 1, 2, 3, 4, 5, 6, 7, 8, 9, or 10.

The composition can comprise 1 or more, 2 or more, 3 or more, 4 or more, 5 or more, 6 or more, 7 or more, 8 or more, 9 or more, or 10 or more DNA vaccines encoding an antigen. The composition may comprise 1 or more, 2 or more, 3 or more, 4 or more, 5 or more, 6 or more, 7 or more, 8 or more, 9 or more, or 10 or more DNA encoded synthetic antibodies or fragments thereof.

The DNA vaccine and the DMAb may be administered at the same time or at different times. In one embodiment, the DNA vaccine and the DMAb are administered simultaneously. In one embodiment, the DNA vaccine is administered before the DMAb. In one embodiment, the DMAb is administered before the DNA vaccine.

In certain embodiments, the DNA vaccine is administered 1 or more days, 2 or more days, 3 or more days, 4 or more days, 5 or more days, 6 or more days, 7 or more days, 8 or more days, 9 or more days, 10 or more days, 11 or more days, 12 or more days, 13 or more days, or 14 or more days after the DMAb is administered. In certain embodiments, the DNA vaccine is administered 1 or more weeks, 2 or more weeks, 3 or more weeks, 4 or more weeks, 5 or more weeks, 6 or more weeks, 7 or more weeks, 8 or more weeks, 9 or more weeks, or 10 or more weeks after the DMAb is administered. In certain embodiments, the DNA vaccine is administered 1 or more months, 2 or more months, 3 or more months, 4 or more months, 5 or more months, 6 or more months, 7 or more months, 8 or more months, 9 or more months, 10 or more months, 11 or more months, or 12 or more months after the DMAb is administered.

In certain embodiments, the DMAb is administered 1 or more days, 2 or more days, 3 or more days, 4 or more days, 5 or more days, 6 or more days, 7 or more days, 8 or more days, 9 or more days, 10 or more days, 11 or more days, 12 or more days, 13 or more days, or 14 or more days after the DNA vaccine is administered. In certain embodiments, the DMAb is administered 1 or more weeks, 2 or more weeks, 3 or more weeks, 4 or more weeks, 5 or more weeks, 6 or more weeks, 7 or more weeks, 8 or more weeks, 9 or more weeks, or 10 or more weeks after the DNA vaccine is administered. In certain embodiments, the DMAb is administered 1 or more months, 2 or more months, 3 or more months, 4 or more months, 5 or more months, 6 or more months, 7 or more months, 8 or more months, 9 or more months, 10 or more months, 11 or more months, or 12 or more months after the DNA vaccine is administered.

In certain embodiments, the DMAb and DNA vaccine are administered once. In certain embodiments, the DMAb and/or the DNA vaccine are administered more than once. In certain embodiments, administration of the DMAb and DNA vaccine provides immediate, persistent, and systemic immune responses.

The composition dose can be between 1 μg to 10 mg active component/kg body weight/time, and can be 20 μg to 10 mg component/kg body weight/time. The composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of composition doses for effective treatment can be 1, 2, 3, 4, 5, 6, 7, 8, 9, or 10.

15. USE IN COMBINATION WITH ANTIBIOTICS

The present invention also provides a method of treating, protecting against, and/or preventing disease in a subject in need thereof by administering a combination of the synthetic antibody and a therapeutic antibiotic agent.

The synthetic antibody and an antibiotic agent may be administered using any suitable method such that a combination of the synthetic antibody and antibiotic agent are both present in the subject. In one embodiment, the method may comprise administration of a first composition comprising a synthetic antibody of the invention by any of the methods described in detail above and administration of a second composition comprising an antibiotic agent less than 1, less than 2, less than 3, less than 4, less than 5, less than 6, less than 7, less than 8, less than 9 or less than 10 days following administration of the synthetic antibody. In one embodiment, the method may comprise administration of a first composition comprising a synthetic antibody of the invention by any of the methods described in detail above and administration of a second composition comprising an antibiotic agent more than 1, more than 2, more than 3, more than 4, more than 5, more than 6, more than 7, more than 8, more than 9 or more than 10 days following administration of the synthetic antibody. In one embodiment, the method may comprise administration of a first composition comprising an antibiotic agent and administration of a second composition comprising a synthetic antibody of the invention by any of the methods described in detail above less than 1, less than 2, less than 3, less than 4, less than 5, less than 6, less than 7, less than 8, less than 9 or less than 10 days following administration of the antibiotic agent. In one embodiment, the method may comprise administration of a first composition comprising an antibiotic agent and administration of a second composition comprising a synthetic antibody of the invention by any of the methods described in detail above more than 1, more than 2, more than 3, more than 4, more than 5, more than 6, more than 7, more than 8, more than 9 or more than 10 days following administration of the antibiotic agent. In one embodiment, the method may comprise administration of a first composition comprising a synthetic antibody of the invention by any of the methods described in detail above and a second composition comprising an antibiotic agent concurrently. In one embodiment, the method may comprise administration of a first composition comprising a synthetic antibody of the invention by any of the methods described in detail above and a second composition comprising an antibiotic agent concurrently. In one embodiment, the method may comprise administration of a single composition comprising a synthetic antibody of the invention and an antibiotic agent.

Non-limiting examples of antibiotics that can be used in combination with the synthetic antibody of the invention include aminoglycosides (e.g., gentamicin, amikacin, tobramycin), quinolones (e.g., ciprofloxacin, levofloxacin), cephalosporins (e.g., ceftazidime, cefepime, cefoperazone, cefpirome, ceftobiprole), antipseudomonal penicillins: carboxypenicillins (e.g., carbenicillin and ticarcillin) and ureidopenicillins (e.g., mezlocillin, azlocillin, and piperacillin), carbapenems (e.g., meropenem, imipenem, doripenem), polymyxins (e.g., polymyxin B and colistin) and monobactams (e.g., aztreonam).

The present invention has multiple aspects, illustrated by the following non-limiting examples.

16. GENERATION OF ANTIGENS AND SYNTHETIC ANTIBODIES IN VITRO AND EX VIVO

In one embodiment, the MAYV antigen is generated in vitro or ex vivo. For example, in one embodiment, a nucleic acid encoding a MAYV antigen can be introduced and expressed in an in vitro or ex vivo cell. In one embodiment, the synthetic antibody is generated in vitro or ex vivo. For example, in one embodiment, a nucleic acid encoding a synthetic antibody can be introduced and expressed in an in vitro or ex vivo cell.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

17. EXAMPLES

The present invention is further illustrated in the following Examples. It should be understood that these Examples, while indicating preferred embodiments, of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

The data presented herein describes a scMAYV-E vaccine which encodes a synthetically designed, consensus full-length MAYV envelope antigen sequence. EP-enhanced delivery of scMAYV-E into immunocompetent mice induced high levels of cellular responses to multiple MAYV-E epitopes along with robust antibody responses that could neutralize MAYV infection in vitro. Immunization of interferon a/b receptor knockout mice (IFNAR$^{-/-}$; A129) with scMAYV-E protected the mice from morbidity and mortality following MAYV challenge, where the protection in this model was primarily due to vaccine-induced humoral responses. The robust immunogenicity of the scMAYV-E vaccine demonstrates that this vaccine as a viable means to halt the spread of this virus and protect individuals from MAYV disease.

Materials and methods are now described
Cell Culture

Human embryonic kidney 293T (HEK293T; ATCC-CLR-N268) and Vero CCL-81 (ATCC #CCL-81) (ATCC, Manassas, VA, USA) cells were cultured in D10 media: Dulbecco Modified Eagle's Medium (Invitrogen Life Science Technologies, San Diego, CA, USA) supplemented with 10% heat-inactivated fetal calf serum (FCS), 3 mM glutamine, 100 U/ml penicillin, and 100 U/ml streptomycin (Muthumani et al., 2016, NPJ Vaccines 1:16021). Mouse splenocytes were cultured in R10 media: (RPMI1640, Invitrogen Life Science Technologies, San Diego, CA, USA) supplemented with 10% heat-inactivated FCS, 3 mM glutamine, 100 U/ml penicillin, and 100 U/ml streptomycin. All cell types were cultured in incubators set to 37° C. and 5% $CO_2$.

MAYV Vaccine Construction and Expression

The synthetic MAYV vaccine DNA construct encodes a full-length MAYV envelope sequence. The consensus gene insert was computationally optimized for improved expression. The construct was synthesized commercially (Genscript, NJ, USA) and then sub-cloned into a modified pVax1 vaccine expression vector under the control of the cytomegalovirus immediate-early promoter.

HEK293T cells were plated in six-well plates at $6 \times 10^5$ cells/well and transfected 24 hours later with scMAYV-E and pVax1 empty vector control plasmids using GeneJammer transfection reagent according to the manufacturer's instructions. The transfection was carried out in Opti-MEM medium. The transfected supernatants and cell lysates were collected 48 hours post transfection, and antigen expression was confirmed by western blot analysis. Cells were washed with phosphate-buffered saline (PBS) and lysed with lysis buffer containing 50 mM HCl, 150 mM NaCl, 1% Nonidet P-40, 1% Triton X-100, 0.1% sodium dodecyl sulfate, and a cocktail of protease inhibitors on ice for 30 minutes with intermediate vortexing. After 10 minutes of centrifugation at 13,000 rpm, the supernatant was collected and analyzed by sodium dodecyl sulfate-12% polyacrylamide gel electrophoresis and transferred to a nitrocellulose membrane for immunoblotting with antisera (1:100 dilution) against scMAYV-E. Secondary antibodies coupled to horseradish peroxidase (HRP) were used at a dilution of 1:5,000. For Immunofluorescence analysis, cells were seeded on top of coverslips in a 6-well cell culture plate. After washing three times with PBS, the cells were incubated for an hour at 37° C. with a Fluorescein isothiocyanate (FITC)-conjugated goat anti-human IgG (Santa Cruz Biotechnology Inc., USA). The nucleus was stained with 4',6-diamidino-2-phenylindole (DAPI) at room temperature for 20 minutes. PBS washes were performed after each incubation step. The samples were subsequently mounted onto glass slides using Fluoroshield Mounting Medium (Abcam, USA) and were viewed under a confocal microscope (LSM710). The resulting images were analyzed using Zen software.

Animals & DNA Immunizations with Electroporation

Five- to eight-week old female C57BL/6 mice (The Jackson Laboratory, Bar Harbor, ME, USA) were housed and vaccinated in a light-cycled, temperature- and humidity-controlled animal facility. Four- to six-week old mice of C57BL/6 background deficient in the interferon-α/β receptors (IFNAR$^{-/-}$, A129) were purchased from The Jackson Laboratory (MMRRC Repository-The Jackson Laboratory, USA).

For DNA immunization, five- to eight-week-old female C57BL/6 mice and four- to six-week old IFNAR$^{-/-}$ mice of mixed sex were delivered 25 μg of DNA in a total volume of 30 μl of sterile water by a syringe into the anterior tibialis (TA) muscle. The same site is immediately electroporated by the CELLECTRA® adaptive constant current enhanced electroporation (EP) delivery device (Inovio Pharmaceuticals, PA, USA), where a three-pronged minimally invasive device is inserted 2 mm into the TA muscle. Each prong consists of 26-gauge, solid stainless-steel electrode, and triangulated square-wave pulses of 0.1 Amps are delivered at 52 msec/pulse twice with a 1 second delay at the insertion site. Blood was collected by the submandibular method preceding the DNA injection and EP procedure. All mice were anesthetized with 2-5% isoflurane (Phoenix, Clipper, MO, USA) during procedures. Each group received one, two, or three immunizations at 2-week intervals, and mice were euthanized one week following the last immunization.

Splenocyte Isolation and IFN-γ ELISpot Assay

Spleens were dissected and individually crushed with the use of a Stomacher device (Seward, UK). Splenocytes were strained with a 40 μm cell strainer (ThermoFisher, USA) and treated 5 minutes with Ammonium-Chloride-Potassium (ACK) lysis buffer (Quality Biologicals, MD, USA) to lyse red blood cells. The splenocytes were resuspended in R10 and used in the Mouse IFN-γ ELISpot PLUS assay (Mabtech, USA) according to the manufacturer's instructions. Briefly, $2 \times 10^5$ splenocytes from the scMAYV-E or pVax1 control immunized mice were added to each well and incubated for 18 hours at 37° C. in 5% $CO_2$, either in the presence of media alone (negative control), media with Cell Activation Cocktail (BioLegend, USA) containing premixed phorbol 12-myristate-13-acetate (PMA) and ionomycin (positive control), or media with peptide pools (1 μg/ml) consisting of linearly pooled 20 individual peptides that are 15-mers overlapping by 9 amino acids spanning the length of the MAYV envelope protein. Spots were formed by the addition of 5-bromo-4-chloro-3-indolyl-phosphate/nitro blue tetrazolium (BCIP/NBT) color development substrate (R&D Systems, USA). Spot forming units (SFU) were quantified by an automated ELISpot reader (CTL Limited, USA). The average number of SFU from the media alone wells was subtracted from each stimulated well, and the data was adjusted to SFU per $10^6$ splenocytes.

ELISA for Detection of Ag-Specific Antibody

MaxiSorp high-binding 96-well ELISA plates (ThermoFisher, USA) were coated with purified recombinant protein at a concentration of 0.5 μg/mL in coating buffer (0.012 M $Na_2CO_3$, 0.038 M NaHCO3, pH 9.6) at 4° C. overnight. Plates were washed 5 times with PBS buffer solution containing 0.01% Tween-20 (PBST) (ThermoFisher, USA), and blocked with 10% FBS in PBS at 37° C. for 1 hour. Serum samples were serially diluted (starting 1:50, dilution factor 3.16) in PBS containing 1% FBS, and 100 μl was added to each well. After incubation at 37° C. for 2 hours, the plates were washed 5 times with PBST and then incubated with HRP-labeled goat anti-mouse IgG (Sigma-Aldrich, USA), at 37° C. for 1 hour. After the final wash, 100 μl of fresh TMB Substrate (Sigma-Aldrich) was added per well and incubated for 10 minutes. The reaction was stopped by adding 50 μl of 2 M $H_2SO_4$, and the optical density of the plate was measured at 450 nm by Biotek ELISA plate reader (Biotek, USA). The antibody endpoint titer was defined as the highest dilution of a serum sample with OD values >(mean+3SD) of pVax1 vaccinated mice. Samples with a titer <50 were given an endpoint titer of 1. All assays were done in triplicate. For mouse IgG subtyping, Pierce™ Rapid Antibody Isotyping Kit (ThermoFisher, USA) was used with 1:100 dilution of pVax1 mouse sera or scMAYV-E immune sera from C57BL/6 background.

Flow Cytometry and Intracellular Cytokine Staining Assay $2\times10^6$ single-cell suspended mouse splenocytes were added per well to a U-bottom 96-well plate (ThermoFisher). Cells were stimulated for 5 hours at 37° C. in 5% $CO_2$, either in the presence of media alone (negative control), media with Cell Activation Cocktail (BioLegend) containing premixed PMA and ionomycin (positive control), or media with MAYV envelope peptides (1 μg/ml) spanning the length of the entire protein, where all of the samples contained a protein transport inhibitor cocktail (eBioscience, San Diego, CA, USA). Upon completed stimulation, the cells are washed with FACS buffer (PBS containing 0.1% sodium azide and 1% FBS). Cells were stained for the surface proteins using fluorochrome-conjugated antibodies per the manufacturer's instructions (BD Biosciences, San Diego, CA, USA). The cells were washed again with FACS buffer, then fixed and permeabilized using BD Cytofix/Cytoperm™ (BD Biosciences) per the manufacturer's protocol before the intracellular cytokines were stained using fluorchrome conjugated antibodies (BD Biosciences). The following antibodies were used for surface staining: LIVE/DEAD Fixable Violet Dead Cell stain kit (Invitrogen); CD19 (V450; clone 1D3; BD Biosciences); CD4 (FITC; clone RM4-5; eBioscience); CD8α (APC-Cy7; clone 53-6.7; BD Biosciences); CD44 (A700; clone IM7; BioLegend). For intracellular staining the following antibodies were used: IFN-γ (APC; clone XMG1.2; Biolegend); TNF-α (PE; clone MP6-XT22; eBioscience); $CD3_ε$ (PerCP/Cy5.5; clone 145-2C11; Biolegend); IL-2 (PeCy7; clone JES6-SH4; ebioscience). The LSRII flow cytometer was outfitted with the following lasers and bandpass filters: (i) violet (405 nm) −450/50, 525/50, 560/40, 585/42, 605/40, 660/40, 705/70, 780/60; (ii) blue (488 nm) −530/30, 695/40; (iii) green (532 nm) −575/25, 610/20, 660/20, 710/50, 780/60; and (iv) red (640 nm) −670/30, 710/50, 780/60. All data was collected using an LSRII flow cytometer (BD Biosciences) and analyzed using FlowJo software (Tree Star, Ashland, OR, USA) and SPICE v5. Boolean gating was performed using FlowJo software to examine the polyfunctionality of the T cells from vaccinated animals.

Mayaro Viral Challenge Experiments in $IFNAR^{-/-}$ Mice

The Trinidad Regional Virus Laboratory (TRVL) 15537 strain of MAYV was obtained from ATCC® (ATCC® VR-1863TM), passaged once through cell culture, and quantified as previously described (Weise et al., 2014, PLoS Negl Trop Dis 8(8):e2969; Santiago et al., PLoS Negl Trop Dis 9(10):e0004104). One week after the second immunization, 10 mice from either scMAYV-E vaccinated or pVax1 vaccinated groups were challenged with $10^2$ plaque-forming units (PFU) of MAYV diluted in 100 μl of sterile PBS delivered by a gradual intraperitoneal (i.p.) inoculation. Mice were weighed daily and evaluated for clinical signs of infection as follows: (1) decreased mobility; (2) hunched posture; (3) footpad swelling; (4) decreased grip strength of the hindlimb; (5) paralysis of hindlimb(s); (6) moribund. The Wistar Institute IACUC does not approve death as an endpoint. Mice were euthanized if (1) weight loss was sustained for 3 days or more and total weight loss reaches 20% of the body weight, (2) mice exhibited 3 or more signs of clinical symptoms as listed above concurrently for over 3 days, or (3) mice were moribund. All mice that exhibited signs and symptoms of MAYV infection lasted no more than 7 days during the experiment(s). Whole blood was collected on day 6 post challenge for Mayaro viral titer quantification as described previously (Weise et al., 2014, PLoS Negl Trop Dis 8(8):e2969; Santiago et al., PLoS Negl Trop Dis 9(10):e0004104), and the footpad swelling of individual mouse was measured with a caliper on the same day. Eight days post challenge, the number of surviving mice was noted and humanely euthanized.

Passive Transfer of Immune Sera from Immunized $IFNAR^{-/-}$ to Naive $IFNAR^{-/-}$ Mice Four- to six-week old $IFNAR^{-/-}$ mice were immunized twice at a two-week interval. One week after the second immunization, immune sera were isolated from whole blood and combined into a single pool per group. Passive transfer of immune sera was performed by intraperitoneal (i.p.) injection at 200 μl per mouse into four- to six-week old naive IFNAR−/− mice. Mice receiving immune sera from the pVax1 immunized group or PBS served as negative controls. All groups were challenged with $10^2$ PFU of wild-type TRVL 15537 strain of MAYV and monitored daily.

Adoptive Transfer of Splenocytes from Immunized IFNAR$^{-/-}$ to Naive IFNAR$^{-/-}$ Mice Four- to six-week old IFNAR$^{-/-}$ mice were immunized twice at a two-week interval. One week after the second immunization, all mice were euthanized, and spleens were collected and processed as single-cell suspensions. The cell viability was examined by Trypan Blue dye exclusion staining using a Countess™ II Automated Cell Counter (ThermoFisher). Adoptive transfer was performed by i.p. inoculation ($2\times10^6$ cells/200 µl) into four- to six-week old naive IFNAR−/− mice. A group receiving splenocytes i.p. (200 µl) from the pVax1 immunized mice or PBS served as negative controls. All groups were challenged with $10^2$ PFU of wild-type TRVL 15537 strain of MAYV and monitored daily.

Neutralization Assay

PRNT assay was carried out to detect and quantify the presence of neutralizing antibodies in the immunized mouse serum samples (Muthumani et al., 2016, J Infect Dis 214 (3):369-78; Mallilankaraman et al., 2011, PLoS Negl Trop Dis 5(1):e298; Wang et al., 2011, J Virol 85(17):9249-52). Heat-inactivated (56° C., 30 minutes) immune sera were diluted serially and 150 µl of each diluted sample was mixed with an equal volume of $10^2$ PFU of wild-type TRVL 15537 strain of MAYV, followed by incubation at 37° C. for 1.5 hour for a virus-antibody neutralization reaction. 100 µl of the virus and serum mixture was then used to inoculate a monolayer of Vero cells in a 12-well plate followed by an incubation at 37° C. for 1.5 hour with rocking every 15 minutes. Next, the supernatant was removed from each well, and a layer of 2% methyl cellulose was added. After further incubation at 37° C. with 5% CO2 for 3 days, the cells were fixed, stained with Crystal Violet (ThermoFisher), and plaque numbers were recorded. MAYV alone without serum incubation served as negative control. After washing the stained cells with distilled water and air-drying the plates, the number of foci per well were counted using a stereomicroscope. The percentage of infectivity was calculated as: % reduction in infection={1−(number of plaques from serum samples/number of plaques from negative control)}×100.

Macrophage Infection of MAYV and Cell Viability Assay

Purified CD14$^+$ human monocytes were obtained. Human monocyte-derived macrophages (MDM; $1\times10^6$/well) were cultured in a 6-well plate in Macrophage Base Medium DXF (PromoCell GmbH, Germany) supplemented with 60 ng/mL of granulocyte-macrophage colony stimulating factor (GM-CSF) recombinant protein (R&D Systems, USA). The culture was incubated without disturbance at 37° C. with 5% $CO_2$ for 3 days. and MDMs were washed once with PBS prior to infection. Cells were infected with the multiplicity of infection (MOI) of 0.01 with TRVL 15537 strain of MAYV that was preincubated for 1 hour at 37° C. with either pVax1 immune sera or a 100-fold dilution of pooled day 35 immune sera from scMAYV-E vaccinated mice. The same media containing virus-pVax1 sera or virus scMAYV-E sera mixtures were added to washed MDMs in a 6-well plate that were then kept for 1 hour at 37° C. with a rocking interval of 15 minutes. The supernatant was removed following incubation, and Macrophage Base Medium DXF (Promo-Cell GmbH, Germany) was added to each well and further incubated at 37° C. with 5% $CO_2$ for 48 hours. Uninfected and infected macrophages were stained with Live Cell Labeling Kit-Green Fluorescence-Cytopainter (Abcam, Cambridge, MA, USA) according to the manufacturer's instructions. Stained macrophages were imaged on a microscope (EVOS Cell Imaging Systems; Life Technologies) and % live cells (i.e., Labeling Dye Green+) were assessed by visual inspection of images from six different reviewers assessing the inhibited infection relative to base-line by 90%. A monolayer of Vero CCL-81 cells plated on 12-well plates were inoculated with 200 µl of supernatants from MAYV-infected MDMs that were previously pre-incubated MAYV with either pVax1 or scMAYV-E sera. After 36 hours of incubation, viability of the Vero CCL-81 cells was examined by Trypan Blue dye exclusion staining using a Countess™ II Automated Cell Counter (ThermoFisher). The assays were done in triplicates, and each dot represents the cell viability from a single well+/−SEM. The experiment was repeated twice.

Statistical Analysis

All results are representative of those from at least two independent experiments with similar results. Graphs, standard curves, and pie charts were made using GraphPad Prism (version 4.0) software. $IC_{50}$ values were calculated using a non-linear regression of the reciprocal of the serum dilution compared to the control. The survival data for mouse experiments were graphed using Kaplan-Meier survival curves. Two-tailed p values were calculated by log-rank (Mantel-Cox) test for nonparametric data using Graph-Pad Prism (version 4.0) software.

The results are now described.

Synthetic Consensus Mayaro DNA Vaccine Development and Characterization

Figures 1B, 1C:
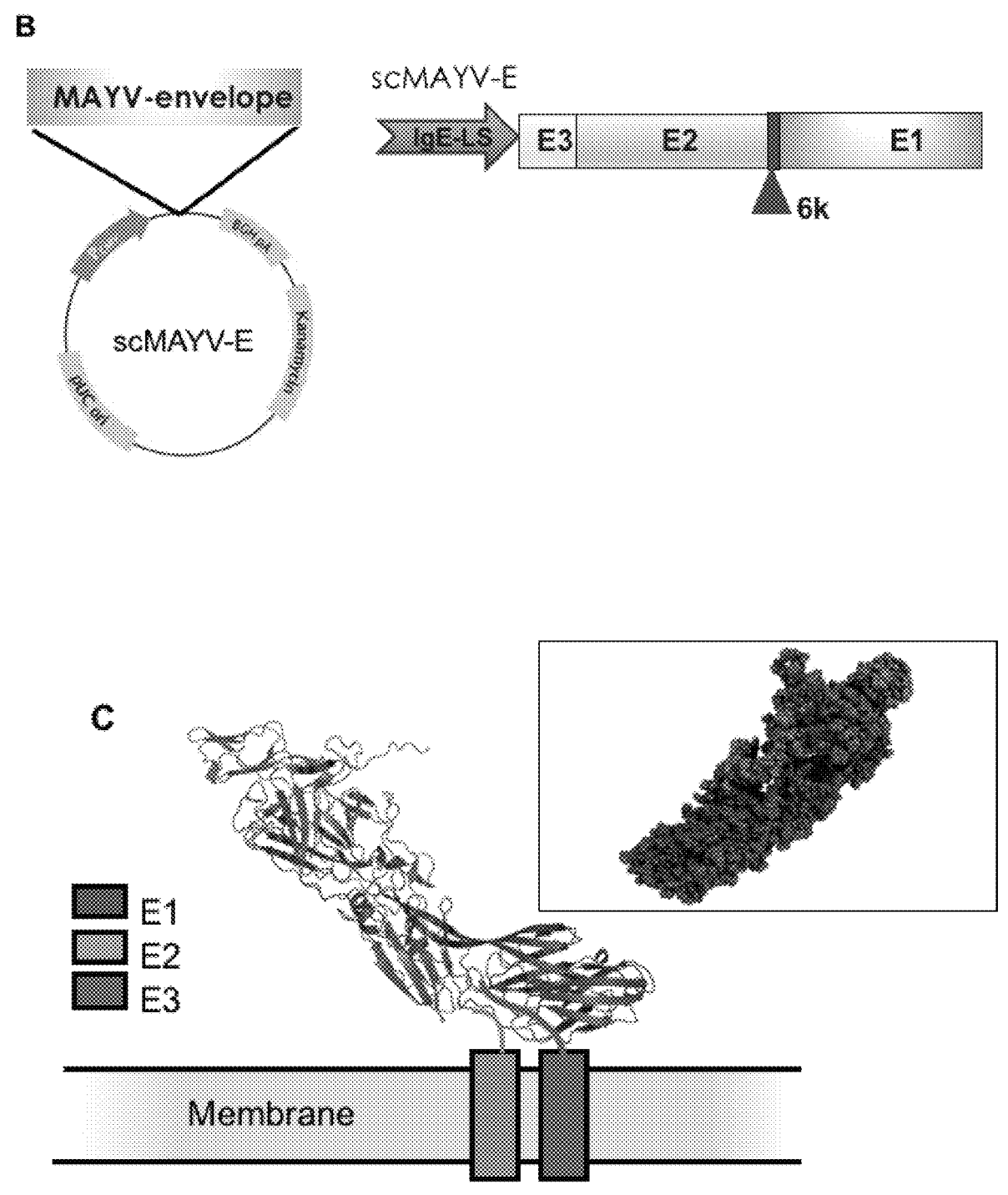
Figures 1D, 1E:
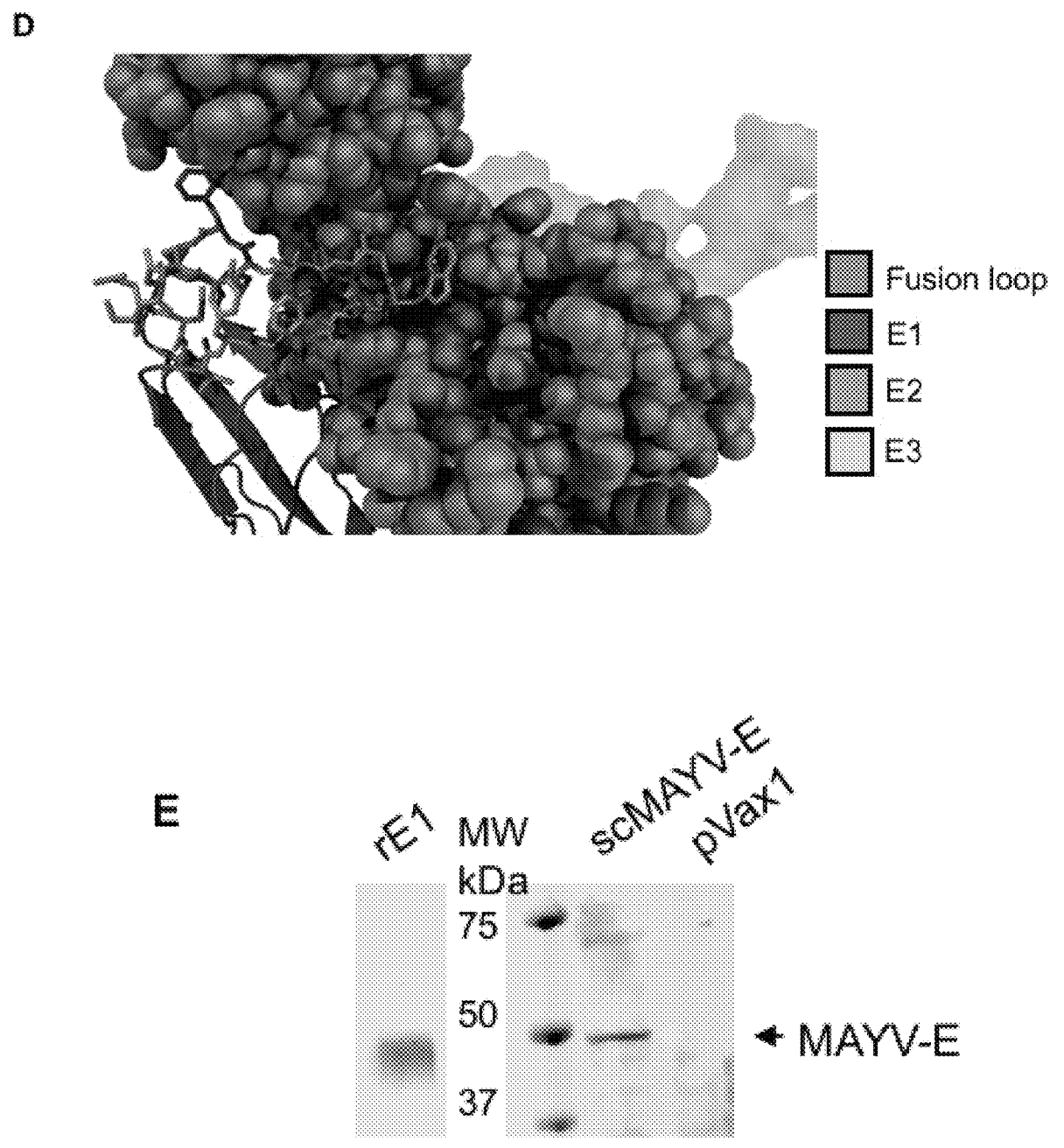

Bioinformatics and synthetic DNA technologies were employed to create a novel DNA vaccine encoding a full-length MAYV envelope gene sequence comprised of the E1, E2, and E3 glycoprotein domains as well as the 6K/TF polypeptides. The synthetic DNA insert was created by aligning full-length envelope genomic sequences from multiple MAYV strains deposited in the GenBank-NCBI (National Center for Biotechnology Information) database and determining the most common conserved amino acid at each position. Consensus antigen sequences account for genetic variability that occurs over time in a sequence and thus mapped at the phylogenetic midpoint (FIG. 1A). Studies show that synthetic consensus sequences can focus immune responses against conserved sites as well as broaden T cell immunity (Muthumani et al., 2016, NPJ Vaccines 1:16021, Duperret et al., 2018, Mol Ther 26(2):435-45). To improve the transcription and translation of the vaccine inserts, modifications to the insert sequences were made prior to cloning into the modified pVax1 vaccine expression vector including the addition of an immunoglobulin E (IgE) leader sequence to the N-terminus (FIG. 1B) along with codon and RNA optimization of the sequences (Muthumani et al., 2015, Sci Transl. Med. 7(301):301ra132). Reference models of the scMAYV-E antigen made using Discovery Studio 4.5. software indicate that its predicted structure matches that of a wild-type MAYV envelope with the fusion loop at the end of domain E1 tucked into a fold in domain E2 (FIG. 1C-D), thus preserving important envelope functional sites. Expression of the scMAYV-E antigen was confirmed in vitro through western analyses of lysates from 293T cells transfected with vaccine (FIG. 1E).

Figure 2D:
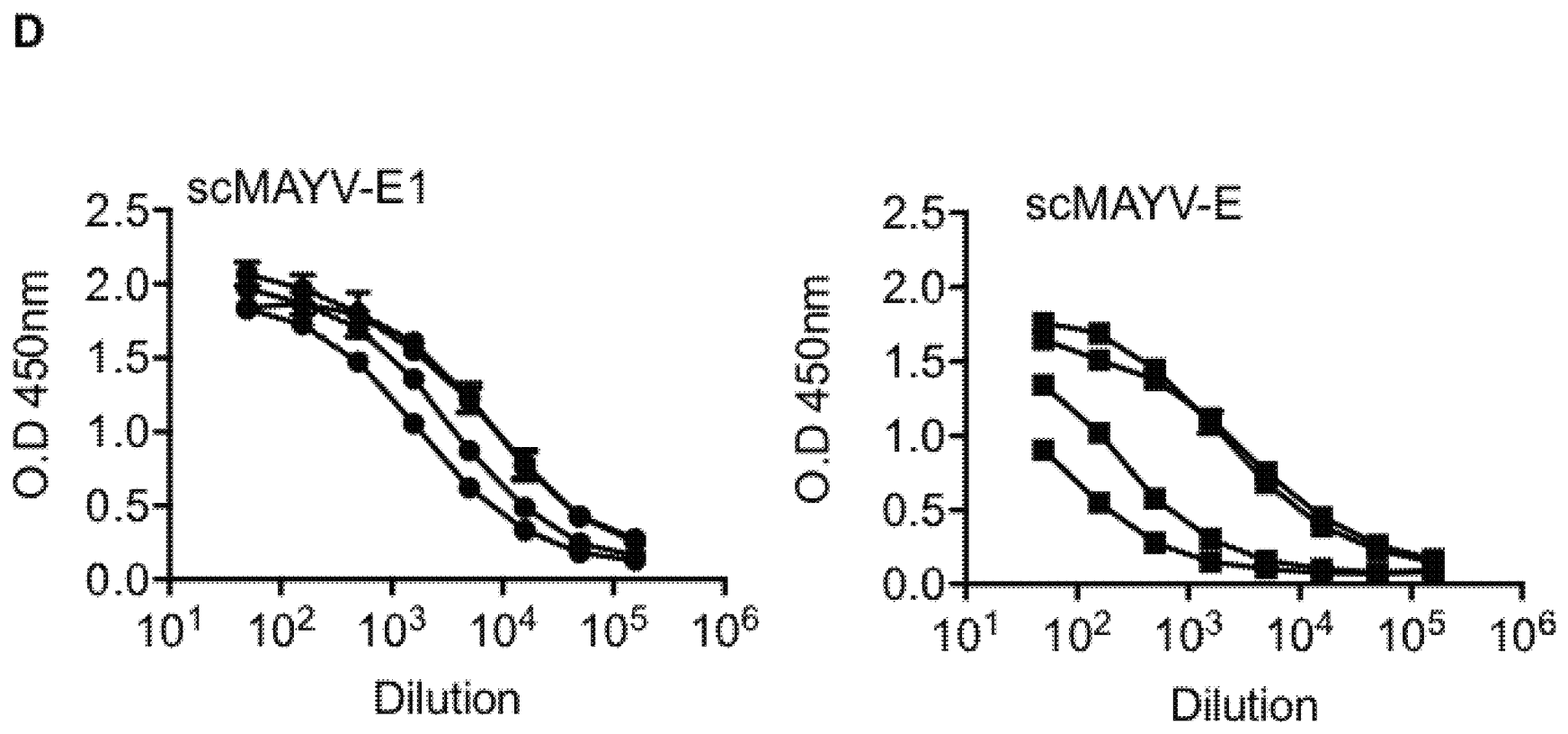

Due to a paucity of commercially available reagents for evaluating anti-MAYV immune responses, a recombinant MAYV-E1 (rE1) protein was generated for use in the immunoassays (FIG. 2A). The E1 glycoprotein is the immunodominant portion of MAYV envelope that is varied amongst alphaviruses, and the E2 region highly conserved;

thus, the E1 domain was chosen for development over full-length envelope due to significant time and cost requirements needed to prepare the latter. The consensus MAYV-E1 domain sequence was obtained from the scMAYV-E consensus described above and cloned into the pET30A *E. coli* expression vector (Muthumani et al., 2016, NPJ Vaccines 1:16021). The rE1 protein was purified from transfected *E. coli* cultures using nickel column chromatography (FIG. 2B), and a pan alphavirus monoclonal antibody (clone: G77L; ThermoFisher) was used to verify the final rE1 product by western analyses (FIG. 2C). Further confirmation of the identity of the purified protein was made using ELISA with sera collected from mice immunized with scMAYV-E1 or scMAYV-E DNA plasmids (FIG. 2D). Based on this result, this recombinant protein was utilized for investigating MAYV-specific humoral immunogenicity.

scMAYV-E Induces Binding and Neutralizing Antibody Responses in Mice

Figure 3A:
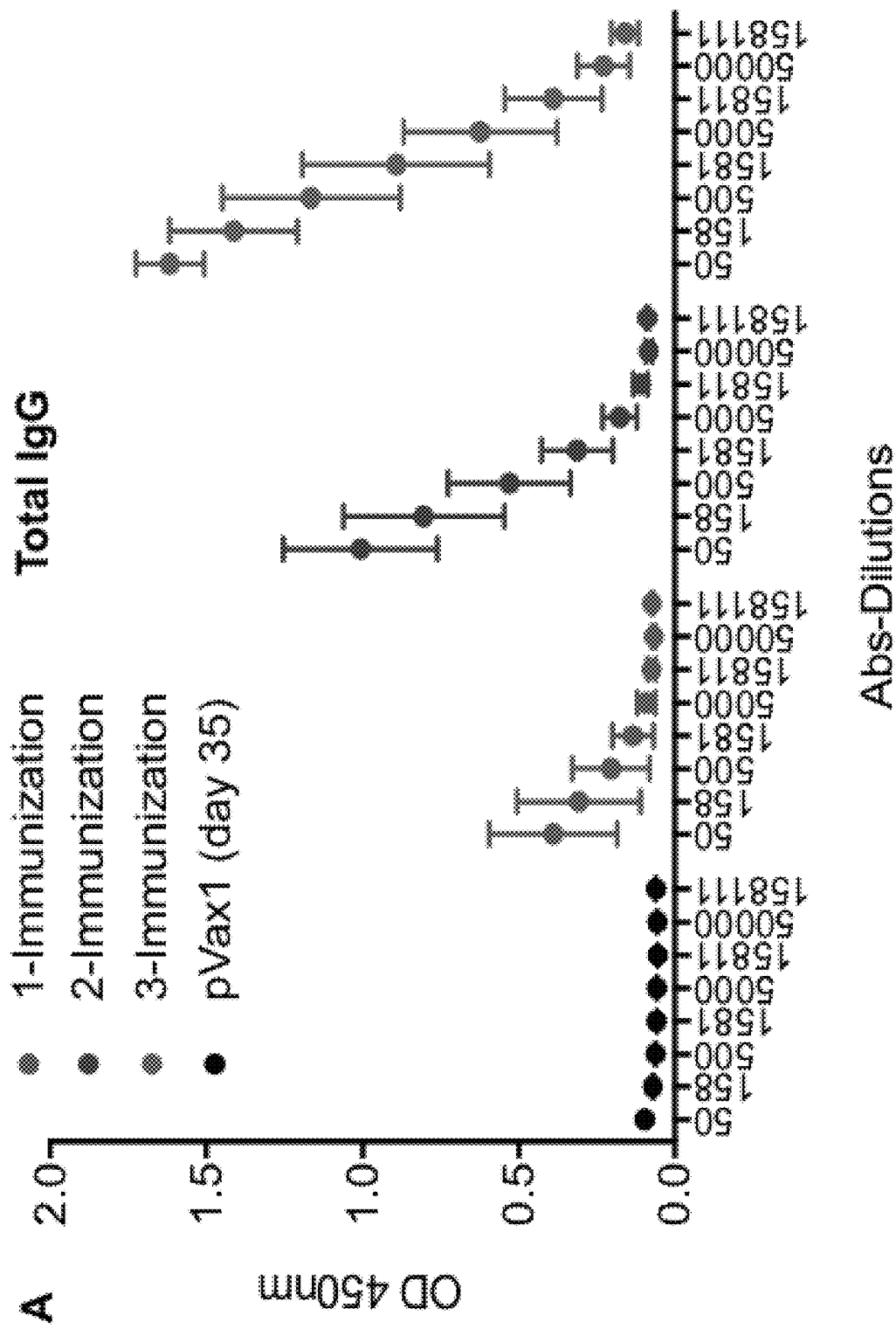
Figures 3B, 3C:
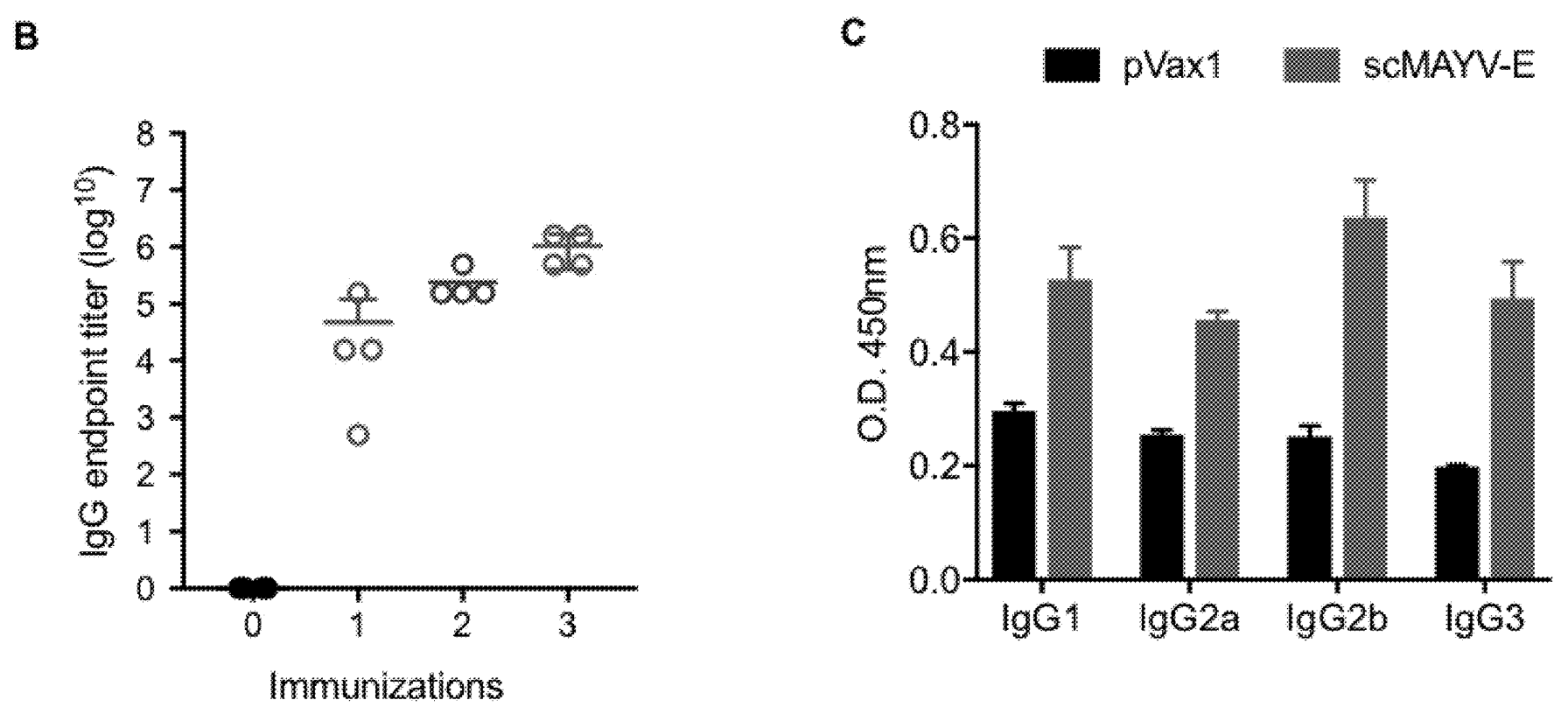
Figure 3D:
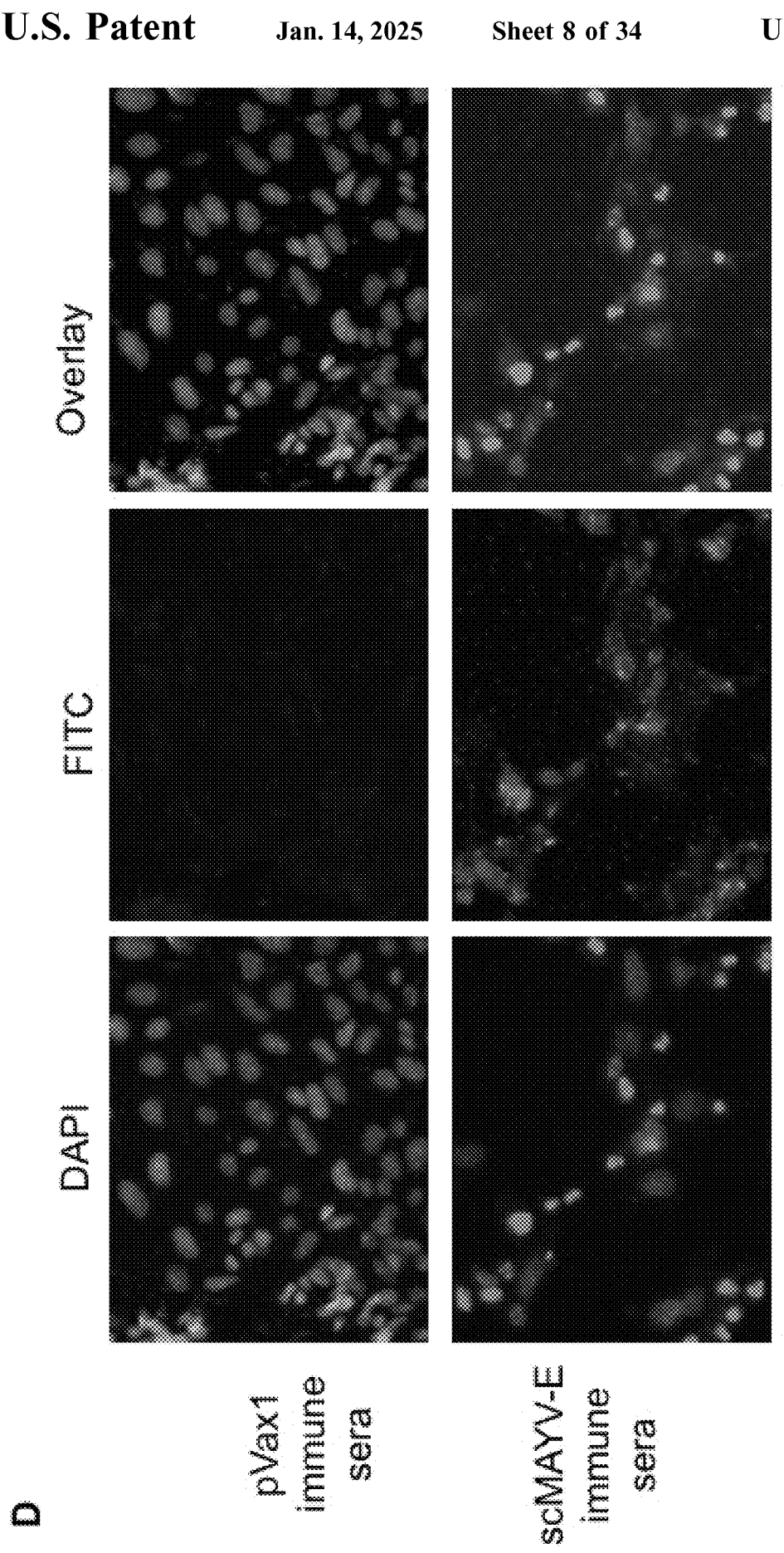

The immunogenicity of the scMAYV-E vaccine was evaluated in C57BL/6 mice. Initially, groups of mice were immunized three times, two weeks apart, with 25 μg of either scMAYV-E or an pVax1 empty vector plasmid using EP-enhanced i.m. delivery (Fisher et al., 2017, Gene Ther 24(12):757-67). Immunized mice were bled on day 0 and one week after each injection to obtain sera, which were assayed for the presence of antibodies to MAYV envelope using ELISA with the rE1 protein. The results show that all mice develop anti-MAYV antibodies after a single immunization, and the MAYV envelope-specific IgG responses were boosted by both a second and third immunization (FIG. 3A). Multiple immunizations also enhanced the affinity of the vaccine-induced anti-MAYV responses as evidenced by increasing endpoint titers after the second immunization (FIG. 3B). There is a comparable increase in IgG1, IgG2a, IgG2b, and IgG3 subtypes after the third immunization (FIG. 3C). Both Vero-CCL81 (FIG. 3D) and U-87 MG neuronal cells (FIG. 3E) infected with the wild-type MAYV could be identified by indirect immunofluorescence assay using pooled day 35 sera from scMAYV-E immunized mice but not when using pooled day 35 pVax1 sera.

Figures 3E, 3F:
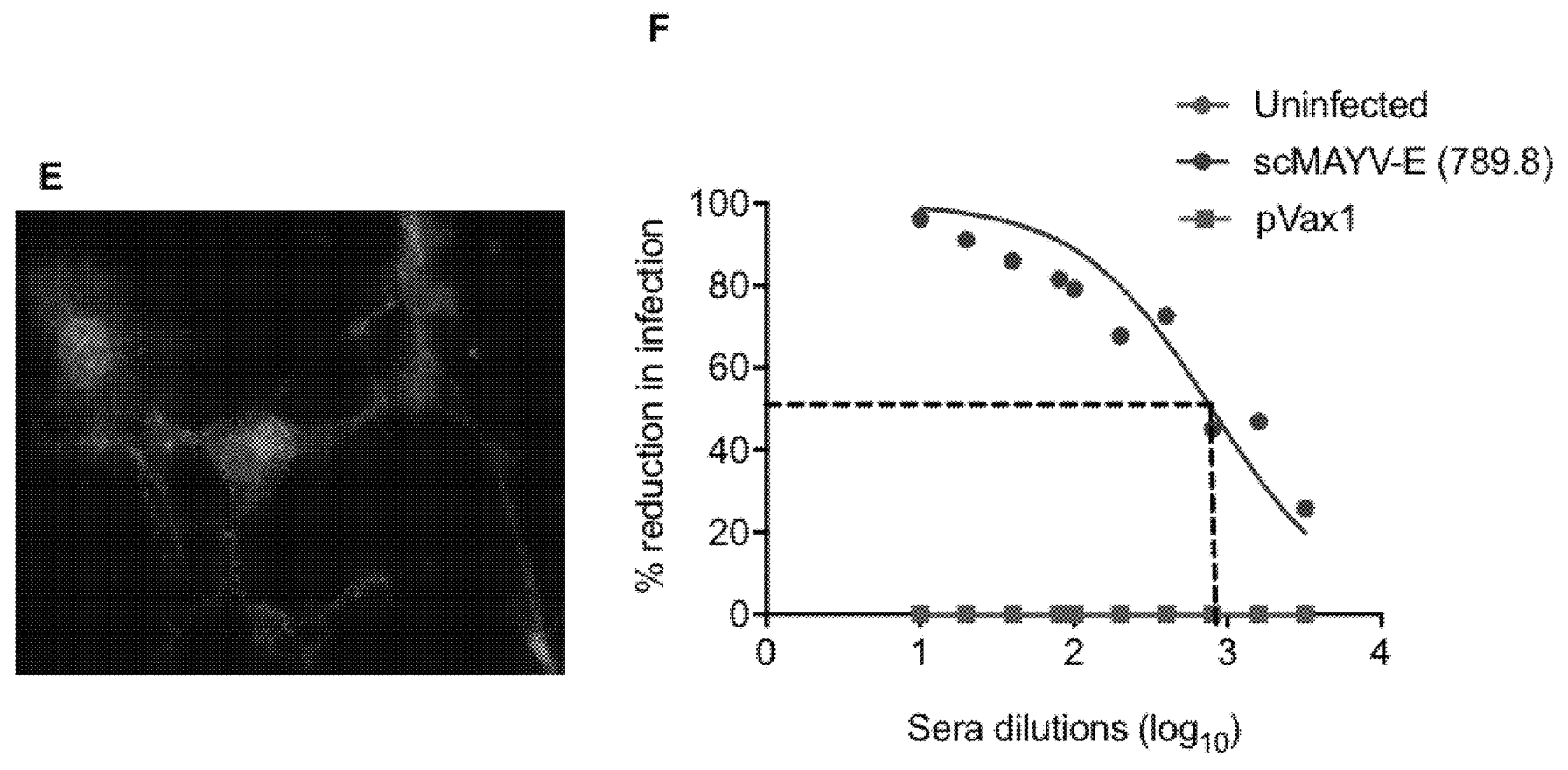
Figure 4A:
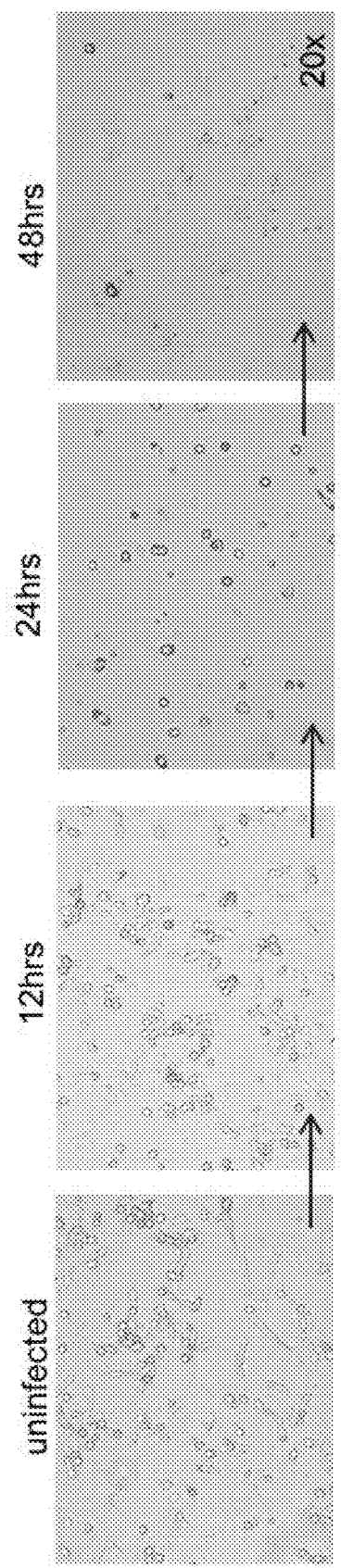
FIG. 4A through FIG. 4D, depicts experimental results demonstrating scMAYV-E immune sera protect monocyte derived macrophages (MDMs) from MAYV infection-induced cell death.
Figure 4B:
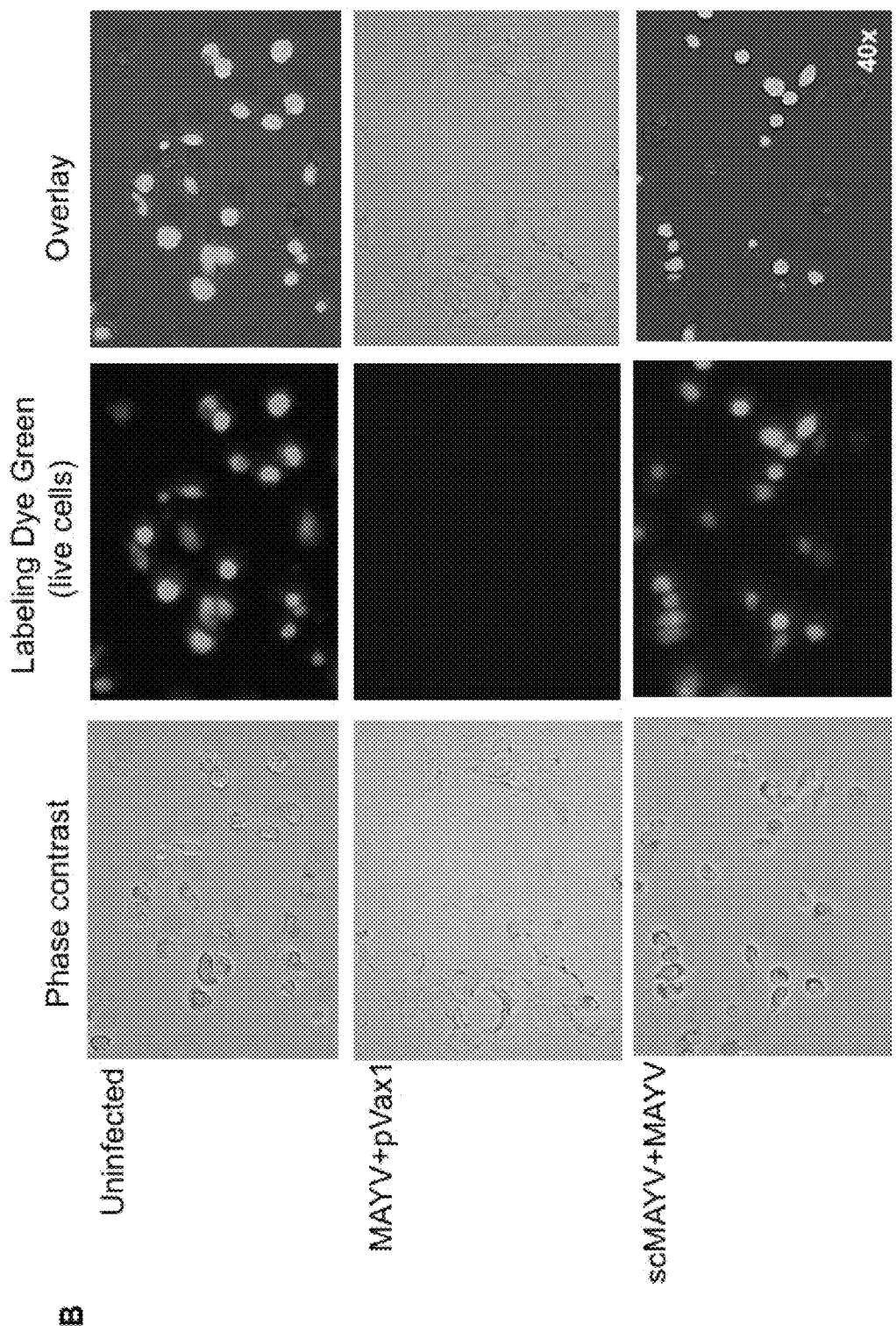
Figures 4C, 4D:
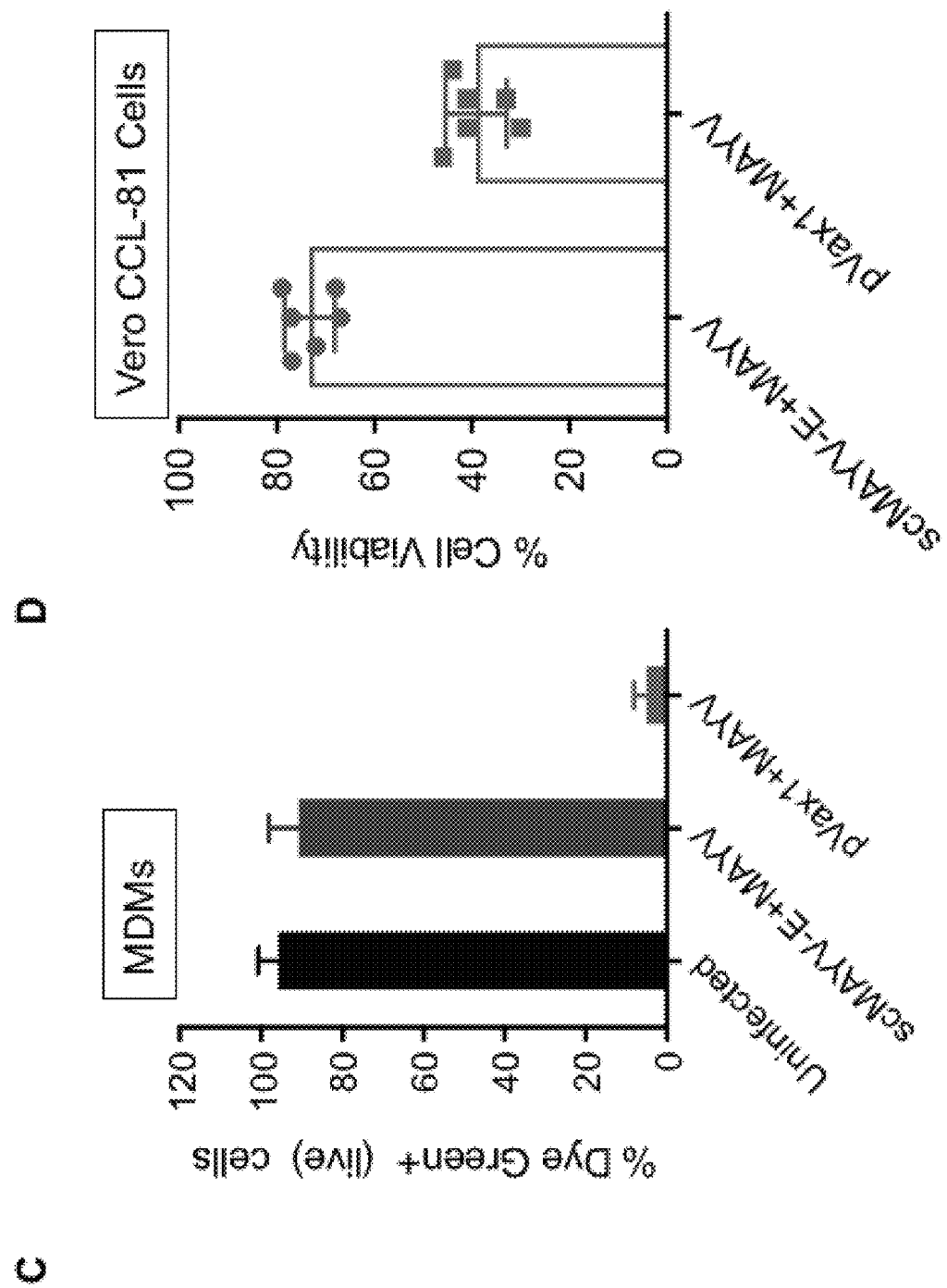

Studies on related alphaviruses including CHIKV have established anti-viral antibodies as a primary correlate of protection (Mallilankaraman et al., 2011, PLoS Negl Trop Dis 5(1):e298; Fox et al., 2016, J Immunol 197(11):4210-19; Fox et al., 2015, Cell 163(5):1095-107). Next, it was evaluated whether the antibody response elicited by the scMAYV-E vaccine in mice could neutralize MAYV infection in vitro. A plaque reduction neutralization test (PRNT) performed on pooled day 35 sera from scMAYV-E immunized or pVax1 control mice found that antibodies in scMAYV-E vaccinated mice could neutralize MAYV infection of Vero-CCL81 cells with a high neutralizing titer (PRNT50=789.8). These results indicate that scMAYV-E induces robust, MAYV-specific humoral responses in mice that are capable of blocking MAYV infection in vitro (FIG. 3F).

scMAYV-E Immune Sera Protect Human Macrophages from MAYV Infection-Induced Death Multiple alphaviruses are known to infect macrophage cells, which are believed to play a role in alphavirus-induced arthritis (Herrero et al., 2013, Arthritis Rheum 65(10):2724-36; Haist et al., 2017, PLoS Pathog. 13(12):e1006748). To assess the potential of scMAYV-E immune sera to protect against macrophage infection, an in vitro infection assay was performed. Addition of wild-type MAYV TRVL 15337 to human monocyte-derived macrophages (MDMs) decreased cell viability at 48 hours post infection (FIG. 4A). Importantly, preincubation of MAYV infection with pooled immune sera from scMAYV-E immunized mice significantly increased the viability of MDMs whereas MDMs incubated with virus plus pVax1 sera demonstrated high levels of cell death. This was observed in all visual fields on a fluorescent microscope (FIG. 4B) as well as by the Labelling Dye Green positive cells evaluated by six independent reviewers (FIG. 4C). These results led to the conclusion that while MAYV was likely inducing cell death, the immune sera from scMAYV-E immunized mice can prevent this process from killing the cells. To further investigate this observation, Vero CCL-81 cells were cultured with supernatants from the infected MDM cultures described above for 36 hours. Vero cells grown in the presence of supernatant from MDMs incubated with MAYV+scMAYV-E immune sera had a cell viability over 60% when compared to a 40% cell viability of Vero cell cultured in the presence of supernatant from MDMs incubated with MAYV+pVax1 sera (FIG. 4D). Taken together, these results suggest that scMAYV-E immune sera are capable of inhibiting viral entry into the target cells.

scMAYV-E Induces Potent Antigen-Specific Cellular Immune Responses

Figure 5A:
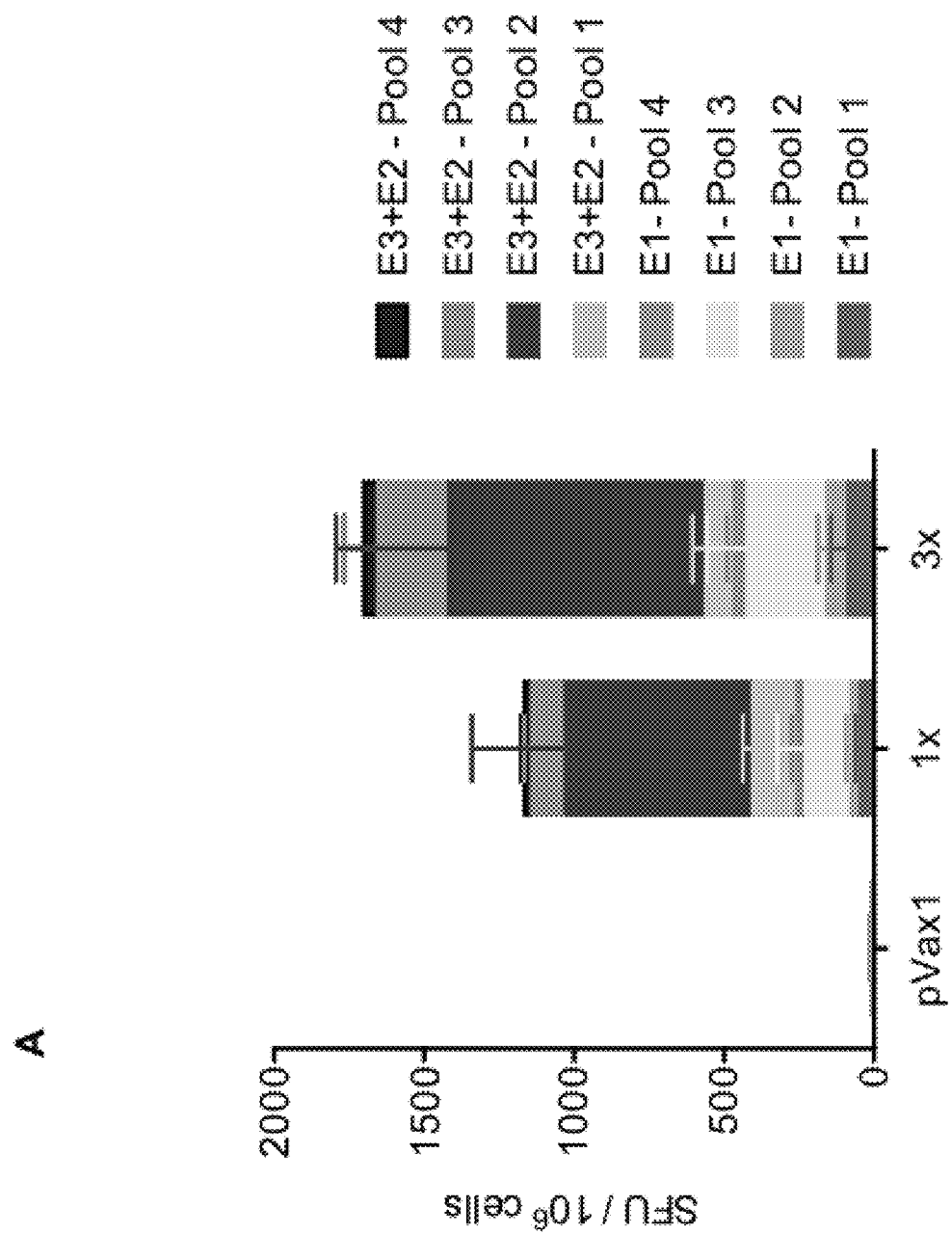

Next, anti-MAYV cellular immunity was evaluated in splenocytes collected from the scMAYV-E immunized C57BL/6 mice mentioned previously. One week after the third immunization (day 35), pVax1 control and scMAYV-E immunized mice were euthanized, and bulk splenocytes were obtained for evaluation in ELISpot assay. Briefly, harvested splenocytes from mice were ex vivo stimulated with various peptide pools encompassing the full-length MAYV envelope protein (i.e., glycoprotein E1, E2, and E3). The identity of each peptide pool is shown in Table 1. The antigen specific production of interferon gamma (IFN-γ) by the cells is reported as spot forming units (SFUs) per million cells. Mice immunized with scMAYV-E exhibit a robust cellular response to multiple peptide pools throughout the MAYV envelope glycoprotein domains. A similar strong cellular response to multiple MAYV peptide pools was also observed in a separate cohort of mice that were euthanized two weeks after a single immunization with the scMAYV-E vaccine (FIG. 5A).

TABLE 1

Peptide pools encompassing the scMAYV-E sequence.

| Linear Pools | | Matrix Pools | | | |
| --- | --- | --- | --- | --- | --- |
| scMAYV-E | Peptides included | E1 | Peptides included | E3 + E2 | Peptides included |
| E1 - Pool 1 | 1-20 (E1) | Pool 1 | 1-9 (E1) | Pool 18 | 1-9 (E3 + E2) |
| E1 - Pool 2 | 21-40 (E1) | Pool 2 | 10-18 (E1) | Pool 19 | 10-18 (E3 + E2) |
| E1 - Pool 3 | 41-60 (E1) | Pool 3 | 19-27 (E1) | Pool 20 | 19-27 (E3 + E2) |

TABLE 1-continued

Peptide pools encompassing the scMAYV-E sequence.

| Linear Pools | | Matrix Pools | | | |
|---|---|---|---|---|---|
| scMAYV-E | Peptides included | E1 | Peptides included | E3 + E2 | Peptides included |
| E1 - Pool 4 | 61-72 (E1) | Pool 4 | 28-36 (E1) | Pool 21 | 28-36 (E3 + E2) |
| E3 + E2 - Pool 1 | 1-20 (E3 + E2) | Pool 5 | 37-45 (E1) | Pool 22 | 37-45 (E3 + E2) |
| E3 + E2 - Pool 2 | 21-40 (E3 + E2) | Pool 6 | 46-54 (E1) | Pool 23 | 46-54 (E3 + E2) |
| E3 + E2 - Pool 3 | 41-60 (E3 + E2) | Pool 7 | 55-63 (E1) | Pool 24 | 55-63 (E3 + E2) |
| E3 + E2 - Pool 4 | 61-81 (E3 + E2) | Pool 8 | 64-72 (E1) | Pool 25 | 64-72 (E3 + E2) |
| | | Pool 9 | 1, 10, 19, 28, 37, 46, 55, 64 (E1) | Pool 26 | 73-81 (E3 + E2) |
| | | Pool 10 | 2, 11, 20, 29, 38, 47, 56, 65 (E1) | Pool 27 | 1, 10, 19, 28, 37, 46, 55, 64, 73 (E3 + E2) |
| | | Pool 11 | 3, 12, 21, 30, 39, 48, 57, 66 (E1) | Pool 28 | 2, 11, 20, 29, 38, 47, 56, 65, 74 (E3 + E2) |
| | | Pool 12 | 4, 13, 22, 31, 40, 49, 58, 67 (E1) | Pool 29 | 3, 12, 21, 30, 39, 48, 57, 66, 75 (E3 + E2) |
| | | Pool 13 | 5, 14, 23, 32, 41, 50, 59, 68 (E1) | Pool 30 | 4, 13, 22, 31, 40, 49, 58, 67, 76 (E3 + E2) |
| | | Pool 14 | 6, 15, 24, 33, 42, 51, 60, 69 (E1) | Pool 31 | 5, 14, 23, 32, 41, 50, 59, 68, 77 (E3 + E2) |
| | | Pool 15 | 7, 16, 25, 34, 43, 52, 61, 70 (E1) | Pool 32 | 6, 15, 24, 33, 42, 51, 60, 69, 78 (E3 + E2) |
| | | Pool 16 | 8, 17, 26, 35, 44, 53, 62, 71 (E1) | Pool 33 | 7, 16, 25, 34, 43, 52, 61, 70, 79 (E3 + E2) |
| | | Pool 17 | 9, 18, 27, 36, 45, 54, 63, 72 (E1) | Pool 34 | 8, 17, 26, 35, 44, 53, 62, 71, 80 (E3 + E2) |
| | | | | Pool 35 | 9, 18, 27, 36, 45, 54, 63, 72, 81 (E3 + E2) |

15-mer peptides overlapping by 9 amino acids spanning the entire length of the scMAYV-E sequence were created. 72 peptides comprise the E1 domain of scMAYV-E, and 81 peptides comprise the E3 + E2 region. The E1 peptides were grouped into linear Pools 1-4 and E3 + E2 into Pools 1-4, all of which consist of 20 or fewer peptides per pool. Matrix pools for E1 peptides and E3 + E2 peptides were created separately.

Figure 5B:
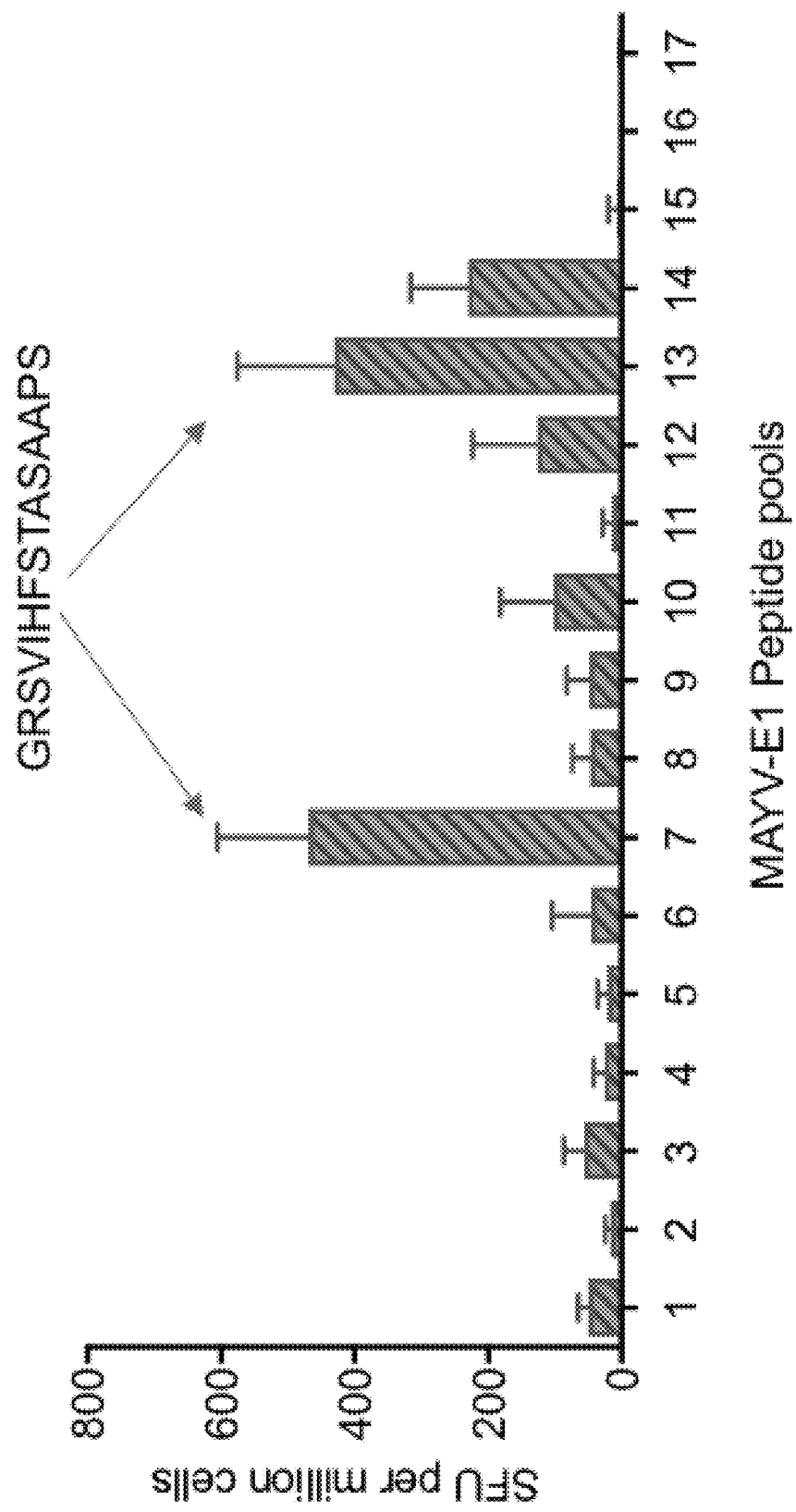
Figure 5C:
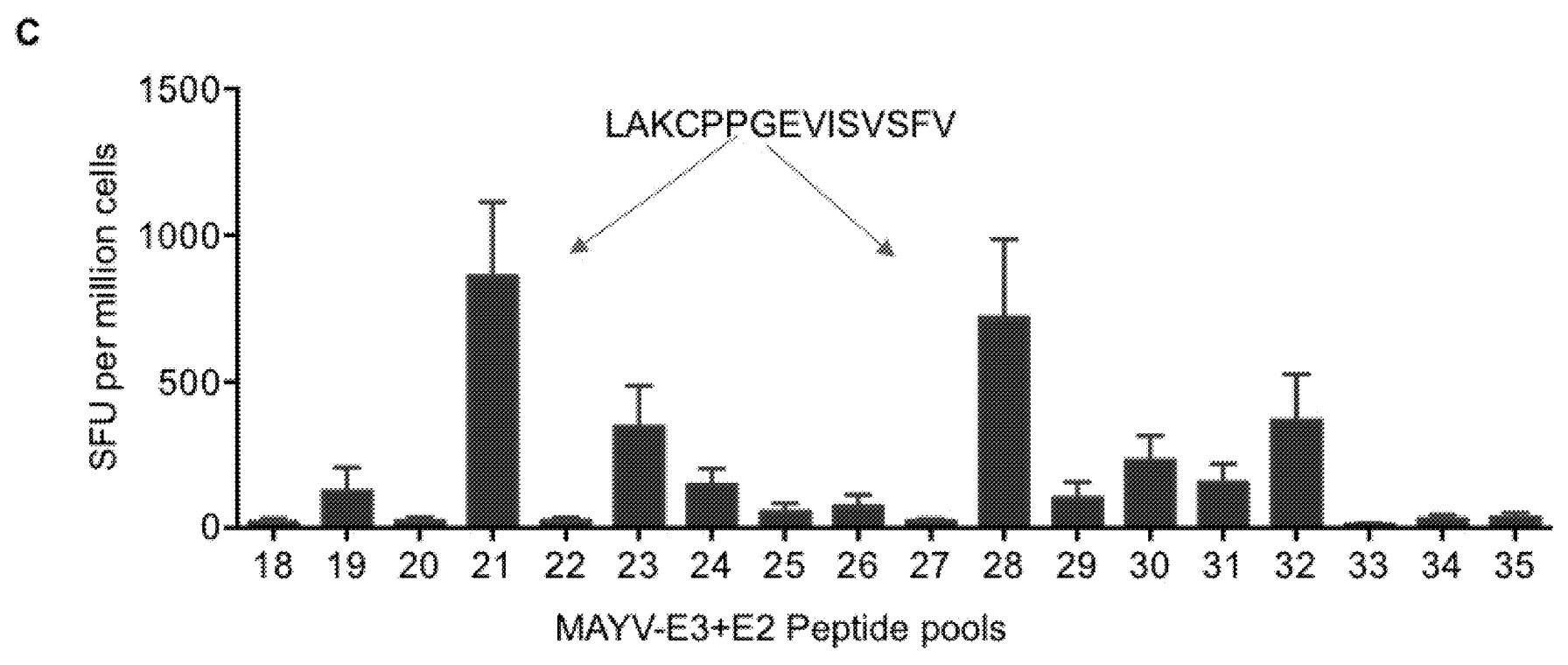

To better define the dominant epitope(s) of scMAYV-E that elicit cellular responses in the C57BL/6 mouse model, an ELISpot mapping analysis was performed on bulk splenocytes from the mice that received three immunizations with scMAYV-E. Thirty-five matrix peptide pools encompassing the entire MAYV envelope protein, each comprised of individual 15-mer peptides that overlap by 9 amino acids, were created (Table. 1) and used to ex vivo stimulate splenocytes for the IFN-γ ELISpot assay as previously described. Several matrix pools from different regions of the MAYV envelope stimulated IFN-γ production by T cells in the bulk splenocytes, with peptide pools 7, 13, 21, and 28 eliciting the highest responses (FIG. 5B-C). Subsequent mapping analysis identified dominant epitopes within the MAYV E1 glycoprotein, 'GRSVIHFSTASAAPS' (FIG. 5B) and within the MAYV-E3+E2 glycoproteins as 'LAKCPP-GEVISVSFV' (FIG. 5C). The amino acid sequences of the dominant epitopes determined from the ELISpot mapping analysis were confirmed using the immune epitope database analysis resources tools (http://tools.iedb.org), substantiating the effective antigen processing of scMAYV-E vaccine in this strain of mice.

scMAYV-E Generates Significant Polyfunctionality in Both CD4+ and CD8+ T Cells

Figures 6A, 6B:
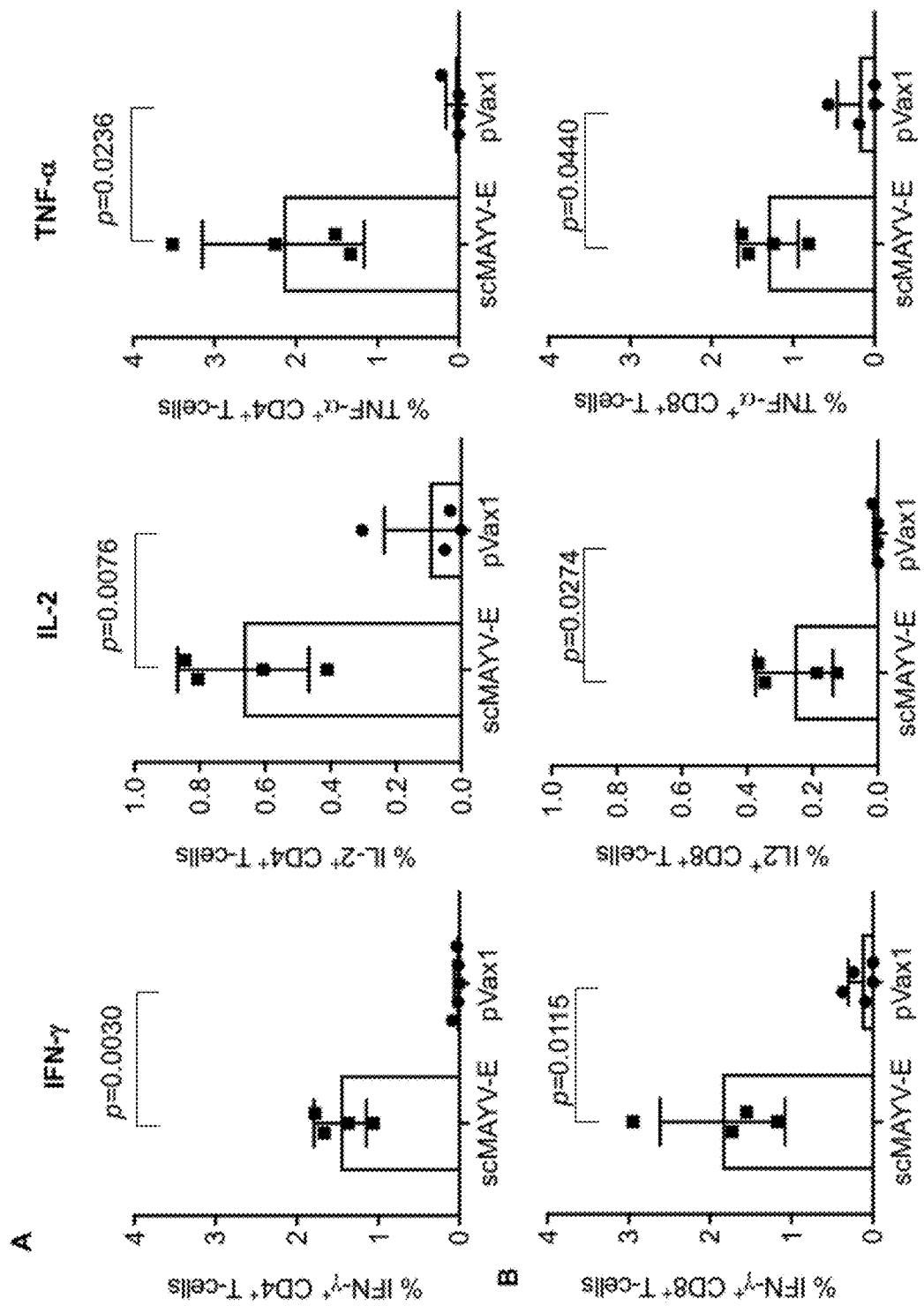
FIG. 6A through FIG. 6C, depicts experimental results demonstrating scMAYV-E induces both CD4+ and CD8+ T cell responses in mice.
Figure 6C:
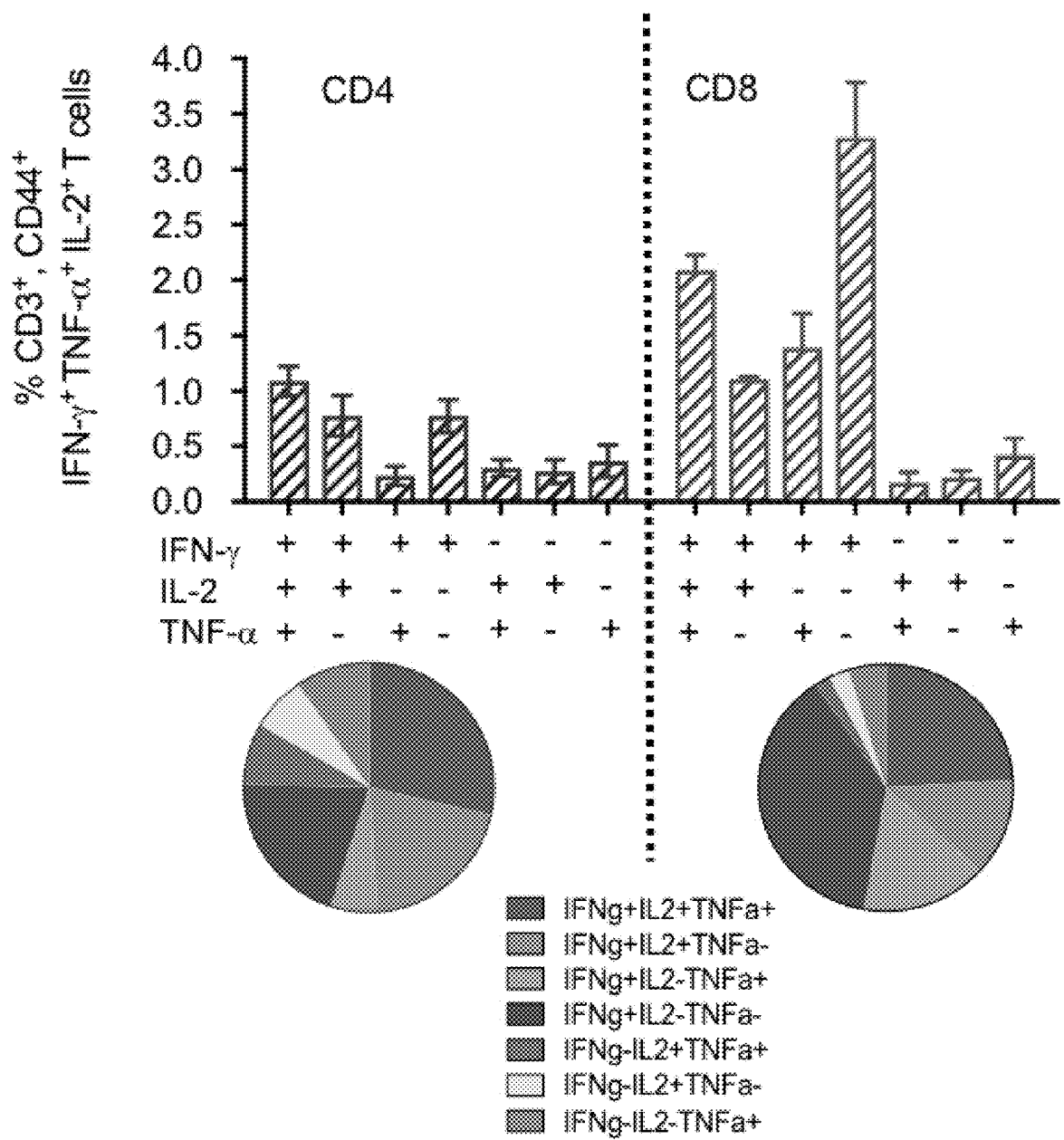

To further characterize the cellular response induced by the scMAYV-E vaccine, splenocytes collected from the C57BL/6 mice receiving three immunizations of scMAYV-E as described above were evaluated by polychromatic flow cytometry. A panel of fluorophore-tagged antibodies was created and used to characterize production of the activated-state cytokines such as IFN-γ tumor necrosis factor-α (TNF-α), and interleukin 2 (IL-2), by helper (CD4¹) and cytotoxic (CD8¹) T cells present in bulk splenocytes from pVax1 or scMAYV-E immunized mice after ex vivo stimulation with all peptides comprising MAYV full-length envelope. Both CD4+ and CD8+ T cells isolated only from scMAYV-E vaccinated mice were able to produce each cytokine upon stimulation with MAYV peptides (FIG. 6A-B). Vaccination also induced a large polyfunctional response in both T cell subsets (i.e., production of multiple activated-state cytokines) (FIG. 6C). Combined with the ELISpot results, these results show that the scMAYV-E DNA vaccine both induces cellular immunity to MAYV and provides polyfunctionality of the antigen specific T cells.

scMAYV-E Induced Immunity Protects Mice from MAYV Disease

Next, it was evaluated whether these MAYV-specific immune responses could protect against MAYV infection or disease in a challenge model. Previous studies showed that older immunocompetent mouse models do not exhibit arthritogenic signs of disease upon alphavirus challenge (Wang et al., 2011, J Virol 85(17):9249-52; Gorchakov et al., 2012, J Virol 86(11):6084-96). Therefore the interferon α/β receptor knockout mouse (IFNAR$^{-/-}$; A129) model was chosen, which has a defective innate immune response to pathogens. A dose of $10^2$ PFU of MAYV administered i.p. produced measurable clinical signs of disease including weight loss, foot swelling, and death.

Figures 7A, 7B:
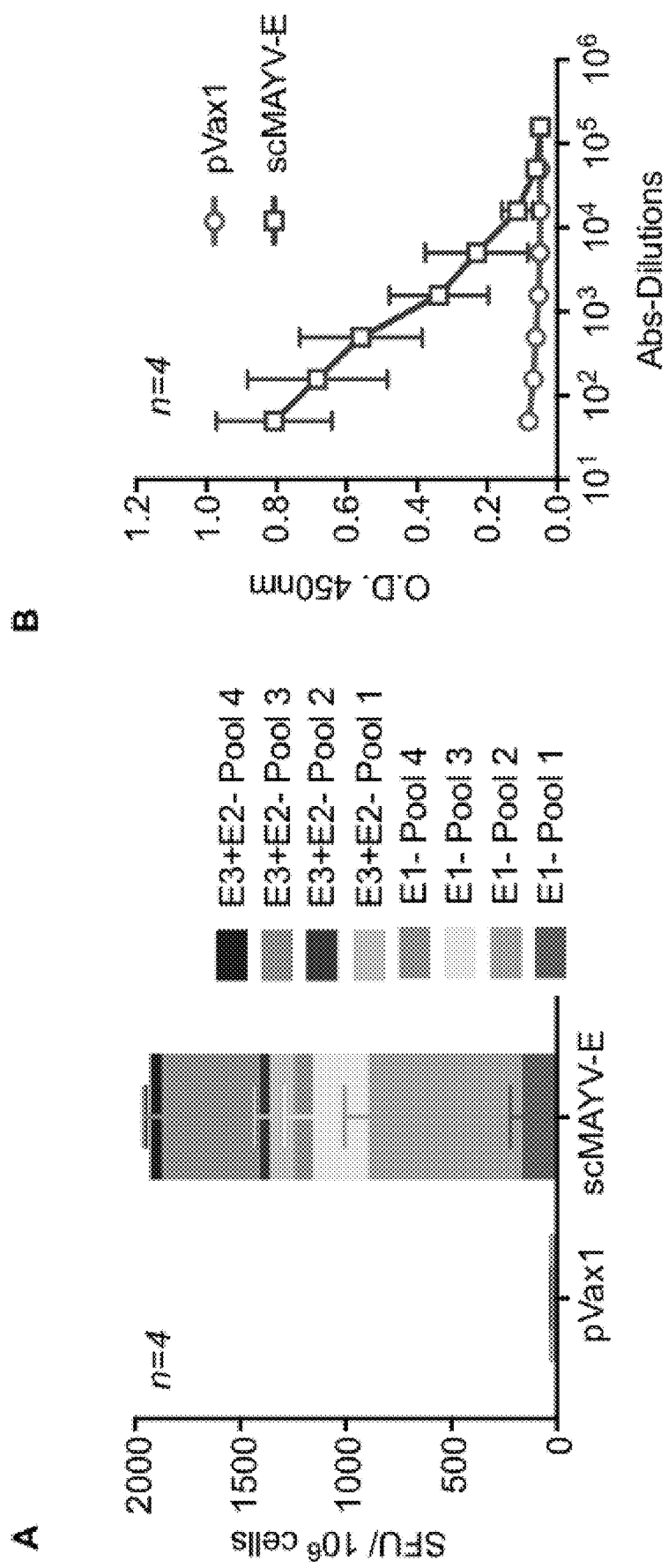
Figures 7C, 7D:
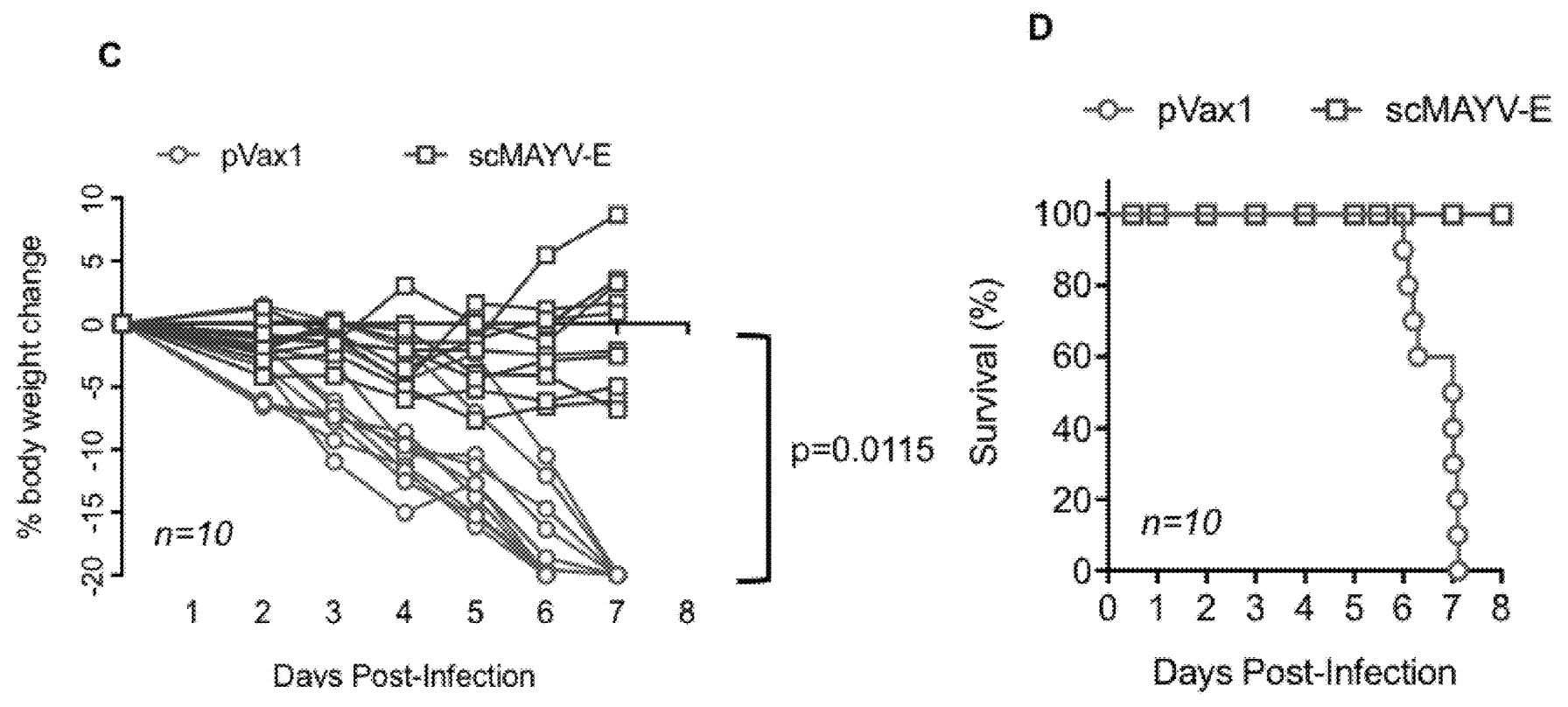
Figure 7E:
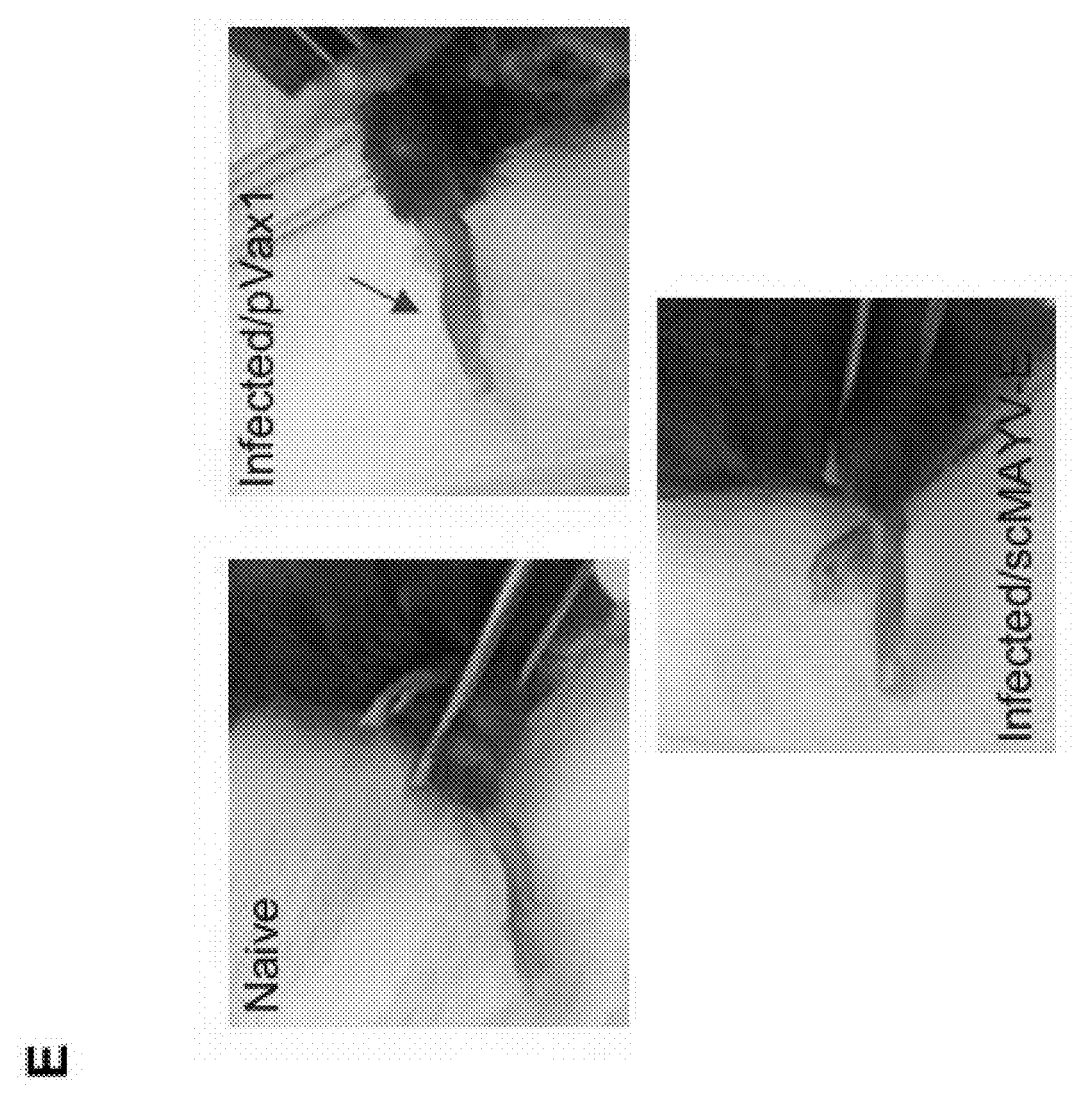
Figures 7F, 7G:
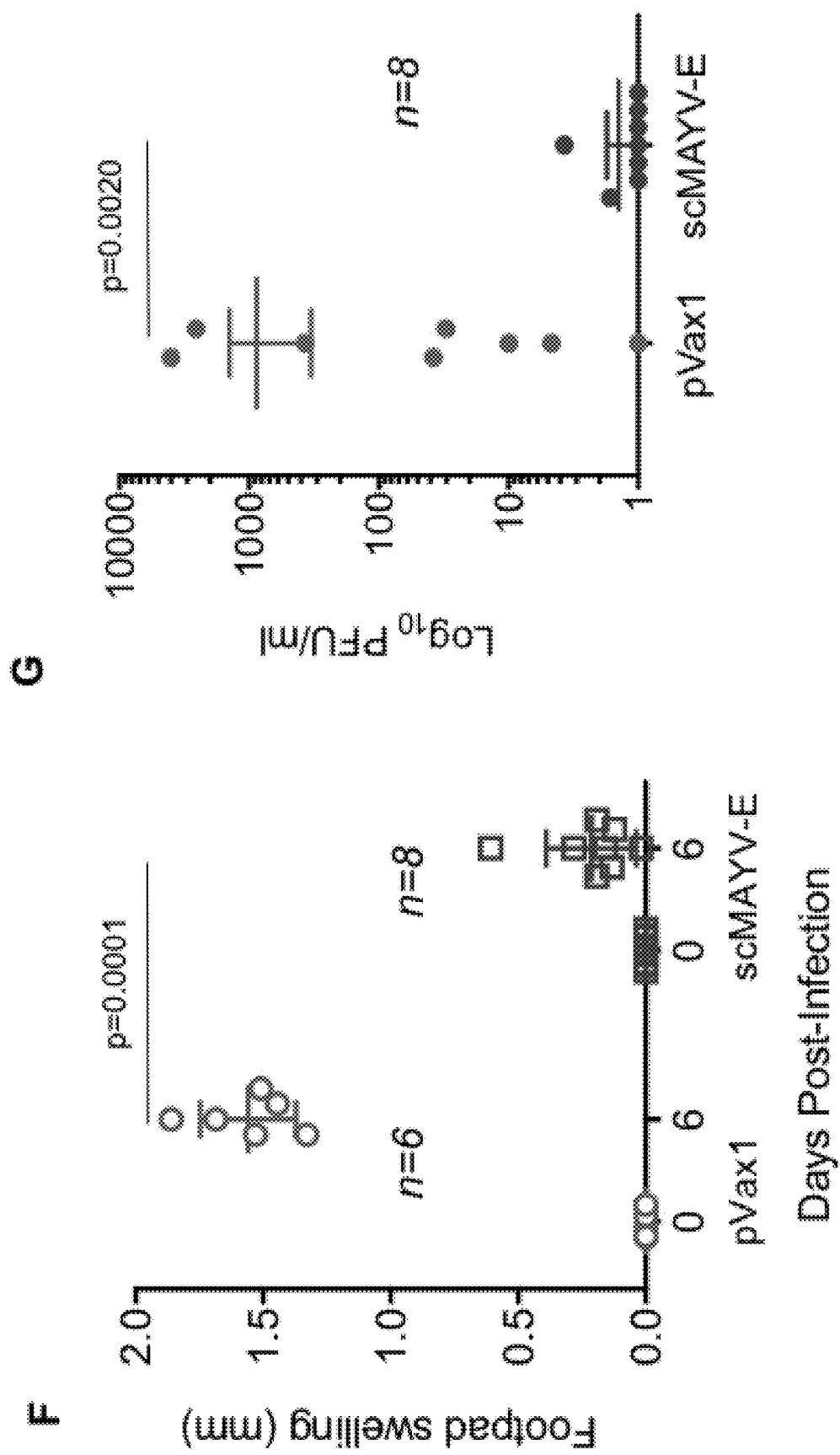

First, the cellular and humoral immunogenicity of scMAYV-E vaccinated IFNAR$^{-/-}$ mice were evaluated as previously described with C67BL/6 mice to confirm that they would mount a similar adaptive immune response. IFN-γ ELISpot responses (FIG. 7A) and total IgG binding antibody levels (FIG. 7B) were very comparable to those observed in the C56BL/6 mice. For the challenge studies, cohorts of 10 four- to six-week old IFNAR$^{-/-}$ mice were similarly immunized twice, two weeks apart, with either 25 µg scMAYV-E vaccine or pVax1 empty vector plasmid as a control. Animals were challenged on day 21, one week after the second immunization, with $10^2$ PFU of wild-type MAYV and were checked daily for 8 days for clinical signs of infection. All 556 mice receiving pVax1 empty vector plasmid exhibited significant and progressive weight loss (FIG. 7C). In contrast, mice vaccinated with scMAYV-E initially had minor weight loss over the first 4 days of challenge but exhibited slight weight gain after day 5 post challenge (FIG. 7C). Importantly, 100% of vaccinated mice survived the challenge, while all control mice met euthanasia criteria by 6-7 days post challenge (FIG. 7D). They also had significant footpad swelling at day 6 post challenge (FIG. 7E-F). Quantification of MAYV in sera from both groups of mice collected 6 days post challenge showed that scMAYV-E vaccinated mice had a significant reduction in circulating virus compared to pVax1 injected mice (FIG. 7G). Combined, these data demonstrate that immune responses induced by the scMAYV-E vaccine provide protection from morbidity and viral load following MAYV challenge in this murine challenge model.

scMAYV-E Induced Humoral Responses are Required to Confer Protection From Viral Challenge The relative contribution of the scMAYV-E vaccine induced humoral and cellular responses was evaluated in an in vivo passive transfer MAYV challenge model. In this investigation, a cohort of 6 four- to six-week-old IFNAR$^{-/-}$ mice were immunized twice at a two-week interval with 25 µg of scMAYV-E or pVax1. One week following the final immunization, the mice were euthanized and blood and bulk splenocytes were collected from each animal. Sera and splenocytes from each group were pooled. Cohorts of 6 naive, four- to six-week old IFNAR$^{-/-}$ mice were injected with either PBS, 200 µl of pooled immune sera, or $2 \times 10^6$ pooled splenocytes containing T cells, and subsequently challenged with $10^2$ PFU of MAYV. Challenged mice were monitored for up to 8 days for clinical signs of disease. All mice receiving PBS prior to challenge progressively lost weight and were eventually euthanized due to severe disease as expected. Adoptive transfer of T cells from immunized mice provided some protection from weight loss (FIG. 8A) and partial protection from disease (FIG. 8B). Significantly, 100% of mice receiving immune sera from vaccinated mice exhibited no weight loss (FIG. 8A) and all survived the challenge (FIG. 8B). Combined, these data establish the scMAYV-E induced humoral response as the main driver of its protective efficacy in this murine MAYV challenge model.

Discussion

Mayaro virus is an emerging infectious disease agent endemic in tropical regions of South America, but recent evidence suggests that its range may be expanding into Central America and island nations of the Caribbean Sea (Rodriguez-Morales et al., 2017, Travel Med Infect Dis 15:72-3, Mackay et al., 2016, Microbes Infect 18(12):724-34). The virus causes an acute febrile illness with symptoms including rash, headache, nausea, and diarrhea that can turn into a debilitating, long-term arthralgia in some patients after acute infection has cleared (El-Bacha et al., 2004, Mol Cell Biochem 266(1-2):191-8; Lednicky et al., 2016, Emerg Infect Dis 22(11):2000-2). There are currently no approved vaccines or therapeutics to combat MAYV disease and spread. The data presented herein demonstrates the generation and immunogenicity of a synthetic, enhanced DNA vaccine encoding a novel consensus-designed sequence of the MAYV envelope protein. The vaccine encoding MAYV envelope antigen sequence was designed to focus on conserved amino acids of the full-length envelope sequences to improve the specificity of the anti-MAYV immune responses induced by the vaccine. Immunization of mice with scMAYV-E using enhanced EP delivery induced robust, MAYV-specific humoral and cellular responses. Importantly, these responses can neutralize MAYV infection in vitro and can fully protect susceptible mice from morbidity and mortality following MAYV challenge. The results show that scMAYV-E is a highly immunogenic vaccine candidate that warrants further testing in additional systems and animal models for developing countermeasures against MAYV infection and diseases.

The precise correlates of protection for MAYV have not been defined. A recent one-year longitudinal study of confirmed MAYV-infected individuals in Peru found that infection elicited robust anti-viral immune responses including strong neutralizing antibody responses and promoted secretion of pro-inflammatory immune cytokines including IL-13, IL-7, and VEGF (Santiago et al., 2015, PLoS Negl Trop Dis 9(10):e0004104). They also report that the strong neutralizing antibody response was not sufficient to prevent long-term negative outcomes of MAYV infection; however, these responses developed post infection. Studies on related alphaviruses, including CHIKV, strongly suggest that a potent, neutralizing antibody response primarily mediates protection from infection, but non-neutralizing antibodies may contribute to protection as well through alternative effector functions (Fox et al., 2015, Cell 163(5):1095-107). Post infection, there is likely an important role for cellular immunity that may complement the humoral responses.

The scMAYV-E DNA vaccine elicits both humoral and cellular responses against MAYV, and thus might be an important tool to provide comprehensive protection from MAYV infection and disease. Antibodies to MAYV are generated after the initial priming immunization with scMAYV-E, and these responses increase after both one and two boosts in terms of binding capacity and affinity to rE1. Immune sera from vaccinated mice was able to detect full-length MAYV envelope in scMAYV-E transfected cells as well as MAYV infected cells. scMAYV-E vaccination of mice was able to induce neutralizing antibodies that can block viral entry and inhibit cell death induced by MAYV infection in human MDMs. Passive transfer of immune sera from scMAYV-E vaccinated mice to susceptible naive IFNAR$^{-/-}$ mice prior to MAYV challenge completely protected animals from illness, further confirming the importance of a strong humoral response for conferring protection from alphavirus infection.

Although the anti-MAYV T cell response appears less important for an immediate protection against MAYV infection, it may still be essential for the prevention of chronic disease by eliminating virus-infected cells. The cellular components induced by the scMAYV-E DNA vaccine target multiple epitopes along the full-length MAYV envelope glycoprotein. The strongest cellular responses were directed to epitopes in the E3+E2 glycoprotein domains of envelope, and the responses to epitopes in the E1 glycoprotein were less robust. The ELISpot mapping studies conducted here identified two immunodominant epitopes, 'LAKCPPGE-VISVSFV' in the E3+E2 domain and 'GRSVIHFS-TASAAPS' within the E1 glycoprotein, providing important and useful reagents for studies of the T cell immune response in this haplotype. Interestingly, passive transfer of splenocytes from scMAYV-E immunized mice to susceptible naive IFNAR$^{-/-}$ mice prior to MAYV challenge provided partial protection from weight loss and clinical symptoms of MAYV disease, suggesting that MAYV-specific cellular responses do contribute to protection. In this adoptive transfer experiment, MAYV-specific T cells were not purified or enriched from bulk splenocytes prior to transfer, thus it is possible that the partial protection observed here could be enhanced with a larger dose of antigen-specific T cells.

The immunogenicity of the scMAYV-E DNA vaccine mirrors what were observed in a previous DNA vaccine candidate targeting chikungunya virus (CHIKV-E) which encodes a synthetic consensus sequence of the full-length chikungunya envelope protein (Mallilankaraman et al., 2011, PLoS Negl Trop Dis 5(1):e298). The CHIKV-E vaccine was similarly able to generate humoral and cellular responses directed towards the CHIKV envelope protein, and these responses could protect mice from morbidity and mortality following a CHIKV challenge (Mallilankaraman et al., 2011, PLoS Negl Trop Dis 5(1):e298).

The synthetic DNA vaccines have some practical advantages for development including simplicity of production and stability at warmer temperatures, likely reducing the requirement for a cold chain. They are non-live and nonreplicating and do not integrate, thus providing conceptual safety advantages as well. Since DNA vaccine vectors do not induce anti-vector serology, they can be administered multiple times with no loss of potency and without interfering with other vaccine protocols. Such logistical and safety advantages warrant further studies of this vaccine approach, especially pertaining to diseases prevalent in tropical settings like MAYV. scMAYV-E is the third vaccine candidate for MAYV developed. The first vaccine was an inactivated Mayaro virus, and the second vaccine reported was a live-attenuated MAYV virus (Robinson et al., 1976, Mil Med 141(3):163-6; Weise et al., 2014, PLoS Negl Trop Dis 8(8):e2969). Both prior vaccines were shown to induce anti-MAYV humoral responses that could protect mice from MAYV challenge, but neither study reported on the induction of cFwellular responses to MAYV. The synthetic scMAYV-E DNA vaccine described here generates MAYV-specific humoral and cellular responses without replication, which is likely important for immune-challenged, young, pregnant, and elderly populations of potential travelers and residents in endemic areas in need of vaccine-induced immune protection.

Example 2

Consensus MAYV-ENV DNA vaccines are rationally designed based on alphavirus phylogenetics. Antigen-specific cellular and humoral responses to Env-DNA vaccines are tested in vivo. Antibodies possessing functional activity undergo epitope mapping against MAYV Env proteins using overlapping peptide libraries. These analyses include the measurement of the cellular immunogenicity of DNA vaccine constructs in mice and specific memory responses.

Mayaro virus (MAYV) is a member of the Family Togaviridae.(alphavirus) Genetically its divided into two genotypes, "D" (widely Dispersed), "N" (New) and "L" (Limited).

Figure 9:
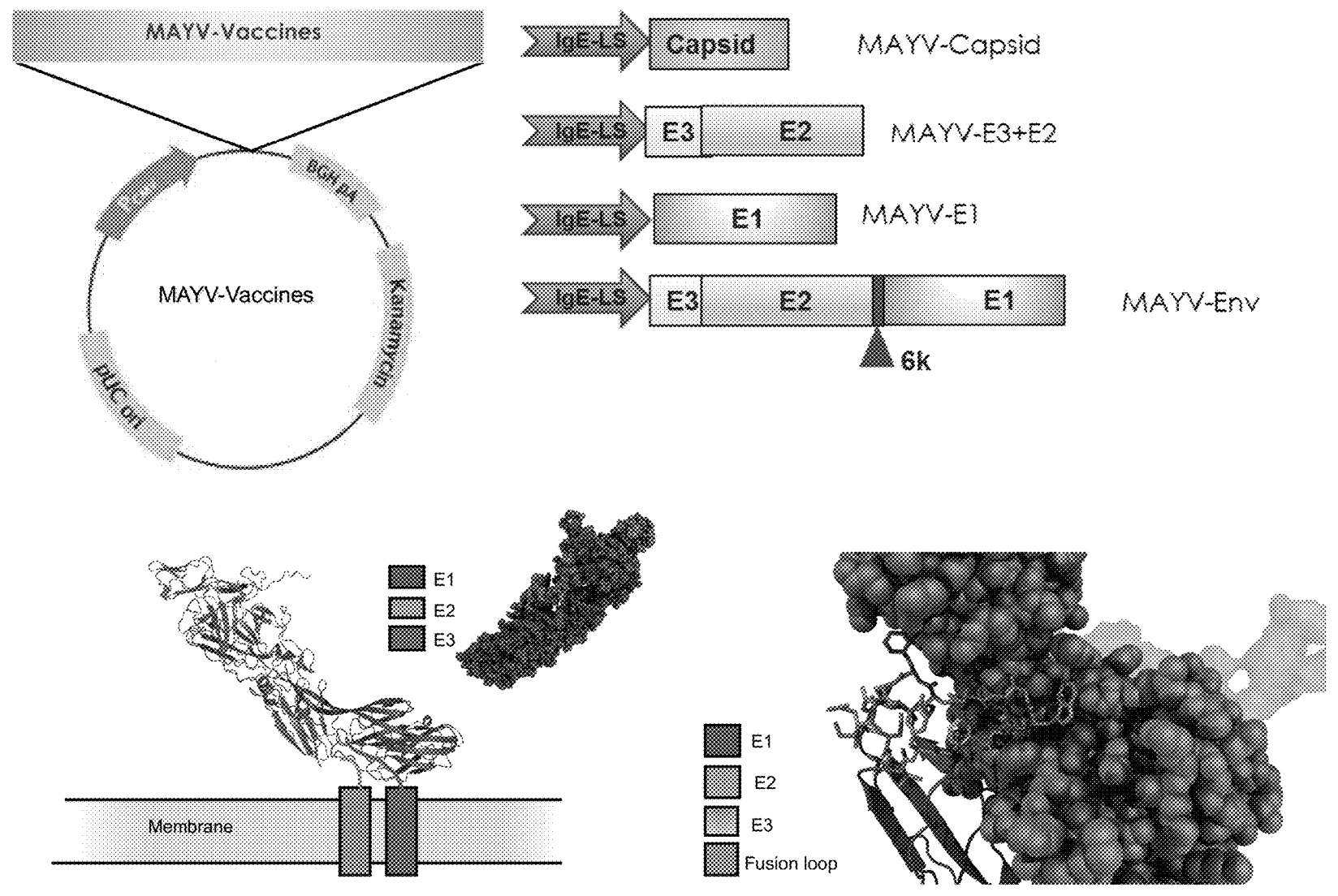

Synthetic Consensus Mayaro-Envelope, E1, E2+E3 and Capsid were developed (FIG. 1A, FIG. 9)

Figure 11:
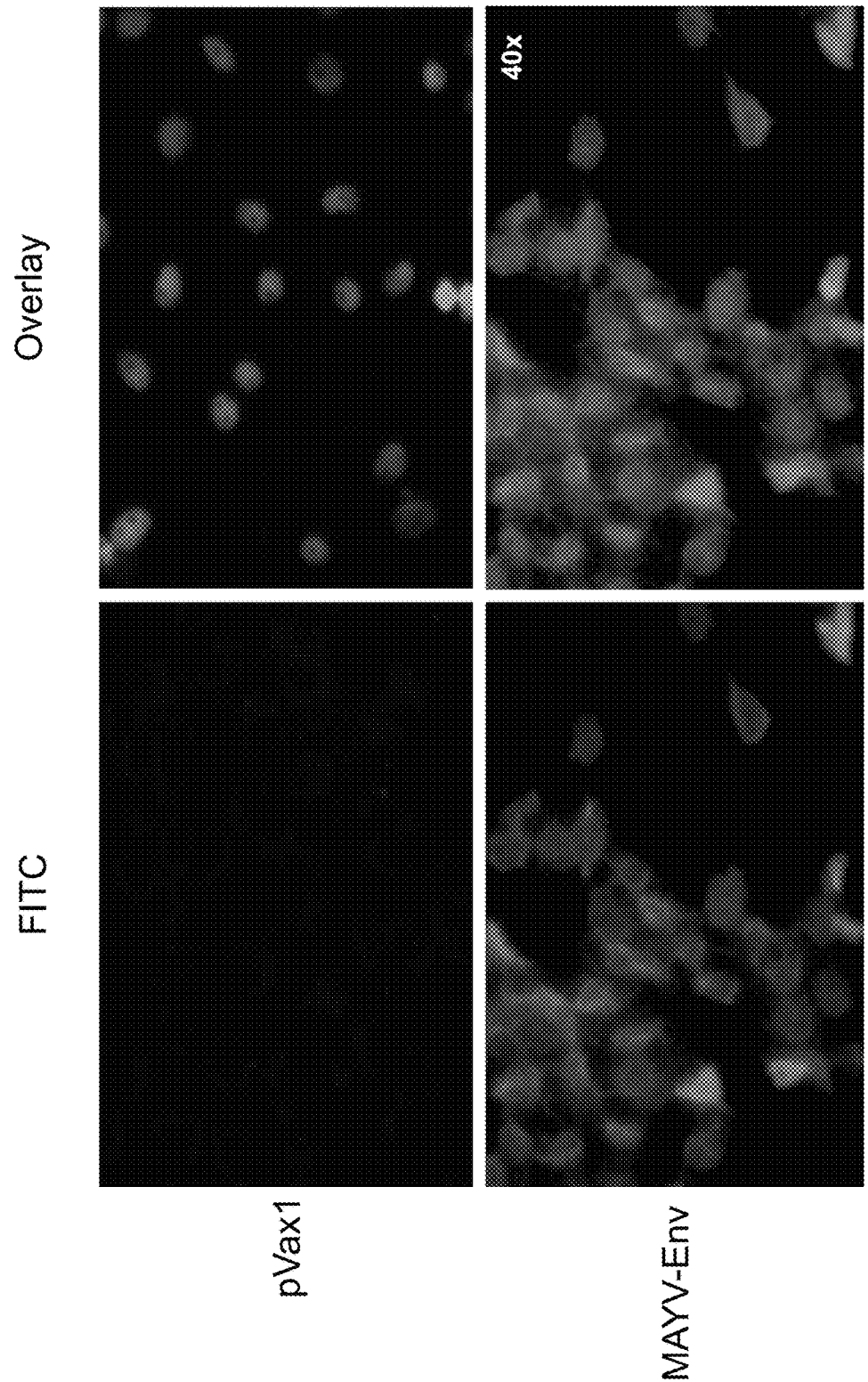
FIG. 11 depicts an immunofluorescence assay demonstrating that IgG generated from MAYV-Env administered mice was capable of binding to MAYV-infected Vero cells.
Figure 12:
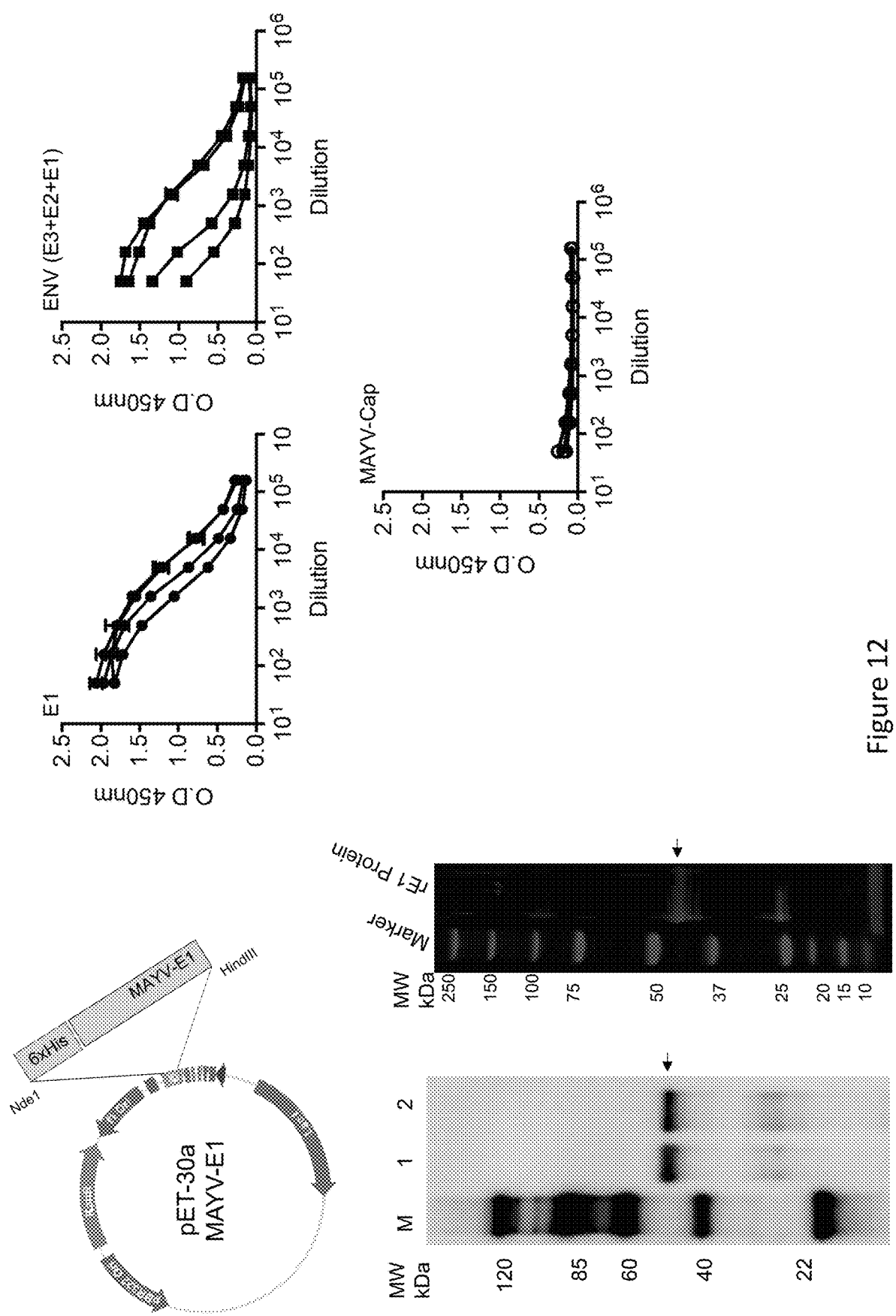
FIG. 12 depicts the development, expression, purification, and characterization of MAYV-Envelope Protein-(E1) purification.

Characterization of MAYV-Vaccine by Western blot analysis demonstrated that the vaccines are well expressed in vitro. The immunoblot indicates that the MAYV-Env sera recognized Envelope protein, confirming the specificity of the envelope protein expression as well as optimized DNA vaccines induce very strong humoral responses and was shown to be immunogenic (FIG. 10). An immunofluorescence assay demonstrated that IgG generated from MAYV-Env administered mice was capable of binding to MAYV-infected Vero cells (FIG. 11). The Immune profile of E1, E2 & E3 appear particularly relevant for vaccine development (FIG. 12).

Figure 13:
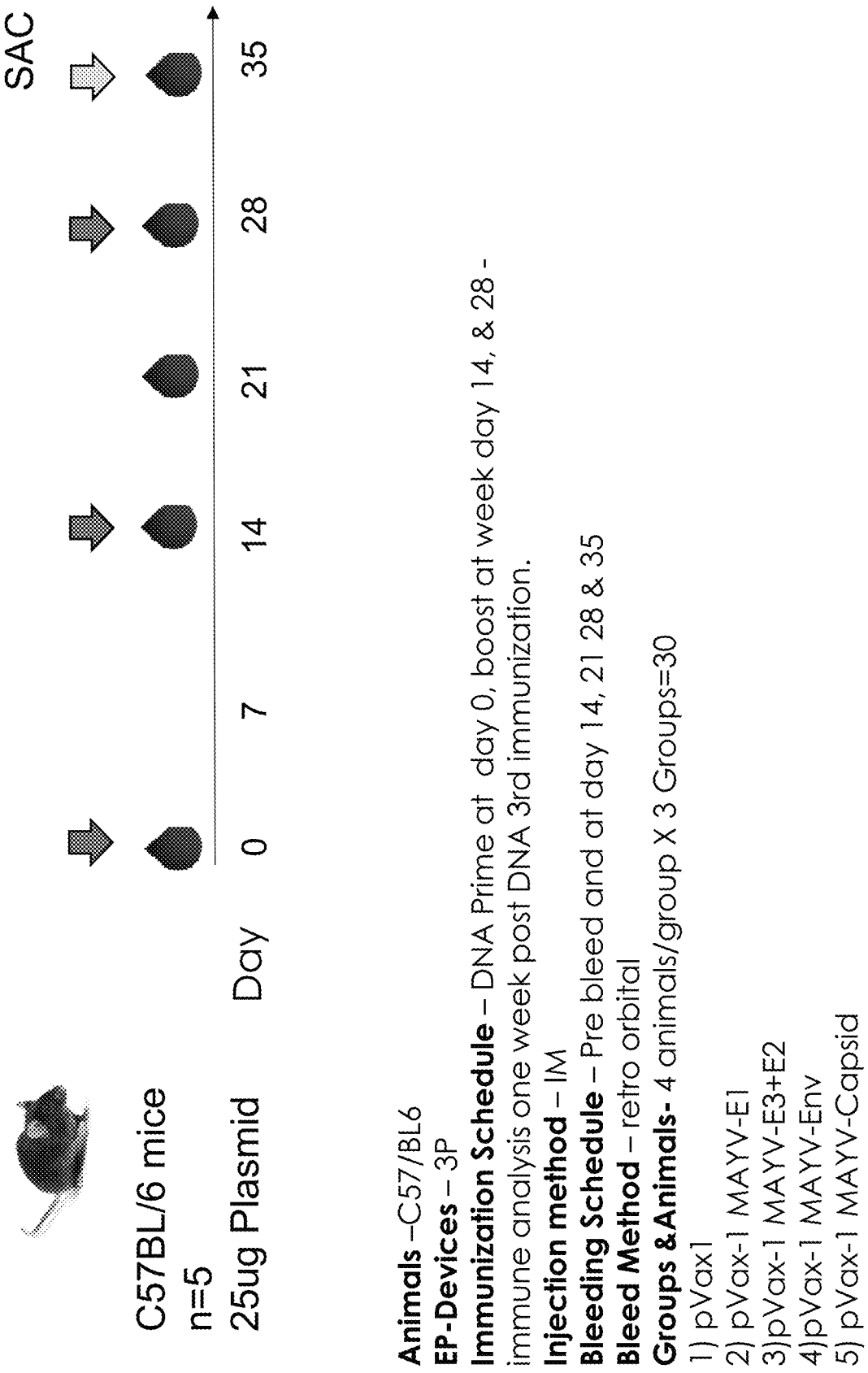
FIG. 13 depicts the design of MAYV vaccine immunization studies in mice.

Immunization studies of the MAYV vaccine in mice were carried out. C57/BL6 mice were DNA primed at day 0, and received a boost at week day 14, & 28. Immune analysis was carried out one week post DNA 3rd immunization. Mice (4 animals/group) received one of: pVAX-1; pVAX-1 MAYV-E1; pVAX-1 MAYV-E3: E2; pVAX-1 MAYV-ENV or pVAX-1 MAYV-Capsid (FIG. 13).

A study of the MAYV-vaccines induces high levels of seroconversion in mice. MAYV-antibodies react to MAYV-Env or MAYV-Capsid antigen appear specific and react in western blot analysis. 100% Seroconversion is observed after a single immunization of MAYV-Env vaccine. Potent cellular immune responses are induced and dominant epitopes for each vaccine were characterized. Induction of polyfunctionality is also induced driving $CD3^+/CD4^+$ and $CD3^+/CD8^+$ T cells (FIGS. 5, 7, 14-18).

Experiments were performed to examine the ability of immunization with MAYV-Env vaccine to protect against MAYV challenge. A129 mice (n=10/group) which are lacking the type I interferon a/b receptor and thus prone to MAYV infection were immunized twice with 25 µg of control pVax1 or MAYV-Env vaccine at 2-week intervals into the quadriceps muscles by i.m injection with electroporation. Animals were challenged on day 21, one week after the second immunization with $1\times10^2$ plaque-forming units (PFU) of MAYV virus (VR1277 viral strain) and were checked daily for clinical signs of infection. It was observed that 100% of MAYV-Env immunized mice were protected against infection (FIG. 7A), and that 100% of MAYV-Env immunized mice displayed no signs of weight loss (FIG. 7B).

In conclusion, the data presented herein demonstrates that the MAYV novel consensus DNA vaccine can be effectively delivered using in vivo EP, which results in the activation of a broad immune response (both cellular and humoral responses).

Example 3

Anti-Mayaro virus (MAYV) "DNA monoclonal antibodies" (DMAb) can be generated via intramuscular electroporation of plasmid DNA.

Figures 14A, 14B:
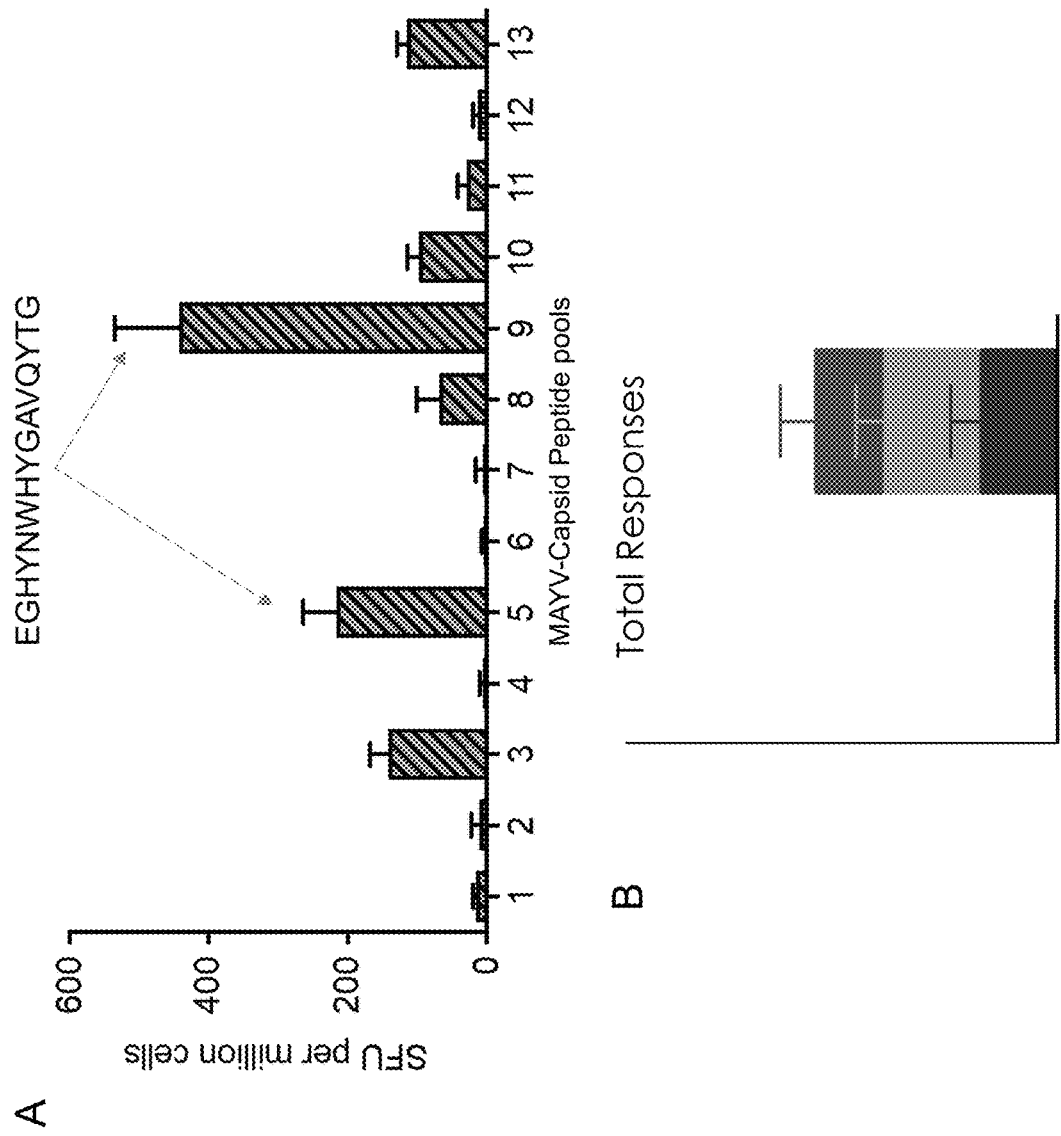
FIG. 14 depicts experimental results demonstrating cellular immune responses induction by MAYV-Capsid and the MHC-class 1 binding prediction.

As described herein, an optimized, synthetic DNA vector platform (DMAb) to deliver encoded mAb heavy and light chains directly into skeletal muscle was designed, employing the cells as biological factories that will secrete a functional antibody at detectable levels in systemic circulation. DMAbs encoding anti-MAYV mAbs that target the MAYV Capsid or Envelope proteins are developed. DMAb nucleotide and amino acid optimized before insertion into a highly-optimized plasmid backbone. A plasmid capable of producing full-length, anti-MAYV mAbs was designed using coding sequences for the variable heavy (VH) and light (VL) immunoglobulin (Ig) chains procured from DNA immunized hybridoma (FIG. 14).

Figure 15:
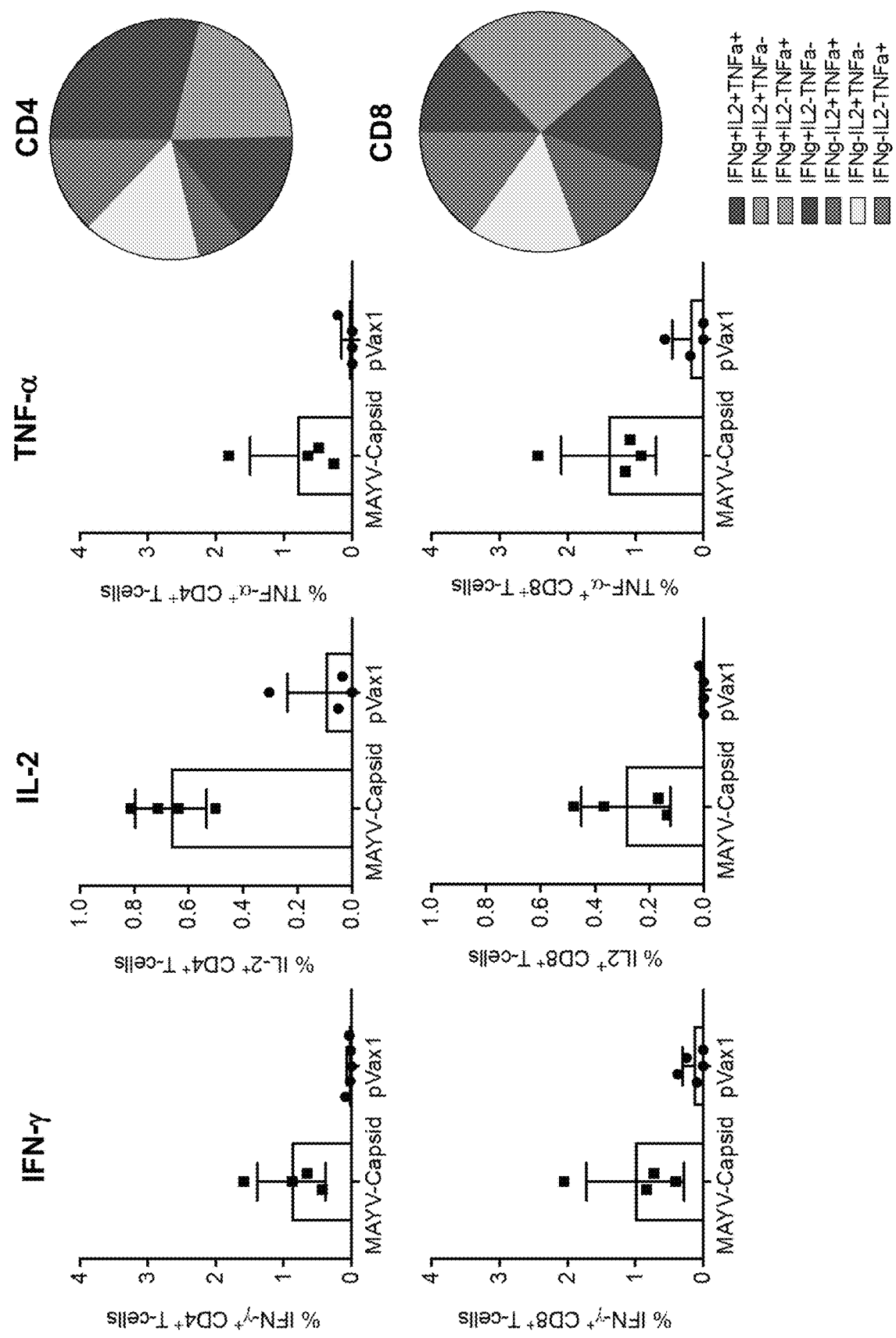
FIG. 15 depicts the functional profile of CD4+ and CD8+ T cell responses elicited by MAYV-Capsid vaccine.
Figure 16:
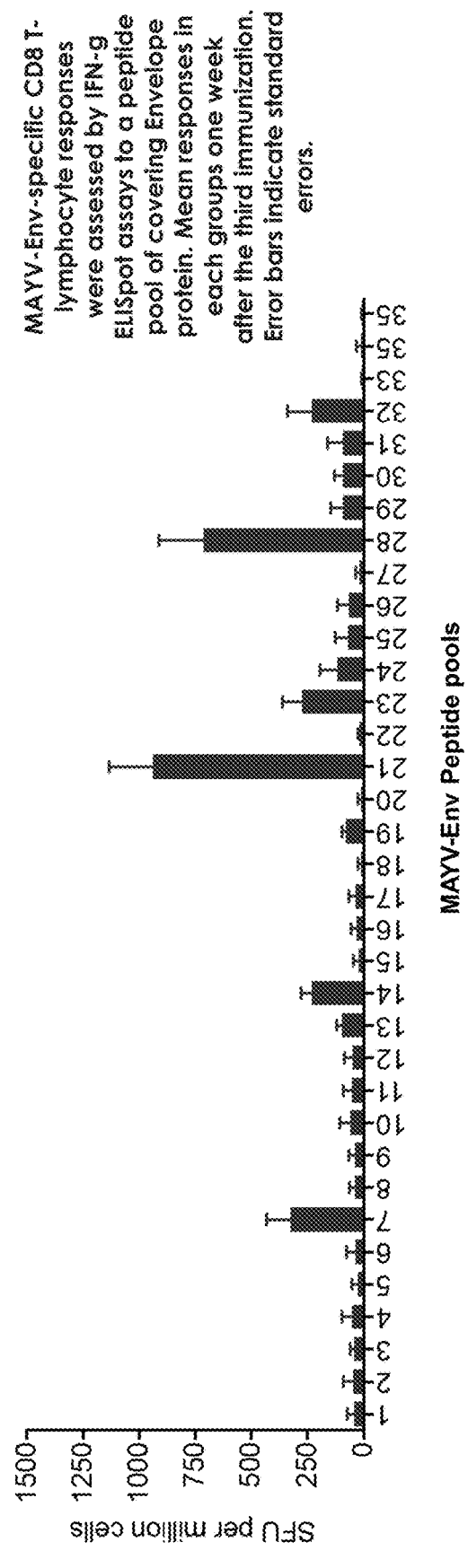
FIG. 16 depicts experimental results demonstrating cellular immune responses elicited by MAYV-Env vaccines.
Figure 16:
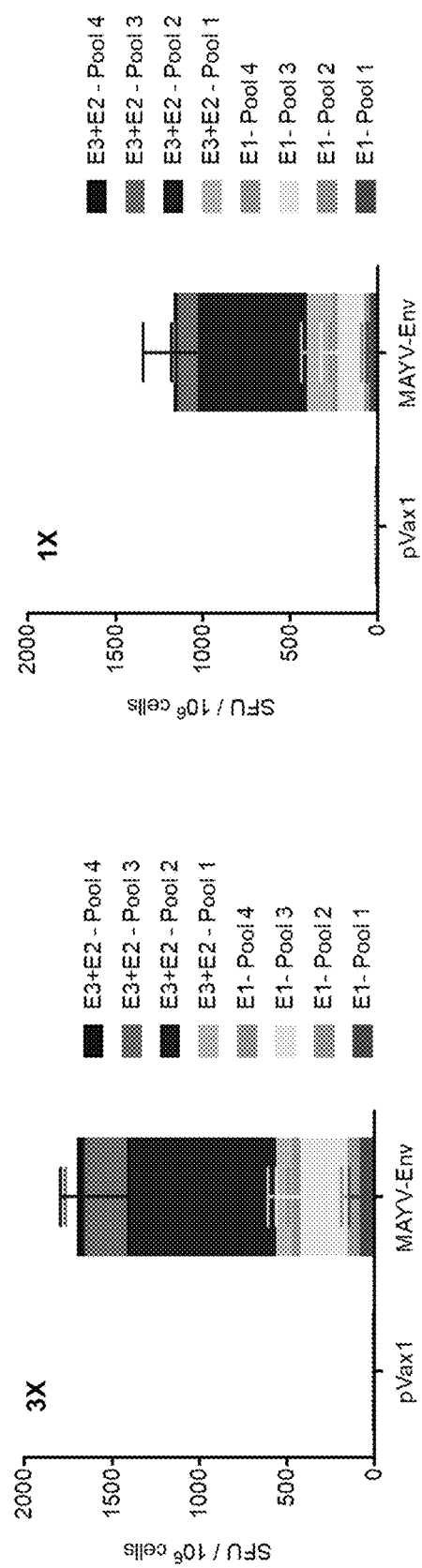
Figure 17:
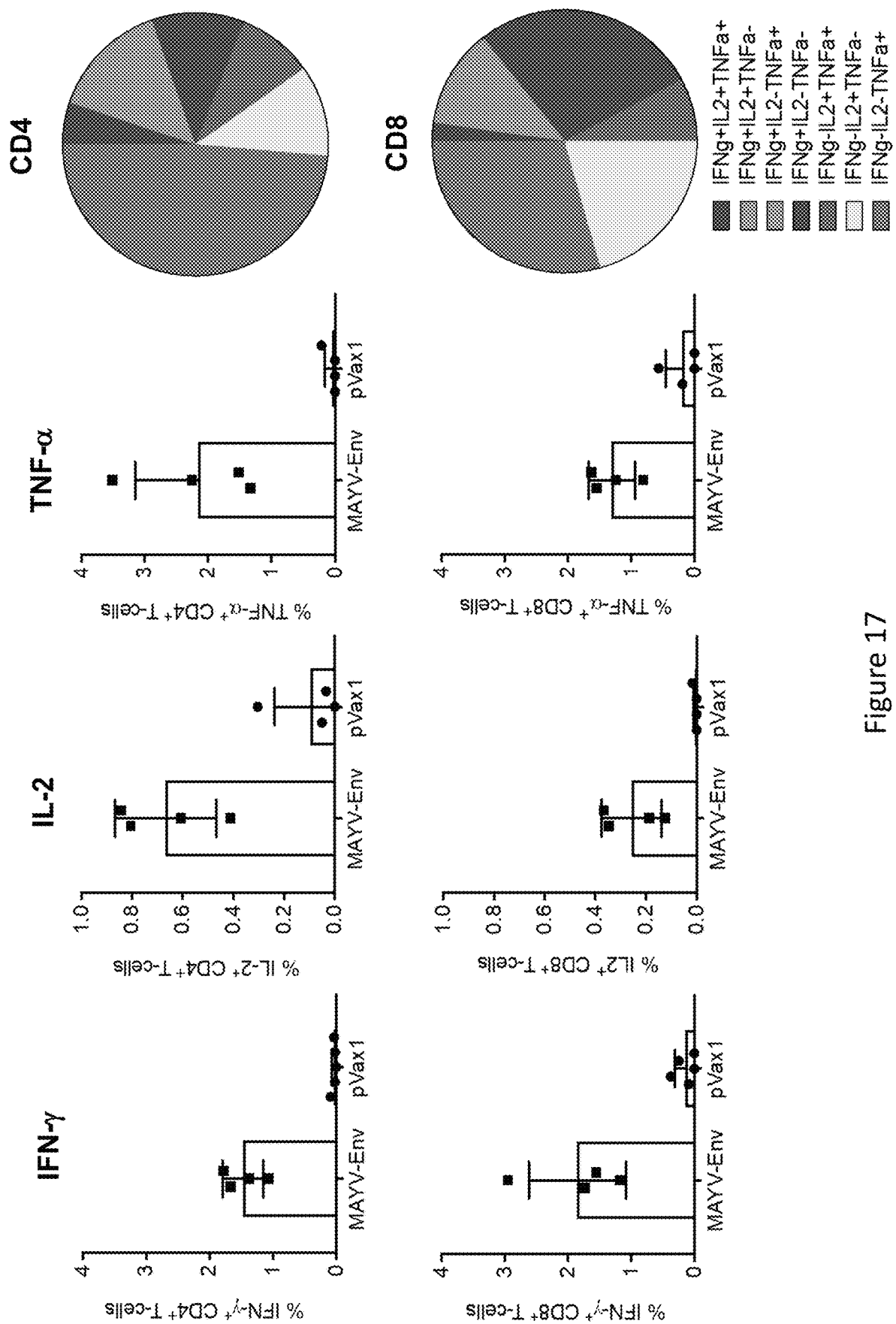
FIG. 17 depicts experimental results demonstrating the functional profile of CD4+ and CD8+ T cell responses elicited by MAYV-Env vaccine.
Figure 18:
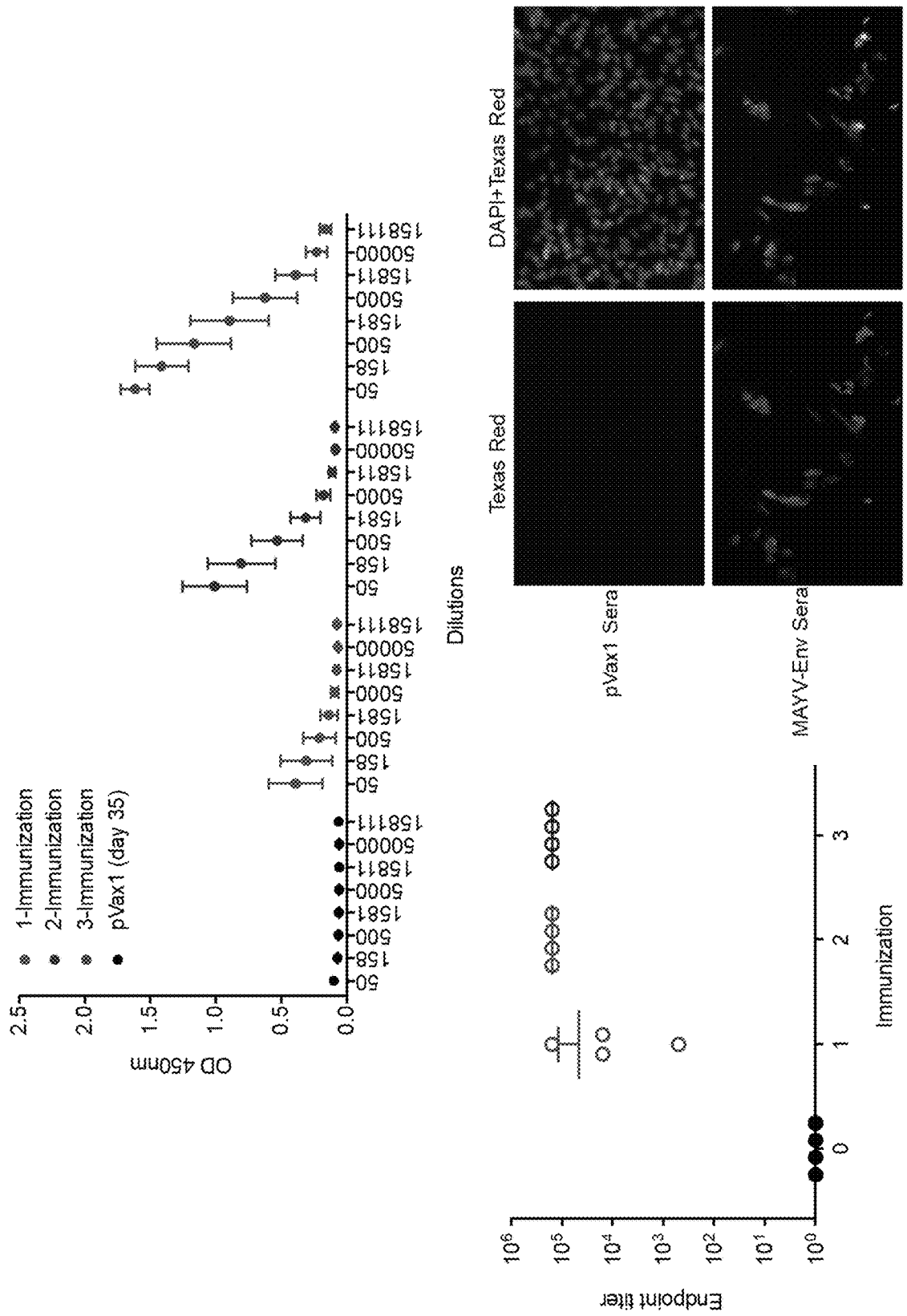
FIG. 18 depicts experimental results demonstrating induction of antibodies in mice-MAYV-Env Vaccine.

Quantification of total human IgG levels were evaluated by ELISA of supernatants from cells transfected with anti-MAYV-DMAb plasmids. Plasmids are capable of producing detectable human anti-MAYV-Env-IgG1 in serum on post DNA immunization. Results confirm plasmids are capable of directing IgG production (FIG. 15).

Administration of one or more nucleic acid molecules encoding anti-MAYV DMAbs in a subject via intramuscular (IM) or intradermal (ID) injection, followed by in vivo electroporation (EP) produces MAYV DMAbs detectable in serum for >3 months, with Cmax serum levels comparable to protein-delivered human IgG1. The muscle expresses, assembles, and secretes functional mAb in vivo at levels detectable in systemic circulation. In the field, MAYV DMAbs could be administered in advance during a possible MAYV outbreak.

MAYV DMAbs provide preventative protection against lethal MAYV challenge and offer long-lasting preventative protection against MAYV infection. Further, MAYV DMAbs protect against MAYV-related diseases or disorders including weight loss and arthropathies.

Example 4

Vaccination is known to exhibit a lag phase before generation of immunity; thus, there is a gap of time during infection before an immune response is in effect. The following provides specific novel approaches that utilizes the benefit of vaccines and the native immune response along with a rapid generation of effective immunity using the DNA synthetic antibodies or dMabs.

An antibody-based prophylaxis/therapy entailing the electroporation mediated delivery of synthetic plasmids, encoding biologically active anti-Mayaro virus (MAYV) mAb (designated dMAb), was designed and evaluated for antiviral efficacy as well as for the ability to overcome shortcomings inherent with conventional active vaccination by a novel passive immune-based strategy. One intramuscular injection of the MAYV-dMAb produces antibodies in vivo more rapidly than active vaccination with a MAYV-DNA vaccine. This dMAb neutralizes diverse MAYV clinical isolates and protected mice from viral challenge. Combinations of both afford rapid as well as long-lived protection.

Thus, it is disclosed herein that a DNA based dMAb strategy induces rapid protection against an emerging viral infection, which can be combined with DNA vaccination providing a uniquely both short term and long-term protection against this emerging infectious disease. These studies have implications for pathogen treatment and control strategies.

Development of MAYV-DNA vaccines and anti-MAYV dMABs are described in Examples 2 and 3, respectively.

One potential issue of combining antibody delivery with vaccination approaches is that the antibodies can neutralize many traditional vaccines and thus are incompatible platforms. The co-administration of anti-MAYV dMAb and MAYV antigen-DNA results in anti-MAYV dMAb mediated rapid protection from infection and death after MAYV challenge and strong T-cell responses mediated by MAYV antigen-DNA. This demonstrates the lack of interference of these approaches. Accordingly, both anti-MAYV dMAb and MAYV-DNA vaccines can be administered simultaneously without reciprocal interference, providing immediate and long-lived protection via systemic humoral and cellular immunity.

Subjects administered anti-MAYV dMAbs are fully protected from viral challenge shortly after administration, whereas subjects do not survive infection following a single immunization with MAYV-DNA vaccine, owing presumably to an insufficient time to mount protective immunity. However, MAYV-DNA provides complete protection after an immunization regimen followed by challenge at later time points. A similar level of protection occurs in subjects administered a single dose of anti-MAYV dMAbs, although protection wanes over time. Notably, the co-delivery of anti-MAYV dMAbs and MAYV-DNA produces rapid and persistent humoral and cellular immunity, suggesting that a combination approach can have additive or synergistic effects. Importantly, co-delivery of anti-MAYV dMAbs and MAYV-DNA are not antagonistic in terms of the development of short- or long-term protective immune responses.

It is understood that the foregoing detailed description and accompanying examples are merely illustrative and are not to be taken as limitations upon the scope of the invention, which is defined solely by the appended claims and their equivalents.

Various changes and modifications to the disclosed embodiments, will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A composition composition comprising a nucleic acid molecule comprising a nucleotide sequence encoding a Mayaro virus (MAYV) antigen wherein the MAYV antigen comprises MAYV-E1, MAYV-E2, MAYV-E3, and MAYV-6K, wherein the MAYV antigen comprises SEQ ID NO:116.

2. The composition of claim 1, wherein the nucleic acid molecule encoding MAYV antigen comprises a nucleotide sequence selected from the group consisting of: SEQ ID NO:117, a nucleotide sequence that is 90% identical or greater to SEQ ID NO:117, a fragment of SEQ ID NO:117 and a fragment of a nucleotide sequence that is 90% identical or greater to SEQ ID NO:117.

3. The composition of claim 1, wherein
a) the composition further comprises nucleic acid sequences that encode one or more proteins selected from the group consisting of: IL-12, IL-15 and IL-28; or
b) the MAYV antigen is linked to an IgE leader sequence.

4. A method of inducing an immune response comprising administering the composition of claim 1 to an individual in an amount effective to induce an immune response in said individual.

5. A nucleic acid molecule comprising SEQ ID NO: 117 or a nucleotide sequence that is 90% identical or greater to SEQ ID NO:117.

6. The nucleic acid molecule of claim 5, wherein
a) the nucleic acid molecule further comprises a nucleotide sequence encoding a cleavage domain;
b) the nucleic acid molecule comprises an expression vector; or
c) the nucleotide sequence encodes a leader sequence.

7. A composition comprising the nucleic acid molecule of claim 5.

8. The composition of claim 7, further comprising a pharmaceutically acceptable excipient.

9. A protein comprising SEQ ID NO:116.

10. A method of inducing an immune response comprising administering the nucleic acid molecule of claim 5 or a composition thereof to an individual in an amount effective to induce an immune response in said individual.

11. The method of claim 10, wherein the immune response is an anti-MAYV immune response.

* * * * *

SEQUENCE LISTING

<160> NUMBER OF SEQ ID NOS: 126

<210> SEQ ID NO 1
<211> LENGTH: 729
<212> TYPE: PRT
<213> ORGANISM: Artificial Sequence
<220> FEATURE:
<223> OTHER INFORMATION: MAYV-M17H32

<400> SEQUENCE: 1

```
Met Asp Trp Thr Trp Arg Ile Leu Phe Leu Val Ala Ala Thr Gly
1               5                   10                  15

Thr His Ala Gln Val Gln Leu Gln Gln Ser Gly Ala Glu Leu Met Lys
                20                  25                  30

Pro Gly Ala Ser Val Lys Leu Ser Cys Lys Ala Thr Gly Tyr Thr Phe
            35                  40                  45

Thr Gly Tyr Trp Ile Glu Trp Val Lys Gln Arg Pro Gly His Gly Leu
        50                  55                  60

Glu Trp Ile Gly Glu Ile Leu Pro Gly Ser Gly Ser Thr Asn Tyr Asn
65                  70                  75                  80

Glu Lys Phe Lys Gly Lys Ala Thr Phe Thr Ala Asp Thr Ser Ser Asn
                85                  90                  95

Thr Ala Tyr Met Gln Leu Ser Ser Leu Thr Thr Glu Asp Ser Ala Ile
            100                 105                 110

Tyr Tyr Cys Ala Arg Gly Tyr Tyr Gly Ser Ser Tyr Pro Arg Ala Met
        115                 120                 125

Asp Tyr Trp Gly Gln Gly Thr Ser Val Thr Val Ser Ser Ala Ser Thr
```

```
              130                 135                 140
Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Lys Thr Tyr Thr Cys
210                 215                 220

Asn Val Asp His Lys Pro Ser Asn Thr Lys Val Asp Lys Arg Val Ser
225                 230                 235                 240

Pro Asn Met Val Pro His Ala His His Ala Gln Ala Pro Glu Phe Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
            275                 280                 285

Gln Glu Asp Pro Glu Val Gln Phe Asn Trp Tyr Val Asp Gly Val Glu
290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
                340                 345                 350

Ile Glu Lys Thr Ile Ser Lys Ala Lys Gly Gln Pro Arg Glu Pro Gln
            355                 360                 365

Val Tyr Thr Leu Pro Pro Ser Gln Glu Glu Met Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
                420                 425                 430

Val Asp Lys Ser Arg Trp Gln Glu Gly Asn Val Phe Ser Cys Ser Val
            435                 440                 445

Met His Glu Ala Leu His Asn His Tyr Thr Gln Lys Ser Leu Ser Leu
450                 455                 460

Ser Leu Gly Lys Arg Gly Arg Lys Arg Arg Ser Gly Ser Gly Ala Thr
465                 470                 475                 480

Asn Phe Ser Leu Leu Lys Gln Ala Gly Asp Val Glu Glu Asn Pro Gly
                485                 490                 495

Pro Met Val Leu Gln Thr Gln Val Phe Ile Ser Leu Leu Leu Trp Ile
                500                 505                 510

Ser Gly Ala Tyr Gly Glu Ile Val Leu Thr Gln Ser Ile Pro Ser Leu
            515                 520                 525

Ser Val Ser Val Gly Glu Thr Val Thr Ile Thr Cys Arg Ala Ser Glu
530                 535                 540

Asn Ile Tyr Ser Asn Leu Ala Trp Tyr Gln Gln Lys Gln Gly Lys Ser
545                 550                 555                 560
```

```
Pro Gln Leu Leu Val Tyr Ala Ala Thr Asn Leu Ala Asp Gly Val Pro
                565                 570                 575

Ser Arg Phe Ser Gly Ser Gly Ser Gly Thr Gln Tyr Ser Leu Lys Ile
            580                 585                 590

Asn Ser Leu Gln Ser Glu Asp Phe Gly Ser Tyr Tyr Cys Gln His Phe
        595                 600                 605

Trp Gly Thr Pro Ser Arg Ser Val Leu Gly Pro Ser Trp Lys Asn Thr
    610                 615                 620

Val Ala Ala Pro Ser Val Phe Ile Phe Pro Pro Ser Asp Glu Gln Leu
625                 630                 635                 640

Lys Ser Gly Thr Ala Ser Val Val Cys Leu Leu Asn Asn Phe Tyr Pro
                645                 650                 655

Arg Glu Ala Lys Val Gln Trp Lys Val Asp Asn Ala Leu Gln Ser Gly
            660                 665                 670

Asn Ser Gln Glu Ser Val Thr Glu Gln Asp Ser Lys Asp Ser Thr Tyr
        675                 680                 685

Ser Leu Ser Ser Thr Leu Thr Leu Ser Lys Ala Asp Tyr Glu Lys His
    690                 695                 700

Lys Val Tyr Ala Cys Glu Val Thr His Gln Gly Leu Ser Ser Pro Val
705                 710                 715                 720

Thr Lys Ser Phe Asn Arg Gly Glu Cys
                725
```

<210> SEQ ID NO 2
<211> LENGTH: 2187
<212> TYPE: DNA
<213> ORGANISM: Artificial Sequence
<220> FEATURE:
<223> OTHER INFORMATION: MAYV-M17H32

<400> SEQUENCE: 2

```
atggattgga catggaggat tctgtttctg gtcgccgccg ccactggaac tcacgctcag      60
gtgcagctgc agcagtcagg ggccgagctg atgaagcctg gcgcctccgt gaagctgtct     120
tgcaaggcca ccggctacac cttcacaggc tattggatcg agtgggtgaa gcagcggccc     180
ggacacggcc tggagtggat cggcgagatc ctgcctggct ccggctctac aaactacaat     240
gagaagttca agggcaaggc cacctttaca gccgacacca gctccaacac agcctatatg     300
cagctgtcta gcctgaccac agaggatagc gccatctact attgtgccag ggctactat      360 ggctcctctt accctcgcgc catggactat tggggccagg gcacctccgt gacagtgagc     420
tccgcctcta ccaagggccc aagcgtgttt ccactggcac cttgcagccg ctccacctct     480
gagagcacag ccgccctggg ctgtctggtg aaggattact tcccagagcc cgtgacagtg     540
tcctggaact ctggcgccct gacctctggc gtgcacacat ttccagccgt gctgcagtct     600
agcggcctgt actccctgtc ctctgtggtg accgtgccca gctcctctct gggcaccaag     660
acatatacct gcaacgtgga ccacaagcct tccaatacaa aggtggataa gagggtgtct     720
cctaatatgg tgccacacgc ccaccacgca caggcaccag agttcctggg cggccctagc     780
gtgttcctgt ttccccctaa gcctaaggac accctgatga tctccagaac ccagaggtg      840 acatgcgtgg tggtggacgt gtctcaggag gaccccgagg tgcagttcaa ctggtacgtg     900
gatggcgtgg aggtgcacaa tgccaagacc aagcccaggg aggagcagtt taacagcacc     960
tacagagtgg tgtccgtgct gacagtgctg caccaggact ggctgaacgg caaggagtat    1020
aagtgcaagg tgagcaataa gggcctgccc agctccatcg agaagaccat ctccaaggca    1080
```

```
aagggacagc caagggagcc acaggtgtac acactgccac ccagccagga ggagatgacc   1140
aagaaccagg tgtccctgac atgtctggtg aagggcttct atccatctga catcgccgtg   1200
gagtgggaga gcaatggcca gcccgagaac aattacaaga ccacacctcc agtgctggac   1260
agcgatggct ccttctttct gtattccagg ctgaccgtgg ataagtctag atggcaggag   1320
ggcaacgtgt tttcctgctc tgtgatgcac gaggccctgc acaatcacta cacccagaag   1380
agcctgtccc tgtctctggg caagagggga aggaagagga gaagcggctc cggcgccaca   1440
aacttcagcc tgctgaagca ggccggcgat gtggaggaga tcctggcccc aatggtgctg   1500
cagacccagg tgtttatctc tctgctgctg tggatcagcg cgccctacgg cgagatcgtg   1560
ctgacacaga gcatcccctc tctgagcgtg tccgtgggcg agacagtgac catcacatgt   1620
agggcctccg agaacatcta ctctaatctg gcctggtatc agcagaagca gggcaagtcc   1680
cctcagctgc tggtgtacgc agcaaccaac ctggcagacg gagtgccatc tcggttctct   1740
ggcagcggct ccggcacaca gtatagcctg aagatcaatt ctctgcagag cgaggatttc   1800
ggcagctact attgccagca cttttgggga accccatctc gcagcgtgct gggaccctcc   1860
tggaagaaca cagtggccgc ccccagcgtg ttcatctttc cccttccga cgagcagctg   1920
aagagcggaa ccgcatccgt ggtgtgcctg ctgaacaact tctaccctcg ggaggccaag   1980
gtgcagtgga aggtggataa cgccctgcag tccggcaatt ctcaggagag cgtgaccgag   2040
caggactcca aggattctac atatagcctg tctagcaccc tgacactgag caaggccgac   2100
tacgagaagc acaaggtgta tgcctgcgag gtcacccacc aggggctgtc ttcacccgtc   2160
acaaaatcct tcaatagagg ggaatgt                                      2187
```

<210> SEQ ID NO 3
<211> LENGTH: 733
<212> TYPE: PRT
<213> ORGANISM: Artificial Sequence
<220> FEATURE:
<223> OTHER INFORMATION: MAYV-M17B82

<400> SEQUENCE: 3

Met Asp Trp Thr Trp Arg Ile Leu Phe Leu Val Ala Ala Ala Thr Gly
1               5                   10                  15

Thr His Ala Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Trp Ile Thr Trp Val Lys Gln Arg Pro Gly Gln Gly Leu
    50                  55                  60

Glu Trp Ile Gly Asp Ile Tyr Pro Gly Ser Gly Ser Thr Asn Tyr Asn
65                  70                  75                  80

Glu Lys Phe Lys Ser Lys Ala Thr Leu Thr Val Asp Thr Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Lys Ala Asn Trp Asp Met Ala Trp Phe Ala Tyr
        115                 120                 125

Trp Gly Gln Gly Thr Ser Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

-continued

```
Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Ser Pro Asn
225                 230                 235                 240

Met Val Pro His Ala His His Ala Gln Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460

Gly Lys Arg Gly Arg Lys Arg Arg Ser Gly Ser Gly Ala Thr Asn Phe
465                 470                 475                 480

Ser Leu Leu Lys Gln Ala Gly Asp Val Glu Glu Asn Pro Gly Pro Met
                485                 490                 495

Val Leu Gln Thr Gln Val Phe Ile Ser Leu Leu Leu Trp Ile Ser Gly
            500                 505                 510

Ala Tyr Gly Asp Ile Val Met Thr Gln Ser Pro Lys Phe Leu Pro Val
        515                 520                 525

Ser Leu Gly Asp Gln Ala Ser Ile Ser Cys Arg Ser Ser Gln Ser Leu
    530                 535                 540

Val His Ser Asn Gly Asn Thr Tyr Leu His Trp Tyr Leu Gln Lys Pro
545                 550                 555                 560

Gly Gln Ser Pro Lys Leu Leu Ile Tyr Lys Val Ser Asn Arg Phe Ser
                565                 570                 575

Gly Val Pro Asp Arg Phe Ser Gly Ser Gly Ser Gly Thr Asp Phe Thr
```

-continued

```
            580                 585                 590

Leu Lys Ile Ser Arg Val Glu Ala Glu Asp Leu Gly Val Tyr Phe Cys
        595                 600                 605

Ser Gln Ser Thr His Val Pro Tyr Thr Phe Gly Ser Gly Thr Lys Leu
    610                 615                 620

Glu Ile Lys Thr Val Ala Ala Pro Ser Val Phe Ile Phe Pro Pro Ser
625                 630                 635                 640

Asp Glu Gln Leu Lys Ser Gly Thr Ala Ser Val Val Cys Leu Leu Asn
                645                 650                 655

Asn Phe Tyr Pro Arg Glu Ala Lys Val Gln Trp Lys Val Asp Asn Ala
            660                 665                 670

Leu Gln Ser Gly Asn Ser Gln Glu Ser Val Thr Glu Gln Asp Ser Lys
        675                 680                 685

Asp Ser Thr Tyr Ser Leu Ser Ser Thr Leu Thr Leu Ser Lys Ala Asp
    690                 695                 700

Tyr Glu Lys His Lys Val Tyr Ala Cys Glu Val Thr His Gln Gly Leu
705                 710                 715                 720

Ser Ser Pro Val Thr Lys Ser Phe Asn Arg Gly Glu Cys
                725                 730

<210> SEQ ID NO 4
<211> LENGTH: 2199
<212> TYPE: DNA
<213> ORGANISM: Artificial Sequence
<220> FEATURE:
<223> OTHER INFORMATION: MAYV-M17B82

<400> SEQUENCE: 4
atggactgga cttggaggat tctgtttctg gtcgccgccg caactggaac tcacgctcag      60
gtgcagctgc agcagcctgg ggccgagctg gtgaagcctg gcgcctccgt gaagatgtct     120
tgcaaggcca gcggctacac cttcacatcc tattggatca cctgggtgaa gcagaggcca     180
ggacagggcc tggagtggat cggcgacatc taccccggct ctggcagcac aaactataat     240
gagaagttta agagcaaggc caccctgaca gtggatacaa gctcctctac cgcctacatg     300
cagctgagct ccctgacctc cgaggactct gccgtgtact attgtgcccg gaaggccaac     360
tgggatatgg cctggttcgc ctattggggc cagggcacat ccgtgaccgt gtctagcgcc     420
tccaccaagg gaccaagcgt gttcccactg gcaccttgct cccgctctac aagcgagtcc     480
accgccgccc tgggatgtct ggtgaaggac tacttcccag agcccgtgac agtgagctgg     540
aactccggcg ccctgacatc tggcgtgcac acctttcctg ccgtgctgca gtcctctggc     600
ctgtacagcc tgagctccgt ggtgaccgtg ccctctagct ccctgggcac caagacatat     660
acctgcaacg tggaccacaa gcctagcaat acaaaggtgg ataagagggt gtcccctaat     720
atggtgccac acgcacacca cgcacaggca cctgagttcc tgggcggccc aagcgtgttc     780
ctgtttcccc ctaagcccaa ggacaccctg atgatctcca gaacacctga ggtgacctgc     840
gtggtggtgg acgtgtctca ggaggacccc gaggtgcagt tcaactggta cgtggatggc     900
gtggaggtgc acaatgccaa gaccaagcca agggaggagc agtttaatag cacctacaga     960
gtggtgtccg tgctgacagt gctgcaccag gactggctga acggcaagga gtataagtgc    1020
aaggtgagca ataagggcct gccctctagc atcgagaaga ccatctccaa ggcaaaggga    1080
cagccaaggg agccacaggt gtacacactg ccaccctctc aggaggagat gaccaagaac    1140
caggtgagcc tgacatgtct ggtgaagggc ttctatcctt ccgacatcgc cgtggagtgg    1200
```

```
gagtctaatg gccagccaga gaacaattac aagaccacac ctccagtgct ggactctgat    1260
ggcagcttct ttctgtattc caggctgacc gtggataagt ctagatggca ggagggcaac    1320
gtgttctctt gcagcgtgat gcacgaggcc ctgcacaatc actacaccca gaagtccctg    1380
tctctgagcc tgggcaagag gggaaggaag aggagatccg gctctggcgc cacaaacttt    1440
tccctgctga agcaggccgg cgatgtggag gagaatcctg gcccaatggt gctgcagacc    1500
caggtgttca tctctctgct gctgtggatc agcggcgcct acggcgacat cgtgatgaca    1560
cagagcccca gtttctgccg cgtgagcctg ggcgatcagg caagcatctc ctgtcggtcc    1620
tctcagtccc tggtgcactc taacggcaat acctacctgc actggtatct gcagaagcca    1680
ggccagagcc ccaagctgct gatctataag gtgagcaacc ggttctccgg cgtgccagac    1740
cgcttttctg gcagcggctc cggcacagat ttcaccctga agatctcccg cgtggaggca    1800
gaggacctgg gcgtgtactt ctgctctcag agcacacacg tgccatatac ctttggcagc    1860
ggcacaaagc tggagatcaa gaccgtggcc gcccccagcg tgttcatctt tccccctagc    1920
gacgagcagc tgaagtctgg cacagccagc gtggtgtgcc tgctgaacaa cttctacccc    1980
cgggaggcca aggtgcagtg gaaggtggat aacgccctgc agtccggcaa ttctcaggag    2040
agcgtgaccg agcaggactc caaggattct acatatagcc tgagctccac actgaccctg    2100
agcaaggccg attacgagaa gcacaaggtg tatgcctgcg aggtcaccca ccagggactg    2160
agcagccccg tcaccaaatc tttcaataga ggagaatgt                          2199
```

<210> SEQ ID NO 5
<211> LENGTH: 119
<212> TYPE: PRT
<213> ORGANISM: Artificial Sequence
<220> FEATURE:
<223> OTHER INFORMATION: MAYV-VH-C12-2 Heavy Chain

<400> SEQUENCE: 5

```
Thr Ala Thr Gly Val His Ser Gln Ile Gln Leu Val Gln Ser Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Asn Pro Asn Asn Gly Gly Thr Asn Tyr Asn Gln Lys Phe
    50                  55                  60

Lys Gly Lys Ala Thr Phe Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Arg Glu Tyr Gly Asn Pro Phe Ala Tyr Trp Gly Gln Gly
            100                 105                 110

Thr Thr Val Thr Val Ser Ser
        115
```

<210> SEQ ID NO 6
<211> LENGTH: 121
<212> TYPE: PRT
<213> ORGANISM: Artificial Sequence
<220> FEATURE:
<223> OTHER INFORMATION: MAYV-VH-C9-2 Heavy Chain

<400> SEQUENCE: 6

Glu Val Gln Leu Gln Gln Ser Gly Ala Glu Leu Val Arg Pro Gly Ala

```
                1               5                   10                  15
            Ser Val Lys Leu Ser Cys Lys Ala Ser Gly Cys Thr Phe Thr Ser Tyr
                            20                  25                  30

Trp Ile Asn Trp Val Lys Gln Arg Pro Gly Gln Gly Leu Glu Trp Ile
                            35                  40                  45

Gly Asn Ile Tyr Pro Ser Asp Ser Tyr Thr Asn Tyr Asn Gln Lys Phe
                            50                  55                  60

Lys Gly Lys Ala Thr Leu Thr Val Asp Lys Ser Ser Thr Ala Tyr
             65                 70                  75                  80

Met Gln Leu Ser Ser Pro Thr Ser Glu Asp Ser Ala Val Tyr Tyr Cys
                            85                  90                  95

Thr Arg Trp Ala Tyr Tyr Gly Asn Tyr Tyr Ala Met Asp Tyr Trp Gly
                            100                 105                 110

Gln Gly Thr Ser Val Thr Val Ser Ser
                            115                 120
```

<210> SEQ ID NO 7
<211> LENGTH: 120
<212> TYPE: PRT
<213> ORGANISM: Artificial Sequence
<220> FEATURE:
<223> OTHER INFORMATION: MAYV-VH-C7-1 Heavy Chain

<400> SEQUENCE: 7

```
            Gln Val Gln Leu Gln Gln Ser Gly Ala Glu Leu Val Lys Pro Gly Ala
             1               5                   10                  15

Ser Val Lys Ile Ser Cys Lys Ala Ser Gly Tyr Ala Phe Ser Ser Tyr
                            20                  25                  30

Trp Met Asn Trp Val Lys Gln Arg Pro Gly Lys Gly Leu Glu Trp Ile
                            35                  40                  45

Gly Gln Ile Tyr Pro Gly Asp Gly Asp Thr Ser Tyr Ser Gly Lys Phe
                            50                  55                  60

Lys Gly Lys Ala Thr Leu Thr Ala Asp Lys Ser Ser Thr Ala Tyr
             65                 70                  75                  80

Met Gln Leu Ser Ser Leu Thr Ser Glu Asp Ser Ala Val Tyr Phe Cys
                            85                  90                  95

Ala Arg Leu Gly Ala Tyr Tyr Ser Asn Tyr Glu Ala Tyr Trp Gly Gln
                            100                 105                 110

Gly Thr Ser Val Thr Val Ser Ser
                            115                 120
```

<210> SEQ ID NO 8
<211> LENGTH: 120
<212> TYPE: PRT
<213> ORGANISM: Artificial Sequence
<220> FEATURE:
<223> OTHER INFORMATION: MAYV-VH-C9-4 Heavy Chain

<400> SEQUENCE: 8

```
            Gln Val Gln Leu Lys Glu Ser Gly Gly Gly Val Val Gln Pro Gly Arg
             1               5                   10                  15

Ser Leu Arg Leu Ser Cys Ala Ala Ser Gly Phe Thr Phe Ser Ser Tyr
                            20                  25                  30

Gly Met Arg Trp Val Arg Gln Ala Pro Gly Lys Gly Leu Glu Trp Val
                            35                  40                  45

Ala Val Ile Trp Tyr Asp Gly Ser Asn Lys Tyr Tyr Ala Asp Ser Val
                            50                  55                  60
```

```
Lys Gly Arg Ser Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ile Ala Val Ala Gly Phe Gly Met Asp Val Trp Gly Gln
            100                 105                 110

Gly Thr Thr Val Thr Val Ser Ser
            115                 120

<210> SEQ ID NO 9
<211> LENGTH: 118
<212> TYPE: PRT
<213> ORGANISM: Artificial Sequence
<220> FEATURE:
<223> OTHER INFORMATION: MAYV-VH-D3-7 Heavy Chain

<400> SEQUENCE: 9

Gln Val Gln Leu Gln Gln Pro Gly Ser Glu Leu Val Arg Pro Gly Ala
 1               5                   10                  15

Ser Val Lys Leu Ser Cys Lys Ala Ser Gly Tyr Thr Phe Thr Ser Tyr
                 20                  25                  30

Trp Met His Trp Val Lys Gln Arg Pro Gly Gln Gly Leu Glu Trp Ile
             35                  40                  45

Gly Asn Ile Tyr Pro Gly Ser Gly Ser Thr Asn Tyr Asp Glu Lys Phe
 50                  55                  60

Lys Ser Lys Ala Thr Leu Thr Val Asp Thr Ser Ser Thr Ala Tyr
 65                  70                  75                  80

Met Gln Leu Ser Ser Leu Thr Ser Glu Asp Ser Ala Val Tyr Tyr Cys
                 85                  90                  95

Thr Arg Thr Leu Thr Gly Thr Trp Phe Ala Tyr Trp Gly Gln Gly Thr
            100                 105                 110

Leu Val Thr Val Ser Ala
            115

<210> SEQ ID NO 10
<211> LENGTH: 112
<212> TYPE: PRT
<213> ORGANISM: Artificial Sequence
<220> FEATURE:
<223> OTHER INFORMATION: MAYV-VH-F5-8 Heavy Chain

<400> SEQUENCE: 10

Glu Ala Lys Leu Val Glu Ser Gly Ala Glu Leu Val Arg Pro Gly Ala
 1               5                   10                  15

Ser Val Thr Leu Ser Cys Lys Ala Ser Gly Tyr Thr Phe Thr Asp Tyr
                 20                  25                  30

Glu Met His Trp Val Lys Gln Thr Pro Val His Gly Leu Glu Trp Ile
             35                  40                  45

Gly Ala Ile Asp Pro Glu Thr Gly Gly Thr Ala Tyr Asn Gln Lys Phe
 50                  55                  60

Lys Gly Lys Ala Thr Leu Thr Ala Asp Lys Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Thr Arg Gly Pro Trp Trp Gly Gln Gly Thr Leu Thr Val Ser Ser
            100                 105                 110

<210> SEQ ID NO 11
```

```
<211> LENGTH: 113
<212> TYPE: PRT
<213> ORGANISM: Artificial Sequence
<220> FEATURE:
<223> OTHER INFORMATION: MAYV-VH-B2-2 Heavy Chain
<220> FEATURE:
<221> NAME/KEY: misc_feature
<222> LOCATION: (10)..(10)
<223> OTHER INFORMATION: Xaa can be any naturally occurring amino acid

<400> SEQUENCE: 11

Gln Val Gln Leu Gln Gln Pro Gly Ala Xaa Leu Val Arg Pro Gly Ala
1               5                   10                  15

Le

<223> OTHER INFORMATION: Xaa can be any naturally occurring amino acid

<400> SEQUENCE: 13

```
Gln Val Gln Leu Gln Gln Pro Gly Ala Glu Leu Val Lys Ser Gly Ala
1               5                   10                  15

Ser Val Lys Leu Ser Cys Thr Ala Ser Gly Phe Asn Ile Lys Asp Tyr
            20                  25                  30

Phe Ile His Trp Val Lys Gln Arg Pro Glu Gln Gly Leu Glu Trp Ile
        35                  40                  45

Gly Trp Ile Asp Pro Glu Asn Asp Asp Thr Glu Tyr Ala Pro Lys Phe
    50                  55                  60

Gln Gly Lys Ala Thr Leu Ala Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Asp Asp Gly Tyr Pro Phe Ala Tyr Trp Gly Gln Gly Thr Xaa
            100                 105                 110

Val Thr Val Ser Ser
        115
```

<210> SEQ ID NO 14
<211> LENGTH: 118
<212> TYPE: PRT
<213> ORGANISM: Artificial Sequence
<220> FEATURE:
<223> OTHER INFORMATION: MAYV-VH-F4-1 Heavy Chain

<400> SEQUENCE: 14

```
Glu Ile Gln Leu Gln Gln Ser Gly Gly Gly Leu Val Gln Pro Gly Gly
1               5                   10                  15

Ser Leu Gly Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Arg Met Asn Thr Leu Arg Ala Glu Asp Ser Ala Thr Tyr
                85                  90                  95

Tyr Cys Ala Arg Asp Gly Asn Tyr Phe Asp Tyr Trp Gly Gln Gly Thr
            100                 105                 110

Thr Leu Thr Val Ser Ser
        115
```

<210> SEQ ID NO 15
<211> LENGTH: 122
<212> TYPE: PRT
<213> ORGANISM: Artificial Sequence
<220> FEATURE:
<223> OTHER INFORMATION: MAYV-VH-H3-2 Heavy Chain

<400> SEQUENCE: 15

```
Gln Val Gln Leu Gln Gln Ser Gly Ala Glu Leu Met Lys Pro Gly Ala
1               5                   10                  15

Ser Val Lys Leu Ser Cys Lys Ala Thr Gly Tyr Thr Phe Thr Gly Tyr
            20                  25                  30

Trp Ile Glu Trp Val Lys Gln Arg Pro Gly His Gly Leu Glu Trp Ile
```

```
        35                  40                  45

Gly Glu Ile Leu Pro Gly Ser Gly Ser Thr Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Thr Glu Asp Ser Ala Ile Tyr Tyr Cys
                85                  90                  95

Ala Arg Gly Tyr Tyr Gly Ser Ser Tyr Pro Arg Ala Met Asp Tyr Trp
            100                 105                 110

Gly Gln Gly Thr Ser Val Thr Val Ser Ser
        115                 120

<210> SEQ ID NO 16
<211> LENGTH: 118
<212> TYPE: PRT
<213> ORGANISM: Artificial Sequence
<220> FEATURE:
<223> OTHER INFORMATION: MAYV-VH-B8-2 Heavy Chain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 16

Gln Leu Xaa Gln Ser Gly Xaa Glu Leu Val Lys Pro Gly Ala Ser Val
1               5                   10                  15

Lys Met Ser Cys Lys Ala Ser Gly Tyr Thr Phe Thr Ser Tyr Trp Ile
            20                  25                  30

Thr Trp Val Lys Gln Arg Pro Gly Gln Gly Leu Glu Trp Ile Gly Asp
        35                  40                  45

Ile Tyr Pro Gly Ser Gly Ser Thr Asn Tyr Asn Glu Lys Phe Lys Ser
    50                  55                  60

Lys Ala Thr Leu Thr Val Asp Thr Ser Ser Ser Thr Ala Tyr Met Gln
65                  70                  75                  80

Leu Ser Ser Leu Thr Ser Glu Asp Ser Ala Val Tyr Tyr Cys Ala Arg
                85                  90                  95

Lys Ala Asn Trp Asp Met Ala Trp Phe Ala Tyr Trp Gly Gln Gly Thr
            100                 105                 110

Ser Val Thr Val Ser Ser
        115

<210> SEQ ID NO 17
<211> LENGTH: 107
<212> TYPE: PRT
<213> ORGANISM: Artificial Sequence
<220> FEATURE:
<223> OTHER INFORMATION: MAYV-VK-A3-3 Light Chain

<400> SEQUENCE: 17

Gln Ile Val Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
```

```
    50                  55                  60

Gly Gly Ser Gly Thr Ser Tyr Ser Leu Thr Ile Gly Thr Met Glu Ala
65                  70                  75                  80

Glu Asp Val Ala Thr Tyr Tyr Cys Gln Gln Gly Ser Ser Ile Pro Leu
                85                  90                  95

Thr Phe Gly Ala Gly Thr Lys Leu Glu Leu Lys
            100                 105

<210> SEQ ID NO 18
<211> LENGTH: 112
<212> TYPE: PRT
<213> ORGANISM: Artificial Sequence
<220> FEATURE:
<223> OTHER INFORMATION: MAYV-VK-B2-2 9 Light Chain

<400> SEQUENCE: 18

Gln Ile Val Leu Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Trp Thr Phe Gly Gly Gly Thr Lys Leu Glu Ile Lys
            100                 105                 110

<210> SEQ ID NO 19
<211> LENGTH: 111
<212> TYPE: PRT
<213> ORGANISM: Artificial Sequence
<220> FEATURE:
<223> OTHER INFORMATION: MAYV-K-G12-2 Light Chain

<400> SEQUENCE: 19

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asp Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Tyr Thr Phe Gly Ala Gly Thr Lys Leu Glu Ile Lys
            100                 105                 110

<210> SEQ ID NO 20
<211> LENGTH: 107
<212> TYPE: PRT
<213> ORGANISM: Artificial Sequence
<220> FEATURE:
```

<223> OTHER INFORMATION: MAYV-K-E10-4 Light Chain

<400> SEQUENCE: 20

Asp Ile Gln Met Thr Gln

```
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Ser Gly Thr Lys Leu Glu Ile Lys
            100                 105                 110

<210> SEQ ID NO 23
<211> LENGTH: 107
<212> TYPE: PRT
<213> ORGANISM: Artificial Sequence
<220> FEATURE:
<223> OTHER INFORMATION: MAYV-K-F12-1 Light Chain

<400> SEQUENCE: 23

Asp Ile Val Met Thr Gln Ser Pro Ser Ser Leu Ser Ala Ser Val Gly
1               5                   10                  15

Glu Thr Val Thr Ile Thr Cys Arg Ala Ser Glu Asn Ile Tyr Ser Ser
            20                  25                  30

Leu Ala Trp Tyr Gln Gln Lys Gln Gly Lys Ser Pro Gln Leu Leu Val
        35                  40                  45

Tyr Asn Val Lys Thr Leu Val Glu Gly Val Pro Ser Arg Phe Gly Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Phe
                85                  90                  95

Thr Phe Gly Ser Gly Thr Lys Leu Glu Ile Lys
            100                 105

<210> SEQ ID NO 24
<211> LENGTH: 107
<212> TYPE: PRT
<213> ORGANISM: Artificial Sequence
<220> FEATURE:
<223> OTHER INFORMATION: MAYV-VK-D3-3 Light Chain

<400> SEQUENCE: 24

Gln Ile Val Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Ile Lys
            100                 105

<210> SEQ ID NO 25
<211> LENGTH: 107
<212> TYPE: PRT
<213> ORGANISM: Artificial Sequence
<220> FEATURE:
<223> OTHER INFORMATION: MAYV-VK-H4-4 Light Chain

<400> SEQUENCE: 25
```

```
Gln Ile Val Leu Thr Gln Ser Pro Ser Ser Leu Ser Ala Ser Val Gly
1               5                   10                  15

Asp Arg Val Thr Ile Thr Cys Arg Ala Ser Gln Asp Ile Arg Ser Asp
            20                  25                  30

Leu Gly Trp Tyr Gln Gln Lys Pro Gly Lys Ala Pro Lys Arg Leu Ile
        35                  40                  45

Phe Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Thr Ser Tyr Pro Trp
                85                  90                  95

Thr Phe Gly Gln Gly Thr Lys Leu Glu Ile Lys
            100                 105

<210> SEQ ID NO 26
<211> LENGTH: 111
<212> TYPE: PRT
<213> ORGANISM: Artificial Sequence
<220> FEATURE:
<223> OTHER INFORMATION: MAYV-VK-A4-1 Light Chain

<400> SEQUENCE: 26

Glu Thr Thr Val Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110

<210> SEQ ID NO 27
<211> LENGTH: 106
<212> TYPE: PRT
<213> ORGANISM: Artificial Sequence
<220> FEATURE:
<223> OTHER INFORMATION: MAYV-VK-H3-4 Light Chain

<400> SEQUENCE: 27

Glu Ile Val Leu Thr Gln Ser Ile Pro Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Ser
```

```
                85                  90                  95
Arg Ser Val Leu Gly Pro Ser Trp Lys Asn
            100                 105

<210> SEQ ID NO 28
<211> LENGTH: 112
<212> TYPE: PRT
<213> ORGANISM: Artificial Sequence
<220> FEATURE:
<223> OTHER INFORMATION: MAYV-VK-B8-3 Light Chain

<400> SEQUENCE: 28

Asp Ile Val Met Thr Gln Ser Pro Lys Phe Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Ser Gly Thr Lys Leu Glu Ile Lys
            100                 105                 110

<210> SEQ ID NO 29
<211> LENGTH: 8
<212> TYPE: PRT
<213> ORGANISM: Artificial Sequence
<220> FEATURE:
<223> OTHER INFORMATION: MAYV-VH-C12-2 CDR1

<400> SEQUENCE: 29

Gly Tyr Thr Phe Thr Glu Tyr Thr
1               5

<210> SEQ ID NO 30
<211> LENGTH: 8
<212> TYPE: PRT
<213> ORGANISM: Artificial Sequence
<220> FEATURE:
<223> OTHER INFORMATION: MAYV-VH-C12-2 CDR2

<400> SEQUENCE: 30

Ile Asn Pro Asn Asn Gly Gly Thr
1               5

<210> SEQ ID NO 31
<211> LENGTH: 12
<212> TYPE: PRT
<213> ORGANISM: Artificial Sequence
<220> FEATURE:
<223> OTHER INFORMATION: MAYV-VH-C12-2 CDR3

<400> SEQUENCE: 31

Ala Arg Gly Arg Glu Tyr Gly Asn Pro Phe Ala Tyr
1               5                   10

<210> SEQ ID NO 32
<211> LENGTH: 8
<212> TYPE: PRT
```

```
<213> ORGANISM: Artificial Sequence
<220> FEATURE:
<223> OTHER INFORMATION: MAYV-VH-C9-2 CDR1

<400> SEQUENCE: 32

Gly Cys Thr Phe Thr Ser Tyr Trp
1               5

<210> SEQ ID NO 33
<211> LENGTH: 8
<212> TYPE: PRT
<213> ORGANISM: Artificial Sequence
<220> FEATURE:
<223> OTHER INFORMATION: MAYV-VH-C9-2 CDR2

<400> SEQUENCE: 33

Ile Tyr Pro Ser Asp Ser Tyr Thr
1               5

<210> SEQ ID NO 34
<211> LENGTH: 14
<212> TYPE: PRT
<213> ORGANISM: Artificial Sequence
<220> FEATURE:
<223> OTHER INFORMATION: MAYV-VH-C9-2 CDR3

<400> SEQUENCE: 34

Thr Arg Trp Ala Tyr Tyr Gly Asn Tyr Tyr Ala Met Asp Tyr
1               5                   10

<210> SEQ ID NO 35
<211> LENGTH: 8
<212> TYPE: PRT
<213> ORGANISM: Artificial Sequence
<220> FEATURE:
<223> OTHER INFORMATION: MAYV-VH-C7-1 CDR1

<400> SEQUENCE: 35

Gly Tyr Ala Phe Ser Ser Tyr Trp
1               5

<210> SEQ ID NO 36
<211> LENGTH: 8
<212> TYPE: PRT
<213> ORGANISM: Artificial Sequence
<220> FEATURE:
<223> OTHER INFORMATION: MAYV-VH-C7-1 CDR2

<400> SEQUENCE: 36

Ile Tyr Pro Ser Asp Ser Tyr Thr
1               5

<210> SEQ ID NO 37
<211> LENGTH: 14
<212> TYPE: PRT
<213> ORGANISM: Artificial Sequence
<220> FEATURE:
<223> OTHER INFORMATION: MAYV-VH-C7-1 CDR3

<400> SEQUENCE: 37

Thr Arg Trp Ala Tyr Tyr Gly Asn Tyr Tyr Ala Met Asp Tyr
1               5                   10

<210> SEQ ID NO 38
<211> LENGTH: 8
<212> TYPE: PRT
<213> ORGANISM: Artificial Sequence
```

-continued

```
<220> FEATURE:
<223> OTHER INFORMATION: MAYV-VH-C9-4 CDR1

<400> SEQUENCE: 38

Gly Phe Thr Phe Ser Ser Tyr Gly
1               5

<210> SEQ ID NO 39
<211> LENGTH: 6
<212> TYPE: PRT
<213> ORGANISM: Artificial Sequence
<220> FEATURE:
<223> OTHER INFORMATION: MAYV-VH-C9-4 CDR2

<400> SEQUENCE: 39

Tyr Asp Gly Ser Asn Lys
1               5

<210> SEQ ID NO 40
<211> LENGTH: 13
<212> TYPE: PRT
<213> ORGANISM: Artificial Sequence
<220> FEATURE:
<223> OTHER INFORMATION: MAYV-VH-C9-4 CDR3

<400> SEQUENCE: 40

Ala Arg Gly Ile Ala Val Ala Gly Phe Gly Met Asp Val
1               5                   10

<210> SEQ ID NO 41
<211> LENGTH: 8
<212> TYPE: PRT
<213> ORGANISM: Artificial Sequence
<220> FEATURE:
<223> OTHER INFORMATION: MAYV-VH-D3-7 CDR1

<400> SEQUENCE: 41

Gly Tyr Thr Phe Thr Ser Tyr Trp
1               5

<210> SEQ ID NO 42
<211> LENGTH: 8
<212> TYPE: PRT
<213> ORGANISM: Artificial Sequence
<220> FEATURE:
<223> OTHER INFORMATION: MAYV-VH-D3-7 CDR2

<400> SEQUENCE: 42

Ile Tyr Pro Gly Ser Gly Ser Thr
1               5

<210> SEQ ID NO 43
<211> LENGTH: 11
<212> TYPE: PRT
<213> ORGANISM: Artificial Sequence
<220> FEATURE:
<223> OTHER INFORMATION: MAYV-VH-D3-7 CDR3

<400> SEQUENCE: 43

Thr Arg Thr Leu Thr Gly Thr Trp Phe Ala Tyr
1               5                   10

<210> SEQ ID NO 44
<211> LENGTH: 8
<212> TYPE: PRT
<213> ORGANISM: Artificial Sequence
<220> FEATURE:
```

<223> OTHER INFORMATION: MAYV-VH-F5-8 CDR1

<400> SEQUENCE: 44

Gly Tyr Thr Phe Thr Asp Tyr Glu
1               5

<210> SEQ ID NO 45
<211> LENGTH: 8
<212> TYPE: PRT
<213> ORGANISM: Artificial Sequence
<220> FEATURE:
<223> OTHER INFORMATION: MAYV-VH-F5-8 CDR2

<400> SEQUENCE: 45

Ile Asp Pro Glu Thr Gly Gly Thr
1               5

<210> SEQ ID NO 46
<211> LENGTH: 5
<212> TYPE: PRT
<213> ORGANISM: Artificial Sequence
<220> FEATURE:
<223> OTHER INFORMATION: MAYV-VH-F5-8 CDR3

<400> SEQUENCE: 46

Thr Arg Gly Pro Trp
1               5

<210> SEQ ID NO 47
<211> LENGTH: 8
<212> TYPE: PRT
<213> ORGANISM: Artificial Sequence
<220> FEATURE:
<223> OTHER INFORMATION: MAYV-VH-B2-2 CDR1

<400> SEQUENCE: 47

Gly Phe Asn Ile Lys Asp Tyr Tyr
1               5

<210> SEQ ID NO 48
<211> LENGTH: 8
<212> TYPE: PRT
<213> ORGANISM: Artificial Sequence
<220> FEATURE:
<223> OTHER INFORMATION: MAYV-VH-B2-2 CDR2

<400> SEQUENCE: 48

Ile Asp Pro Glu Asn Gly Asn Thr
1               5

<210> SEQ ID NO 49
<211> LENGTH: 6
<212> TYPE: PRT
<213> ORGANISM: Artificial Sequence
<220> FEATURE:
<223> OTHER INFORMATION: MAYV-VH-B2-2 CDR3

<400> SEQUENCE: 49

Ala Asn Asp Phe Ala Tyr
1               5

<210> SEQ ID NO 50
<211> LENGTH: 8
<212> TYPE: PRT
<213> ORGANISM: Artificial Sequence
<220> FEATURE:
<223> OTHER INFORMATION: MAYV-VH-B8-3 CDR1

```
<400> SEQUENCE: 50

Gly Tyr Thr Phe Thr Ser Tyr Trp
1               5

<210> SEQ ID NO 51
<211> LENGTH: 8
<212> TYPE: PRT
<213> ORGANISM: Artificial Sequence
<220> FEATURE:
<223> OTHER INFORMATION: MAYV-VH-B8-3 CDR2

<400> SEQUENCE: 51

Ile Tyr Pro Gly Ser Gly Ser Thr
1               5

<210> SEQ ID NO 52
<211> LENGTH: 13
<212> TYPE: PRT
<213> ORGANISM: Artificial Sequence
<220> FEATURE:
<223> OTHER INFORMATION: MAYV-VH-B8-3 CDR3

<400> SEQUENCE: 52

Ala Arg Lys Ala Asn Trp Asp Met Ala Trp Phe Ala Tyr
1               5                   10

<210> SEQ ID NO 53
<211> LENGTH: 8
<212> TYPE: PRT
<213> ORGANISM: Artificial Sequence
<220> FEATURE:
<223> OTHER INFORMATION: MAYV-VH-E1-5 CDR1

<400> SEQUENCE: 53

Gly Phe Asn Ile Lys Asp Tyr Phe
1               5

<210> SEQ ID NO 54
<211> LENGTH: 8
<212> TYPE: PRT
<213> ORGANISM: Artificial Sequence
<220> FEATURE:
<223> OTHER INFORMATION: MAYV-VH-E1-5 CDR2

<400> SEQUENCE: 54

Ile Asp Pro Glu Asn Asp Asp Thr
1               5

<210> SEQ ID NO 55
<211> LENGTH: 10
<212> TYPE: PRT
<213> ORGANISM: Artificial Sequence
<220> FEATURE:
<223> OTHER INFORMATION: MAYV-VH-E1-5 CDR3

<400> SEQUENCE: 55

Asn Ala Asp Asp Gly Tyr Pro Phe Ala Tyr
1               5                   10

<210> SEQ ID NO 56
<211> LENGTH: 8
<212> TYPE: PRT
<213> ORGANISM: Artificial Sequence
<220> FEATURE:
<223> OTHER INFORMATION: MAYV-VH-F4-1 CDR1
```

```
<400> SEQUENCE: 56

Gly Phe Thr Phe Thr Asp Tyr Tyr
1 5

<210> SEQ ID NO 57
<211> LENGTH: 10
<212> TYPE: PRT
<213> ORGANISM: Artificial Sequence
<220> FEATURE:
<223> OTHER INFORMATION: MAYV-VH-F4-1 CDR2

<400> SEQUENCE: 57

Ile Arg Asn Lys Ala Asn Gly Tyr Thr Thr
1 5 10

<210> SEQ ID NO 58
<211> LENGTH: 9
<212> TYPE: PRT
<213> ORGANISM: Artificial Sequence
<220> FEATURE:
<223> OTHER INFORMATION: MAYV-VH-F4-1 CDR3

<400> SEQUENCE: 58

Ala Arg Asp Gly Asn Tyr Phe Asp Tyr
1 5

<210> SEQ ID NO 59
<211> LENGTH: 8
<212> TYPE: PRT
<213> ORGANISM: Artificial Sequence
<220> FEATURE:
<223> OTHER INFORMATION: MAYV-VH-H3-2 CDR1

<400> SEQUENCE: 59

Gly Tyr Thr Phe Thr Gly Tyr Trp
1 5

<210> SEQ ID NO 60
<211> LENGTH: 8
<212> TYPE: PRT
<213> ORGANISM: Artificial Sequence
<220> FEATURE:
<223> OTHER INFORMATION: MAYV-VH-H3-2 CDR2

<400> SEQUENCE: 60

Ile Leu Pro Gly Ser Gly Ser Thr
1 5

<210> SEQ ID NO 61
<211> LENGTH: 15
<212> TYPE: PRT
<213> ORGANISM: Artificial Sequence
<220> FEATURE:
<223> OTHER INFORMATION: MAYV-VH-H3-2 CDR3

<400> SEQUENCE: 61

Ala Arg Gly Tyr Tyr Gly Ser Ser Tyr Pro Arg Ala Met Asp Tyr
1 5 10 15

<210> SEQ ID NO 62
<211> LENGTH: 8
<212> TYPE: PRT
<213> ORGANISM: Artificial Sequence
<220> FEATURE:
<223> OTHER INFORMATION: MAYV-VH-B8-2 CDR1

<400> SEQUENCE: 62

Gly Tyr Thr Phe Thr Ser Tyr Trp
1               5

<210> SEQ ID NO 63
<211> LENGTH: 8
<212> TYPE: PRT
<213> ORGANISM: Artificial Sequence
<220> FEATURE:
<223> OTHER INFORMATION: MAYV-VH-B8-2 CDR2

<400> SEQUENCE: 63

Ile Tyr Pro Gly Ser Gly Ser Thr
1               5

<210> SEQ ID NO 64
<211> LENGTH: 13
<212> TYPE: PRT
<213> ORGANISM: Artificial Sequence
<220> FEATURE:
<223> OTHER INFORMATION: MAYV-VH-B8-2 CDR3

<400> SEQUENCE: 64

Ala Arg Lys Ala Asn Trp Asp Met Ala Trp Phe Ala Tyr
1               5                   10

<210> SEQ ID NO 65
<211> LENGTH: 7
<212> TYPE: PRT
<213> ORGANISM: Artificial Sequence
<220> FEATURE:
<223> OTHER INFORMATION: MAYV-VK-A3-3 CDR1

<400> SEQUENCE: 65

Ser Ser Ile Ser Ser Asn Tyr
1               5

<210> SEQ ID NO 66
<211> LENGTH: 3
<212> TYPE: PRT
<213> ORGANISM: Artificial Sequence
<220> FEATURE:
<223> OTHER INFORMATION: MAYV-VK-A3-3 CDR2

<400> SEQUENCE: 66

Arg Thr Ser
1

<210> SEQ ID NO 67
<211> LENGTH: 9
<212> TYPE: PRT
<213> ORGANISM: Artificial Sequence
<220> FEATURE:
<223> OTHER INFORMATION: MAYV-VK-A3-3 CDR3

<400> SEQUENCE: 67

Gln Gln Gly Ser Ser Ile Pro Leu Thr
1               5

<210> SEQ ID NO 68
<211> LENGTH: 12
<212> TYPE: PRT
<213> ORGANISM: Artificial Sequence
<220> FEATURE:
<223> OTHER INFORMATION: MAYV-VK-B2-2 9 CDR1

<400> SEQUENCE: 68

```
Gln Ser Leu Leu Asn Ser Arg Thr Arg Lys Asn Tyr
1               5                   10

<210> SEQ ID NO 69
<211> LENGTH: 3
<212> TYPE: PRT
<213> ORGANISM: Artificial Sequence
<220> FEATURE:
<223> OTHER INFORMATION: MAYV-VK-B2-2 9 CDR2

<400> SEQUENCE: 69

Trp Ala Ser
1

<210> SEQ ID NO 70
<211> LENGTH: 8
<212> TYPE: PRT
<213> ORGANISM: Artificial Sequence
<220> FEATURE:
<223> OTHER INFORMATION: MAYV-VK-B2-2 9 CDR3

<400> SEQUENCE: 70

Lys Gln Ser Tyr Asn Leu Trp Thr
1               5

<210> SEQ ID NO 71
<211> LENGTH: 10
<212> TYPE: PRT
<213> ORGANISM: Artificial Sequence
<220> FEATURE:
<223> OTHER INFORMATION: MAYV-K-G12-2 CDR1

<400> SEQUENCE: 71

Glu Ser Val Asp Asp Tyr Gly Asn Ser Phe
1               5                   10

<210> SEQ ID NO 72
<211> LENGTH: 3
<212> TYPE: PRT
<213> ORGANISM: Artificial Sequence
<220> FEATURE:
<223> OTHER INFORMATION: MAYV-K-G12-2 CDR2

<400> SEQUENCE: 72

Leu Ala Ser
1

<210> SEQ ID NO 73
<211> LENGTH: 9
<212> TYPE: PRT
<213> ORGANISM: Artificial Sequence
<220> FEATURE:
<223> OTHER INFORMATION: MAYV-K-G12-2 CDR3

<400> SEQUENCE: 73

Gln Gln Asn Asn Glu Asp Pro Tyr Thr
1               5

<210> SEQ ID NO 74
<211> LENGTH: 6
<212> TYPE: PRT
<213> ORGANISM: Artificial Sequence
<220> FEATURE:
<223> OTHER INFORMATION: MAYV-K-E10-4 CDR1

<400> SEQUENCE: 74

Gln Ser Ile Ser Asp Tyr
```

```
<210> SEQ ID NO 75
<211> LENGTH: 3
<212> TYPE: PRT
<213> ORGANISM: Artificial Sequence
<220> FEATURE:
<223> OTHER INFORMATION: MAYV-K-E10-4 CDR2

<400> SEQUENCE: 75

Tyr Ala Ser
1

<210> SEQ ID NO 76
<211> LENGTH: 9
<212> TYPE: PRT
<213> ORGANISM: Artificial Sequence
<220> FEATURE:
<223> OTHER INFORMATION: MAYV-K-E10-4 CDR3

<400> SEQUENCE: 76

Gln Asn Gly His Ser Phe Pro Tyr Thr
1               5

<210> SEQ ID NO 77
<211> LENGTH: 6
<212> TYPE: PRT
<213> ORGANISM: Artificial Sequence
<220> FEATURE:
<223> OTHER INFORMATION: MAYV-VK-C3-2 CDR1

<400> SEQUENCE: 77

Thr Asp Ile Asp Asp Asp
1               5

<210> SEQ ID NO 78
<211> LENGTH: 3
<212> TYPE: PRT
<213> ORGANISM: Artificial Sequence
<220> FEATURE:
<223> OTHER INFORMATION: MAYV-VK-C3-2 CDR2

<400> SEQUENCE: 78

Glu Gly Asn
1

<210> SEQ ID NO 79
<211> LENGTH: 9
<212> TYPE: PRT
<213> ORGANISM: Artificial Sequence
<220> FEATURE:
<223> OTHER INFORMATION: MAYV-VK-C3-2 CDR3

<400> SEQUENCE: 79

Leu Gln Ser Asp Asn Met Pro Tyr Thr
1               5

<210> SEQ ID NO 80
<211> LENGTH: 11
<212> TYPE: PRT
<213> ORGANISM: Artificial Sequence
<220> FEATURE:
<223> OTHER INFORMATION: MAYV-K-A10-3 CDR1

<400> SEQUENCE: 80

Gln Ser Leu Val His Ser Asn Gly Asn Thr Tyr
1               5                   10
```

<210> SEQ ID NO 81
<211> LENGTH: 3
<212> TYPE: PRT
<213> ORGANISM: Artificial Sequence
<220> FEATURE:
<223> OTHER INFORMATION: MAYV-K-A10-3 CDR2

<400> SEQUENCE: 81

Lys Val Ser
1

<210> SEQ ID NO 82
<211> LENGTH: 9
<212> TYPE: PRT
<213> ORGANISM: Artificial Sequence
<220> FEATURE:
<223> OTHER INFORMATION: MAYV-K-A10-3 CDR3

<400> SEQUENCE: 82

Ser Gln Ser Thr His Val Pro Tyr Thr
1               5

<210> SEQ ID NO 83
<211> LENGTH: 6
<212> TYPE: PRT
<213> ORGANISM: Artificial Sequence
<220> FEATURE:
<223> OTHER INFORMATION: MAYV-K-F12-1 CDR1

<400> SEQUENCE: 83

Glu Asn Ile Tyr Ser Ser
1               5

<210> SEQ ID NO 84
<211> LENGTH: 3
<212> TYPE: PRT
<213> ORGANISM: Artificial Sequence
<220> FEATURE:
<223> OTHER INFORMATION: MAYV-K-F12-1 CDR2

<400> SEQUENCE: 84

Asn Val Lys
1

<210> SEQ ID NO 85
<211> LENGTH: 9
<212> TYPE: PRT
<213> ORGANISM: Artificial Sequence
<220> FEATURE:
<223> OTHER INFORMATION: MAYV-K-F12-1 CDR3

<400> SEQUENCE: 85

Gln His His Tyr Gly Thr Pro Phe Thr
1               5

<210> SEQ ID NO 86
<211> LENGTH: 6
<212> TYPE: PRT
<213> ORGANISM: Artificial Sequence
<220> FEATURE:
<223> OTHER INFORMATION: MAYV-VK-D3-3 CDR1

<400> SEQUENCE: 86

Gln Asn Val Gly Th

```
<210> SEQ ID NO 87
<211> LENGTH: 3
<212> TYPE: PRT
<213> ORGANISM: Artificial Sequence
<220> FEATURE:
<223> OTHER INFORMATION: MAYV-VK-D3-3 CDR2

<400> SEQUENCE: 87

Ser Ala Ser
1

<210> SEQ ID NO 88
<211> LENGTH: 9
<212> TYPE: PRT
<213> ORGANISM: Artificial Sequence
<220> FEATURE:
<223> OTHER INFORMATION: MAYV-VK-D3-3 CDR3

<400> SEQUENCE: 88

Gln Gln Tyr Asn Ser Tyr Pro Leu Thr
1               5

<210> SEQ ID NO 89
<211> LENGTH: 6
<212> TYPE: PRT
<213> ORGANISM: Artificial Sequence
<220> FEATURE:
<223> OTHER INFORMATION: MAYV-VK-H4-4 CDR1

<400> SEQUENCE: 89

Gln Asp Ile Arg Ser Asp
1               5

<210> SEQ ID NO 90
<211> LENGTH: 3
<212> TYPE: PRT
<213> ORGANISM: Artificial Sequence
<220> FEATURE:
<223> OTHER INFORMATION: MAYV-VK-H4-4 CDR2

<400> SEQUENCE: 90

Ala Ser Ser
1

<210> SEQ ID NO 91
<211> LENGTH: 9
<212> TYPE: PRT
<213> ORGANISM: Artificial Sequence
<220> FEATURE:
<223> OTHER INFORMATION: MAYV-VK-H4-4 CDR3

<400> SEQUENCE: 91

Leu Gln His Thr Ser Tyr Pro Trp Thr
1               5

<210> SEQ ID NO 92
<211> LENGTH: 14
<212> TYPE: PRT
<213> ORGANISM: Artificial Sequence
<220> FEATURE:
<223> OTHER INFORMATION: MAYV-VK-A4-1 CDR1

<400> SEQUENCE: 92

Glu Ser Val Asp Asn Tyr Gly Ile Ser Phe Met Asn Trp Phe
1               5                   10
```

```
<210> SEQ ID NO 93
<211> LENGTH: 3
<212> TYPE: PRT
<213> ORGANISM: Artificial Sequence
<220> FEATURE:
<223> OTHER INFORMATION: MAYV-VK-A4-1 CDR2

<400> SEQUENCE: 93

Ala Ala Ser
1

<210> SEQ ID NO 94
<211> LENGTH: 9
<212> TYPE: PRT
<213> ORGANISM: Artificial Sequence
<220> FEATURE:
<223> OTHER INFORMATION: MAYV-VK-A4-1 CDR3

<400> SEQUENCE: 94

Gln Gln Ser Lys Glu Val Pro Trp Thr
1               5

<210> SEQ ID NO 95
<211> LENGTH: 6
<212> TYPE: PRT
<213> ORGANISM: Artificial Sequence
<220> FEATURE:
<223> OTHER INFORMATION: MAYV-VK-H3-4 CDR1

<400> SEQUENCE: 95

Glu Asn Ile Tyr Ser Asn
1               5

<210> SEQ ID NO 96
<211> LENGTH: 3
<212> TYPE: PRT
<213> ORGANISM: Artificial Sequence
<220> FEATURE:
<223> OTHER INFORMATION: MAYV-VK-H3-4 CDR2

<400> SEQUENCE: 96

Ala Ala Thr
1

<210> SEQ ID NO 97
<211> LENGTH: 8
<212> TYPE: PRT
<213> ORGANISM: Artificial Sequence
<220> FEATURE:
<223> OTHER INFORMATION: MAYV-VK-H3-4 CDR3

<400> SEQUENCE: 97

Gln His Phe Trp Gly Thr Pro Ser
1               5

<210> SEQ ID NO 98
<211> LENGTH: 11
<212> TYPE: PRT
<213> ORGANISM: Artificial Sequence
<220> FEATURE:
<223> OTHER INFORMATION: MAYV-VK-B8-3 CDR1

<400> SEQUENCE: 98

Gln Ser Leu Val His Ser Asn Gly Asn Thr Tyr
1               5                   10

<210> SEQ ID NO 99
```

```
<211> LENGTH: 3
<212> TYPE: PRT
<213> ORGANISM: Artificial Sequence
<220> FEATURE:
<223> OTHER INFORMATION: MAYV-VK-B8-3 CDR2

<400> SEQUENCE: 99

Lys Val Ser
1

<210> SEQ ID NO 100
<211> LENGTH: 9
<212> TYPE: PRT
<213> ORGANISM: Artificial Sequence
<220> FEATURE:
<223> OTHER INFORMATION: MAYV-VK-B8-3 CDR3

<400> SEQUENCE: 100

Ser Gln Ser Thr His Val Pro Tyr Thr
1               5

<210> SEQ ID NO 101
<211> LENGTH: 15
<212> TYPE: PRT
<213> ORGANISM: Artificial Sequence
<220> FEATURE:
<223> OTHER INFORMATION: MAYV CA antigen fragment

<400> SEQUENCE: 101

Glu Gly His Tyr Asn Trp His Tyr Gly Ala Val Gln Tyr Thr Gly
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: MAYV ENV antigen fragment

<400> SEQUENCE: 102

Gly Arg Ser Val Ile His Phe Ser Thr Ala Ser Ala Ala Pro Ser
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: MAYV ENV antigen fragment

<400> SEQUENCE: 103

Leu Ala Lys Cys Pro Pro Gly Glu Val Ile Ser Val Ser Phe Val
1               5                   10                  15

<210> SEQ ID NO 104
<211> LENGTH: 257
<212> TYPE: PRT
<213> ORGANISM: Artificial Sequence
<220> FEATURE:
<223> OTHER INFORMATION: MAYV-Capsid

<400> SEQUENCE: 104

Asp Phe Leu Pro Thr Gln Val Phe Tyr Gly Arg Arg Trp Arg Pro Arg
1               5                   10                  15

Met Pro Pro Arg Pro Trp Arg Pro Arg Pro Thr Ile Gln Arg Pro
            20                  25                  30
```

```
Asp Gln Gln Ala Arg Gln Met Gln Gln Leu Ile Ala Ala Val Ser Thr
        35                  40                  45

Leu Ala Leu Arg Gln Asn Ala Ala Ala Pro Gln Arg Gly Arg Lys Lys
    50                  55                  60

Gln Pro Arg Arg Lys Lys Pro Lys Pro Gln Pro Glu Lys Pro Lys Lys
65                  70                  75                  80

Gln Glu Gln Lys Pro Lys Gln Lys Lys Thr Pro Lys Lys Lys Pro Gly
                85                  90                  95

Arg Arg Glu Arg Met Cys Met Lys Ile Glu His Asp Cys Ile Phe Glu
            100                 105                 110

Val Lys His Glu Gly Lys Val Thr Gly Tyr Ala Cys Leu Val Gly Asp
        115                 120                 125

Lys Val Met Lys Pro Ala His Val Pro Gly Val Ile Asp Asn Ile Asp
    130                 135                 140

Leu Ala Arg Leu Ser Tyr Lys Lys Ser Ser Lys Tyr Asp Leu Glu Cys
145                 150                 155                 160

Ala Gln Ile Pro Val Ala Met Lys Ser Asp Ala Ser Lys Tyr Thr His
                165                 170                 175

Glu Lys Pro Glu Gly His Tyr Asn Trp His Tyr Gly Ala Val Gln Tyr
            180                 185                 190

Thr Gly Gly Arg Phe Thr Val Pro Thr Gly Val Gly Lys Pro Gly Asp
        195                 200                 205

Ser Gly Arg Pro Ile Phe Asp Asn Lys Gly Arg Val Val Ala Ile Val
    210                 215                 220

Leu Gly Gly Ala Asn Glu Gly Ala Arg Thr Ala Leu Ser Val Val Thr
225                 230                 235                 240

Trp Asn Lys Asp Met Val Thr Lys Ile Thr Pro Glu Gly Thr Glu Glu
                245                 250                 255

Trp
```

```
<210> SEQ ID NO 105
<211> LENGTH: 771
<212> TYPE: DNA
<213> ORGANISM: Artificial Sequence
<220> FEATURE:
<223> OTHER INFORMATION: MAYV-Capsid

<400> SEQUENCE: 105
gacttcctgc ctactcaggt cttctacggg aggaggtgga ggcccaggat gccccctcgc      60
ccttggcgcc caaggccacc caccatccag cgccccgacc agcaggccag gcagatgcag     120
cagctgatcg cagccgtgag cacactggcc ctgaggcaga acgcagcagc ccctcagaga     180
ggacggaaga agcagcctag gagaaagaag cctaagccac agcccgagaa gcctaagaag     240
caggagcaga agccaaagca gaagaagacc cccaagaaga agcctggcag gagggagcgc     300
atgtgcatga agatcgagca cgactgtatc ttcgaggtga agcacgaggg caaggtgaca     360
ggctacgcct gcctggtggg cgataaagtg atgaagccag cccacgtgcc cggcgtgatc     420
gacaacatcg atctggcccg gctgtcctac aagaagagct ccaagtatga cctggagtgt     480
gcccagatcc cagtggccat gaagtctgat gccagcaagt acacccacga gaagcccgag     540
ggccactaca attggcacta tggcgccgtg cagtatacag gcggcagatt caccgtgcct     600
acaggagtgg gcaagccagg cgactccggc agacccatct ttgataacaa gggaagggtg     660
gtggcaatcg tgctgggcgg cgccaatgag ggcgcccgga ccgccctgtc tgtggtcacc     720
tggaataagg atatggtcac aaagattaca cccgaaggga cagaggaatg g              771
```

<210> SEQ ID NO 106
<211> LENGTH: 436
<212> TYPE: PRT
<213> ORGANISM: Artificial Sequence
<220> FEATURE:
<223> OTHER INFORMATION: MAYV-E1

<400> SEQUENCE: 106

```
Tyr Glu His Thr Ala Val Ile Pro Asn Gln Val Gly Phe Pro Tyr Lys
1               5                   10                  15

Ala His Val Ala Arg Glu Gly Tyr Ser Pro Leu Thr Leu Gln Met Gln
            20                  25                  30

Val Val Glu Thr Ser Leu Glu Pro Thr Leu Asn Leu Glu Tyr Ile Thr
        35                  40                  45

Cys Asp Tyr Lys Thr Lys Val Pro Ser Pro Tyr Val Lys Cys Cys Gly
    50                  55                  60

Thr Ala Glu Cys Arg Thr Gln Asp Lys Pro Glu Tyr Lys Cys Ala Val
65                  70                  75                  80

Phe Thr Gly Val Tyr Pro Phe Met Trp Gly Gly Ala Tyr Cys Phe Cys
                85                  90                  95

Asp Ser Glu Asn Thr Gln Met Ser Glu Ala Tyr Val Glu Arg Ala Asp
            100                 105                 110

Val Cys Lys His Asp Tyr Ala Ala Ala Tyr Arg Ala His Thr Ala Ser
        115                 120                 125

Leu Arg Ala Lys Ile Lys Val Thr Tyr Gly Thr Val Asn Gln Thr Val
    130                 135                 140

Glu Ala Tyr Val Asn Gly Asp His Ala Val Thr Ile Ala Gly Thr Lys
145                 150                 155                 160

Phe Ile Phe Gly Pro Val Ser Thr Ala Trp Thr Pro Phe Asp Thr Lys
                165                 170                 175

Ile Val Val Tyr Lys Gly Glu Val Tyr Asn Gln Asp Phe Pro Pro Tyr
            180                 185                 190

Gly Ala Gly Gln Pro Gly Arg Phe Gly Asp Ile Gln Ser Arg Thr Leu
        195                 200                 205

Asp Ser Lys Asp Leu Tyr Ala Asn Thr Gly Leu Lys Leu Ala Arg Pro
    210                 215                 220

Ala Ala Gly Asn Ile His Val Pro Tyr Thr Gln Thr Pro Ser Gly Phe
225                 230                 235                 240

Lys Thr Trp Gln Lys Asp Arg Asp Ser Pro Leu Asn Ala Lys Ala Pro
                245                 250                 255

Phe Gly Cys Thr Ile Gln Thr Asn Pro Val Arg Ala Met Asn Cys Ala
            260                 265                 270

Val Gly Asn Ile Pro Val Ser Met Asp Ile Ala Asp Ser Ala Phe Thr
        275                 280                 285

Arg Leu Thr Asp Ala Pro Ile Ile Ser Glu Leu Leu Cys Thr Val Ser
    290                 295                 300

Thr Cys Thr His Ser Ser Asp Phe Gly Gly Val Ala Val Leu Ser Tyr
305                 310                 315                 320

Lys Val Glu Lys Ala Gly Arg Cys Asp Val His Ser His Ser Asn Val
                325                 330                 335

Ala Val Leu Gln Glu Val Ser Ile Glu Ala Glu Gly Arg Ser Val Ile
            340                 345                 350

His Phe Ser Thr Ala Ser Ala Ala Pro Ser Phe Ile Val Ser Val Cys
        355                 360                 365
```

Ser Ser Arg Ala Thr Cys Thr Ala Lys Cys Glu Pro Pro Lys Asp His
    370                 375                 380

Val Val Thr Tyr Pro Ala Asn His Asn Gly Ile Thr Leu Pro Asp Leu
385                 390                 395                 400

Ser Ser Thr Ala Met Thr Trp Ala Gln His Leu Ala Gly Gly Val Gly
                405                 410                 415

Leu Leu Ile Ala Leu Ala Val Leu Ile Leu Val Ile Val Thr Cys Ile
            420                 425                 430

Thr Leu Arg Arg
        435

<210> SEQ ID NO 107
<211> LENGTH: 1308
<212> TYPE: DNA
<213> ORGANISM: Artificial Sequence
<220> FEATURE:
<223> OTHER INFORMATION: MAYV-E1

<400> SEQUENCE: 107
tacgagcata ctgccgtgat tcccaaccag gtcggcttcc catacaaggc ccacgtggcc        60
agagagggct atagccccct gaccctgcag atgcaggtgg tggagacaag cctggagccc       120
acactgaacc tggagtacat cacctgcgat tataagacaa aggtgcctag cccatacgtg       180
aagtgctgtg gcaccgccga gtgcagaaca caggacaagc tgagtataaa gtgtgccgtg       240
ttcaccggcg tgtaccccct catgtggggc ggcgcctatt gcttctgtga ttctgagaat       300
acacagatga gcgaggccta cgtggagagg gccgacgtgt gcaagcacga ttacgcagca       360
gcatataggg cacacaccgc atctctgaga gccaagatca aggtgaccta cggcacagtg       420
aaccagacag tggaggccta tgtgaatggc gaccacgcag tgaccatcgc aggaacaaag       480
ttcatctttg gccccgtgag caccgcctgg acaccatttg acaccaagat cgtggtgtac       540
aagggcgagt gtataaacca ggatttccct ccctacggag caggacagcc aggcaggttt       600
ggcgacatcc agagccgcac cctggactcc aaggatctgt acgccaacac aggcctgaag       660
ctggccagac ccgcagcagg aaatatccac gtgccctata cccagacacc ttccggcttc       720
aagacctggc agaaggaccg ggattctcca ctgaacgcca ggccccctt tggctgcacc        780 atccagacaa atcccgtgag agccatgaac tgtgccgtgg caatatccc cgtgagcatg        840 gacatcgccg attctgcctt cacccggctg acagatgccc tatcatcag cgagctgctg        900 tgcaccgtgt ccacctgtac acacagctcc gattttggcg gcgtggccgt gctgtcctac       960
aaggtggaga aggcaggcag gtgcgacgtg cacagccact ccaatgtggc cgtgctgcag      1020
gaggtgtcta tcgaggccga gggccgcagc gtgatccact tctctacagc cagcgccgcc      1080
ccaagcttca tcgtgagcgt gtgcagcagc cgggccacct gcacagccaa gtgtgagcca      1140
cccaaggatc acgtggtgac ctatcccgcc aaccacaatg gcatcacact gcctgacctg      1200
tcctctaccg ccatgacatg ggcccagcac ctggccggcg gcgtgggcct gctgattgcc      1260
ctggctgtgc tgattctggt catcgtcacc tgtattaccc tgcggaga              1308

<210> SEQ ID NO 108
<211> LENGTH: 422
<212> TYPE: PRT
<213> ORGANISM: Artificial Sequence
<220> FEATURE:
<223> OTHER INFORMATION: MAYV-E2

<400> SEQUENCE: 108

-continued

```
Ser Thr Ala Asn His Phe Asn Ala Tyr Lys Leu Thr Arg Pro Tyr Val
1               5                   10                  15

Ala Tyr Cys Ala Asp Cys Gly Met Gly His Ser Cys His Ser Pro Ala
                20                  25                  30

Met Ile Glu Asn Val Gln Ala Asp Ala Thr Asp Gly Thr Leu Lys Ile
            35                  40                  45

Gln Phe Ala Ser Gln Ile Gly Leu Thr Lys Thr Asp Thr His Asp His
    50                  55                  60

Thr Lys Ile Arg Tyr Ala Glu Gly His Asp Ile Ala Glu Ala Ala Arg
65                  70                  75                  80

Ser Thr Leu Lys Val His Ser Ser Glu Cys Ala Val Thr Gly Thr
                85                  90                  95

Met Gly His Phe Ile Leu Ala Lys Cys Pro Gly Glu Val Ile Ser
            100                 105                 110

Val Ser Phe Val Asp Ser Lys Asn Glu Gln Arg Thr Cys Arg Ile Ala
        115                 120                 125

Tyr His His Glu Gln Arg Leu Ile Gly Arg Glu Arg Phe Thr Val Arg
    130                 135                 140

Pro His His Gly Ile Glu Leu Pro Cys Thr Thr Tyr Gln Leu Thr Thr
145                 150                 155                 160

Ala Glu Thr Ser Glu Glu Ile Asp Met His Met Pro Pro Asp Ile Pro
                165                 170                 175

Asp Arg Thr Ile Leu Ser Gln Gln Ser Gly Asn Val Lys Ile Thr Val
            180                 185                 190

Asn Gly Arg Thr Val Lys Tyr Ser Cys Ser Cys Gly Ser Lys Pro Ser
        195                 200                 205

Gly Thr Thr Thr Thr Asp Lys Thr Ile Asn Ser Cys Thr Val Asp Lys
    210                 215                 220

Cys Gln Ala Tyr Val Thr Ser His Thr Lys Trp Gln Phe Asn Ser Pro
225                 230                 235                 240

Phe Val Pro Arg Ala Glu Gln Ala Glu Arg Lys Gly Lys Val His Ile
                245                 250                 255

Pro Phe Pro Leu Ile Asn Thr Thr Cys Arg Val Pro Leu Ala Pro Glu
            260                 265                 270

Ala Leu Val Arg Ser Gly Lys Arg Glu Ala Thr Leu Ser Leu His Pro
        275                 280                 285

Ile His Pro Thr Leu Leu Ser Tyr Arg Thr Leu Gly Arg Glu Pro Val
    290                 295                 300

Phe Asp Glu Gln Trp Ile Thr Thr Gln Thr Glu Val Thr Ile Pro Val
305                 310                 315                 320

Pro Val Glu Gly Val Glu Tyr Arg Trp Gly Asn His Lys Pro Gln Arg
                325                 330                 335

Leu Trp Ser Gln Leu Thr Thr Glu Gly Arg Ala His Gly Trp Pro His
            340                 345                 350

Glu Ile Ile Glu Tyr Tyr Tyr Gly Leu His Pro Thr Thr Thr Ile Val
        355                 360                 365

Val Val Val Ala Val Ser Val Val Leu Leu Ser Val Ala Ala Ser
    370                 375                 380

Val Tyr Met Cys Val Val Ala Arg Asn Lys Cys Leu Thr Pro Tyr Ala
385                 390                 395                 400

Leu Thr Pro Gly Ala Val Val Pro Val Thr Ile Gly Val Leu Cys Cys
                405                 410                 415
```

Ala Pro Lys Ala His Ala
          420

<210> SEQ ID NO 109
<211> LENGTH: 1266
<212> TYPE: DNA
<213> ORGANISM: Artificial Sequence
<220> FEATURE:
<223> OTHER INFORMATION: MAYV-E2

<400> SEQUENCE: 109

```
agcaccgcca accacttcaa tgcctacaag ctgacaaggc cctatgtggc ctactgcgcc      60
gattgtggca tgggccacag ctgtcactcc cctgccatga tcgagaatgt gcaggccgac     120
gccaccgatg gcacact Lys Arg
65

<210> SEQ ID NO 111
<211> LENGTH: 198
<212> TYPE: DNA
<213> ORGANISM: Artificial Sequence
<220> FEATURE:
<223> OTHER INFORMATION: MAYV-E3

<400> SEQUENCE: 111
gccgccccca ccgtcaccgc aatgtgcctg ctggccaacg tgtccttccc ttgctttcag    60
ccatcttgta gccctgctg ttacgagaag ggaccagagc ccaccctgag gatgctggag    120
gagaacgtga attctgaggg ctactatgag ctgctgcacg ccgccgtgta ttgcaagaac    180
agctcccggt ccaagagg                                                 198

<210> SEQ ID NO 112
<211> LENGTH: 60
<212> TYPE: PRT
<213> ORGANISM: Artificial Sequence
<220> FEATURE:
<223> OTHER INFORMATION: MAYV-6K

<400> SEQUENCE: 112

Ala Ser Phe Ala Glu Gly Met Ala Tyr Leu Trp Asp Asn Asn Gln Ser
1               5                   10                  15

Met Phe Trp Met Glu Leu Thr Gly Pro Leu Ala Leu Leu Ile Leu Thr
20 25 30

Thr Cys Cys Ala Arg Ser Leu Leu Ser Cys Cys Lys Gly Ser Phe Leu
35 40 45

Val Ala Val Ser Val Gly Ser Ala Val Ala Ser Ala
50 55 60

<210> SEQ ID NO 113
<211> LENGTH: 180
<212> TYPE: DNA
<213> ORGANISM: Artificial Sequence
<220> FEATURE:
<223> OTHER INFORMATION: MAYV-6K

<400> SEQUENCE: 113
gcaagcttcg ccgagggaat ggcatatctg tgggacaaca atcagtccat gttttggatg 60
gagctgaccg gacctctggc cctgctgatc ctgacaacct gctgtgccag aagcctgctg 120
tcctgctgta agggcagctt cctggtggcc gtgtctgtgg gcagcgccgt ggcctccgcc 180

<210> SEQ ID NO 114
<211> LENGTH: 488
<212> TYPE: PRT
<213> ORGANISM: Artificial Sequence
<220> FEATURE:
<223> OTHER INFORMATION: MAYV-E3+E2

<400> SEQUENCE: 114

Ala Ala Pro Thr Val Thr Ala Met Cys Leu Leu Ala Asn Val Ser Phe
1 5 10 15

Pro Cys Phe Gln Pro Ser Cys Ser Pro Cys Cys Tyr Glu Lys Gly Pro
20 25 30

Glu Pro Thr Leu Arg Met Leu Glu Glu Asn Val Asn Ser Glu Gly Tyr
35 40 45

Tyr Glu Leu Leu His Ala Ala Val Tyr Cys Lys Asn Ser Ser Arg Ser

-continued

```
            50                  55                  60
Lys Arg Ser Thr Ala Asn His Phe Asn Ala Tyr Lys Leu Thr Arg Pro
 65                  70                  75                  80

Tyr Val Ala Tyr Cys Ala Asp Cys Gly Met Gly His Ser Cys His Ser
                 85                  90                  95

Pro Ala Met Ile Glu Asn Val Gln Ala Asp Ala Thr Asp Gly Thr Leu
                100                 105                 110

Lys Ile Gln Phe Ala Ser Gln Ile Gly Leu Thr Lys Thr Asp Thr His
                115                 120                 125

Asp His Thr Lys Ile Arg Tyr Ala Glu Gly His Asp Ile Ala Glu Ala
                130                 135                 140

Ala Arg Ser Thr Leu Lys Val His Ser Ser Glu Cys Ala Val Thr
145                 150                 155                 160

Gly Thr Met Gly His Phe Ile Leu Ala Lys Cys Pro Pro Gly Glu Val
                165                 170                 175

Ile Ser Val Ser Phe Val Asp Ser Lys Asn Glu Gln Arg Thr Cys Arg
                180                 185                 190

Ile Ala Tyr His His Glu Gln Arg Leu Ile Gly Arg Glu Arg Phe Thr
                195                 200                 205

Val Arg Pro His His Gly Ile Glu Leu Pro Cys Thr Thr Tyr Gln Leu
210                 215                 220

Thr Thr Ala Glu Thr Ser Glu Glu Ile Asp Met His Met Pro Pro Asp
225                 230                 235                 240

Ile Pro Asp Arg Thr Ile Leu Ser Gln Gln Ser Gly Asn Val Lys Ile
                245                 250                 255

Thr Val Asn Gly Arg Thr Val Lys Tyr Ser Cys Ser Cys Gly Ser Lys
                260                 265                 270

Pro Ser Gly Thr Thr Thr Asp Lys Thr Ile Asn Ser Cys Thr Val
                275                 280                 285

Asp Lys Cys Gln Ala Tyr Val Thr Ser His Thr Lys Trp Gln Phe Asn
290                 295                 300

Ser Pro Phe Val Pro Arg Ala Glu Gln Ala Glu Arg Lys Gly Lys Val
305                 310                 315                 320

His Ile Pro Phe Pro Leu Ile Asn Thr Thr Cys Arg Val Pro Leu Ala
                325                 330                 335

Pro Glu Ala Leu Val Arg Ser Gly Lys Arg Glu Ala Thr Leu Ser Leu
                340                 345                 350

His Pro Ile His Pro Thr Leu Leu Ser Tyr Arg Thr Leu Gly Arg Glu
                355                 360                 365

Pro Val Phe Asp Glu Gln Trp Ile Thr Thr Gln Thr Glu Val Thr Ile
                370                 375                 380

Pro Val Pro Val Glu Gly Val Glu Tyr Arg Trp Gly Asn His Lys Pro
385                 390                 395                 400

Gln Arg Leu Trp Ser Gln Leu Thr Thr Glu Gly Arg Ala His Gly Trp
                405                 410                 415

Pro His Glu Ile Ile Glu Tyr Tyr Gly Leu His Pro Thr Thr Thr
                420                 425                 430

Ile Val Val Val Ala Val Ser Val Val Leu Leu Ser Val Ala
                435                 440                 445

Ala Ser Val Tyr Met Cys Val Ala Arg Asn Lys Cys Leu Thr Pro
450                 455                 460

Tyr Ala Leu Thr Pro Gly Ala Val Pro Val Thr Ile Gly Val Leu
465                 470                 475                 480
```

Cys Cys Ala Pro Lys Ala His Ala
485

<210> SEQ ID NO 115
<211> LENGTH: 1464
<212> TYPE: DNA
<213> ORGANISM: Artificial Sequence
<220> FEATURE:
<223> OTHER INFORMATION: MAYV-E3+E2

<400> SEQUENCE: 115
gccgctccta ccgtcactgc tatgtgcctg ctggccaacg tgagcttccc ttgctttcag 60
ccatcttgta gcccctgctg ttatgagaag ggccctgagc caaccctgag gatgctggag 120
gagaacgtga attccgaggg ctactatgag ctgctgcacg ccgccgtgta ttgcaagaac 180
agctcccggt ctaagcgcag caccgccaac cacttcaatg cctacaagct gacaagacca 240
tatgtggcct actgcgccga ctgtggcatg ggccactcct gtcactctcc cgccatgatc 300
gagaatgtgc aggccgacgc caccgatggc acactgaaga tccagtttgc ctcccagatc 360
ggcctgacaa agaccgacac acacgatcac accaagatca gatacgcaga gggacacgac 420
atcgcagagg cagcaagatc tacactgaag gtgcactcta gctccgagtg cgcagtgacc 480
ggaacaatgg gacacttcat cctggccaag tgtccccctg gcgaagtgat ctccgtgtct 540
tttgtggatt ccaagaacga gcagaggacc tgcagaatcg cctatcacca cgagcagcgg 600
ctgatcggca gggagagatt caccgtgcgc cctcaccacg gaatcgagct gccatgtacc 660
acataccagc tgaccacagc cgagacaagc gaggagatcg acatgcacat gccacccgac 720
atccctgatc ggacaatcct gagccagcag tccggcaacg tgaagatcac cgtgaatggc 780
cgcacagtga agtatagctg ctcctgtggc tctaagccaa gcggcaccac aaccacagac 840
aagaccatca actcctgcac agtggataag tgtcaggcct acgtgaccag ccacacaaag 900
tggcagttca attccccttt tgtgccacgg gccgagcagg cagagaggaa gggcaaggtg 960
cacatcccct tccctctgat caataccaca tgcagggtgc cactggcacc tgaggccctg 1020
gtgcggtctg gcaagaggga ggccaccctg agcctgcacc caatccaccc caccctgctg 1080
agctatagga cactgggcag agagcccgtg tttgatgagc agtggatcac cacacagacc 1140
gaggtgacaa tcccagtgcc agtggaggga gtggagtaca gatggggcaa ccacaagcct 1200
cagagactgt ggagccagct gaccacagag ggaagggcac acggatggcc acacgagatc 1260
atcgagtact attacggcct gcaccctacc acaaccatcg tggtggtggt ggccgtgagc 1320
gtggtggtgc tgctgtccgt ggcagccagc gtgtacatgt gcgtggtggc ccgcaataag 1380
tgtctgaccc cctacgccct gacacctggc gctgtggtcc ctgtgacaat cggggtgctg 1440
tgctgtgctc ccaaagctca tgcc 1464

<210> SEQ ID NO 116
<211> LENGTH: 993
<212> TYPE: PRT
<213> ORGANISM: Artificial Sequence
<220> FEATURE:
<223> OTHER INFORMATION: MAYV-Env

<400> SEQUENCE: 116

Ala Ala Pro Thr Val Thr Ala Met Cys Leu Leu Ala Asn Val Ser Phe
1 5 10 15

Pro Cys Phe Gln Pro Ser Cys Ser Pro Cys Cys Tyr Glu Lys Gly Pro
20 25 30

```
Glu Pro Thr Leu Arg Met Leu Glu Glu Asn Val Asn Ser Glu Gly Tyr
            35                  40                  45

Tyr Glu Leu Leu His Ala Ala Val Tyr Cys Lys Asn Ser Ser Arg Ser
    50                  55                  60

Lys Arg Ser Thr Ala Asn His Phe Asn Ala Tyr Lys Leu Thr Arg Pro
65                  70                  75                  80

Tyr Val Ala Tyr Cys Ala Asp Cys Gly Met Gly His Ser Cys His Ser
                85                  90                  95

Pro Ala Met Ile Glu Asn Val Gln Ala Asp Ala Thr Asp Gly Thr Leu
                100                 105                 110

Lys Ile Gln Phe Ala Ser Gln Ile Gly Leu Thr Lys Thr Asp Thr His
            115                 120                 125

Asp His Thr Lys Ile Arg Tyr Ala Glu Gly His Asp Ile Ala Glu Ala
            130                 135                 140

Ala Arg Ser Thr Leu Lys Val His Ser Ser Glu Cys Ala Val Thr
145                 150                 155                 160

Gly Thr Met Gly His Phe Ile Leu Ala Lys Cys Pro Pro Gly Glu Val
                165                 170                 175

Ile Ser Val Ser Phe Val Asp Ser Lys Asn Glu Gln Arg Thr Cys Arg
                180                 185                 190

Ile Ala Tyr His His Glu Gln Arg Leu Ile Gly Arg Glu Arg Phe Thr
                195                 200                 205

Val Arg Pro His His Gly Ile Glu Leu Pro Cys Thr Thr Tyr Gln Leu
            210                 215                 220

Thr Thr Ala Glu Thr Ser Glu Glu Ile Asp Met His Met Pro Pro Asp
225                 230                 235                 240

Ile Pro Asp Arg Thr Ile Leu Ser Gln Gln Ser Gly Asn Val Lys Ile
                245                 250                 255

Thr Val Asn Gly Arg Thr Val Lys Tyr Ser Cys Ser Cys Gly Ser Lys
                260                 265                 270

Pro Ser Gly Thr Thr Thr Thr Asp Lys Thr Ile Asn Ser Cys Thr Val
            275                 280                 285

Asp Lys Cys Gln Ala Tyr Val Thr Ser His Thr Lys Trp Gln Phe Asn
            290                 295                 300

Ser Pro Phe Val Pro Arg Ala Glu Gln Ala Glu Arg Lys Gly Lys Val
305                 310                 315                 320

His Ile Pro Phe Pro Leu Ile Asn Thr Thr Cys Arg Val Pro Leu Ala
                325                 330                 335

Pro Glu Ala Leu Val Arg Ser Gly Lys Arg Glu Ala Thr Leu Ser Leu
                340                 345                 350

His Pro Ile His Pro Thr Leu Leu Ser Tyr Arg Thr Leu Gly Arg Glu
                355                 360                 365

Pro Val Phe Asp Glu Gln Trp Ile Thr Thr Gln Thr Glu Val Thr Ile
    370                 375                 380

Pro Val Pro Val Glu Gly Val Glu Tyr Arg Trp Gly Asn His Lys Pro
385                 390                 395                 400

Gln Arg Leu Trp Ser Gln Leu Thr Thr Glu Gly Arg Ala His Gly Trp
                405                 410                 415

Pro His Glu Ile Ile Glu Tyr Tyr Gly Leu His Pro Thr Thr Thr
                420                 425                 430

Ile Val Val Val Val Ala Val Ser Val Val Leu Leu Ser Val Ala
            435                 440                 445
```

```
Ala Ser Val Tyr Met Cys Val Val Ala Arg Asn Lys Cys Leu Thr Pro
    450             455                 460
Tyr Ala Leu Thr Pro Gly Ala Val Val Pro Val Thr Ile Gly Val Leu
465             470                 475                 480
Cys Cys Ala Pro Lys Ala His Ala Arg Gly Lys Arg Arg Ser Ala
                485                 490                 495
Thr Ala Ser Phe Ala Glu Gly Met Ala Tyr Leu Trp Asp Asn Asn Gln
                500                 505                 510
Ser Met Phe Trp Met Glu Leu Thr Gly Pro Leu Ala Leu Ile Leu
            515                 520                 525
Thr Thr Cys Cys Ala Arg Ser Leu Leu Ser Cys Cys Lys Gly Ser Phe
    530                 535                 540
Leu Val Ala Val Ser Val Gly Ser Ala Val Ala Ser Ala Tyr Glu His
545                 550                 555                 560
Thr Ala Val Ile Pro Asn Gln Val Gly Phe Pro Tyr Lys Ala His Val
                565                 570                 575
Ala Arg Glu Gly Tyr Ser Pro Leu Thr Leu Gln Met Gln Val Val Glu
                580                 585                 590
Thr Ser Leu Glu Pro Thr Leu Asn Leu Glu Tyr Ile Thr Cys Asp Tyr
    595                 600                 605
Lys Thr Lys Val Pro Ser Pro Tyr Val Lys Cys Cys Gly Thr Ala Glu
    610                 615                 620
Cys Arg Thr Gln Asp Lys Pro Glu Tyr Lys Cys Ala Val Phe Thr Gly
625                 630                 635                 640
Val Tyr Pro Phe Met Trp Gly Gly Ala Tyr Cys Phe Cys Asp Ser Glu
                645                 650                 655
Asn Thr Gln Met Ser Glu Ala Tyr Val Glu Arg Ala Asp Val Cys Lys
            660                 665                 670
His Asp Tyr Ala Ala Ala Tyr Arg Ala His Thr Ala Ser Leu Arg Ala
        675                 680                 685
Lys Ile Lys Val Thr Tyr Gly Thr Val Asn Gln Thr Val Glu Ala Tyr
    690                 695                 700
Val Asn Gly Asp His Ala Val Thr Ile Ala Gly Thr Lys Phe Ile Phe
705             710                 715                 720
Gly Pro Val Ser Thr Ala Trp Thr Pro Phe Asp Thr Lys Ile Val Val
                725                 730                 735
Tyr Lys Gly Glu Val Tyr Asn Gln Asp Phe Pro Pro Tyr Gly Ala Gly
                740                 745                 750
Gln Pro Gly Arg Phe Gly Asp Ile Gln Ser Arg Thr Leu Asp Ser Lys
        755                 760                 765
Asp Leu Tyr Ala Asn Thr Gly Leu Lys Leu Ala Arg Pro Ala Ala Gly
    770                 775                 780
Asn Ile His Val Pro Tyr Thr Gln Thr Pro Ser Gly Phe Lys Thr Trp
785             790                 795                 800
Gln Lys Asp Arg Asp Ser Pro Leu Asn Ala Lys Ala Pro Phe Gly Cys
                805                 810                 815
Thr Ile Gln Thr Asn Pro Val Arg Ala Met Asn Cys Ala Val Gly Asn
                820                 825                 830
Ile Pro Val Ser Met Asp Ile Asp Ser Ala Phe Thr Arg Leu Thr
                835                 840                 845
Asp Ala Pro Ile Ile Ser Glu Leu Leu Cys Thr Val Ser Thr Cys Thr
850                 855                 860
His Ser Ser Asp Phe Gly Gly Val Ala Val Leu Ser Tyr Lys Val Glu
```

Lys Ala Gly Arg Cys Asp Val His Ser His Ser Asn Val Ala Val Leu
            885                 890                 895

Gln Glu Val Ser Ile Glu Ala Glu Gly Arg Ser Val Ile His Phe Ser
            900                 905                 910

Thr Ala Ser Ala Ala Pro Ser Phe Ile Val Ser Val Cys Ser Ser Arg
            915                 920                 925

Ala Thr Cys Thr Ala Lys Cys Glu Pro Pro Lys Asp His Val Val Thr
        930                 935                 940

Tyr Pro Ala Asn His Asn Gly Ile Thr Leu Pro Asp Leu Ser Ser Thr
945                 950                 955                 960

Ala Met Thr Trp Ala Gln His Leu Ala Gly Gly Val Gly Leu Leu Ile
            965                 970                 975

Ala Leu Ala Val Leu Ile Leu Val Ile Val Thr Cys Ile Thr Leu Arg
            980                 985                 990

Arg

<210> SEQ ID NO 117
<211> LENGTH: 2979
<212> TYPE: DNA
<213> ORGANISM: Artificial Sequence
<220> FEATURE:
<223> OTHER INFORMATION: MAYV-Env

<400> SEQUENCE: 117

| | |
|---|---|
| gccgccccca ccgtcaccgc aatgtgcctg ctggccaacg tgtccttccc ttgctttcag | 60 |
| ccatcttgta gcccctgctg ttacgagaag ggaccagagc ccaccctgag gatgctggag | 120 |
| gagaacgtga attctgaggg ctactatgag ctgctgcacg ccgccgtgta ttgcaagaac | 180 |
| agctcccggt ccaagaggag caccgccaac cacttcaatg cctacaagct gacaaggccc | 240 |
| tatgtggcct actgcgccga ttgtggcatg ggccacagct gtcactcccc tgccatgatc | 300 |
| gagaatgtgc aggccgacgc caccgatggc acactgaaga tccagtttgc ctctcagatc | 360 |
| ggcctgacaa agaccgacac acacgatcac accaagatca gatacgcaga gggacacgat | 420 |
| atcgcagagg cagccagaag cacactgaag gtgcactcta gctccgagtg cgcagtgacc | 480 |
| ggaacaatgg gacacttcat cctggccaag tgtcccccctg cgaagtgat ctccgtgtct | 540 |
| tttgtggact ccaagaacga gcagaggacc tgcagaatcg cctatcacca cgagcagcgg | 600 |
| ctgatcggaa gggagaggtt caccgtgagg ccccaccacg gaatcgagct gccatgtacc | 660 |
| acataccagc tgaccacagc cgagacaagc gaggagatcg acatgcacat gccacccgac | 720 |
| atccctgatc ggacaatcct gtctcagcag agcggcaacg tgaagatcac cgtgaatggc | 780 |
| cgcacagtga agtatagctg ctcctgtggc tccaagccat ctggcaccac aaccacagac | 840 |
| aagaccatca actcctgcac agtggataag tgtcaggcct acgtgacctc ccacacaaag | 900 |
| tggcagttca attctccttt tgtgccacgg gccgagcagg cagagaggaa gggcaaggtg | 960 |
| cacatccctt tcccactgat caataccaca tgcagggtgc cactggcacc tgaggccctg | 1020 |
| gtgcggagcg gcaagcgcga ggccacccct tccctgcacc caatccaccc caccctgctg | 1080 |
| agctatagga cactgggcag agagcccgtg tttgatgagc agtggatcac cacacagacc | 1140 |
| gaggtgacaa tccccgtgcc tgtggagggc gtggagtaca tgggcaa cacaagcct | 1200 |
| cagagactgt ggagccagct gaccacagag ggaagggcac acggatggcc tcacgagatc | 1260 |
| atcgagtact attacggcct gcacccaacc acaaccatcg tggtggtggt ggccgtgtcc | 1320 |

```
gtggtggtgc tgctgagcgt ggcagcctcc gtgtatatgt gcgtggtggc caggaataag    1380
tgtctgaccc cttacgcact gacaccagga gcagtggtgc cagtgaccat cggcgtgctg    1440
tgctgtgcac caaaggcaca cgccagggc agaaagagga gatctgccac agcaagcttc    1500
gccgagggaa tggcatatct gtgggacaac aatcagtcca tgttttggat ggagctgacc    1560
ggacctctgg ccctgctgat cctgacaacc tgctgtgcca gaagcctgct gtcctgctgt    1620
aagggcagct tcctggtggc cgtgtctgtg ggcagcgccg tggcctccgc ctacgagcac    1680
accgccgtga tccccaacca gtgggctttt ccttataagg cacacgtggc ccgggaggga    1740
tactcccctc tgaccctgca gatgcaggtg gtggagacaa gcctggagcc aacactgaat    1800
ctggagtata tcacctgcga ttacaagaca aaggtgccaa gccccatgt gaagtgctgt    1860
ggcaccgccg agtgcagaac acaggacaag cccgagtaca gtgtgccgt gttcaccggc    1920
gtgtatcctt ttatgtgggg cggcgcctac tgcttctgtg attctgagaa cacacagatg    1980
agcgaggcat acgtggagag ggcagacgtg tgcaagcacg attatgcagc agcatacagg    2040
gcacacaccg catctctgag agccaagatc aaggtgacct atggcacagt gaaccagaca    2100
gtggaggcct acgtgaatgg cgaccacgca gtgaccatcg caggaacaaa gttcatcttt    2160
ggccccgtga gcaccgcctg gacacctttc gacaccaaga tcgtggtgta agggccgag    2220
gtgtacaatc aggatttccc tccatacgga gcaggacagc caggccggtt tggcgacatc    2280
cagagccgca ccctggactc caaggatctg tatgccaaca caggcctgaa gctggccaga    2340
cccgcagcag gaaatatcca cgtgccttac acccagacac atctggcgtt caagacctgg    2400
cagaaggaca gggatagccc actgaacgcc aaggccccct ttggctgcac catccagaca    2460
aatccagtga gagccatgaa ctgtgccgtg ggcaatatcc ccgtgtccat ggacatcgcc    2520
gattctgcct tcacccggct gacagacgcc cccatcatca gcgagctgct gtgcaccgtg    2580
tccacctgta cacactctag cgattttggc ggcgtggccg tgctgtccta aggtggag    2640
aaggcaggcc ggtgcgacgt gcactctcac agcaacgtgg ccgtgctgca ggaggtgtct    2700
atcgaggccg agggccgcag cgtgatccac ttctccaccg catctgccgc accaagcttc    2760
atcgtgagcg tgtgcagcag cagggccacc tgcacagcca gtgtgagcc ccctaaggat    2820
cacgtggtga cctacccagc caaccacaat ggcatcacac tgcccgacct gagctccacc    2880
gccatgacat gggcccagca cctggccggc ggcgtgggcc tgctgattgc tctggctgtg    2940
ctgattctgg tcattgtcac ctgtattact ctgcggaga                           2979
```

<210> SEQ ID NO 118
<211> LENGTH: 275
<212> TYPE: PRT
<213> ORGANISM: Artificial Sequence
<220> FEATURE:
<223> OTHER INFORMATION: MAYV-Capsid with leader Sequence

<400> SEQUENCE: 118

Met Asp Trp Thr Trp Ile Leu Phe Leu Val Ala Ala Thr Arg Val
1               5                   10                  15

His Ser Asp Phe Leu Pro Thr Gln Val Phe Tyr Gly Arg Arg Trp Arg
                20                  25                  30

Pro Arg Met Pro Pro Arg Pro Trp Arg Pro Arg Pro Thr Ile Gln
            35                  40                  45

Arg Pro Asp Gln Gln Ala Arg Gln Met Gln Gln Leu Ile Ala Ala Val
        50                  55                  60

Ser Thr Leu Ala Leu Arg Gln Asn Ala Ala Ala Pro Gln Arg Gly Arg

```
                65                   70                   75                   80
Lys Lys Gln Pro Arg Arg Lys Lys Pro Lys Pro Gln Pro Glu Lys Pro
                    85                   90                   95

Lys Lys Gln Glu Gln Lys Pro Lys Gln Lys Lys Thr Pro Lys Lys Lys
                100                  105                 110

Pro Gly Arg Arg Glu Arg Met Cys Met Lys Ile Glu His Asp Cys Ile
            115                  120                 125

Phe Glu Val Lys His Glu Gly Lys Val Thr Gly Tyr Ala Cys Leu Val
        130                  135                 140

Gly Asp Lys Val Met Lys Pro Ala His Val Pro Gly Val Ile Asp Asn
145                  150                  155                 160

Ile Asp Leu Ala Arg Leu Ser Tyr Lys Lys Ser Ser Lys Tyr Asp Leu
                165                  170                 175

Glu Cys Ala Gln Ile Pro Val Ala Met Lys Ser Asp Ala Ser Lys Tyr
                180                  185                 190

Thr His Glu Lys Pro Glu Gly His Tyr Asn Trp His Tyr Gly Ala Val
            195                  200                 205

Gln Tyr Thr Gly Gly Arg Phe Thr Val Pro Thr Gly Val Gly Lys Pro
        210                  215                 220

Gly Asp Ser Gly Arg Pro Ile Phe Asp Asn Lys Gly Arg Val Val Ala
225                  230                  235                 240

Ile Val Leu Gly Gly Ala Asn Glu Gly Ala Arg Thr Ala Leu Ser Val
                245                  250                 255

Val Thr Trp Asn Lys Asp Met Val Thr Lys Ile Thr Pro Glu Gly Thr
                260                  265                 270

Glu Glu Trp
        275

<210> SEQ ID NO 119
<211> LENGTH: 825
<212> TYPE: DNA
<213> ORGANISM: Artificial Sequence
<220> FEATURE:
<223> OTHER INFORMATION: MAYV-Capsid with leader Sequence

<400> SEQUENCE: 119
atggactgga cttggattct gtttctggtc gccgctgcta cacgggtgca ttccgacttc     60
ctgcctactc aggtcttcta cgggaggagg tggaggccca ggatgccccc tcgcccttgg    120
cgcccaaggc cacccaccat ccagcgcccc gaccagcagg ccaggcagat gcagcagctg    180
atcgcagccg tgagcacact ggccctgagg cagaacgcag cagcccctca gagaggacgg    240
aagaagcagc ctaggagaaa gaagcctaag ccacagcccg agaagcctaa gaagcaggag    300
cagaagccaa agcagaagaa gacccccaag aagaagcctg caggagggga cgcatgtgc    360 atgaagatcg agcacgactg tatcttcgag gtgaagcacg agggcaaggt gacaggctac    420
gcctgcctgg tgggcgataa agtgatgaag ccagcccacg tgcccggcgt gatcgacaac    480
atcgatctgg cccggctgtc ctacaagaag agctccaagt atgacctgga gtgtgcccag    540
atcccagtgg ccatgaagtc tgatgccagc aagtacaccc acgagaagcc cgagggccac    600
tacaattggc actatggcgc cgtgcagtat acaggcggca gattcaccgt gcctacagga    660
gtgggcaagc caggcgactc cggcagaccc atctttgata caagggaag ggtggtggca    720 atcgtgctgg gcggcgccaa tgagggcgcc cggaccgccc tgtctgtggt cacctggaat    780
aaggatatgg tcacaaagat tacacccgaa gggacagagg aatgg                    825
```

```
<210> SEQ ID NO 120
<211> LENGTH: 454
<212> TYPE: PRT
<213> ORGANISM: Artificial Sequence
<220> FEATURE:
<223> OTHER INFORMATION: MAYV-E1 with leader sequence

<400> SEQUENCE: 120
```

Met Asp Trp Thr Trp Ile Leu Phe Leu Val Ala Ala Thr Arg Val
1               5                   10                  15

His Ser Tyr Glu His Thr Ala Val Ile Pro Asn Gln Val Gly Phe Pro
            20                  25                  30

Tyr Lys Ala His Val Ala Arg Glu Gly Tyr Ser Pro Leu Thr Leu Gln
        35                  40                  45

Met Gln Val Val Glu Thr Ser Leu Glu Pro Thr Leu Asn Leu Glu Tyr
    50                  55                  60

Ile Thr Cys Asp Tyr Lys Thr Lys Val Pro Ser Pro Tyr Val Lys Cys
65                  70                  75                  80

Cys Gly Thr Ala Glu Cys Arg Thr Gln Asp Lys Pro Glu Tyr Lys Cys
                85                  90                  95

Ala Val Phe Thr Gly Val Tyr Pro Phe Met Trp Gly Gly Ala Tyr Cys
            100                 105                 110

Phe Cys Asp Ser Glu Asn Thr Gln Met Ser Glu Ala Tyr Val Glu Arg
        115                 120                 125

Ala Asp Val Cys Lys His Asp Tyr Ala Ala Ala Tyr Arg Ala His Thr
    130                 135                 140

Ala Ser Leu Arg Ala Lys Ile Lys Val Thr Tyr Gly Thr Val Asn Gln
145                 150                 155                 160

Thr Val Glu Ala Tyr Val Asn Gly Asp His Ala Val Thr Ile Ala Gly
                165                 170                 175

Thr Lys Phe Ile Phe Gly Pro Val Ser Thr Ala Trp Thr Pro Phe Asp
            180                 185                 190

Thr Lys Ile Val Val Tyr Lys Gly Glu Val Tyr Asn Gln Asp Phe Pro
        195                 200                 205

Pro Tyr Gly Ala Gly Gln Pro Gly Arg Phe Gly Asp Ile Gln Ser Arg
    210                 215                 220

Thr Leu Asp Ser Lys Asp Leu Tyr Ala Asn Thr Gly Leu Lys Leu Ala
225                 230                 235                 240

Arg Pro Ala Ala Gly Asn Ile His Val Pro Tyr Thr Gln Thr Pro Ser
                245                 250                 255

Gly Phe Lys Thr Trp Gln Lys Asp Arg Asp Ser Pro Leu Asn Ala Lys
            260                 265                 270

Ala Pro Phe Gly Cys Thr Ile Gln Thr Asn Pro Val Arg Ala Met Asn
        275                 280                 285

Cys Ala Val Gly Asn Ile Pro Val Ser Met Asp Ile Ala Asp Ser Ala
    290                 295                 300

Phe Thr Arg Leu Thr Asp Ala Pro Ile Ile Ser Glu Leu Leu Cys Thr
305                 310                 315                 320

Val Ser Thr Cys Thr His Ser Ser Asp Phe Gly Gly Val Ala Val Leu
                325                 330                 335

Ser Tyr Lys Val Glu Lys Ala Gly Arg Cys Asp Val His Ser His Ser
            340                 345                 350

Asn Val Ala Val Leu Gln Glu Val Ser Ile Glu Ala Glu Gly Arg Ser
        355                 360                 365

```
Val Ile His Phe Ser Thr Ala Ser Ala Ala Pro Ser Phe Ile Val Ser
            370                 375                 380

Val Cys Ser Ser Arg Ala Thr Cys Thr Ala Lys Cys Glu Pro Pro Lys
385                 390                 395                 400

Asp His Val Val Thr Tyr Pro Ala Asn His Asn Gly Ile Thr Leu Pro
                405                 410                 415

Asp Leu Ser Ser Thr Ala Met Thr Trp Ala Gln His Leu Ala Gly Gly
                420                 425                 430

Val Gly Leu Leu Ile Ala Leu Ala Val Leu Ile Leu Ile Val Thr
            435                 440                 445

Cys Ile Thr Leu Arg Arg
    450

<210> SEQ ID NO 121
<211> LENGTH: 1362
<212> TYPE: DNA
<213> ORGANISM: Artificial Sequence
<220> FEATURE:
<223> OTHER INFORMATION: MAYV-E1 with leader sequence

<400> SEQUENCE: 121
atggactgga catggattct gtttctggtc gccgccgcta ctagagtgca ttcctacgag     60
catactgccg tgattcccaa ccaggtcggc ttcccataca aggcccacgt ggccagagag    120
ggctatagcc ccctgaccct gcagatgcag gtggtggaga caagcctgga gcccacactg    180
aacctggagt acatcacctg cgattataag acaaaggtgc ctagcccata cgtgaagtgc    240
tgtggcaccg ccgagtgcag aacacaggac aagcctgagt ataagtgtgc cgtgttcacc    300
ggcgtgtacc ccttcatgtg gggcggcgcc tattgcttct gtgattctga aatacacag    360 atgagcgagg cctacgtgga gagggccgac gtgtgcaagc acgattacgc agcagcatat    420
agggcacaca ccgcatctct gagagccaag atcaaggtga cctacggcac agtgaaccag    480
acagtggagg cctatgtgaa tggcgaccac gcagtgacca tcgcaggaac aaagttcatc    540
tttggccccg tgagcaccgc ctggacacca tttgacacca agatcgtggt gtacaagggc    600
gaggtgtata accaggattt ccctccctac ggagcaggac agccaggcag gtttggcgac    660
atccagagcc gcaccctgga ctccaaggat ctgtacgcca cacaggcct gaagctggcc    720 agacccgcag caggaaatat ccacgtgccc tatacccaga caccttccgg cttcaagacc    780
tggcagaagg accgggattc tccactgaac gccaaggccc cctttggctg caccatccag    840
acaaatcccg tgagagccat gaactgtgcc gtgggcaata tccccgtgag catggacatc    900
gccgattctg ccttcacccg gctgacagat gcccctatca tcagcgagct gctgtgcacc    960
gtgtccacct gtacacacag ctccgatttt ggcggcgtgg ccgtgctgtc ctacaaggtg   1020
gagaaggcag gcaggtgcga cgtgcacagc cactccaatg tggccgtgct gcaggaggtg   1080
tctatcgagg ccgagggccg cagcgtgatc cacttctcta cagccagcgc cgccccaagc   1140
ttcatcgtga gcgtgtgcag cagccggccc acctgcacag ccaagtgtga gccacccaag   1200
gatcacgtgg tgacctatcc cgccaaccac aatggcatca cactgcctga cctgtcctct   1260
accgccatga catgggccca gcacctggcc ggcggcgtgg gcctgctgat tgccctggct   1320
gtgctgattc tggtcatcgt cacctgtatt accctgcgga ga                      1362

<210> SEQ ID NO 122
<211> LENGTH: 506
<212> TYPE: PRT
<213> ORGANISM: Artificial Sequence
```

<220> FEATURE:
<223> OTHER INFORMATION: MAYV-E3+E2 with leader sequence

<400> SEQUENCE: 122

```

```
Thr Ile Pro Val Pro Val Glu Gly Val Glu Tyr Arg Trp Gly Asn His
            405                 410                 415

Lys Pro Gln Arg Leu Trp Ser Gln Leu Thr Thr Glu Gly Arg Ala His
        420                 425                 430

Gly Trp Pro His Glu Ile Ile Glu Tyr Tyr Gly Leu His Pro Thr
            435                 440                 445

Thr Thr Ile Val Val Val Ala Val Ser Val Val Leu Leu Ser
    450                 455                 460

Val Ala Ala Ser Val Tyr Met Cys Val Val Arg Asn Lys Cys Leu
465                 470                 475                 480

Thr Pro Tyr Ala Leu Thr Pro Gly Ala Val Val Pro Val Thr Ile Gly
                485                 490                 495

Val Leu Cys Cys Ala Pro Lys Ala His Ala
            500                 505

<210> SEQ ID NO 123
<211> LENGTH: 1518
<212> TYPE: DNA
<213> ORGANISM: Artificial Sequence
<220> FEATURE:
<223> OTHER INFORMATION: MAYV-E3+E2 with leader sequence

<400> SEQUENCE: 123
atggactgga cctggattct gttcctggtc gccgccgcaa ctcgcgtgca ttcagccgct      60
cctaccgtca ctgctatgtg cctgctggcc aacgtgagct cccttgctt tcagccatct     120 tgtagcccct gctgttatga agggccct gagccaaccc tgaggatgct ggaggagaac      180
gtgaattccg agggctacta tgagctgctg cacgccgccg tgtattgcaa gaacagctcc     240
cggtctaagc gcagcaccgc caaccacttc aatgcctaca gctgacaag accatatgtg      300 gcctactgcg ccgactgtgg catgggccac tcctgtcact ctcccgccat gatcgagaat     360
gtgcaggccg acgccaccga tggcacactg aagatccagt ttgcctccca gatcggcctg     420
acaaagaccg acacacacga tcacaccaag atcagatacg cagagggaca cgacatcgca     480
gaggcagcaa gatctacact gaaggtgcac tctagctccg agtgcgcagt gaccggaaca     540
atgggacact tcatcctggc caagtgtccc cctggcgaag tgatctccgt gtcttttgtg     600
gattccaaga cgagcagag gacctgcaga atcgcctatc accacgagca gcggctgatc     660
ggcagggaga gattcaccgt gcgccctcac cacggaatcg agctgccatg taccacatac     720
cagctgacca cagccgagac aagcgaggag atcgacatgc acatgccacc cgacatccct     780
gatcggacaa tcctgagcca gcagtccggc aacgtgaaga tcaccgtgaa tggccgcaca     840
gtgaagtata ctgctcctg tggctctaag ccaagcggca ccacaaccac agacaagacc     900
atcaactcct gcacagtgga taagtgtcag gcctacgtga ccagccacac aaagtggcag     960
ttcaattccc cttttgtgcc acgggccgag caggcagaga ggaagggcaa ggtgcacatc    1020
cccttccctc tgatcaatac cacatgcagg gtgccactgg cacctgaggc cctggtgcgg    1080
tctggcaaga gggaggccac cctgagcctg cacccaatcc accccacct gctgagctat     1140 aggacactgg gcagagagcc cgtgtttgat gagcagtgga tcaccacaca gaccgaggtg    1200
acaatcccag tgccagtgga gggagtggag tacagatggg gcaaccacaa gcctcagaga    1260
ctgtggagcc agctgaccac agagggaagg gcacacggat ggccacacga gatcatcgag    1320
tactattacg gcctgcaccc taccacaacc atcgtggtgg tggtggccgt gagcgtggtg    1380
gtgctgctgt ccgtggcagc cagcgtgtac atgtgcgtgg tggcccgcaa taagtgtctg    1440
```

```
acccctacg ccctgacacc tggcgctgtg gtccctgtga caatcggggt gctgtgctgt    1500
gctcccaaag ctcatgcc                                                 1518
```

<210> SEQ ID NO 124
<211> LENGTH: 1011
<212> TYPE: PRT
<213> ORGANISM: Artificial Sequence
<220> FEATURE:
<223> OTHER INFORMATION: MAYV-Env with leader sequence

<400> SEQUENCE: 124

```
Met Asp Trp Thr Trp Ile Leu Phe Leu Val Ala Ala Thr Arg Val
1               5                   10                  15

His Ser Ala Ala Pro Thr Val Thr Ala Met Cys Leu Leu Ala Asn Val
            20                  25                  30

Ser Phe Pro Cys Phe Gln Pro Ser Cys Ser Pro Cys Cys Tyr Glu Lys
        35                  40                  45

Gly Pro Glu Pro Thr Leu Arg Met Leu Glu Glu Asn Val Asn Ser Glu
    50                  55                  60

Gly Tyr Tyr Glu Leu Leu His Ala Ala Val Tyr Cys Lys Asn Ser Ser
65                  70                  75                  80

Arg Ser Lys Arg Ser Thr Ala Asn His Phe Asn Ala Tyr Lys Leu Thr
                85                  90                  95

Arg Pro Tyr Val Ala Tyr Cys Ala Asp Cys Gly Met Gly His Ser Cys
            100                 105                 110

His Ser Pro Ala Met Ile Glu Asn Val Gln Ala Asp Ala Thr Asp Gly
        115                 120                 125

Thr Leu Lys Ile Gln Phe Ala Ser Gln Ile Gly Leu Thr Lys Thr Asp
    130                 135                 140

Thr His Asp His Thr Lys Ile Arg Tyr Ala Glu Gly His Asp Ile Ala
145                 150                 155                 160

Glu Ala Ala Arg Ser Thr Leu Lys Val His Ser Ser Ser Glu Cys Ala
                165                 170                 175

Val Thr Gly Thr Met Gly His Phe Ile Leu Ala Lys Cys Pro Pro Gly
            180                 185                 190

Glu Val Ile Ser Val Ser Phe Val Asp Ser Lys Asn Glu Gln Arg Thr
        195                 200                 205

Cys Arg Ile Ala Tyr His His Glu Gln Arg Leu Ile Gly Arg Glu Arg
    210                 215                 220

Phe Thr Val Arg Pro His His Gly Ile Glu Leu Pro Cys Thr Thr Tyr
225                 230                 235                 240

Gln Leu Thr Thr Ala Glu Thr Ser Glu Glu Ile Asp Met His Met Pro
                245                 250                 255

Pro Asp Ile Pro Asp Arg Thr Ile Leu Ser Gln Gln Ser Gly Asn Val
            260                 265                 270

Lys Ile Thr Val Asn Gly Arg Thr Val Lys Tyr Ser Cys Ser Cys Gly
        275                 280                 285

Ser Lys Pro Ser Gly Thr Thr Thr Asp Lys Thr Ile Asn Ser Cys
    290                 295                 300

Thr Val Asp Lys Cys Gln Ala Tyr Val Thr Ser His Thr Lys Trp Gln
305                 310                 315                 320

Phe Asn Ser Pro Phe Val Pro Arg Ala Glu Gln Ala Glu Arg Lys Gly
                325                 330                 335

Lys Val His Ile Pro Phe Pro Leu Ile Asn Thr Thr Cys Arg Val Pro
```

```
              340             345             350
Leu Ala Pro Glu Ala Leu Val Arg Ser Gly Lys Arg Glu Ala Thr Leu
            355                 360                 365
Ser Leu His Pro Ile His Pro Thr Leu Leu Ser Tyr Arg Thr Leu Gly
            370                 375                 380
Arg Glu Pro Val Phe Asp Glu Gln Trp Ile Thr Thr Gln Thr Glu Val
385                 390                 395                 400
Thr Ile Pro Val Pro Val Glu Gly Val Glu Tyr Arg Trp Gly Asn His
                405                 410                 415
Lys Pro Gln Arg Leu Trp Ser Gln Leu Thr Thr Glu Gly Arg Ala His
                420                 425                 430
Gly Trp Pro His Glu Ile Ile Glu Tyr Tyr Gly Leu His Pro Thr
            435                 440                 445
Thr Thr Ile Val Val Val Ala Val Ser Val Val Leu Leu Ser
            450                 455                 460
Val Ala Ala Ser Val Tyr Met Cys Val Ala Arg Asn Lys Cys Leu
465                 470                 475                 480
Thr Pro Tyr Ala Leu Thr Pro Gly Ala Val Pro Val Thr Ile Gly
                485                 490                 495
Val Leu Cys Cys Ala Pro Lys Ala His Ala Arg Gly Arg Lys Arg Arg
                500                 505                 510
Ser Ala Thr Ala Ser Phe Ala Glu Gly Met Ala Tyr Leu Trp Asp Asn
                515                 520                 525
Asn Gln Ser Met Phe Trp Met Glu Leu Thr Gly Pro Leu Ala Leu Leu
            530                 535                 540
Ile Leu Thr Thr Cys Cys Ala Arg Ser Leu Leu Ser Cys Cys Lys Gly
545                 550                 555                 560
Ser Phe Leu Val Ala Val Ser Val Gly Ser Ala Val Ala Ser Ala Tyr
                565                 570                 575
Glu His Thr Ala Val Ile Pro Asn Gln Val Gly Phe Pro Tyr Lys Ala
            580                 585                 590
His Val Ala Arg Glu Gly Tyr Ser Pro Leu Thr Leu Gln Met Gln Val
            595                 600                 605
Val Glu Thr Ser Leu Glu Pro Thr Leu Asn Leu Glu Tyr Ile Thr Cys
            610                 615                 620
Asp Tyr Lys Thr Lys Val Pro Ser Pro Tyr Val Lys Cys Cys Gly Thr
625                 630                 635                 640
Ala Glu Cys Arg Thr Gln Asp Lys Pro Glu Tyr Lys Cys Ala Val Phe
                645                 650                 655
Thr Gly Val Tyr Pro Phe Met Trp Gly Gly Ala Tyr Cys Phe Cys Asp
            660                 665                 670
Ser Glu Asn Thr Gln Met Ser Glu Ala Tyr Val Glu Arg Ala Asp Val
            675                 680                 685
Cys Lys His Asp Tyr Ala Ala Ala Tyr Arg Ala His Thr Ala Ser Leu
            690                 695                 700
Arg Ala Lys Ile Lys Val Thr Tyr Gly Thr Val Asn Gln Thr Val Glu
705                 710                 715                 720
Ala Tyr Val Asn Gly Asp His Ala Val Thr Ile Ala Gly Thr Lys Phe
                725                 730                 735
Ile Phe Gly Pro Val Ser Thr Ala Trp Thr Pro Phe Asp Thr Lys Ile
            740                 745                 750
Val Val Tyr Lys Gly Glu Val Tyr Asn Gln Asp Phe Pro Pro Tyr Gly
            755                 760                 765
```

Ala Gly Gln Pro Gly Arg Phe Gly Asp Ile Gln Ser Arg Thr Leu Asp
        770                 775                 780

Ser Lys Asp Leu Tyr Ala Asn Thr Gly Leu Lys Leu Ala Arg Pro Ala
785                 790                 795                 800

Ala Gly Asn Ile His Val Pro Tyr Thr Gln Thr Pro Ser Gly Phe Lys
            805                 810                 815

Thr Trp Gln Lys Asp Arg Asp Ser Pro Leu Asn Ala Lys Ala Pro Phe
            820                 825                 830

Gly Cys Thr Ile Gln Thr Asn Pro Val Arg Ala Met Asn Cys Ala Val
        835                 840                 845

Gly Asn Ile Pro Val Ser Met Asp Ile Ala Asp Ser Ala Phe Thr Arg
    850                 855                 860

Leu Thr Asp Ala Pro Ile Ile Ser Glu Leu Leu Cys Thr Val Ser Thr
865                 870                 875                 880

Cys Thr His Ser Ser Asp Phe Gly Gly Val Ala Val Leu Ser Tyr Lys
            885                 890                 895

Val Glu Lys Ala Gly Arg Cys Asp Val His Ser His Ser Asn Val Ala
        900                 905                 910

Val Leu Gln Glu Val Ser Ile Glu Ala Glu Gly Arg Ser Val Ile His
    915                 920                 925

Phe Ser Thr Ala Ser Ala Ala Pro Ser Phe Ile Val Ser Val Cys Ser
930                 935                 940

Ser Arg Ala Thr Cys Thr Ala Lys Cys Glu Pro Pro Lys Asp His Val
945                 950                 955                 960

Val Thr Tyr Pro Ala Asn His Asn Gly Ile Thr Leu Pro Asp Leu Ser
            965                 970                 975

Ser Thr Ala Met Thr Trp Ala Gln His Leu Ala Gly Gly Val Gly Leu
            980                 985                 990

Leu Ile Ala Leu Ala Val Leu Ile Leu Val Ile Val Thr Cys Ile Thr
    995                 1000                1005

Leu Arg Arg
    1010

<210> SEQ ID NO 125
<211> LENGTH: 3033
<212> TYPE: DNA
<213> ORGANISM: Artificial Sequence
<220> FEATURE:
<223> OTHER INFORMATION: MAYV-Env with leader sequence

<400> SEQUENCE: 125
atggactgga cttggattct gttcctggtc gctgccgcaa ctcgcgtgca tagtgccgcc      60
cccaccgtca ccgcaatgtg cctgctggcc aacgtgtcct ccccttgctt tcagccatct     120
tgtagcccct gctgttacga aagggaccca gagcccaccc tgaggatgct ggaggagaac     180
gtgaattctg agggctacta tgagctgctg cacgccgccg tgtattgcaa gaacagctcc     240
cggtccaaga ggagcaccgc caaccacttc aatgcctaca gctgacaag gccctatgtg      300 gcctactgcg ccgattgtgg catgggccac agctgtcact cccctgccat gatcgagaat     360
gtgcaggccg acgccaccga tggcacactg aagatccagt tgcctctca gatcggcctg     420 acaaagaccg acacacacga tcacaccaag atcagatacg cagagggaca cgatatcgca     480
gaggcagcca gaagcacact gaaggtgcac tctagctccg agtgcgcagt gaccggaaca     540
atgggacact tcatcctggc caagtgtccc cctggcgaag tgatctccgt gtcttttgtg     600

```
gactccaaga acgagcagag gacctgcaga atcgcctatc accacgagca gcggctgatc    660
ggaagggaga ggttcaccgt gaggccccac cacggaatcg agctgccatg taccacatac    720
cagctgacca cagccgagac aagcgaggag atcgacatgc acatgccacc cgacatccct    780
gatcggacaa tcctgtctca gcagagcggc aacgtgaaga tcaccgtgaa tggccgcaca    840
gtgaagtata gctgctcctg tggctccaag ccatctggca ccacaaccac agacaagacc    900
atcaactcct gcacagtgga taagtgtcag gcctacgtga cctcccacac aaagtggcag    960
ttcaattctc cttttgtgcc acgggccgag caggcagaga ggaagggcaa ggtgcacatc   1020
cctttcccac tgatcaatac cacatgcagg gtgccactgg cacctgaggc cctggtgcgg   1080
agcggcaagc gcgaggccac cctgtccctg cacccaatcc accccaccct gctgagctat   1140
aggacactgg gcagagagcc cgtgtttgat gagcagtgga tcaccacaca gaccgaggtg   1200
acaatccccg tgcctgtgga gggcgtggag tacagatggg gcaaccacaa gcctcagaga   1260
ctgtggagcc agctgaccac agagggaagg gcacacggat ggcctcacga gatcatcgag   1320
tactattacg gcctgcaccc aaccacaacc atcgtggtgg tggtgccgt gtccgtggtg   1380
gtgctgctga gcgtggcagc ctccgtgtat atgtgcgtgg tggccaggaa taagtgtctg   1440
acccccttacg cactgacacc aggagcagtg gtgccagtga ccatcggcgt gctgtgctgt   1500
gcaccaaagg cacacgccag gggcagaaag aggagatctg ccacagcaag cttcgccgag   1560
ggaatggcat atctgtggga caacaatcag tccatgtttt ggatggagct gaccggacct   1620
ctggccctgc tgatcctgac aacctgctgt gccagaagcc tgctgtcctg ctgtaagggc   1680
agcttcctga tggccgtgtc tgtgggcagc gccgtggcct ccgcctacga gcacaccgcc   1740
gtgatcccca accaagtggg cttttccttat aaggcacacg tggcccggga gggatactcc   1800
cctctgaccc tgcagatgca ggtggtggag acaagcctgg agccaacact gaatctggag   1860
tatatcacct gcgattacaa gacaaaggtg ccaagcccct atgtgaagtg ctgtggcacc   1920
gccgagtgca gaacacagga caagcccgag tacaagtgtg ccgtgttcac cggcgtgtat   1980
cctttatgt ggggcggcgc ctactgcttc tgtgattctg agaacacaca gatgagcgag   2040
gcatacgtgg agagggcaga cgtgtgcaag cacgattatg cagcagcata cagggcacac   2100
accgcatctc tgagagccaa gatcaaggtg acctatggca cagtgaacca gacagtggag   2160
gcctacgtga atggcgacca cgcagtgacc atcgcaggaa caaagttcat ctttggcccc   2220
gtgagcaccg cctggacacc tttcgacacc aagatcgtgg tgtataaggg cgaggtgtac   2280
aatcaggatt ccctccata cggagcagga cagccaggcc ggtttggcga catccagagc   2340
cgcaccctgg actccaagga tctgtatgcc aacacaggcc tgaagctggc cagacccgca   2400
gcaggaaata tccacgtgcc ttacacccag acaccatctg gcttcaagac ctggcagaag   2460
gacagggata gcccactgaa cgccaaggcc ccctttggct gcaccatcca gacaaatcca   2520
gtgagagcca tgaactgtgc cgtgggcaat atccccgtgt ccatggacat cgccgattct   2580
gccttcaccc ggctgacaga cgcccccatc atcagcgagc tgctgtgcac cgtgtccacc   2640
tgtacacact ctagcgattt tggcggcgtg gccgtgctgt cctataaggt ggagaaggca   2700
ggccggtgcg acgtgcactc tcacagcaac gtggccgtgc tgcaggaggt gtctatcgag   2760
gccgagggcc gcagcgtgat ccacttctcc accgcatctg ccgcaccaag cttcatcgtg   2820
agcgtgtgca gcagcagggc cacctgcaca gccaagtgtg agcccctaa ggatcacgtg   2880
gtgacctacc agccaaccaa caatggcatc acactgcccg acctgagctc caccgccatg   2940
acatggggcc agcacctggc cggcggcgtg ggcctgctga ttgctctggc tgtgctgatt   3000
```

```
ctggtcattg tcacctgtat tactctgcgg aga                              3033
```

<210> SEQ ID NO 126
<211> LENGTH: 7
<212> TYPE: PRT
<213> ORGANISM: Artificial Sequence
<220> FEATURE:
<223> OTHER INFORMATION: Furin Protease Sequence

<400> SEQUENCE: 126

```
Arg Gly Arg Lys Arg Arg Ser
1               5
```